US012491257B2

(12) United States Patent
Missinato et al.

(10) Patent No.: US 12,491,257 B2
(45) Date of Patent: Dec. 9, 2025

(54) COMPOSITIONS AND METHODS OF USING PRKAG2-TARGETING ANTIBODY-OLIGONUCLEOTIDE CONJUGATES

(71) Applicant: Avidity Biosciences, Inc., San Diego, CA (US)

(72) Inventors: Maria Azzurra Missinato, San Diego, CA (US); Georgios Karamanlidis, Thousand Oaks, CA (US); Sami Abdulwahab Abdulkadir, San Diego, CA (US); Subbarao Nallagatla, San Diego, CA (US); Maryam Jordan, Escondido, CA (US)

(73) Assignee: AVIDITY BIOSCIENCES, INC., San Diego, CA (US)

( * ) Notice: Subject to any disclaimer, the term of this patent is extended or adjusted under 35 U.S.C. 154(b) by 0 days.

(21) Appl. No.: 18/755,579

(22) Filed: Jun. 26, 2024

(65) Prior Publication Data

US 2025/0108120 A1 Apr. 3, 2025

Related U.S. Application Data

(60) Provisional application No. 63/510,531, filed on Jun. 27, 2023.

(51) Int. Cl.

| | |
|---|---|
| ***A61K 47/68*** | (2017.01) |
| ***A61P 9/00*** | (2006.01) |
| ***C07K 16/28*** | (2006.01) |
| ***C12N 15/113*** | (2010.01) |

(52) U.S. Cl.

CPC ...... *A61K 47/6807* (2017.08); *A61K 47/6849* (2017.08); *A61P 9/00* (2018.01); *C07K 16/2881* (2013.01); *C12N 15/113* (2013.01); *C12N 2310/11* (2013.01); *C12N 2310/14* (2013.01); *C12N 2310/313* (2013.01); *C12N 2310/321* (2013.01)

(58) Field of Classification Search

None

See application file for complete search history.

(56) References Cited

U.S. PATENT DOCUMENTS

| | | | | |
|---|---|---|---|---|
| 4,694,778 | A | 9/1987 | Learn et al. | |
| 5,142,047 | A | 8/1992 | Summerton et al. | |
| 5,185,444 | A | 2/1993 | Summerton et al. | |
| 5,334,711 | A | 8/1994 | Sproat et al. | |
| 5,627,053 | A | 5/1997 | Usman et al. | |
| 5,716,824 | A | 2/1998 | Beigelman et al. | |
| 5,736,557 | A | 4/1998 | Hofheinz et al. | |
| 5,885,803 | A | 3/1999 | Bandman et al. | |
| 5,889,136 | A | 3/1999 | Scaringe et al. | |
| 6,008,400 | A | 12/1999 | Scaringe et al. | |
| 6,111,086 | A | 8/2000 | Scaringe | |
| 6,821,783 | B1 | 11/2004 | Comely et al. | |
| 6,884,869 | B2 | 4/2005 | Senter et al. | |
| 7,498,298 | B2 | 3/2009 | Doronina et al. | |
| 7,850,975 | B2 | 12/2010 | Mullis | |
| 8,090,542 | B2 | 1/2012 | Khvorova et al. | |
| 8,288,352 | B2 | 10/2012 | Doronina et al. | |
| 8,501,930 | B2 | 8/2013 | Rozema et al. | |
| 8,591,910 | B2 | 11/2013 | Mullis | |
| 8,604,184 | B2 | 12/2013 | Mullis et al. | |
| 8,609,105 | B2 | 12/2013 | Senter et al. | |
| 8,697,688 | B2 | 4/2014 | Howard et al. | |
| 8,936,910 | B2 | 1/2015 | Mitsch et al. | |
| 9,089,614 | B2 | 7/2015 | Lin et al. | |
| 10,550,188 | B2 | 2/2020 | Geall et al. | |
| 10,612,027 | B2 | 4/2020 | Maier et al. | |
| 10,881,743 | B2 | 1/2021 | Geall et al. | |
| 10,913,800 | B2 | 2/2021 | Darimont et al. | |
| 10,994,020 | B2 | 5/2021 | Levin et al. | |
| 11,110,180 | B2 | 9/2021 | Geall et al. | |
| 11,555,190 | B2 | 1/2023 | Malecova et al. | |
| 2006/0275770 | A1* | 12/2006 | Bednarik | G01N 33/5308 435/7.1 |
| 2008/0113351 | A1 | 5/2008 | Naito et al. | |
| 2011/0097335 | A1 | 4/2011 | Sugimoto | |
| 2011/0229484 | A1* | 9/2011 | Baumert | C12N 15/113 435/7.1 |
| 2013/0028919 | A1 | 1/2013 | Howard et al. | |
| 2013/0171242 | A1* | 7/2013 | Lim | C12N 15/113 435/375 |
| 2013/0309256 | A1 | 11/2013 | Lyon et al. | |
| 2014/0099666 | A1 | 4/2014 | Rossomando et al. | |

(Continued)

FOREIGN PATENT DOCUMENTS

| | | | |
|---|---|---|---|
| EP | 1579015 | A2 | 9/2005 |
| WO | WO-9207065 | A1 | 4/1992 |

(Continued)

OTHER PUBLICATIONS

*Homo sapiens* protein kinase AMP-activated non-catalytic subunit gamma 2 (PRKAG2) transcript variant a, mRNA, NCBI reference No. NM_016203.4, retrieved on-line from National Library of Medicine, NCBI on Feb. 5, 2025, pp. 1-6. (Year: 2018).*

Michael Gollb Circulation vol. 117 pp. 134-135, pp. 1-4 (Year: 2008).*

Pendergraff et al. Nucleic Acid Therapeutics vol. 26, pp. 1-10 (Year: 2016).*

Abramova, Tatyana V. et al. Novel Oligonucleotide Analogues Based on Morpholino Nucleoside Subunits Antisense Technologies: New Chemical Possibilities. Indian Journal of Chemistry 48B:1721-1726 (2009).

Agarwal, Paresh. et al. A Pictet-Spengler Ligation for Protein Chemical Modification. PNAS USA 110(1):46-51 (2013).

(Continued)

*Primary Examiner* — Brian Whiteman

(74) *Attorney, Agent, or Firm* — WILSON SONSINI GOODRICH & ROSATI

(57) ABSTRACT

Disclosed herein are polynucleic acid molecules, pharmaceutical compositions, and methods of use for PRKAG2 antibody oligonucleotide conjugates (AOC).

22 Claims, 26 Drawing Sheets

Specification includes a Sequence Listing.

(56) References Cited

U.S. PATENT DOCUMENTS

2014/0127239 A1 5/2014 Howard
2014/0194610 A1 7/2014 Verdine et al.
2014/0286970 A1 9/2014 Jeffrey et al.
2014/0294851 A1 10/2014 Nguyen
2015/0037360 A1 2/2015 Smith
2015/0105539 A1 4/2015 Miao et al.
2015/0105540 A1 4/2015 Miao et al.
2015/0211006 A1 7/2015 Butler et al.
2018/0028557 A1* 2/2018 Ozsolak ............ A61K 31/7105
2018/0030452 A1* 2/2018 Ozsolak ................ C12N 15/63
2019/0192681 A1 6/2019 Geall et al.
2021/0254056 A1 8/2021 Liu et al.
2021/0261679 A1 8/2021 Darimont et al.

FOREIGN PATENT DOCUMENTS

WO WO-9315187 A1 8/1993
WO WO-9726270 A2 7/1997
WO WO-9734631 A1 9/1997
WO WO-9813526 A1 4/1998
WO WO-2009099942 A2 8/2009
WO WO-2009126933 A2 10/2009
WO WO-2013166155 A1 11/2013
WO WO-2014080251 A1 5/2014
WO WO-2014140317 A2 9/2014
WO WO-2014145090 A1 9/2014
WO WO-2014177042 A1 11/2014
WO WO-2014197854 A1 12/2014
WO WO-2015038426 A1 3/2015
WO WO-2015057699 A2 4/2015
WO WO-2015069587 A2 5/2015
WO WO-2015107425 A2 7/2015
WO WO-2025006639 A2 1/2025

OTHER PUBLICATIONS

Albarran, Brian. et al. Efficient intracellular delivery of a pro-apoptotic peptide with a pH-responsive carrier. Reactive and Functional Polymers 71(3):261-265 (2011).
Alegre, Maria-Luisa. et al. Effect of a Single Amino Acid Mutation on the Activating and Immunosuppressive Properties of a "Humanized" OKT3 Monoclonal Antibody. Journal of Immunology 148(11):3461-3468 (1992).
Axup, Jun Y. et al. Synthesis of Site-specific Antibody-drug Conjugates Using Unnatural Amino Acids. PNAS USA 109(40):16101-16106 (2012).
Beigelman, Leonid. et al. Chemical Modification of Hammerhead Ribozymes: Catalytic Activity and Nuclease Resistance. Journal of Biological Chemistry 270(43):25702-25708 (1995).
Bird, Robert E. et al. Single-chain Antigen-binding Proteins. Science 242(4877):423-426 (1988).
Blaney, Paul. et al. Traceless Solid-phase Organic Synthesis. Chemical Reviews 102(7):2607-2624 (2002).
Burlina, Fabienne. et al. Chemical Engineering of RNase Resistant and Catalytically Active Hammerhead Ribozymes. Bioorganic and Medicinal Chemistry 5(11):1999-2010 (1997).
Casi, Giulio. et al. Site-specific Traceless Coupling of Potent Cytotoxic Drugs to Recombinant Antibodies for Pharmacodelivery. Journal of the American Chemical Society 134(13):5887-5892 (2012).
Clackson, Tim. et al. Making antibody fragments using phage display libraries. Nature 352(6336):624-628 (1991).
Colberre-Garapin, Florence. et al. A New Dominant Hybrid Selective Marker for Higher Eukaryotic Cells. Journal of Molecular Biology 150(1):1-14 (1981).
Cole, S.P.C. et al. The EBV-Hybridoma Technique and its Application to Human Lung Cancer. Monoclonal Antibodies and Cancer Therapy 27:77-96 (1985).
Crouse, Gray F. et al. Expression and Amplification of Engineered Mouse Dihydrofolate Reductase Minigenes. Molecular Cell Biology 3(2):257-266 (1983).
Dawson, Philip E. et al. Modulation of Reactivity in Native Chemical Ligation through the Use of Thiol Additives. Journal of American Chemical Society 119(19):4325-4329 (1997).
Dawson, Philip E. et al. Synthesis of Proteins by Native Chemical Ligation. 266(5186):776-779 (1994).
Dimasi, Nazzareno. et al. Development of a Trispecific Antibody Designed to Simultaneously and Efficiently Target Three Different Antigens on Tumor Cells. Molecular Pharmaceutics 12(9):3490-3501 (2015).
Earnshaw, David J. et al. Modified Oligoribonucleotides as Site-Specific Probes of RNA Structure and Function. Biopolymers (Nucleic Acid Sciences) 48(1):39-55 (1998).
Goldspiel, Barry R. et al. Human Gene Therapy. Clinical Pharmacy 12(7):488-505 (1993).
Griffey, Richard H. et al. 2'-O-aminopropyl Ribonucleotides: A Zwitterionic Modification that Enhances the Exonuclease Resistance and Biological Activity of Antisense Oligonucleotides. Journal of Medicinal Chemistry 39(26):5100-5109 (1997).
Hackeng, Tilman M. et al. Protein Synthesis by Native Chemical Ligation: Expanded Scope by Using Straightforward Methodology. PNAS USA 96(18):10068-10073 (1999).
Hanes, Jozef, and A Pluckthun. In Vitro Selection and Evolution of Functional Proteins by Using Ribosome Display. PNAS USA 94(10):4937-4942 (1997).
Hejesen, Christian. et al. A Traceless Aryl-triazene Linker for DNA-directed Chemistry. Organic and Biomolecular Chemistry 11(15):2493-2497 (2013).
Huse, William D. et al. Generation of a Large Combinatorial Library of the Immunoglobulin Repertoire in Phage Lambda. Science 246(4935):1275-1281 (1989).
Huston, James S. et al. Protein engineering of antibody binding sites: recovery of specific activity in an anti-digoxin single-chain fv analogue produced in *Escherichia coli*. PNAS USA 85(16):5879-5883 (1988).
Idusogie, Esohe E. et al. Engineered Antibodies with Increased Activity to Recruit Complement. Journal of Immunology 166(4):2571-2575 (2001).
Kaneko, Etsuji. et al. Optimizing Therapeutic Antibody Function: Progress with Fc Domain Engineering. Bio Drugs 25(1):1-11 (2011).
Karpeisky, Alexander. et al. Highly Efficient Synthesis of 2-O-amino Nucleosides and their Incorporation in Hammerhead Ribozymes. Tetrahedron Letters 39:1131-1134 (1998).
Kohler, G, and Milstein, C. Continuous Cultures of Fused Cells Secreting Antibody of Predefined Specificity. Nature 256(5517):495-497 (1975).
Koizumi, Makoto. ENA Oligonucleotides as Therapeutics. Current Opinion in Molecular Therapeutics 8(2):144-149 (2006).
Kozbor, Danuta, and J C Roder. The Production of Monoclonal Antibodies From Human Lymphocytes. Immunology Today 4(3):72-79 (1983).
Kutmeier, G. et al. Assembly of Humanized Antibody Genes from Synthetic Oligonucleotides Using a Single-round PCR. Biotechniques 17(2):242-246 (1994).
Lazar, Greg A. et al. Engineered Antibody Fc Variants with Enhanced Effector Function. PNAS USA 103(11):4005-4010 (2006).
Loakes, David. Survey and Summary: The applications of universal DNA base analogues. Nucleic Acids Research 29(12):2437-2447 (2001).
Lowy, Israel. et al. Isolation of Transforming DNA: Cloning the Hamster Aprt Gene. Cell 22(3):817-823 (1980).
Lyon, Robert P. et al. Self-Hydrolyzing Maleimides improve the Stability and Pharmacological Properties of Antibody-drug Conjugates. Nature Biotechnology 32(10):1059-1062 (2014).
Martinez, Javier. et al. Single-Stranded Antisense siRNAs Guide Target RNA Cleavage in RNAi. Cell 110(5):563-574 (2002).
McEnaney, Patrick J. et al. Antibody-Recruiting Molecules: An Emerging Paradigm for Engaging Immune Function in Treating Human Disease. ACS Chemical Biology 7(7):1139-1151 (2012).
Moore, Gregory L. et al. Engineered Fc Variant Antibodies with Enhanced Ability to Recruit Complement and Mediate Effector Functions. mAbs 2(2):181-189 (2010).
Morgan, Richard A, and W F Anderson. Human Gene Therapy. Annual Review of Biochemistry 62:191-217 (1993).

(56) References Cited

OTHER PUBLICATIONS

Morrison, Sherie L. et al. Chimeric Human Antibody Molecules: Mouse Antigen-binding Domains With Human Constant Region Domains. PNAS USA 81(21):6851-6855 (1984).
Mulligan, Richard C, and P Berg. Selection for Animal Cells that Express the *Escherichia coli* Gene Coding for Xanthine-guanine Phosphoribosyltransferase. PNAS USA 78(4):2072-2076 (1981).
Mulligan, Richard C. The Basic Science of Gene Therapy. Science 260(5110):926-932 (1993).
Naisbitt, D J. et al. Disposition of Amodiaquine and Related Antimalarial Agents in Human Neutrophils: Implications for Drug Design. The Journal of Pharmacology and Experimental Therapeutics 280(2):884-893 (1997).
Natsume, Akito et al. Engineered Antibodies of IgG1/IgG3 Mixed Isotype with Enhanced Cytotoxic Activities. Cancer Research 68(10):3863-3872 (2008).
Neuberger, Michael S. et al. Recombinant Antibodies Possessing Novel Effector Functions. Nature 312(5995):604-608 (1984).
Obika, Satosh et al. Synthesis of 2'-0,4'-C-methyleneuridine and -cytidine. Novel bicyclic nucleosides having a fixed C3'-endo sugar puckering. Tetrahedron Letters 38(50):8735-8738 (1997).
O'Hare, K. et al. Transformation of Mouse Fibroblasts to Methotrexate Resistance by a Recombinant Plasmid Expressing a Prokaryotic Dihydrofolate Reductase. PNAS USA 78(3):1527-1531 (1981).
Perrault, Jean-Pierre. et al. Mixed Deoxyribo- and Ribo-Oligonucleotides with Catalytic Activity. Nature 344(6266):565-568 (1990).
Pieken, Wolfgang A. et al. Kinetic Characterization of Ribonuclease-Resistant 2'-Modified Hammerhead Ribozymes. Science 253(5017):314-317 (1991).
Santerre, Robert F. et al. Expression of Prokaryotic Genes for Hygromycin B and G418 Resistance as Dominant-selection Markers in Mouse L Cells. Gene 30(3):147-156 (1984).
Schwarz, Dianne S. et al. Evidence that siRNAs Function as Guides, not Primers, in the *Drosophila* and Human RNAi Pathways. Molecular Cell 10:537-548 (2002).
Shields, Robert L. et al. High Resolution Mapping of the Binding Site on Human IgG1 for Fc Gamma RI, Fc Gamma RII, Fc Gamma RIII, and FcRn and design of IgG1 variants with improved binding to the Fc gamma R. Journal of Biological Chemistry 276(9):6591-6604 (2001).
Skerra, Arne, and A Pluckthun. Assembly of a Functional Immunoglobulin Fv Fragment in *Escherichia coli*. Science 240(4855):1038-1041 (1988).
Stavenhagen, Jeffrey B. et al. Enhancing the Potency of Therapeutic Monoclonal Antibodies via Fc Optimization. Advances in Enzyme Regulation 48:152-64 (2008).
Stavenhagen, Jeffrey B. et al. Fc Optimization of Therapeutic Antibodies Enhances their Ability to Kill Tumor Cells In vitro and Controls Tumor Expansion In vivo via Low-Affinity Activating Fcgamma Receptors. Cancer Research 67(18):8882-8890 (2007).
Strop, Pavel. et al. Location Matters: Site of Conjugation Modulates Stability and Pharmacokinetics of Antibody Drug Conjugates. Chemistry and Biology 20(2):161-167 (2013).
Szybalska, Elizabeth H, and W Szybalski. Genetics of Human Cell Lines, IV. DNA-Mediated Heritable Transformation of a Biochemical Trait. PNAS USA 48(12):2026-2034 (1962).
Takeda, Shun-Ichi. et al. Construction of Chimaeric Processed Immunoglobulin Genes Containing Mouse Variable and Human Constant Region Sequences. Nature 314(6010):452-454 (1985).
Tolstoshev, Paul. Gene Therapy, Concepts, Current Trials and Future Directions. Annual Review Pharmacology and Toxicology 32:573-596 (1993).
US Food and Drug Administration. Guide for the Care and Use of Laboratory Animals. US National Institutes of Health:1-246 (2011).
Usman, Nassim, and Cedergren, Robert. Exploiting the Chemical Synthesis of RNA. Trends in Biochemical Sciences 17:334-339 (1992).
Verma, Sandeep. et al. Modified Oligonucleotides: Synthesis and Strategy for Users. Annual Review of Biochemistry 67:99-134 (1998).
Ward, E Sally. et al. Binding Activities of a Repertoire of Single Immunoglobulin Variable Domains Secreted from *Escherichia coli*. Nature 341(6242):544-546 (1989).
Wigler, Michael. et al. Transfer of Purified Herpes Virus Thymidine Kinase Gene to Cultured Mouse Cells. Cell 11(1):223-232 (1977).
Wigler, Michael. et al. Transformation of Mammalian Cells With an Amplifiable Dominant-acting Gene. PNAS USA 77(6):3567-3570 (1980).
Wu, Bin. et al. Building Complex Glycopeptides: Development of a Cysteine-free Native Chemical Ligation Protocol. Angewandte Chemie 45(25):4116-4125 (2006).
Wu, George Y, and C H Wu et al. Delivery systems for Gene Therapy. Biotherapy 3(1):87-95 (1991).
Wu, Peng. et al. Site-specific Chemical Modification of Recombinant Proteins Produced in Mammalian Cells by Using the Genetically Encoded Aldehyde Tag. PNAS USA 106(9):3000-3005 (2009).
Zhang, Andrew X. et al. A Remote Arene-Binding Site on Prostate Specific Membrane Antigen Revealed by Antibody-Recruiting Small Molecules. Journal of the American Chemical Society 132(36):12711-12716 (2010).
PCT/US2024/035667 International Search Report and Written Opinion dated Jan. 17, 2025.
PCT/US2024/035667 Invitation to Pay Additional Fees dated Nov. 22, 2024.

* cited by examiner

PBS

AOC PRKAG2_Seq61 –VP
(3mg/Kg)

AOC PRKAG2_Seq61 +VP
(3mg/Kg)

COMPOSITIONS AND METHODS OF USING PRKAG2-TARGETING ANTIBODY-OLIGONUCLEOTIDE CONJUGATES

CROSS-REFERENCE

This application claims the benefit of U.S. Provisional Application No. 63/510,531 filed Jun. 27, 2023, which is incorporated herein by reference in its entirety.

REFERENCE TO A SEQUENCE LISTING XML

This application contains a Sequence Listing which has been submitted electronically in XML format. The Sequence Listing XML is incorporated herein by reference. Said XML file, created on Jul. 29, 2025, is named 45532-773_201_Replacement_SL.xml and is 433,956 bytes in size.

BACKGROUND OF THE DISCLOSURE

Gene suppression by RNA-induced gene silencing provides several levels of control: transcription inactivation, small interfering RNA (siRNA)-induced mRNA degradation, and siRNA-induced transcriptional attenuation. In some instances, RNA interference (RNAi) provides long lasting effects over multiple cell divisions. As such, RNAi represents a viable method useful for drug target validation, gene function analysis, pathway analysis, and disease therapeutics.

AMP-activated protein kinase (AMPK) is an energy sensor kinase, composed of 3 subunits: a catalytic subunit (α1 or α2) and 2 regulatory subunits (β1 or β2 subunit and γ1, γ2, or γ3 subunit). The Protein Kinase AMP-Activated Non-Catalytic Subunit Gamma 2 (PRKAG2) gene encodes the γ2 regulatory subunit of the AMPK, which responds to AMP/ATP fluctuations. PRKAG2 is predominantly a cardiac isoform and the human PRKAG2 gene shares high homology (~90%) with the non-human primate and murine PRKAG2 gene. Binding of AMP to the γ2 regulatory subunit encoded by PRKAG2 activates AMPK and induces its conformational changes. As such, mutations in PRKAG2 result in decreased affinity to ATP to so maintain AMPK inactive such that the AMPK loses its ability to sense AMP and ATP levels. Elevated AMPK activity promotes glucose transporter 4 (GLUT4) shuttling to the plasma membrane and increases glucose uptake and intracellular glucose 6-phosphate (G6P) concentration. This leads to an allosteric activation of glycogen synthase (GS), which overrides the inhibitory effect of AMPK on GS, resulting in a net increase in GS activity and excess glycogen storage in muscle cells.

PRKAG2 cardiac syndrome is an autosomal dominant metabolic heart disease characterized by left ventricular hypertrophy (LVH), progressive conduction abnormalities, and ventricular pre-excitation. PRKAG2 cardiac syndrome causes cardiac hypertrophy and electrophysiologic abnormalities, particularly preexcitation (Wolff-Parkinson-White syndrome) and atrioventricular conduction block, glycogen storage disease of the heart. The prevalence of PRKAG2 syndrome is 0.23-1% in patients with suspected HCM. The glycogen accumulation is often associated with an eccentric pattern of hypertrophy and conduction abnormalities that characterize the PRKAG2 cardiac syndrome. Cardiomyopathies caused by glycogen storage diseases including PRKAG2 mutations are distinguished from other types of hypertrophic cardiomyocyte (HCM) by the formation of glycogen filled vacuoles in myocytes. Most of the mutations on PRKAG2 are gain of function (GOF) mutations. Numerous human PRKAG2 GOF mutations have been identified and each of these mutations is associated with a point mutation within the PRKAG2 gene resulting in an amino acid substitution of the PRKAG2 protein. Most commonly identified amino acid substitutions of the PRKAG2 protein include H142R, R302Q, L341S, H383R, R384T, T400N, H401D, K475E, K485I, Y487H, N488I, S548P, and R531G. These PRKAG2 GOF mutations in cardiac cells result in glycogen accumulation in the heart muscle cells, leading to glycogen storage cardiomyopathy.

Current treatments for PRKAG2 cardiac syndrome that include standard heart failure and antiarrhythmic treatment, pacemaker, defibrillator implantation and surgical ablation alleviate the symptoms but do not treat the genetic cause of the cardiac abnormalities. However, there are no specific treatments available that target PRKAG2 mRNA. There is a need to develop therapeutics for treating cardiomyopathy caused by PRKAG2 cardiac syndrome.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE DISCLOSURE

In the present disclosure, methods and compositions of antibody-oligonucleotide conjugates (AOC) targeting PRKAG2 mRNA are provided to inhibit the expression of PRKAG2. In addition, the present disclosure provides methods and compositions to treat cardiomyopathy caused by mutations of PRKAG2 with antibody oligonucleotide conjugates to deliver nucleic acids that target the expression of PRKAG2 in tissue. In addition, the present disclosure provides methods and compositions to treat cardiomyopathy caused by PRKAG2 cardiac syndrome with antibody-oligonucleotide conjugates to deliver nucleic acids that target the expression of PRKAG2 in cardiac tissue.

Disclosed herein, in certain embodiments, are polynucleotides and pharmaceutical compositions comprising the polynucleotides for modulating a gene associated with cardiomyopathy, especially PRKAG2 cardiac syndrome. In some aspects, also described herein are methods of treating cardiomyopathy, especially PRKAG2 cardiac syndrome, with a polynucleotide or a polynucleotide-conjugate disclosed herein.

Disclosed herein, in certain aspects, is a polynucleotide conjugate comprising an anti-transferrin antibody or antigen binding fragment thereof conjugated to a polynucleotide that hybridizes to a target sequence of PRKAG2 mRNA, and the polynucleic acid molecule conjugate mediates RNA interference against the PRKAG2 mRNA. In some instances, is a polynucleotide conjugate comprising an anti-transferrin antibody or antigen binding fragment thereof conjugated to a polynucleic acid molecule that hybridizes to a target sequence of a mutated PRKAG2, and the polynucleic acid molecule conjugate mediates RNA interference against the PRKAG2 mRNA. In some instances, the target sequence is a PRKAG2 mRNA having a mutation. In some instances, the mutation is a gain of function mutation. In some instances, the polynucleotide hybridizes to at least 8 contiguous bases of the target sequence of the PRKAG2 mRNA. In some instances, the polynucleotide is from about 8 to about 50 nucleotides in length or from about 10 to about 30 nucleotides in length. In some instances, the polynucleotide is a single-stranded antisense polynucleotide or a double-stranded polynucleotide. In some instances, the single-stranded polynucleotide is an antisense oligonucleotide (ASO). In some instances, the polynucleotide hybridizes to a target sequence of the PRKAG2 mRNA and mediates RNA interference against the PRKAG2 mRNA via RNase H activity in the muscle cell. In some instances, the target sequence is a mutated PRKAG2. In some instances, the mutated PRKAG2 is a gain of function mutation. In some instances, the gain of function mutation of the PRKAG2 gene is associated with a point mutation within the PRKAG2 gene resulting in an amino acid substitution of the PRKAG2 protein. In some instances, the ASO comprises a nucleic acid sequence having at least 80%, 85%, 90%, 95%, or 100% homology with a sequence selected from SEQ ID NOs: 1-102. In some instances, the ASO comprises a nucleic acid sequence having at least 14, 15, 16, 17, 18 consecutive nucleotides from a sequence selected from SEQ ID NOs: 1-102, with no more than 1, 2, 3 mismatches. In some instances, the ASO comprises a nucleic acid sequence selected from SEQ ID NOs: 233-236. In some instances, the double-stranded polynucleotide is a small interfering RNA (siRNA) comprising a guide strand and a passenger strand. In some instances, the passenger strand comprises a nucleic acid sequence having at least 80%, 85%, 90%, 95%, or 100% homology with a sequence selected from SEQ ID NOs: 103-204. In some instances, the guide strand of comprises a nucleic acid sequence having at least 80%, 85%, 90%, 95%, or 100% homology with a sequence selected from SEQ ID NOs: 1-102. In some instances, the passenger strand comprises a nucleic acid sequence having at least 16, 17, 18, or 19 consecutive nucleotides from a sequence selected from SEQ ID NOs: 103-204, with no more than 1, 2, 3 mismatches. In some instances, the guide strand comprises a nucleic acid sequence having at least 16, 17, 18, or 19 consecutive nucleotides from a sequence selected from SEQ ID NOs: 1-102, with no more than 1, 2, 3 mismatches. In some instances, the polynucleotide comprises at least one 2' modified nucleotide, at least one modified internucleotide linkage, or at least one inverted abasic moiety. In some instances, the at least one 2' modified nucleotide comprises 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified nucleotide; comprises locked nucleic acid (LNA) or ethylene nucleic acid (ENA); or comprises a combination thereof. In some instances, the at least one modified internucleotide linkage comprises a phosphorothioate linkage or a phosphorodithioate linkage. In some instances, wherein the polynucleotide comprises a 5'-terminal vinylphosphonate modified nucleotide. In some instances, the passenger strand comprises a nucleic acid sequence having at least 80%, 85%, 90%, 95%, or 100% homology with a sequence selected from SEQ ID NOs: 221-232. In some instances, the passenger strand of comprises a nucleic acid sequence having at least 16, 17, 18, or 19 consecutive nucleotides from a sequence selected from SEQ ID NOs: 221-232, with no more than 1, 2, 3 mismatches. In some instances, the guide strand comprises a nucleic acid sequence having at least 80%, 85%, 90%, 95%, or 100% homology with a sequence selected from SEQ ID NOs: 209-220. In some instances, the guide strand of comprises a nucleic acid sequence having at least 16, 17, 18, or 19 consecutive nucleotides from a sequence selected from SEQ ID NOs: 209-220, with no more than 1, 2, 3 mismatches. In some instances, the guide strand comprises a nucleic acid sequence of SEQ ID NOs: 1-102 or 209-220, and a passenger strand comprises a nucleic acid sequence of SEQ ID NOs: 103-204 or 221-232. In some instances, the guide strand comprises a nucleic acid sequence of any one of SEQ ID NOs: 209-212, and a passenger strand comprises a nucleic acid sequence of any one of SEQ ID NOs: 221-224. In some instances, the polynucleotide conjugate has a polynucleotide to antibody ratio of from about 1 to about 4. In some instances, the anti-transferrin receptor antibody or antigen binding fragment thereof comprises a non-human antibody or antigen binding fragment thereof, a human antibody or antigen binding fragment thereof, a humanized antibody or antigen binding fragment thereof, a chimeric antibody or antigen binding fragment thereof, a monoclonal antibody or antigen binding fragment thereof, a monovalent Fab', a divalent Fab2, a single-chain variable fragment (scFv), a diabody, a minibody, a nanobody, a single-domain antibody (sdAb), or a camelid antibody or antigen binding fragment thereof. In some instances, the anti-transferrin receptor antibody is conjugated to the 5' end of the polynucleotide. In some instances, the anti-transferrin receptor antibody is conjugated to the 5' end of the passenger strand. In some instances, polynucleotide conjugate comprises a linker connecting the anti-transferrin receptor antibody or antigen-binding fragment thereof to the polynucleotide. In some instances, the muscle cell is a cardiac muscle cell or skeletal muscle cell. In some instances, mediation of RNA interference against the PRKAG2 mRNA in the muscle cell modulates cardiomyopathy in a subject. In some instances, the cardiomyopathy is caused by a glycogen storage disease. In some instances, the cardiomyopathy is caused by PRKAG2 syndrome or PRKAG2 cardiac syndrome. In some instances, the PRKAG2 syndrome or PRKAG2 cardiac syndrome is caused by a mutated PRKAG2 that has a gain of function.

Also disclosed herein, in certain aspects, is a polynucleotide molecule for modulating PRKAG2 mRNA expression, comprising a nucleic acid sequence at least 80%, 85%, 90%, 95%, or 100% homology with a sequence selected from SEQ ID NOs: 1-102 or SEQ ID NO: 233-236. Also disclosed herein, in certain aspects, is a polynucleotide molecule for modulating PRKAG2 mRNA expression, comprising a nucleic acid sequence at least sequence having at least 16, 17, 18, or 19 consecutive nucleotides from a sequence selected from SEQ ID NOs: 1-102, or SEQ ID NOs: 233-236 with no more than 1, 2, 3 mismatches. In some instances, the polynucleotide molecule is a single stranded antisense oligonucleotide (ASO), and the ASO comprises a nucleic acid sequence selected from SEQ ID NOs: 233-236.

Also disclosed herein, in certain aspects, is a polynucleotide molecule for modulating PRKAG2 mRNA expression, comprising a guide strand and a passenger strand, wherein the guide strand comprises a nucleic acid sequence at least 80%, 85%, 90%, 95%, or 100% homology with a sequence selected from SEQ ID NOs: 1-102 or SEQ ID NOs: 209-220. Also disclosed herein, in certain aspects, is a polynucleotide molecule for modulating PRKAG2 mRNA expression, comprising a guide strand and a passenger strand, wherein the guide strand comprises a nucleic acid sequence at least sequence having at least 16, 17, 18, or 19 consecutive nucleotides from a sequence selected from SEQ ID NOs: 1-102, or SEQ ID NOs: 209-220 with no more than 1, 2, 3 mismatches. In some instances, the passenger strand comprises a nucleic acid sequence at least 80%, 85%, 90%, 95%, or 100% homology with a sequence selected from SEQ ID NOs: 103-204 or SEQ ID NOs: 221-232. In some instances, the passenger strand comprises a nucleic acid sequence comprises a nucleic acid sequence at least sequence having at least 16, 17, 18, or 19 consecutive nucleotides from a sequence selected from SEQ ID NOs: 103-204, or SEQ ID NO: 221-232 with no more than 1, 2, 3 mismatches. In some instances, the guide strand comprises a nucleic acid sequence of SEQ ID NOs: 209-212, and a passenger strand comprises a nucleic acid sequence of SEQ ID NOs: 221-225.

Also disclosed herein, in certain aspects, is a pharmaceutical composition comprising the polynucleotide conjugate as disclosed herein or the polynucleotide molecule as disclosed herein, and a pharmaceutically acceptable excipient.

Also disclosed herein, in certain aspects, is a method of treating cardiomyopathy in a subject in need thereof comprising administering to said subject a polynucleotide conjugate as disclosed herein or a polynucleotide molecule of as disclosed herein or a pharmaceutical composition of as disclosed herein, thereby treating cardiomyopathy in said subject. In some instances, the cardiomyopathy is caused by a glycogen storage disease. In some instances, the cardiomyopathy is caused by PRKAG2 syndrome or PRKAG2 cardiac syndrome. In some instances, PRKAG2 syndrome or PRKAG2 cardiac syndrome is caused by a mutated PRKAG2 that has a gain of function. In some instances, the polynucleotide conjugate is administered parenterally, orally, intranasally, buccally, rectally, transdermally, intravenously, subcutaneously, or intrathecally.

Also disclosed herein, in certain aspects, is a method of modulating PRKAG2 expression or activity in a muscle cell comprising contacting the muscle cell with a polynucleotide conjugate as disclosed herein or a polynucleotide molecule as disclosed herein or a pharmaceutical composition as disclosed herein, thereby modulating PRKAG2 expression or activity in the muscle cell. Also disclosed herein, in certain aspects, is a method of modulating PRKAG2 expression or activity in a subject in need thereof comprising administering to said subject a polynucleotide conjugate as disclosed herein or a polynucleotide molecule as disclosed herein or a pharmaceutical composition as disclosed herein, thereby modulating PRKAG2 expression or activity in the subject.

Disclosed herein, in certain embodiments, is a kit comprising the polynucleotide conjugate or the pharmaceutical composition as described herein.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings below.

FIG. 19A is a representative bar graph showing in vivo PRKAG2 mRNA expression levels in the left ventricles (LV) of hearts obtained from wild-type mice or TAC mice 42 days after a single injection of PRKAG2 AOC (PRKAG2 siRNA Seq 61+Vp conjugated to an a-mouse TfR1 antibody) at a concentration of 3 mg/kg of AOC (siRNA dose).

FIG. 19B is a representative bar graph showing in vivo tissue concentration (TC) of siRNA Seq 61+Vp in the left ventricles (LV) of hearts obtained from TAC mice 42 days after a single injection of PRKAG2 AOC (PRKAG2 siRNA Seq 61+Vp conjugated to an a-mouse TfR1 antibody) at a concentration of 3 mg/kg of AOC (siRNA dose).

FIG. 19C is a representative bar graph showing normalized in vivo SERCA2a mRNA expression levels in the left ventricles (LV) of hearts obtained from wild-type mice or TAC mice 42 days after a single injection of PRKAG2 AOC (PRKAG2 siRNA Seq 61+Vp conjugated to an a-mouse TfR1 antibody) at a concentration of 3 mg/kg of AOC (siRNA dose).

FIG. 19D is a representative bar graph showing Percentage of Fractional Shortening (FS %) measured by Echocardiogram in hearts obtained from wild-type mice or TAC mice 56 days post TAC surgery and 42 days after a single injection of PRKAG2 AOC (PRKAG2 siRNA Seq 61+Vp conjugated to an a-mouse TfR1 antibody) at a concentration of 3 mg/kg of AOC (siRNA dose).

FIG. 19E is a representative bar graph showing Left Ventricular Diastolic Diameter (LVDD) measured by echocardiogram in hearts obtained from wild-type mice or TAC mice 56 days post TAC surgery and 42 days after a single injection of PRKAG2 AOC (PRKAG2 siRNA Seq 61+Vp conjugated to an a-mouse TfR1 antibody) at a concentration of 3 mg/kg of AOC (siRNA dose).

FIG. 19F is a representative bar graph showing heart weight normalized to tibia length obtained from wild-type mice or TAC mice 56 days post TAC surgery and 42 days after a single injection of PRKAG2 AOC (PRKAG2 siRNA Seq 61+Vp conjugated to a mouse TfR1 antibody) at a dose of 3 mg/kg of AOC (siRNA dose).

FIG. 21A is a representative bar graph showing PRKAG2 mRNA expression levels in hearts obtained from Male Cynomolgus monkey 28 days after a single injection of PRKAG2 AOC (siRNA Seq61+Vp conjugated to a a-human TfR1 antibody) at a dose of 3 mg/kg of AOC.

FIG. 21B is a representative bar graph showing PRKAG2 siRNA Seq61+Vp tissue concentrations in hearts obtained from Male Cynomolgus monkey 28 days (dosing at day 1) after a single injection of PRKAG2 siRNA AOC (siRNA Seq61+Vp conjugated to a human TfR1 antibody) at a dose of 3 mg/kg of AOC.

FIG. 21C is a representative plot showing the body weight of Male Cynomolgus monkey 28 days (dosing at day 1) after a single injection of PRKAG2 siRNA AOC (siRNA Seq61+Vp conjugated to a human TfR1 antibody) at a dose of 3 mg/kg of AOC.

FIG. 21D is a representative bar graph showing the weight of hearts obtained from Male Cynomolgus monkey 28 days after a single injection of PRKAG2 siRNA AOC (siRNA Seq 61+Vp conjugated to a human TfR1 antibody) at a dose of 3 mg/kg of AOC.

FIG. 21E is a representative bar graph showing heart/body weight ratios of Male Cynomolgus monkey 28 days (dosing at day 1) after a single injection of PRKAG2 siRNA AOC (siRNA Seq61+Vp conjugated to a humanTfR1 antibody) at a dose of 3 mg/kg of AOC.

DETAILED DESCRIPTION OF THE DISCLOSURE

Figure 1:
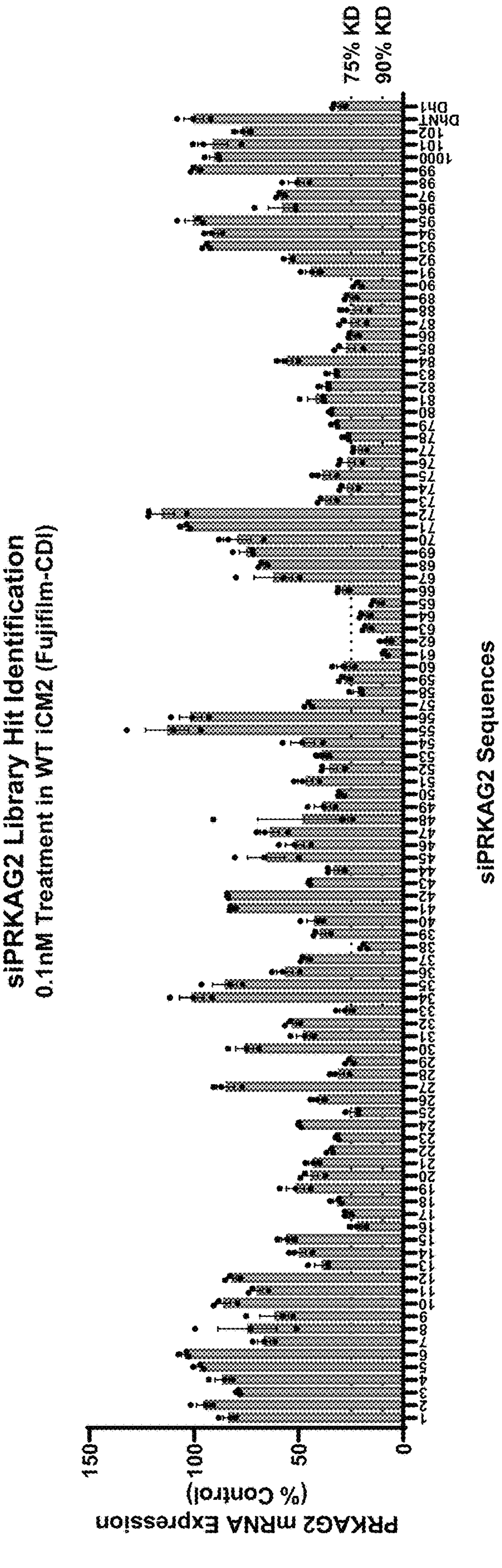
FIG. 1 is a representative plot showing PRKAG2 mRNA expression levels in iCM2 cells transfected with PRKAG2 siRNA at a concentration of 0.1 nM 3 days post transfection.

Mutations in PRKAG2, the gene encoding the γ2 regulatory subunit of AMPK, cause cardiac hypertrophy and electrophysiologic abnormalities, particularly preexcitation (Wolff-Parkinson-White syndrome) and atrioventricular conduction block. Because of the complex electrophysiological impact of the disease, an incidence rate of premature (<40 years) sudden cardiac death (SCD) as high as 20% has been suggested. Most of these carriers end up needing a pacemaker, ablation surgery and/or implantation of a defibrillator. Incidents of heart failure, and atrial fibrillation are also very high.

The PRKAG2 isoform is predominantly expressed in the heart. Transgenic mice overexpressing the human PRKAG2 disease variants, recapitulate the human syndrome and display excessive accumulation of glycogen in the heart, hypertrophy, and preexcitation. The activity of AMPK is increased in the hearts expressing the disease variants, suggesting a gain of function role. Furthermore, several pan-AMPK activators have been previously developed to treat diabetes, but they all resulted in cardiac hypertrophy (rodents, non-human primates (NHP) and humans) and were not further pursued. Mice with cardiac PRKAG2 deletion have no adverse phenotype and normal cardiac function. The lack of PRKAG2 is compensated for by an increase in PRKAG1 (skeletal muscle isoform), thus the total AMPK activity remains unchanged.

Clinical presentation ranges from asymptomatic condition to sudden cardiac death (SCD). PRKAG2 syndrome onset of symptoms frequently occurs within the first 3 decades of age, and it is often characterized by tachyarrhythmias and bradyarrhythmia. Much less frequently, heart failure symptoms or SCD can be the first manifestations of the disease. Prolonged dynamic ECG monitoring and exercise stress testing could be useful tools in those patients with syncope, palpitations, or with a familial history of SCD. Ultrasound imaging and cardiovascular magnetic resonance can be considered gold-standard diagnostic techniques for the identification and characterization of cardiac hypertrophy.

Nucleic acid (e.g., RNAi) therapy is a targeted therapy with high selectivity and specificity. However, in some instances, nucleic acid therapy is also hindered by poor intracellular uptake, limited blood stability and non-specific immune stimulation. To address these issues, various modifications of the nucleic acid composition are explored, such as, for example, novel linkers for better stabilizing and/or lower toxicity, optimization of binding moiety for increased target specificity and/or target delivery, and/or nucleic acid polymer modifications for increased stability and/or reduced off-target effect.

In some aspects, the arrangement or order of the different components that make up the nucleic acid composition further affects intracellular uptake, stability, toxicity, efficacy, and/or non-specific immune stimulation. For example, if the nucleic acid component includes a binding moiety, a polymer, and a polynucleic acid molecule (or polynucleotide), the order or arrangement of the binding moiety, the polymer, and/or the polynucleic acid molecule (or polynucleotide) (e.g., binding moiety-polynucleic acid molecule-polymer, binding moiety-polymer-polynucleic acid molecule, or polymer-binding moiety-polynucleic acid molecule) further effects intracellular uptake, stability, toxicity, efficacy, and/or non-specific immune stimulation.

The present disclosure provides, in certain aspects, oligonucleotide molecules or antibody-oligonucleotides conjugates (AOC) targeting PRKAG2 mRNA, which are capable of inhibiting or modulating the expression of PRKAG2. In some aspects, the present disclosure provides methods of modulating PRKAG2 mRNA expression using the oligonucleotide molecules or antibody-oligonucleotides conjugates (AOC) targeting PRKAG2 mRNA. In some aspects, described herein include polynucleic acid molecules (interchangeably used with the terms "polynucleotide" or "oligonucleotide") and polynucleic acid molecule conjugates for the treatment of cardiomyopathy. In some instances, the polynucleic acid molecule conjugates described herein have or show enhanced intracellular uptake, stability, and/or efficacy. In some cases, the polynucleic acid molecule conjugates comprise an antibody or antigen binding fragment thereof conjugated to a polynucleic acid molecule. In some cases, the polynucleic acid molecules hybridize to target sequences of PRKAG2 mRNA, preferably human PRKAG2 mRNA. In some cases, the polynucleic acid molecules that hybridize to target sequences of mutated PRKAG2 that has a gain-of-function or a target sequence of the PRKAG2 mRNA comprising a gain-of-function mutation In some aspects, the present disclosure further provides treatment of cardiomyopathy or its symptoms thereof, associated with PRKAG2 expression in the heart muscle cells. In certain instances, the cardiomyopathy is caused by PRKAG2 syndrome or PRKAG2 cardiac syndrome.

In some aspects, the present disclosure further provides treatment of cardiomyopathy or its symptoms thereof caused by a glycogen storage disease, by administering to a subject a polynucleic acid molecule or a polynucleic acid molecule conjugate. In some aspects, the present disclosure further provides treatment of cardiomyopathy caused by PRKAG2 syndrome or PRKAG2 cardiac syndrome by administering to a subject a polynucleic acid molecule or a polynucleic acid molecule conjugate. In some aspects, the present disclosure further provides treatment of cardiomyopathy caused by a PRKAG gain-of-function mutation by administering to a subject a polynucleic acid molecule or a polynucleic acid molecule conjugate.

Polynucleic Acid Molecules

In certain aspects, a polynucleic acid molecule hybridizes to a target sequence of PRKAG2 gene (e.g., PRKAG2 mRNA). In some instances, a polynucleic acid molecule described herein hybridizes to a target sequence of human PRKAG2 gene (e.g., human PRKAG2 mRNA) and reduces PRKAG2 mRNA in cardiac muscle cells.

In certain aspects, a polynucleic acid molecule hybridizes to a target sequence of PRKAG2 mRNA. In some instances, a polynucleic acid molecule described herein hybridizes to a target sequence of a PRKAG2 variant which includes a point mutation in the PRKAG2 gene and reduces the expression of PRKAG2 mRNA in cardiac muscle cells.

In some aspects, the polynucleic acid molecule comprises a nucleic acid sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 1-102. In some instances, the polynucleic acid molecule comprises a nucleic acid sequence comprising at least 14, 15, 16, 17, 18, 19 consecutive nucleotide sequences with no more than 1, 2, 3 mismatches from SEQ ID NOs: 1-102. In some aspects, the polynucleic acid molecule comprises a nucleic acid sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 103-204. In some instances, the polynucleic acid molecule comprises a nucleic acid sequence comprising at least 14, 15, 16, 17, 18, 19 consecutive nucleotide sequences with no more than 1, 2, or 3 mismatches from SEQ ID NOs: 103-204.

In some aspects, the polynucleic acid molecule is a single-stranded antisense oligonucleotide (ASO) hybridizing to a target sequence of PRKAG2 mRNA. In some instances, the ASO comprises a nucleic acid sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 1-102. In some instances, the ASO comprises a nucleic acid sequence comprising at least 14, 15, 16, 17, 18, or 19 consecutive nucleotide sequences with no more than 1, 2, 3 mismatches from SEQ ID NOs: 1-102. In some instances, the ASO comprises a nucleic acid sequence comprising or consisting of SEQ ID NOs: 233-236.

In some instances, the ASO is a gapmer or a mixmer. In some instances, the ASO comprises a central region of consecutive DNA nucleotides flanked by a 5'-wing region and 3'-wing region, and the flanked 5' and/or 3' wing region comprises one or more modified nucleotides (e.g., locked nucleic acid (LNA) or 2'-methoxyethyl (2'-MOE) RNA). In some instances, the locked nucleic acid comprises at least one or more of a beta-D-oxy LNA, an alpha-L-oxy-LNA, a beta-D-amino-LNA, an alpha-L-amino-LNA, a beta-D-thio-LNA, an alpha-L-thio-LNA, a 5'-methyl-LNA, a beta-D-ENA, or an alpha-L-ENA. In some instances, the ASO comprises 3-10-3 configurations (3 nucleotides for 5'-flanked region, 10 nucleotides of central region, and 3 nucleotides for 3'-flanked region), 5-10-5 configuration (5 nucleotides for 5'-flanked region, 10 nucleotides of central region, and 5 nucleotides for 3'-flanked region), or X—Y—Z configuration where X can be 1-10 nucleotides, Y can be 8-20 nucleotides, Z can be 1-10 nucleotides.

In some aspects, the polynucleic acid molecule is a double-stranded polynucleotides, comprising a first polynucleotide and a second polynucleotide. In some instances, the first polynucleotide comprises a nucleic acid sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 1-102. In some instances, the first nucleotide comprises a nucleic acid sequence comprising at least 14, 15, 16, 17, 18, or 19 consecutive nucleotide sequences with no more than 1, 2, 3 mismatches from SEQ ID NOs: 1-102. In some cases, the second polynucleotide comprises a nucleic acid sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 103-204. In some instances, the second nucleotide comprises a nucleic acid sequence comprising at least 14, 15, 16, 17, 18, 19 consecutive nucleotide sequences with no more than 1, 2, 3 mismatches from SEQ ID NOs: 103-204.

In some aspects, the polynucleic acid molecule described herein comprises RNA or DNA. In some cases, the polynucleic acid molecule comprises RNA. In some instances, RNA comprises short interfering RNA (siRNA), short hairpin RNA (shRNA), microRNA (miRNA), double-stranded RNA (dsRNA), transfer RNA (tRNA), ribosomal RNA (rRNA), or heterogeneous nuclear RNA (hnRNA). In some instances, RNA comprises shRNA. In some instances, RNA comprises miRNA. In some instances, RNA comprises dsRNA. In some instances, RNA comprises tRNA. In some instances, RNA comprises rRNA. In some instances, RNA comprises hnRNA. In some instances, the polynucleic acid molecule is a phosphorodiamidate morpholino oligomer (PMO), which comprise short single-stranded oligonucleotide analogs that are built upon a backbone of morpholine rings connected by phosphorodiamidate linkages. In some instances, the RNA comprises siRNA. In some instances, the polynucleic acid molecule comprises siRNA.

In some aspects, the polynucleic acid molecule comprises a sense strand (e.g., a passenger strand) and an antisense strand (e.g., a guide strand). In some instances, the sense strand (e.g., the passenger strand) comprises a nucleic acid sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 103-204. In some instances, the sense strand (e.g., the passenger strand) comprises a nucleic acid sequence comprising at least 14, 15, 16, 17, 18, or 19 consecutive nucleotide sequences with no more than 1, 2, 3 mismatches from SEQ ID NOs: 103-204. In some instances, the antisense strand (e.g., the guide strand) comprises a nucleic acid sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 1-102. In some instances, the antisense strand (e.g., the guide strand) comprises a nucleic acid sequence comprising at least 14, 15, 16, 17, 18, 19 consecutive nucleotide sequences with no more than 1, 2, 3 mismatches from SEQ ID NOs: 1-102.

In some instances, the siRNA comprises sense (passenger) strand and antisense (guide) strand as presented in Table 10.

In some aspects, the polynucleic acid molecule is from about 8 to about 50 nucleotides in length. In some aspects, the polynucleic acid molecule is from about 10 to about 50 nucleotides in length. In some instances, the polynucleic acid molecule is from about 10 to about 30, from about 15 to about 30, from about 18 to about 25, form about 18 to about 24, from about 19 to about 23, or from about 20 to about 22 nucleotides in length.

In some aspects, the polynucleic acid molecule is about 50 nucleotides in length. In some instances, the polynucleic acid molecule is about 45 nucleotides in length. In some instances, the polynucleic acid molecule is about 40 nucleotides in length. In some instances, the polynucleic acid molecule is about 35 nucleotides in length. In some instances, the polynucleic acid molecule is about 30 nucleotides in length. In some instances, the polynucleic acid molecule is about 25 nucleotides in length. In some instances, the polynucleic acid molecule is about 20 nucleotides in length. In some instances, the polynucleic acid molecule is about 19 nucleotides in length. In some instances, the polynucleic acid molecule is about 18 nucleotides in length. In some instances, the polynucleic acid molecule is about 17 nucleotides in length. In some instances, the polynucleic acid molecule is about 16 nucleotides in length. In some instances, the polynucleic acid molecule is about 15 nucleotides in length. In some instances, the polynucleic acid molecule is about 14 nucleotides in length. In some instances, the polynucleic acid molecule is about 13 nucleotides in length. In some instances, the polynucleic acid molecule is about 12 nucleotides in length. In some instances, the polynucleic acid molecule is about 11 nucleotides in length. In some instances, the polynucleic acid molecule is about 10 nucleotides in length. In some instances, the polynucleic acid molecule is about 8 nucleotides in length. In some instances, the polynucleic acid molecule is between about 8 and about 50 nucleotides in length. In some instances, the polynucleic acid molecule is between about 10 and about 50 nucleotides in length. In some instances, the polynucleic acid molecule is between about 10 and about 45 nucleotides in length. In some instances, the polynucleic acid molecule is between about 10 and about 40 nucleotides in length. In some instances, the polynucleic acid molecule is between about 10 and about 35 nucleotides in length. In some instances, the polynucleic acid molecule is between about 10 and about 30 nucleotides in length. In some instances, the polynucleic acid molecule is between about 20 and about 30 nucleotides in length. In some instances, the polynucleic acid molecule is between about 10 and about 25 nucleotides in length. In some instances, the polynucleic acid molecule is between about 10 and about 20 nucleotides in length. In some instances, the polynucleic acid molecule is between about 15 and about 25 nucleotides in length. In some instances, the polynucleic acid molecule is between about 15 and about 30 nucleotides in length. In some instances, the polynucleic acid molecule is between about 12 and about 30 nucleotides in length.

In some aspects, the polynucleic acid molecule comprises a first polynucleotide and a second polynucleotide. In some instances, the first polynucleotide is a sense strand (passenger strand) and the second polynucleotide is an antisense strand (guide strand) of a double stranded inhibitory RNA (dsRNA) or an siRNA.

In some aspects, each of the first and/or second polynucleotide is from about 8 to about 50 nucleotides in length. In some aspects, each of the first and/or second polynucleotide is from about 10 to about 50 nucleotides in length. In some instances, each of the first and/or second polynucleotide is from about 10 to about 30, from about 15 to about 30, from about 18 to about 25, form about 18 to about 24, from about 19 to about 23, or from about 20 to about 22 nucleotides in length. In some instances, each of the first and/or second polynucleotide is about 50, 45, 40, 35, 30, 25, 24, 23, 22, 21, 20, 19, 18, 17 nucleotides in length.

In some aspects, the polynucleic acid molecule comprises a first polynucleotide and a second polynucleotide. In some instances, the polynucleic acid molecule further comprises a blunt terminus, an overhang, or a combination thereof. In some instances, the blunt terminus is a 5' blunt terminus, a 3' blunt terminus, or both. In some cases, the overhang is a 5' overhang, 3' overhang, or both. In some cases, the overhang comprises 1, 2, 3, 4, 5, 6, 7, 8, 9, or 10 non-base pairing nucleotides. In some cases, the overhang comprises 1, 2, 3, 4, 5, or 6 non-base pairing nucleotides. In some cases, the overhang comprises 1, 2, 3, or 4 non-base pairing nucleotides. In some cases, the overhang comprises 1 non-base pairing nucleotide. In some cases, the overhang comprises 2 non-base pairing nucleotides. In some cases, the overhang comprises 3 non-base pairing nucleotides. In some cases, the overhang comprises 4 non-base pairing nucleotides. In some aspects, the polynucleic acid molecule comprises a sense strand and an antisense strand, and the antisense strand includes two non-base pairing nucleotides as an overhang at the 3'-end while the sense strand has no overhang. Optionally, in such embodiments, the non-base pairing nucleotides have a sequence of TT, dTdT, or UU. In some aspects, the polynucleic acid molecule comprises a sense strand and an antisense strand, and the sense strand has one or more nucleotides at the 5'-end that are complementary to the antisense sequence.

In some aspects, the nucleic acid sequence of the polynucleic acid molecule is at least 40%, 50%, 55%, 60%, 65%, 70%, 75%, 80%, 85%, 90%, 95%, 98%, 99%, or 99.5% complementary to a target sequence of PRKAG2 mRNA. In some aspects, the target sequence of PRKAG2 mRNA is a nucleic acid sequence of about 10-50 nucleotides in length, about 15-50 nucleotides in length, 15-40 nucleotides in length, 15-30 nucleotides in length, or 15-25 nucleotides in length sequences in PRKAG2 mRNA, in which the first nucleotide of the target sequence starts at any nucleotide in PRKAG2 mRNA transcript in the coding region, or in the 5' or 3'-untranslated region (UTR).

In some aspects, the sequence of the polynucleic acid molecule is at least 50% complementary to a target sequence described herein. In some aspects, the sequence of the polynucleic acid molecule is at least 60% complementary to a target sequence described herein. In some aspects, the sequence of the polynucleic acid molecule is at least 70% complementary to a target sequence described herein. In some aspects, the sequence of the polynucleic acid molecule is at least 80% complementary to a target sequence described herein. In some aspects, the sequence of the polynucleic acid molecule is at least 90% complementary to a target sequence described herein. In some aspects, the sequence of the polynucleic acid molecule is at least 95% complementary to a target sequence described herein. In some aspects, the sequence of the polynucleic acid molecule is at least 99% complementary to a target sequence described herein. In some instances, the sequence of the polynucleic acid molecule is 100% complementary to a target sequence described herein.

In some aspects, the sequence of the polynucleic acid molecule has 5 or less mismatches to a target PRKAG2 mRNA sequence described herein. In some aspects, the sequence of the polynucleic acid molecule has 4 or less mismatches to a target PRKAG2 mRNA sequence described herein. In some instances, the sequence of the polynucleic acid molecule has 3 or less mismatches to a target PRKAG2 mRNA sequence described herein. In some cases, the sequence of the polynucleic acid molecule has 2 or less mismatches to a target PRKAG2 mRNA sequence described herein. In some cases, the sequence of the polynucleic acid molecule has 1 or less mismatches to a target PRKAG2 mRNA sequence described herein.

In some aspects, a group of polynucleic acid molecules among all the polynucleic acid molecules that potentially binds to the target sequence of PRKAG2 mRNA are selected to generate a polynucleic acid molecule library. In certain embodiments, such selection process is conducted in silico via one or more steps of eliminating less desirable polynucleic acid molecules from candidates using one or more selection criteria, e.g., similarity to miRNA sequences, expected off-target effects, etc.

In some aspects, the specificity of the polynucleic acid molecule that hybridizes to a target sequence described herein is a 95%, 98%, 99%, 99.5% or 100% sequence complementarity of the polynucleic acid molecule to a target PRKAG2 mRNA sequence. In some instances, the hybridization is a high stringent hybridization condition.

In some aspects, the polynucleic acid molecule has reduced off-target effect. In some instances, "off-target" or "off-target effects" refer to any instance in which a polynucleic acid polymer directed against a given target causes an unintended effect by interacting either directly or indirectly with another mRNA sequence, a DNA sequence, a cellular protein, or other moiety. In some instances, an "off-target effect" occurs when there is a simultaneous degradation of other transcripts due to partial homology or complementarity between that other transcript and the sense and/or antisense strand of the polynucleic acid molecule.

In some aspects, the polynucleic acid molecule comprises natural or synthetic or artificial nucleotide analogues or bases. In some cases, the polynucleic acid molecule comprises combinations of DNA, RNA and/or synthetic or artificial nucleotide analogues or bases. In some instances, the synthetic or artificial nucleotide analogues or bases comprise modifications at one or more of a ribose moiety, a phosphate moiety, a base moiety, or a combination thereof.

In some aspects, nucleotide analogues or artificial nucleotide base comprise a nucleotide with a modification at a 2' hydroxyl group of the ribose moiety. In some instances, the modification includes an H, OR, R, halo, SH, SR, $NH_2$, NHR, $NR_2$, or CN, wherein R is an alkyl moiety. Exemplary alkyl moieties includes, but are not limited to, halogens, sulfurs, thiols, thioethers, thioesters, amines (primary, secondary, or tertiary), amides, ethers, esters, alcohols and oxygen. In some instances, the alkyl moiety further comprises a modification. In some instances, the modification comprises an azo group, a keto group, an aldehyde group, a carboxyl group, a nitro group, a nitroso, group, a nitrile group, a heterocycle (e.g., imidazole, hydrazino or hydroxylamino) group, an isocyanate or cyanate group, or a sulfur containing group (e.g., sulfoxide, sulfone, sulfide, and disulfide). In some instances, the alkyl moiety further comprises a hetero substitution. In some instances, the carbon of the heterocyclic group is substituted by a nitrogen, oxygen or sulfur. In some instances, the heterocyclic substitution includes but is not limited to, morpholino, imidazole, and pyrrolidino.

In some instances, the modification at the 2' hydroxyl group is a 2'-O-methyl modification or a 2'-O-methoxyethyl (2'-O-MOE) modification. In some cases, the 2'-O-methyl modification adds a methyl group to the 2' hydroxyl group of the ribose moiety whereas the 2'O-methoxyethyl modification adds a methoxyethyl group to the 2' hydroxyl group of the ribose moiety. Exemplary chemical structures of a 2'-O-methyl modification of an adenosine molecule and 2'O-methoxyethyl modification of a uridine are illustrated below.

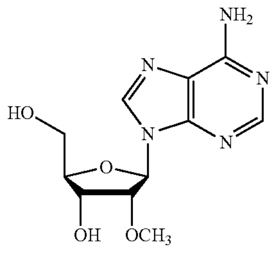

2′-O-methyl-adenosine

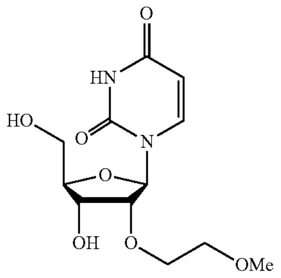

2′-O-methoxyethyl uridine

In some instances, the modification at the 2' hydroxyl group is a 2'-O-aminopropyl modification in which an extended amine group comprising a propyl linker binds the amine group to the 2' oxygen. In some instances, this modification neutralizes the phosphate derived overall negative charge of the oligonucleotide molecule by introducing one positive charge from the amine group per sugar and thereby improves cellular uptake properties due to its zwitterionic properties. An exemplary chemical structure of a 2'-O-aminopropyl nucleoside phosphoramidite is illustrated below.

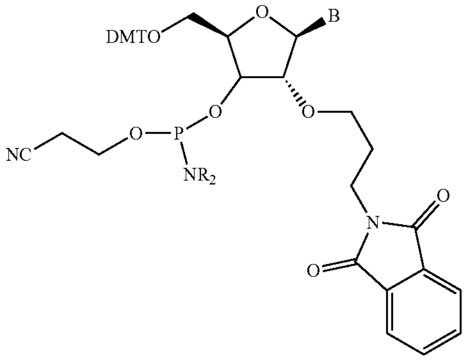

2′-O-aminopropyl nucleoside phosphoramidite

In some instances, the modification at the 2' hydroxyl group is a locked or bridged ribose modification (e.g., locked nucleic acid or LNA) in which the oxygen molecule bound at the 2' carbon is linked to the 4' carbon by a methylene group, thus forming a 2'-C,4'-C-oxy-methylene-linked bicyclic ribonucleotide monomer. Exemplary representations of the chemical structure of LNA are illustrated below. The representation shown to the left highlights the chemical connectivity of an LNA monomer. The representation shown to the right highlights the locked 3'-endo ($^3E$) conformation of the furanose ring of an LNA monomer.

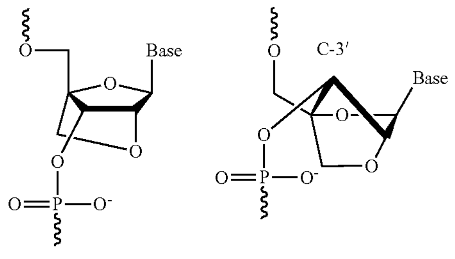

LNA (Locked Nucleic Acids)

In some instances, the modification at the 2' hydroxyl group comprises ethylene nucleic acids (ENA) such as for example 2'-4'-ethylene-bridged nucleic acid, which locks the sugar conformation into a $C_3$'-endo sugar puckering conformation. ENA are part of the bridged nucleic acids class of modified nucleic acids that also comprises LNA. Exemplary chemical structures of the ENA and bridged nucleic acids are illustrated below.

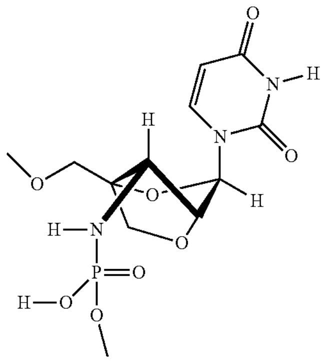

3′-amino-2′,4′-BNA

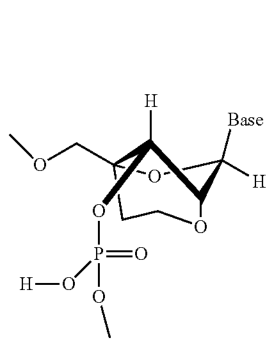

2′,4′-ENA

-continued

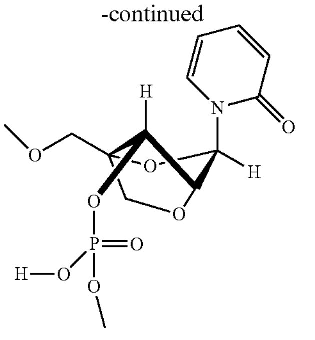

2',4'-BNA-2-pyridone

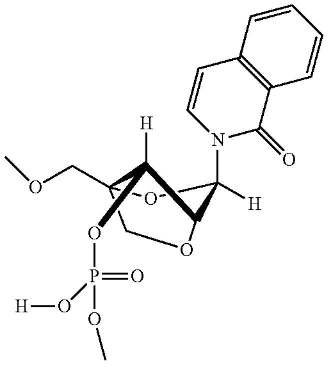

2',4'-BNA-1-isoquinolone

In some aspects, additional modifications at the 2' hydroxyl group include 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA).

In some aspects, nucleotide analogues comprise modified bases such as, but not limited to, 5-propynyluridine, 5-propynylcytidine, 6-methyladenine, 6-methylguanine, N, N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino) propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2, 2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4, 6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties, in some cases are or be based on, mannoses, arabinoses, glucopyranoses, galactopyranoses, 4'-thioribose, and other sugars, heterocycles, or carbocycles. The term nucleotide also includes what are known in the art as universal bases. By way of example, universal bases include but are not limited to 3-nitropyrrole, 5-nitroindole, or nebularine.

In some aspects, nucleotide analogues further comprise morpholinos, peptide nucleic acids (PNAs), methylphosphonate nucleotides, thiolphosphonate nucleotides, 2'-fluoro N3-P5'-phosphoramidites, 1', 5'-anhydrohexitol nucleic acids (HNAs), or a combination thereof. Morpholinos or phosphorodiamidate morpholino oligomers (PMOs) comprise synthetic molecules whose structure mimics a natural nucleic acid structure by deviating from the normal sugar and phosphate structures. In some instances, the five member ribose ring is substituted with a six member morpholino ring containing four carbons, one nitrogen and one oxygen. In some cases, the ribose monomers are linked by a phosphordiamidate group instead of a phosphate group. In such cases, the backbone alterations remove all positive and negative charges making morpholinos neutral molecules capable of crossing cellular membranes without the aid of cellular delivery agents such as those used by charged oligonucleotides.

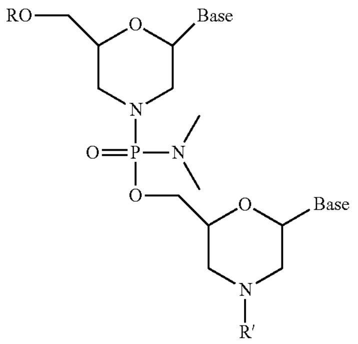

Morpholino

In some aspects, a peptide nucleic acid (PNA) does not contain a sugar ring or a phosphate linkage and the bases are attached and appropriately spaced by oligoglycine-like molecules, therefore, eliminating a backbone charge.

PNA

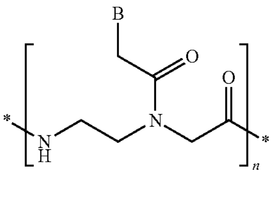

In some aspects, one or more modifications optionally occur at the internucleotide linkage. In some instances, modified internucleotide linkage types include, but are not limited to, phosphorothioates, phosphorodithioates, methylphosphonates, 5'-alkylenephosphonates, 5'-methylphosphonate, 3-alkylene phosphonates, borontrifluoridates, borano phosphate esters and selenophosphates of 3-5' linkages or 2'-5' linkages, phosphotriesters, thionoalkylphosphotriesters, hydrogen phosphonate linkages, alkyl phosphonates, alkylphosphonothioates, arylphosphonothioates, phosphoroselenoates, phosphorodiselenoates, phosphinates, phosphoramidates, 3'-alkylphosphoramidates, aminoalkylphosphoramidates, thionophosphoramidates, phosphoropiperazidates, phosphoroanilothioates, phosphoroanilidates, ketones, sulfones, sulfonamides, carbonates, carbamates, methylenehydrazos, methylenedimethylhydrazos, formacetals, thioformacetals, oximes, methyleneiminos, methylenemethyliminos, thioamidates, linkages with riboacetyl groups, aminoethyl glycine, silyl or siloxane linkages, alkyl or cycloalkyl linkages with or without heteroatoms of, for example, 1 to 10 carbons that are saturated or unsaturated and/or substituted and/or contain heteroatoms, linkages with morpholino structures, amides, polyamides wherein the bases are attached to the aza nitrogens of the backbone directly or indirectly, and combinations thereof. Phosphorothioate antisense oligonucleotides (PS ASO) are antisense oligonucleotides comprising a phosphorothioate linkage. An exemplary PS ASO is illustrated below.

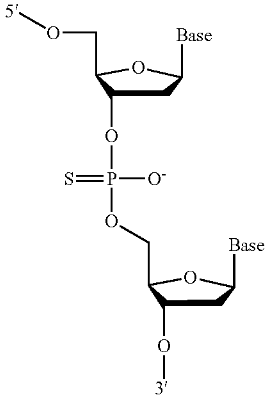

In some instances, the modification is a methyl or thiol modification such as methylphosphonate or thiolphosphonate modification. Exemplary thiolphosphonate nucleotide (left) and methylphosphonate nucleotide (right) are illustrated below.

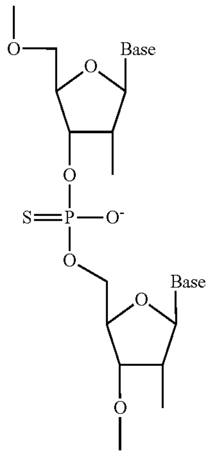

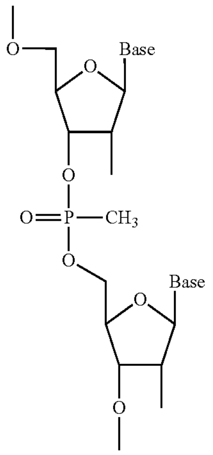

In some instances, a modified nucleotide includes, but is not limited to, 2'-fluoro N3-P5'-phosphoramidites illustrated as:

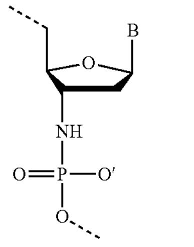

N3'-P5'Phosphoroamidate

In some instances, a modified nucleotide includes, but is not limited to a 5'-vinylphosphonate modified non-natural nucleotide selected from:

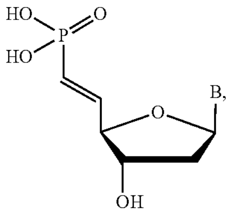

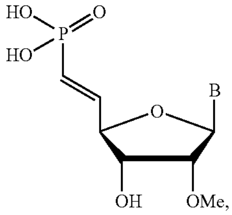

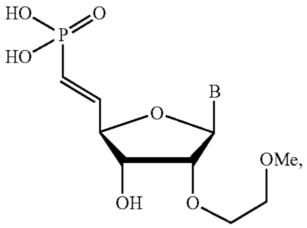

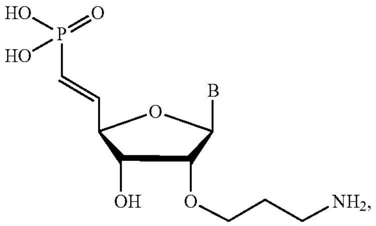

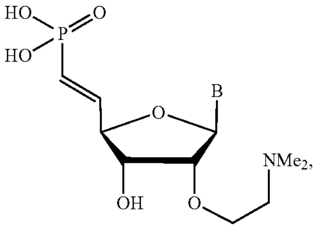

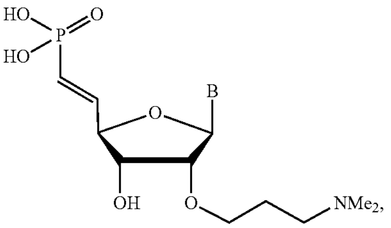

-continued

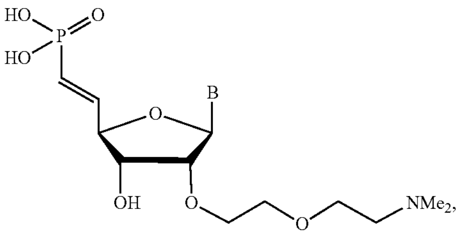

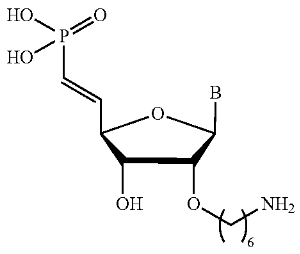

or

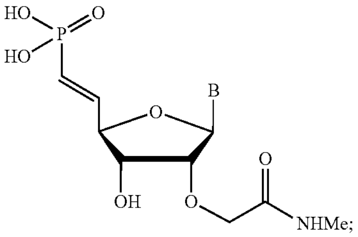

wherein B is a heterocyclic base moiety.

In some instances, a modified nucleotide includes, but is not limited to one 5'-vinylphosphonate modified non-natural nucleotide selected from:

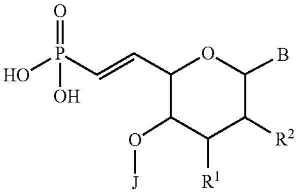

or

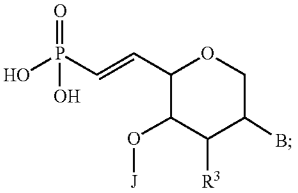

wherein B is a heterocyclic base moiety;

$R^1$, $R^2$, and $R^3$ are independently selected from hydrogen, halogen, alkyl or alkoxy; and J is an internucleotide linking group linking to the adjacent nucleotide of the polynucleotide.

In some instances, a modified nucleotide includes, but is not limited to one 5'-vinylphosphonate modified non-natural nucleotide selected from:

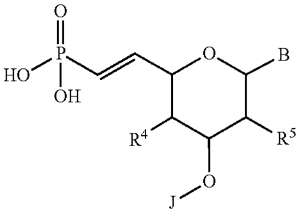

or

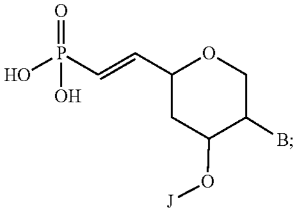

wherein B is a heterocyclic base moiety;

$R^4$, and $R^5$ are independently selected from hydrogen, halogen, alkyl or alkoxy; and J is an internucleotide linking group linking to the adjacent nucleotide of the polynucleotide.

In some instances, a modified nucleotide includes, but is not limited to one 5'-vinylphosphonate modified non-natural nucleotide selected from:

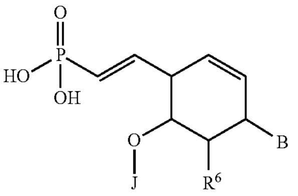

or

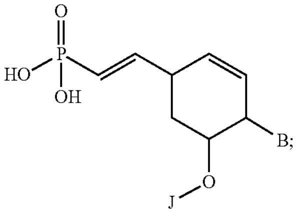

wherein B is a heterocyclic base moiety;

$R^6$ is selected from hydrogen, halogen, alkyl or alkoxy; and

J is an internucleotide linking group linking to the adjacent nucleotide of the polynucleotide.

In some instances, a modified nucleotide includes, but is not limited to one 5'-vinylphosphonate modified non-natural nucleotide selected from locked nucleic acid (LNA) or ethylene nucleic acid (ENA).

In some instances, a modified nucleotide includes, but is not limited to one 5'-vinylphosphonate modified non-natural nucleotide selected from:

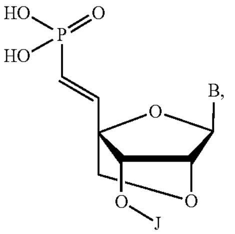

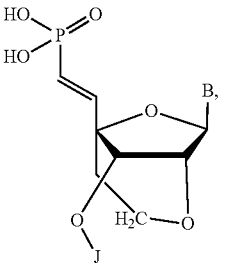

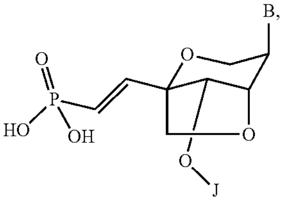

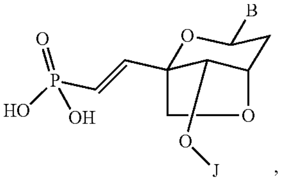

,

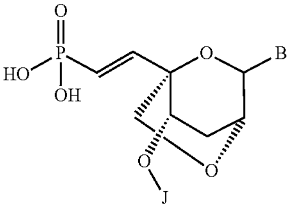

or

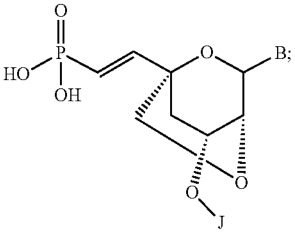

wherein B is a heterocyclic base moiety; and

J is an internucleotide linking group linking to the adjacent nucleotide of the polynucleotide.

In some instances, a modified nucleotide includes, but is not limited to one 5'-vinylphosphonate modified non-natural nucleotide selected from:

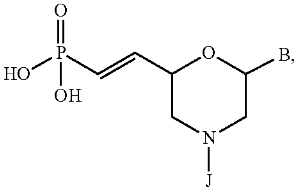

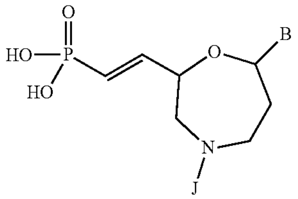

or

-continued

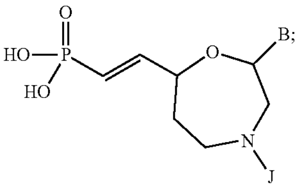

wherein B is a heterocyclic base moiety; and

J is an internucleotide linking group linking to the adjacent nucleotide of the polynucleotide.

In some instances, a modified nucleotide includes, but is not limited to one 5'-vinylphosphonate modified non-natural nucleotide selected from:

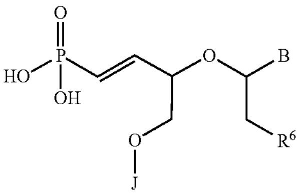

or

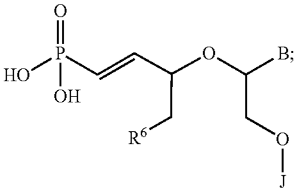

wherein B is a heterocyclic base moiety;

R6 is selected from hydrogen, halogen, alkyl or alkoxy; and

J is an internucleotide linking group linking to the adjacent nucleotide of the polynucleotide.

In some instances, a modified nucleotide includes, but is not limited to one 5'-vinylphosphonate modified non-natural nucleotide is

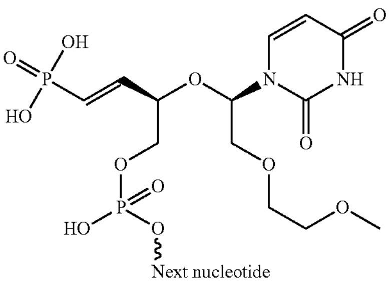

or vpUq

-continued

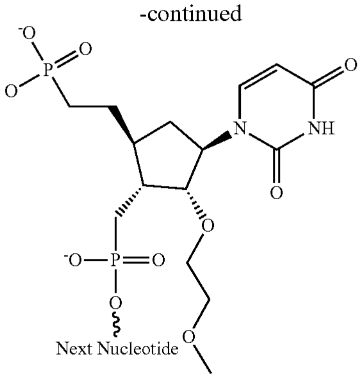

(vpUm)

In some instances, a modified nucleotide includes, but is not limited to, hexitol nucleic acid (or 1', 5'-anhydrohexitol nucleic acids (HNA)) illustrated as:

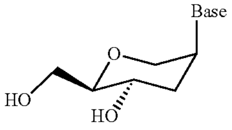

HNA

In some aspects, one or more modifications further optionally include modifications of the ribose moiety, phosphate backbone and the nucleoside, or modifications of the nucleotide analogues at the 3' or the 5' terminus. For example, the 3' terminus optionally include a 3' cationic group, or by inverting the nucleoside at the 3'-terminus with a 3'-3' linkage. In another alternative, the 3'-terminus is optionally conjugated with an aminoalkyl group, e.g., a 3' C5-aminoalkyl dT. In an additional alternative, the 3'-terminus is optionally conjugated with an abasic site, e.g., with an apurinic or apyrimidinic site. In some instances, the 5'-terminus is conjugated with an aminoalkyl group, e.g., a 5'-O-alkylamino substituent. In some cases, the 5'-terminus is conjugated with an abasic site, e.g., with an apurinic or apyrimidinic site.

In some aspects, the polynucleic acid molecule comprises one or more of the artificial nucleotide analogues described herein. In some instances, the polynucleic acid molecule comprises 1, 2, 3, 4, 5, 6, 7, 8, 9, 10, 11, 12, 13, 14, 15, 16, 17, 18, 20, 25, or more of the artificial nucleotide analogues described herein. In some aspects, the artificial nucleotide analogues include 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-0-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the polynucleic acid molecule comprises 1, 2, 3, 4, 5, 6, 7, 8, 9, 10, 11, 12, 13, 14, 15, 16, 17, 18, 20, 25, or more of the artificial nucleotide analogues selected from 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the polynucleic acid molecule comprises 1, 2, 3, 4, 5, 6, 7, 8, 9, 10, 11, 12, 13, 14, 15, 16, 17, 18, 20, 25, or more of 2'-O-methyl modified nucleotides. In some instances, the polynucleic acid molecule comprises 1, 2, 3, 4, 5, 6, 7, 8, 9, 10, 11, 12, 13, 14, 15, 16, 17, 18, 20, 25, or more of 2'-O-methoxyethyl (2'-O-MOE) modified nucleotides. In some instances, the polynucleic acid molecule comprises 1, 2, 3, 4, 5, 6, 7, 8, 9, 10, 11, 12, 13, 14, 15, 16, 17, 18, 20, 25, or more of thiolphosphonate nucleotides.

In some instances, the polynucleic acid molecule comprises at least one of: from about 5% to about 100% modification, from about 10% to about 100%, from about 10% to about 90%, from about 20% to about 100%, from about 10% to about 90%, from about 30% to about 100%, from about 30% to about 90%, from about 40% to about 100%, from about 40% to about 90%, from about 50% to about 100%, from about 50% to about 90%, from about 60% to about 100%, from about 60% to about 90% modification, from about 70% to about 100%, from about 70% to about 90%, from about 80% to about 100%, and from about 90% to about 100% modification.

In some cases, the polynucleic acid molecule comprises at least one of: from about 10% to about 80% modification, from about 20% to about 80%, from about 20% to about 70%, from about 30% to about 80%, from about 30% to about 70%, from about 40% to about 80%, from about 40% to about 70%, from about 50% to about 80%, from about 50% to about 70%, from about 60% to about 80%, from about 60% to about 70%, and from about 70% to about 80% modification.

In some instances, the polynucleic acid molecule comprises at least one of: from about 10% to about 60% modification, from about 20% to about 60% modification, from about 30% to about 60% modification, from about 40% to about 60% modification, and from about 50% to about 60% modification.

In some cases, the polynucleic acid molecule comprises at least one of: from about 10% to about 50% modification, from about 20% to about 50% modification, from about 30% to about 50% modification, and from about 40% to about 50% modification.

In some cases, the polynucleic acid molecule comprises at least one of: from about 10% to about 40% modification, from about 20% to about 40% modification, and from about 30% to about 40% modification.

In some cases, the polynucleic acid molecule comprises at least one of: from about 10% to about 30% modification, and from about 20% to about 30% modification.

In some cases, the polynucleic acid molecule comprises from about 10% to about 20% modification.

In some cases, the polynucleic acid molecule comprises from about 15% to about 90%, from about 20% to about 80%, from about 30% to about 70%, or from about 40% to about 60% modifications.

In additional cases, the polynucleic acid molecule comprises at least about 15%, 20%, 30%, 40%, 50%, 60%, 70%, 80%, 90%, 95%, or 99% modification.

In some aspects, the polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22 or more modifications.

In some instances, from about 5 to about 100% of the polynucleic acid molecule comprise the artificial nucleotide analogues described herein. In some instances, about 5%, 10%, 15%, 20%, 25%, 30%, 35%, 40%, 45%, 50%, 55%, 60%, 65%, 70%, 75%, 80%, 85%, 90%, 95% or 100% of the polynucleic acid molecule comprise the artificial nucleotide analogues described herein. In some instances, about 5% of the polynucleic acid molecule comprises the artificial nucleotide analogues described herein. In some instances, about 10% of the polynucleic acid molecule comprises the artificial nucleotide analogues described herein. In some instances, about 15% of the polynucleic acid molecule comprises the artificial nucleotide analogues described herein. In some instances, about 20% of the polynucleic acid molecule comprises the artificial nucleotide analogues described herein. In some instances, about 25% of the polynucleic acid molecule comprises the artificial nucleotide analogues described herein. In some instances, about 30% of the polynucleic acid molecule comprises the artificial nucleotide analogues described herein. In some instances, about 35% of the polynucleic acid molecule comprises the artificial nucleotide analogues described herein. In some instances, about 40% of the polynucleic acid molecule comprises the artificial nucleotide analogues described herein. In some instances, about 45% of the polynucleic acid molecule comprises the artificial nucleotide analogues described herein. In some instances, about 50% of the polynucleic acid molecule comprises the artificial nucleotide analogues described herein. In some instances, about 55% of the polynucleic acid molecule comprises the artificial nucleotide analogues described herein. In some instances, about 60% of the polynucleic acid molecule comprises the artificial nucleotide analogues described herein. In some instances, about 65% of the polynucleic acid molecule comprises the artificial nucleotide analogues described herein. In some instances, about 70% of the polynucleic acid molecule comprises the artificial nucleotide analogues described herein. In some instances, about 75% of the polynucleic acid molecule comprises the artificial nucleotide analogues described herein. In some instances, about 80% of the polynucleic acid molecule comprises the artificial nucleotide analogues described herein. In some instances, about 85% of the polynucleic acid molecule comprises the artificial nucleotide analogues described herein. In some instances, about 90% of the polynucleic acid molecule comprises the artificial nucleotide analogues described herein. In some instances, about 95% of the polynucleic acid molecule comprises the artificial nucleotide analogues described herein. In some instances, about 96% of the polynucleic acid molecule comprises the artificial nucleotide analogues described herein. In some instances, about 97% of the polynucleic acid molecule comprises the artificial nucleotide analogues described herein. In some instances, about 98% of the polynucleic acid molecule comprises the artificial nucleotide analogues described herein. In some instances, about 99% of the polynucleic acid molecule comprises the artificial nucleotide analogues described herein. In some instances, about 100% of the polynucleic acid molecule comprises the artificial nucleotide analogues described herein. In some aspects, the artificial nucleotide analogues include 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof.

In some aspects, the polynucleic acid molecule comprises from about 1 to about 25 modifications in which the modification comprises an artificial nucleotide analogue described herein. In some aspects, the polynucleic acid molecule comprises about 1, 2, 3, 4, 5, 6, 7, 8, 9, 10, 11, 12, 13, 14, 15, 16, 17, 18, 19, 20, 21, 22, 23, 24, or 25 modification(s) in which the modification comprises an artificial nucleotide analogue described herein.

In some aspects, a polynucleic acid molecule is assembled from two separate polynucleotides wherein one polynucleotide comprises the sense strand and the second polynucleotide comprises the antisense strand of the polynucleic acid molecule. In other embodiments, the sense strand is connected to the antisense strand via a linker molecule, which in some instances is a polynucleotide linker or a non-nucleotide linker.

In some aspects, a polynucleic acid molecule comprises a sense strand and antisense strand, and at least one of sense strand and antisense strands has a plurality of (e.g., two or more, three or more, four or more, five or more, six or more, seven or more, eight or more, etc.) 2'-O-methyl or 2'-deoxy-2'-fluoro modified nucleotides. In some aspects, where at least two out of the plurality of 2'-O-methyl or 2'-deoxy-2'-fluoro modified nucleotides are consecutive nucleotides. In some aspects, where consecutive 2'-O-methyl or 2'-deoxy-2'-fluoro modified nucleotides are located at the 5'-end of the sense strand and/or the antisense strand. In some aspects, where consecutive 2'-O-methyl or 2'-deoxy-2'-fluoro modified nucleotides are located at the 3'-end of the sense strand and/or the antisense strand. In some aspects, the sense strand of polynucleic acid molecule includes at least four, at least five, at least six consecutive 2'-O-methyl modified nucleotides at its 5' end and/or 3' end, or both. Optionally, in such embodiments, the sense strand of polynucleic acid molecule includes at least one, at least two, at least three, at least four 2'-deoxy-2'-fluoro modified nucleotides at the 3' end of the at least four, at least five, at least six consecutive 2'-O-methyl modified nucleotides at the polynucleotides' 5' end, or at the 5' end of the at least four, at least five, at least six consecutive 2'-O-methyl modified nucleotides at polynucleotides' 3' end. Also optionally, such at least two, at least three, at least four 2'-deoxy-2'-fluoro modified nucleotides are consecutive nucleotides.

In some aspects, a polynucleic acid molecule comprises a sense strand and antisense strand, and at least one of sense strand and antisense strands has 2'-O-methyl modified nucleotide located at the 5'-end of the sense strand and/or the antisense strand. In some aspects, at least one of sense strand and antisense strands has 2'-O-methyl modified nucleotide located at the 3'-end of the sense strand and/or the antisense strand. In some aspects, the 2'-O-methyl modified nucleotide located at the 5'-end of the sense strand and/or the antisense strand is a purine nucleotide. In some aspects, the 2'-O-methyl modified nucleotide located at the 5'-end of the sense strand and/or the antisense strand is a pyridine nucleotide.

In some aspects, a polynucleic acid molecule comprises a sense strand and antisense strand, and the antisense strand has two or more consecutive 2'-deoxy-2'-fluoro modified nucleotides at 5'-end. In some aspects, a polynucleic acid molecule comprises a sense strand and antisense strand, and the antisense strand has two or more consecutive 2'-O-methyl modified nucleotides at 3'-end. In some aspects, a polynucleic acid molecule comprises a sense strand and antisense strand, and the antisense strand has at least 2, 3, 4, 5, 6, or 7 consecutive 2'-O-methyl modified nucleotides.

In some aspects, a polynucleic acid molecule comprises a sense strand and antisense strand, wherein the sense strand includes a terminal cap moiety at the 5'-end, the 3'-end, or both of the 5' and 3' ends of the sense strand. In other embodiments, the terminal cap moiety is an inverted deoxy abasic moiety.

In some aspects, a polynucleic acid molecule comprises a sense strand and an antisense strand, wherein the antisense strand comprises a glyceryl modification at the 3' end of the antisense strand.

In some aspects, a polynucleic acid molecule comprises a sense strand and an antisense strand, in which the sense strand comprises one or more, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or about one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and in which the antisense strand comprises about 1 to about 10 or more, specifically about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10, or more, pyrimidine nucleotides of the sense and/or antisense strand are chemically-modified with 2'-deoxy, 2'-O-methyl and/or 2'-deoxy-2'-fluoro nucleotides, with or without one or more, for example about 1, 2, 3, 4, 5, 6, 7, 8, 9, 10, or more, phosphorothioate internucleotide linkages and/or a terminal cap molecule at the 3'-end, the 5'-end, or both of the 3'- and 5'-ends, being present in the same or different strand.

In some aspects, a polynucleic acid molecule comprises a sense strand and an antisense strand, in which the sense strand comprises about 1 to about 25, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10, or more) 2'-deoxy, 2'-O-methyl, 2'-deoxy-2'-fluoro, and/or one or more (e.g., about 1, 2, 3, 4, 5, 6, 7, 8, 9, 10, or more) universal base modified nucleotides, and optionally a terminal cap molecule at the 3-end, the 5'-end, or both of the 3'- and 5'-ends of the sense strand; and in which the antisense strand comprises about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10, or more, pyrimidine nucleotides of the sense and/or antisense strand are chemically-modified with 2'-deoxy, 2'-O-methyl and/or 2'-deoxy-2'-fluoro nucleotides, with or without about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages and/or a terminal cap molecule at the 3'-end, the 5'-end, or both of the 3'- and 5'-ends, being present in the same or different strand.

In some aspects, a polynucleic acid molecule comprises a sense strand and an antisense strand, in which the antisense strand comprises one or more, for example, about 1, 2, 3, 4, 5, 6, 7, 8, 9, 10, 11, 12, 13, 14, 15, 16, 17, 18, 19, 20, or more phosphorothioate internucleotide linkages, and/or about one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides at the 3'-end, the 5'-end, or both of the 3'- and 5'-ends of the sense strand and/or antisense strand, and optionally a terminal cap molecule at the 3'-end, the 5'-end, or both of the 3'- and 5'-ends of the sense strand. In some aspects, the antisense strand comprises about 1 to about 10 or more, specifically about 1, 2, 3, 4, 5, 6, 7, 8, 9, 10 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10, 11, 12, 13, 14, 15, 16, 17, 18, 19, 20, or more pyrimidine nucleotides of the sense and/or antisense strand are chemically-modified with 2'-deoxy, 2'-O-methyl and/or 2'-deoxy-2'-fluoro nucleotides, with or without one or more, for example, about 1, 2, 3, 4, 5, 6, 7, 8, 9, 10 or more phosphorothioate internucleotide linkages and/or a terminal cap molecule at the 3'-end, the 5'-end, or both of the 3' and 5'-ends, being present in the same or different strand.

In some aspects, a polynucleic acid molecule comprises a sense strand and an antisense strand, in which the antisense strand comprises about 1 to about 25 or more, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and the antisense strand comprises about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10 or more pyrimidine nucleotides of the sense and/or antisense strand are chemically-modified with 2'-deoxy, 2'-O-methyl and/or 2'-deoxy-2'-fluoro nucleotides, with or without about 1 to about 5, for example about 1, 2, 3, 4, 5 or more phosphorothioate internucleotide linkages and/or a terminal cap molecule at the 3'-end, the 5'-end, or both of the 3'- and 5'-ends, being present in the same or different strand.

In some aspects, a polynucleic acid molecule described herein is a chemically-modified short interfering nucleic acid molecule having about 1 to about 25, for example, about 1, 2, 3, 4, 5, 6, 7, 8, 9, 10, 11, 12, 13, 14, 15, 16, 17, 18, 19, 20 or more phosphorothioate internucleotide linkages in each strand of the polynucleic acid molecule. In some aspects, a polynucleic acid molecule comprises a sense strand and an antisense strand, and the antisense strand comprises a phosphate backbone modification at the 3' end of the antisense strand. Alternatively and/or additionally, a polynucleic acid molecule comprises a sense strand and an antisense strand, and the sense strand comprises a phosphate backbone modification at the 5' end of the antisense strand. In some instances, the phosphate backbone modification is a phosphorothioate. In some aspects, the sense or antisense strand has three consecutive nucleosides that are coupled via two phosphorothioate backbone.

In another embodiment, a polynucleic acid molecule described herein comprises 2'-5' internucleotide linkages. In some instances, the 2'-5' internucleotide linkage(s) is at the 3'-end, the 5'-end, or both of the 3'- and 5'-ends of one or both sequence strands. In addition instances, the 2'-5' internucleotide linkage(s) is present at various other positions within one or both sequence strands, for example, about 1, 2, 3, 4, 5, 6, 7, 8, 9, 10, or more including every internucleotide linkage of a pyrimidine nucleotide in one or both strands of the polynucleic acid molecule comprise a 2'-5' internucleotide linkage, or about 1, 2, 3, 4, 5, 6, 7, 8, 9, 10, or more including every internucleotide linkage of a purine nucleotide in one or both strands of the polynucleic acid molecule comprise a 2'-5' internucleotide linkage.

In some aspects, a polynucleic acid molecule is a single stranded polynucleic acid molecule that mediates RNAi activity in a cell or reconstituted in vitro system, wherein the polynucleic acid molecule comprises a single stranded polynucleotide having complementarity to a target nucleic acid sequence, and wherein one or more pyrimidine nucleotides present in the polynucleic acid are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the polynucleic acid are 2'-deoxy purine nucleotides (e.g., wherein all purine nucleotides are 2'-deoxy purine nucleotides or alternately a plurality of purine nucleotides are 2'-deoxy purine nucleotides), and a terminal cap modification, that is optionally present at the 3'-end, the 5'-end, or both of the 3' and 5'-ends of the antisense sequence, the polynucleic acid molecule optionally further comprising about 1 to about 4 (e.g., about 1, 2, 3, or 4) terminal 2'-deoxynucleotides at the 3'-end of the polynucleic acid molecule, wherein the terminal nucleotides further comprise one or more (e.g., 1, 2, 3, or 4) phosphorothioate internucleotide linkages, and wherein the polynucleic acid molecule optionally further comprises a terminal phosphate group, such as a 5'-terminal phosphate group.

In some cases, one or more of the artificial nucleotide analogues described herein are resistant toward nucleases such as for example ribonuclease such as RNase H, deoxyribonuclease such as DNase, or exonuclease such as 5'-3' exonuclease and 3'-5' exonuclease when compared to natural polynucleic acid molecules. In some instances, artificial nucleotide analogues comprising 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or combinations thereof are resistant toward nucleases such as for example ribonuclease such as RNase H, deoxyribonuclease such as DNase, or exonuclease such as 5'-3' exonuclease and 3'-5' exonuclease. In some instances, the 5' conjugates described herein inhibit 5'-3' exonucleolytic cleavage. In some instances, the 3' conjugates described herein inhibit 3'-5' exonucleolytic cleavage.

In some aspects, one or more of the artificial nucleotide analogues described herein have increased binding affinity toward their mRNA target relative to an equivalent natural polynucleic acid molecule. The one or more of the artificial nucleotide analogues comprising 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, or 2'-fluoro N3-P5'-phosphoramidites have increased binding affinity toward their mRNA target relative to an equivalent natural polynucleic acid molecule. In some cases, the increased affinity is illustrated with a lower Kd, a higher melt temperature (Tm), or a combination thereof.

In some aspects, a polynucleic acid molecule comprises a sense strand and antisense strand, and the sense strand comprises a nucleic acid of 5'-nsnsnnnnNfNfNfnnnnnnnnsnsa-3' (lower case (n)=2'-O-Me (methyl), Nf=2'-F (fluoro); s=phosphorothioate backbone modification). In some aspects, a polynucleic acid molecule comprises a sense strand and antisense strand, and the antisense strand comprises a nucleic acid of 5'-UfsNfsnnnNfnnnnnnnNfnNfnnnsusu-3' (lower case (n)=2'-O-Me (methyl), Nf=2'-F (fluoro); s=phosphorothioate backbone modification). In some aspects, a polynucleic acid molecule comprises a sense strand and antisense strand, and the sense strand comprises a nucleic acid of 5'-nsnsnnnnNfNfNfnnnnnnnnnsnsa-3' (lower case (n)=2'-O-Me (methyl), Nf=2'-F (fluoro); s=phosphorothioate backbone modification) and the antisense strand comprises a nucleic acid of 5'-UfsNfsnnnNfnnnnnnnNfnNfnnnsusu-3' (lower case (n)=2'-O-Me (methyl), Nf=2'-F (fluoro); s=phosphorothioate backbone modification).

In some aspects, a polynucleic acid molecule comprises a sense strand and antisense strand, and the sense strand comprises a nucleic acid of 5'-nsnsnnnnNfNfNfnnnnnnnnnsnsn-3' (lower case (n)=2'-O-Me (methyl), Nf=2'-F (fluoro); s=phosphorothioate backbone modification), and the antisense strand comprises a nucleic acid of 5'-nsNfsnnnNfnnnnnnnNfnNfnnnnnsnsn-3' (lower case (n)=2'-O-Me (methyl), Nf=2'-F (fluoro); s=phosphorothioate backbone modification). In some aspects, a polynucleic acid molecule comprises a sense strand and antisense strand, and the sense strand comprises a nucleic acid of 5'-nnnnnnnnNfNfNfnnnnnnnnnn-3' (lower case (n)=2'-O-Me (methyl), Nf=2'-F (fluoro); and the antisense strand comprises a nucleic acid of 5'-nNfnnnNfnnnnnnnNfnNfnnnnnnn-3' (lower case (n)=2'-O-Me (methyl), Nf=2'-F (fluoro); s=phosphorothioate backbone modification). In some aspects, a polynucleic acid molecule comprises a sense strand and antisense strand, and the sense strand comprises a nucleic acid of 5'-nsnsnnnnnnNfNfNfnnnnnnnnnsnsn-3' (lower case (n)=2'-O-Me (methyl), Nf=2'-F (fluoro); s=phosphorothioate backbone modification), and the antisense strand comprises a nucleic acid of 5'-nsNfsnnnNfnnnnnnnNfnNfnnnnnsnsn-3' (lower case (n)=2'-O-Me (methyl), Nf=2'-F (fluoro); s=phosphorothioate backbone modification). In some aspects, a polynucleic acid molecule comprises a sense strand and antisense strand, and the sense strand comprises a nucleic acid of 5'-nnnnnnnnNfNfNfnnnnnnnnn-3' (lower case (n)=2'-O-Me (methyl), Nf=2'-F (fluoro); and the antisense strand comprises a nucleic acid of 5'-VpUqNfnnnNfnnnnnnnNfnNfnnnnnnn-3' (lower case (n)=2'-O-Me (methyl), Nf=2'-F (fluoro); s=phosphorothioate backbone modification). In some aspects, a polynucleic acid molecule comprises a sense strand and antisense strand, and the sense strand comprises a nucleic acid of 5'-nsnsnnnnnnNfNfNfnnnnnnnnsnsn-3' (lower case (n)=2'-O-Me (methyl), Nf=2'-F (fluoro); s=phosphorothioate backbone modification), and the antisense strand comprises a nucleic acid of 5'-VpUqsNfsnnnNfnnnnnnnNfnNfnnnnnsnsn-3' (lower case (n)=2'-O-Me (methyl), Nf=2'-F (fluoro); s=phosphorothioate backbone modification).

In some aspects, a polynucleic acid molecule described herein is a chirally pure (or stereo pure) polynucleic acid molecule, or a polynucleic acid molecule comprising a single enantiomer. In some instances, the polynucleic acid molecule comprises L-nucleotide. In some instances, the polynucleic acid molecule comprises D-nucleotides. In some instance, a polynucleic acid molecule composition comprises less than 30%, 25%, 20%, 15%, 10%, 5%, 4%, 3%, 2%, 1%, or less of its mirror enantiomer. In some cases, a polynucleic acid molecule composition comprises less than 30%, 25%, 20%, 15%, 10%, 5%, 4%, 3%, 2%, 1%, or less of a racemic mixture. In some instances, the polynucleic acid molecule is a polynucleic acid molecule described in: U.S. Patent Publication Nos: 2014/194610 and 2015/211006; and PCT Publication No: WO2015107425.

In some aspects, a polynucleic acid molecule described herein is further modified to include an aptamer conjugating moiety. In some instances, the aptamer conjugating moiety is a DNA aptamer conjugating moiety. In some instances, the aptamer conjugating moiety is Alphamer (Centauri Therapeutics), which comprises an aptamer portion that recognizes a specific cell-surface target and a portion that presents a specific epitope for attaching to circulating antibodies. In some instance, a polynucleic acid molecule described herein is further modified to include an aptamer conjugating moiety as described in: U.S. Pat. Nos. 8,604,184, 8,591,910, and 7,850,975.

In additional embodiments, a polynucleic acid molecule described herein is modified to increase its stability. In some embodiment, the polynucleic acid molecule is RNA (e.g., siRNA). In some instances, the polynucleic acid molecule is modified by one or more of the modifications described above to increase its stability. In some cases, the polynucleic acid molecule is modified at the 2' hydroxyl position, such as by 2'-O-methyl, 2'-O-methoxyethyl (2'-O-MOE), 2'-O-aminopropyl, 2'-deoxy, 2'-deoxy-2'-fluoro, 2-O-aminopropyl (2'-O-AP), 2'-0-dimethylaminoethyl (2'-O-DMAOE), 2-O-dimethylaminopropyl (2'-O-DMAP), 2'-O-dimethylaminoethyloxyethyl (2'-O-DMAEOE), or 2'-O—N-methylacetamido (2'-O-NMA) modification or by a locked or bridged ribose conformation (e.g., LNA or ENA). In some cases, the polynucleic acid molecule is modified by 2'-O-methyl and/or 2'-O-methoxyethyl ribose. In some cases, the polynucleic acid molecule also includes morpholinos, PNAs, HNA, methylphosphonate nucleotides, thiolphosphonate nucleotides, and/or 2'-fluoro N3-P5'-phosphoramidites to increase its stability. In some instances, the polynucleic acid molecule is a chirally pure (or stereo pure) polynucleic acid molecule. In some instances, the chirally pure (or stereo pure) polynucleic acid molecule is modified to increase its stability. Suitable modifications to the RNA to increase stability for delivery will be apparent to the skilled person.

In some instances, the polynucleic acid molecule is a double-stranded polynucleotide molecule comprising self-complementary sense and antisense regions, wherein the antisense region comprises nucleotide sequence that is partially or fully complementary to nucleotide sequence in a target nucleic acid molecule or a portion thereof and the sense region having nucleotide sequence partially or fully corresponding to the target nucleic acid sequence or a portion thereof. In some instances, the polynucleic acid molecule is assembled from two separate polynucleotides, where one strand is the sense strand and the other is the antisense strand, wherein the antisense and sense strands are self-complementary (e.g., each strand comprises nucleotide sequence that is complementary to nucleotide sequence in the other strand; such as where the antisense strand and sense strand form a duplex or double stranded structure, for example wherein the double stranded region is about 19, 20, 21, 22, 23, or more base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the polynucleic acid molecule is assembled from a single oligonucleotide, where the self-complementary sense and antisense regions of the polynucleic acid molecule are linked by means of a nucleic acid based or non-nucleic acid-based linker(s).

In some cases, the polynucleic acid molecule is a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. In other cases, the polynucleic acid molecule is a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide is processed either in vivo or in vitro to generate an active polynucleic acid molecule capable of mediating RNAi. In additional cases, the polynucleic acid molecule also comprises a single-stranded polynucleotide having nucleotide sequence complementary to nucleotide sequence in a target nucleic acid molecule or a portion thereof (for example, where such polynucleic acid molecule does not require the presence within the polynucleic acid molecule of nucleotide sequence corresponding to the target nucleic acid sequence or a portion thereof), wherein the single stranded polynucleotide further comprises a terminal phosphate group, such as a 5'-phosphate (see for example Martinez et al., 2002, *Cell.,* 110, 563-574 and Schwarz et al., 2002, *Molecular Cell,* 10, 537-568), or 5', 3'-diphosphate.

In some instances, an asymmetric hairpin is a linear polynucleic acid molecule comprising an antisense region, a loop portion that comprises nucleotides or non-nucleotides, and a sense region that comprises fewer nucleotides than the antisense region to the extent that the sense region has enough complimentary nucleotides to base pair with the antisense region and form a duplex with loop. For example, an asymmetric hairpin polynucleic acid molecule comprises an antisense region having length sufficient to mediate RNAi in a cell or in vitro system (e.g. about 19 to about 22 nucleotides) and a loop region comprising about 4 to about 8 nucleotides, and a sense region having about 3 to about 18 nucleotides that are complementary to the antisense region. In some cases, the asymmetric hairpin polynucleic acid molecule also comprises a 5'-terminal phosphate group that is chemically modified. In additional cases, the loop portion of the asymmetric hairpin polynucleic acid molecule comprises nucleotides, non-nucleotides, linker molecules, or conjugate molecules.

In some aspects, an asymmetric duplex is a polynucleic acid molecule having two separate strands comprising a sense region and an antisense region, wherein the sense region comprises fewer nucleotides than the antisense region to the extent that the sense region has enough complimentary nucleotides to base pair with the antisense region and form a duplex. For example, an asymmetric duplex polynucleic acid molecule comprises an antisense region having length sufficient to mediate RNAi in a cell or in vitro system (e.g., about 19 to about 22 nucleotides) and a sense region having about 3 to about 18 nucleotides that are complementary to the antisense region.

In some cases, a universal base refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see for example Loakes, 2001, *Nucleic Acids Research,* 29, 2437-2447).

Polynucleic Acid Molecule Synthesis

In some aspects, a polynucleic acid molecule described herein is constructed using chemical synthesis and/or enzymatic ligation reactions using procedures known in the art. For example, a polynucleic acid molecule is chemically synthesized using naturally occurring nucleotides or variously modified nucleotides designed to increase the biological stability of the molecules or to increase the physical stability of the duplex formed between the polynucleic acid molecule and target nucleic acids. Exemplary methods include those described in: U.S. Pat. Nos. 5,142,047; 5,185,444; 5,889,136; 6,008,400; and 6,111,086; PCT Publication No. WO2009099942; or European Publication NO. 1579015. Additional exemplary methods include those described in: Griffey et al., "2'-O-aminopropyl ribonucleotides: a zwitterionic modification that enhances the exonuclease resistance and biological activity of antisense oligonucleotides," *J. Med. Chem.* 39 (26):5100-5109 (1997)); Obika, et al. "Synthesis of 2'-0,4'-C-methyleneuridine and -cytidine. Novel bicyclic nucleosides having a fixed C3, -endo sugar puckering". *Tetrahedron Letters* 38 (50): 8735 (1997); Koizumi, M. "ENA oligonucleotides as therapeutics". *Current opinion in molecular therapeutics* 8 (2): 144-149 (2006); and Abramova et al., "Novel oligonucleotide analogues based on morpholino nucleoside subunits-antisense technologies: new chemical possibilities," *Indian Journal of Chemistry* 48B:1721-1726 (2009). Alternatively, the polynucleic acid molecule is produced biologically using an expression vector into which a polynucleic acid molecule has been subcloned in an antisense orientation (i.e., RNA transcribed from the inserted polynucleic acid molecule will be of an antisense orientation to a target polynucleic acid molecule of interest).

In some aspects, a polynucleic acid molecule is synthesized via a tandem synthesis methodology, wherein both strands are synthesized as a single contiguous oligonucleotide fragment or strand separated by a cleavable linker which is subsequently cleaved to provide separate fragments or strands that hybridize and permit purification of the duplex.

In some instances, a polynucleic acid molecule is also assembled from two distinct nucleic acid strands or fragments wherein one fragment includes the sense region and the second fragment includes the antisense region of the molecule.

Additional modification methods for incorporating, for example, sugar, base and phosphate modifications include: Eckstein et al., International Publication PCT No. WO 92/07065; Perrault et al. *Nature,* 1990, 344, 565-568; Pieken et al. *Science,* 1991, 253, 314-317; Usman and Cedergren, *Trends in Biochem. Sci.,* 1992, 17, 334-339; Usman et al. International Publication PCT No. WO 93/15187; Sproat, U.S. Pat. No. 5,334,711 and Beigelman et al., 1995, *J Biol. Chem.,* 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, *Tetrahedron Lett.,* 39, 1131; Eamshaw and Gait, 1998, *Biopolymers* (*Nucleic Acid Sciences*), 48, 39-55; Verma and Eckstein, 1998, *Annu. Rev. Biochem.,* 67, 99-134; and Burlina et al., 1997, *Bioorg. Med. Chem.,* 5, 1999-2010. Such publications describe general methods and strategies to determine the location of incorporation of sugar, base and/or phosphate modifications and the like into nucleic acid molecules without modulating catalysis.

In some instances, while chemical modification of the polynucleic acid molecule internucleotide linkages with phosphorothioate, phosphorodithioate, and/or 5'-methylphosphonate linkages improves stability, excessive modifications sometimes cause toxicity or decreased activity. Therefore, when designing nucleic acid molecules, the amount of these internucleotide linkages in some cases is minimized. In such cases, the reduction in the concentration of these linkages lowers toxicity, increases efficacy and higher specificity of these molecules.

Polynucleic Acid Molecule Conjugates

In some aspects, a polynucleic acid molecule (B) is further conjugated to a polypeptide (A) for delivery to a site of interest. In some instances, at least one polypeptide A is conjugated to at least one B. In some instances, the at least one polypeptide A is conjugated to the at least one B to form an A-B conjugate. In some aspects, at least one A is conjugated to the 5' terminus of B, the 3' terminus of B, an internal site on B, or in any combinations thereof. In some instances, the at least one polypeptide A is conjugated to at least two B. In some instances, the at least one polypeptide A is conjugated to at least 2, 3, 4, 5, 6, 7, 8, or more B.

In some cases, a polynucleic acid molecule is conjugated to a polypeptide (A) and optionally a polymeric moiety (C). In some aspects, at least one polypeptide A is conjugated at one terminus of at least one B while at least one C is conjugated at the opposite terminus of the at least one B to form an A-B-C conjugate. In some instances, at least one polypeptide A is conjugated at one terminus of the at least one B while at least one of C is conjugated at an internal site on the at least one B. In some instances, at least one polypeptide A is conjugated directly to the at least one C. In some instances, the at least one B is conjugated indirectly to the at least one polypeptide A via the at least one C to form an A-C-B conjugate.

In some instances, at least one B and/or at least one C, and optionally at least one D are conjugated to at least one polypeptide A. In some instances, the at least one B is conjugated at a terminus (e.g., a 5' terminus or a 3' terminus) to the at least one polypeptide A or are conjugated via an internal site to the at least one polypeptide A. In some cases, the at least one C is conjugated either directly to the at least one polypeptide A or indirectly via the at least one B. If indirectly via the at least one B, the at least one C is conjugated either at the same terminus as the at least one polypeptide A on B, at opposing terminus from the at least one polypeptide A, or independently at an internal site. In some instances, at least one additional polypeptide A is further conjugated to the at least one polypeptide A, to B, or to C. In additional instances, the at least one D is optionally conjugated either directly or indirectly to the at least one polypeptide A, to the at least one B, or to the at least one C. If directly to the at least one polypeptide A, the at least one D is also optionally conjugated to the at least one B to form an A-D-B conjugate or is optionally conjugated to the at least one B and the at least one C to form an A-D-B-C conjugate. In some instances, the at least one D is directly conjugated to the at least one polypeptide A and indirectly to the at least one B and the at least one C to form a D-A-B-C conjugate. If indirectly to the at least one polypeptide A, the at least one D is also optionally conjugated to the at least one B to form an A-B-D conjugate or is optionally conjugated to the at least one B and the at least one C to form an A-B-D-C conjugate. In some instances, at least one additional D is further conjugated to the at least one polypeptide A, to B, or to C.

Binding Moiety

In some aspects, the binding moiety A is a polypeptide. In some instances, the polypeptide is an antibody or its fragment thereof. In some cases, the fragment is a binding fragment. In some instances, the antibody or antigen binding fragment thereof comprises a humanized antibody or antigen binding fragment thereof, murine antibody or antigen binding fragment thereof, chimeric antibody or antigen binding fragment thereof, monoclonal antibody or antigen binding fragment thereof, a binding fragment having a light chain domain and a heavy chain domain, a binding fragment having two light chain domains and two heavy chain domains, a binding fragment having two or more light chain domains and heavy chain domains, monovalent Fab, Fab', divalent Fab2, $F(ab)'_3$ fragments, single-chain variable fragment (scFv), bis-scFv, $(scFv)_2$, diabody, minibody, nanobody, triabody, tetrabody, disulfide stabilized Fv protein (dsFv), single-domain antibody (sdAb), Ig NAR, camelid antibody or antigen binding fragment thereof, bispecific antibody or biding fragment thereof, or a chemically modified derivative thereof.

In some aspects, the binding moiety A is a bispecific antibody or antigen binding fragment thereof. In some instances, the bispecific antibody is a trifunctional antibody or a bispecific mini-antibody. In some cases, the bispecific antibody is a trifunctional antibody. In some instances, the trifunctional antibody is a full length monoclonal antibody comprising binding sites for two different antigens.

In some cases, the bispecific antibody is a bispecific mini-antibody. In some instances, the bispecific mini-antibody comprises divalent Fab2, $F(ab)'_3$ fragments, bis-scFv, $(scFv)_2$, diabody, minibody, triabody, tetrabody or a bispecific T-cell engager (BiTE). In some aspects, the bispecific T-cell engager is a fusion protein that contains two single-chain variable fragments (scFvs) in which the two scFvs target epitopes of two different antigens.

In some aspects, the binding moiety A is a bispecific mini-antibody. In some instances, A is a bispecific Fab2. In some instances, A is a bispecific $F(ab)'_3$ fragment. In some cases, A is a bispecific bis-scFv. In some cases, A is a bispecific $(scFv)_2$. In some aspects, A is a bispecific diabody. In some aspects, A is a bispecific minibody. In some aspects, A is a bispecific triabody. In other embodiments, A is a bispecific tetrabody. In other embodiments, A is a bi-specific T-cell engager (BiTE).

In some aspects, the binding moiety A is a trispecific antibody. In some instances, the trispecific antibody comprises $F(ab)'_3$ fragments or a triabody. In some instances, A is a trispecific $F(ab)'_3$ fragment. In some cases, A is a triabody. In some aspects, A is a trispecific antibody as described in Dimas, et al., "Development of a trispecific antibody designed to simultaneously and efficiently target three different antigens on tumor cells," *Mol. Pharmaceutics,* 12(9): 3490-3501 (2015).

In some aspects, the binding moiety A is an antibody or antigen binding fragment thereof that recognizes a cell surface protein. In some instances, the binding moiety A is an antibody or antigen binding fragment thereof that recognizes a cell surface protein on a muscle cell. In some cases, the binding moiety A is an antibody or antigen binding fragment thereof that recognizes a cell surface protein on a skeletal muscle cell.

In some aspects, exemplary antibodies include, but are not limited to, an anti-myosin antibody, an anti-transferrin receptor antibody, and an antibody that recognizes Muscle-Specific kinase (MuSK). In some instances, the antibody is an anti-transferrin receptor (anti-CD71) antibody.

In some aspects, where the antibody is an anti-transferrin receptor (anti-CD71) antibody, the anti-transferrin antibody specifically binds to a transferrin receptor (TfR), preferably, specifically binds to transferrin receptor 1 (TfR1), or more preferably, specifically binds to human transferrin receptor 1 (TfR1) (or human CD71).

In some instances, the anti-transferrin receptor antibody comprises a variable heavy chain (VH) region and a variable light chain (VL) region, wherein the VH region comprises HCDR1 sequence comprising SEQ ID NO: 240; HCDR2 sequence $EINPIX_1GRSNYAX_2KFQG$ (SEQ ID NO: 241), wherein $X_1$ is selected from N or Q and $X_2$ is selected from Q or E; and HCDR3 sequence comprising SEQ ID NO: 245.

In some aspects, the VH region of the anti-transferrin receptor antibody comprises HCDR1, HCDR2, and HCDR3 sequences selected from Table 1.

TABLE 1

| Name | HCDR1 | SEQ ID NO: | HCDR2 | SEQ ID NO: | HCDR3 | SEQ ID NO: |
|---|---|---|---|---|---|---|
| 13E4_VH1 | YTFTNYWMH | 240 | EINPINGRS NYAQKFQG | 242 | GTRAMHY | 245 |
| 13E4_VH2* | YTFTNYWMH | 240 | EINPINGRS NYAEKFQG | 243 | GTRAMHY | 245 |

TABLE 1-continued

| Name | HCDR1 | SEQ ID NO: | HCDR2 | SEQ ID NO: | HCDR3 | SEQ ID NO: |
|---|---|---|---|---|---|---|
| 13E4_VH3 | YTFTNYWMH | 240 | EINPIQGRS NYAEKFQG | 244 | GTRAMHY | 245 |

*13E4_VH2 shares the same HCDR1, HCDR2, and HCDR3 sequences with anti-transferrin receptor antibody 13E4_VH4

In some aspects, the VH region comprises HCDR1 sequence comprising SEQ ID NO: 240; HCDR2 sequence comprising SEQ ID NO: 242, 243, or 244; and HCDR3 sequence comprising SEQ ID NO: 245. In some instances, the VH region comprises HCDR1 sequence comprising SEQ ID NO: 240, HCDR2 sequence comprising SEQ ID NO: 242, and HCDR3 sequence comprising SEQ ID NO: 245. In some instances, the VH region comprises HCDR1 sequence comprising SEQ ID NO: 240, HCDR2 sequence comprising SEQ ID NO: 243, and HCDR3 sequence comprising SEQ ID NO: 245. In some instances, the VH region comprises HCDR1 sequence comprising SEQ ID NO: 240, HCDR2 sequence comprising SEQ ID NO: 244, and HCDR3 sequence comprising SEQ ID NO: 245.

In some aspects, the VL region of the anti-transferrin receptor antibody comprises LCDR1 sequence RTSENIYX$_3$NLA (SEQ ID NO: 246), LCDR2 sequence AX$_4$TNLAX$_5$ (SEQ ID NO: 249), and LCDR3 sequence QHFWGTPLTX$_6$ (SEQ ID NO: 253), wherein X$_3$ is selected from N or S, X$_4$ is selected from A or G, X$_5$ is selected from D or E, and X$_6$ is present or absence, and if present, is F.

In some aspects, the VL region of the anti-transferrin receptor antibody comprises LCDR1, LCDR2, and LCDR3 sequences selected from Table 2.

TABLE 2

| Name | LCDR1 | SEQ ID NO: | LCDR2 | SEQ ID NO: | LCDR3 | SEQ ID NO: |
|---|---|---|---|---|---|---|
| 13E4_VL1* | RTSENI YNNLA | 247 | AATNLAD | 250 | QHFWGT PLT | 254 |
| 13E4_VL3 | RTSENI YNNLA | 247 | AATNLAE | 251 | QHFWGT PLTF | 255 |
| 13E4_VL4 | RTSENI YSNLA | 248 | AGTNLAD | 252 | QHFWGT PLTF | 255 |

*13E4_VL1 shares the same LCDR1, LCDR2, and LCDR3 sequences with anti-transferrin receptor antibody 13E4_VL2

In some instances, the VL region comprises LCDR1 sequence RTSENIYX$_3$NLA (SEQ ID NO: 246), LCDR2 sequence comprising SEQ ID NO: 250, 251, or 252, and LCDR3 sequence comprising SEQ ID NO: 254 or 255, wherein X$_3$ is selected from N or S.

In some instances, the VL region comprises LCDR1 sequence comprising SEQ ID NO: 247 or 248, LCDR2 sequence AX$_4$TNLAX$_5$ (SEQ ID NO: 249), and LCDR3 sequence comprising SEQ ID NO: 254 or 255, wherein X$_4$ is selected from A or G, and X$_5$ is selected from D or E.

In some instances, the VL region comprises LCDR1 sequence comprising SEQ ID NO: 247 or 248, LCDR2 sequence SEQ ID NO: 250, 251, or 252, and LCDR3 sequence QHFWGTPLTX$_6$ (SEQ ID NO: 253), wherein X$_6$ is present or absence, and if present, is F.

In some instances, the VL region comprises LCDR1 sequence comprising SEQ ID NO: 247, LCDR2 sequence AX$_4$TNLAX$_5$ (SEQ ID NO: 249), and LCDR3 sequence QHFWGTPLTX$_6$ (SEQ ID NO: 253), wherein X$_4$ is selected from A or G, X$_5$ is selected from D or E and X$_6$ is present or absence, and if present, is F.

In some instances, the VL region comprises LCDR1 sequence comprising SEQ ID NO: 247, LCDR2 sequence comprising SEQ ID NO: 250, and LCDR3 sequence comprising SEQ ID NO: 254.

In some instances, the VL region comprises LCDR1 sequence comprising SEQ ID NO: 247, LCDR2 sequence comprising SEQ ID NO: 251, and LCDR3 sequence comprising SEQ ID NO: 255.

In some instances, the VL region comprises LCDR1 sequence comprising SEQ ID NO: 248, LCDR2 sequence comprising SEQ ID NO: 252, and LCDR3 sequence comprising SEQ ID NO: 255.

In some aspects, the anti-transferrin receptor antibody comprises a VH region and a VL region, wherein the VH region comprises HCDR1 sequence comprising SEQ ID NO: 240; HCDR2 sequence EINPIX$_1$GRSNYAX$_2$KFQG (SEQ ID NO: 241), wherein X$_1$ is selected from N or Q and X$_2$ is selected from Q or E; and HCDR3 sequence comprising SEQ ID NO: 245; and the VL region comprises LCDR1 sequence RTSENIYX$_3$NLA (SEQ ID NO: 246), LCDR2 sequence AX$_4$TNLAX$_5$ (SEQ ID NO: 249), and LCDR3 sequence QHFWGTPLTX$_6$ (SEQ ID NO: 253), wherein X$_3$ is selected from N or S, X$_4$ is selected from A or G, X$_5$ is selected from D or E, and X$_6$ is present or absence, and if present, is F.

In some instances, the anti-transferrin receptor antibody comprises a VH region and a VL region, wherein the VH region comprises HCDR1 sequence comprising SEQ ID NO: 240; HCDR2 sequence EINPIX$_1$GRSNYAX$_2$KFQG (SEQ ID NO: 241), wherein X$_1$ is selected from N or Q and X$_2$ is selected from Q or E; and HCDR3 sequence comprising SEQ ID NO: 245; and the VL region comprises LCDR1 sequence RTSENIYX$_3$NLA (SEQ ID NO: 246), LCDR2 sequence comprising SEQ ID NO: 250, 251, or 252, and LCDR3 sequence comprising SEQ ID NO: 254 or 255, wherein X$_3$ is selected from N or S.

In some instances, the anti-transferrin receptor antibody comprises a VH region and a VL region, wherein the VH region comprises HCDR1 sequence comprising SEQ ID NO: 240; HCDR2 sequence EINPIX$_1$GRSNYAX$_2$KFQG (SEQ ID NO: 241), wherein X$_1$ is selected from N or Q and X$_2$ is selected from Q or E; and HCDR3 sequence comprising SEQ ID NO: 245; and the VL region comprises LCDR1 sequence comprising SEQ ID NO: 247 or 248, LCDR2 sequence AX$_4$TNLAX$_5$ (SEQ ID NO: 249), and LCDR3 sequence comprising SEQ ID NO: 254 or 255, wherein X$_4$ is selected from A or G, and X$_5$ is selected from D or E.

In some instances, the anti-transferrin receptor antibody comprises a VH region and a VL region, wherein the VH region comprises HCDR1 sequence comprising SEQ ID NO: 240; HCDR2 sequence EINPIX$_1$GRSNYAX$_2$KFQG (SEQ ID NO: 241), wherein X$_1$ is selected from N or Q and X$_2$ is selected from Q or E; and HCDR3 sequence comprising SEQ ID NO: 245; and the VL region comprises LCDR1 sequence comprising SEQ ID NO: 247 or 248, LCDR2 sequence SEQ ID NO: 250, 251, or 252, and LCDR3 sequence QHFWGTPLTX$_6$ (SEQ ID NO: 253), wherein X$_6$ is present or absence, and if present, is F.

In some instances, the anti-transferrin receptor antibody comprises a VH region and a VL region, wherein the VH region comprises HCDR1 sequence comprising SEQ ID NO: 240; HCDR2 sequence EINPIX$_1$GRSNYAX$_2$KFQG (SEQ ID NO: 241), wherein X$_1$ is selected from N or Q and X$_2$ is selected from Q or E; and HCDR3 sequence comprising SEQ ID NO: 245; and the VL region comprises LCDR1 sequence comprising SEQ ID NO: 247, LCDR2 sequence $AX_4TNLAX_5$ (SEQ ID NO: 249), and LCDR3 sequence $QHFWGTPLTX_6$ (SEQ ID NO: 253), wherein $X_4$ is selected from A or G, $X_5$ is selected from D or E and $X_6$ is present or absence, and if present, is F.

In some instances, the anti-transferrin receptor antibody comprises a VH region and a VL region, wherein the VH region comprises HCDR1 sequence comprising SEQ ID NO: 240; HCDR2 sequence $EINPIX_1GRSNYAX_2KFQG$ (SEQ ID NO: 241), wherein $X_1$ is selected from N or Q and $X_2$ is selected from Q or E; and HCDR3 sequence comprising SEQ ID NO: 245; and the VL region comprises LCDR1 sequence comprising SEQ ID NO: 247, LCDR2 sequence comprising SEQ ID NO: 250, and LCDR3 sequence comprising SEQ ID NO: 254.

In some instances, the anti-transferrin receptor antibody comprises a VH region and a VL region, wherein the VH region comprises HCDR1 sequence comprising SEQ ID NO: 240; HCDR2 sequence $EINPIX_1GRSNYAX_2KFQG$ (SEQ ID NO: 241), wherein $X_1$ is selected from N or Q and $X_2$ is selected from Q or E; and HCDR3 sequence comprising SEQ ID NO: 245; and the VL region comprises LCDR1 sequence comprising SEQ ID NO: 247, LCDR2 sequence comprising SEQ ID NO: 251, and LCDR3 sequence comprising SEQ ID NO: 255.

In some instances, the anti-transferrin receptor antibody comprises a VH region and a VL region, wherein the VH region comprises HCDR1 sequence comprising SEQ ID NO: 240; HCDR2 sequence $EINPIX_1GRSNYAX_2KFQG$ (SEQ ID NO: 241), wherein $X_1$ is selected from N or Q and $X_2$ is selected from Q or E; and HCDR3 sequence comprising SEQ ID NO: 245; and the VL region comprises LCDR1 sequence comprising SEQ ID NO: 248, LCDR2 sequence comprising SEQ ID NO: 252, and LCDR3 sequence comprising SEQ ID NO: 255.

In some instances, the anti-transferrin receptor antibody comprises a VH region and a VL region, in which the VH region comprises HCDR1 sequence comprising SEQ ID NO: 240, HCDR2 sequence comprising SEQ ID NO: 242, and HCDR3 sequence comprising SEQ ID NO: 245; and the VL region comprises LCDR1 sequence $RTSENIYX_3NLA$ (SEQ ID NO: 246), LCDR2 sequence comprising SEQ ID NO: 250, 251, or 252, and LCDR3 sequence comprising SEQ ID NO: 254 or 255, wherein $X_3$ is selected from N or S.

In some instances, the anti-transferrin receptor antibody comprises a VH region and a VL region, in which the VH region comprises HCDR1 sequence comprising SEQ ID NO: 240, HCDR2 sequence comprising SEQ ID NO: 242, and HCDR3 sequence comprising SEQ ID NO: 245; and the VL region comprises LCDR1 sequence comprising SEQ ID NO: 247 or 248, LCDR2 sequence $AX_4TNLAX_5$ (SEQ ID NO: 249), and LCDR3 sequence comprising SEQ ID NO: 254 or 255, wherein $X_4$ is selected from A or G, and $X_5$ is selected from D or E.

In some instances, the anti-transferrin receptor antibody comprises a VH region and a VL region, in which the VH region comprises HCDR1 sequence comprising SEQ ID NO: 240, HCDR2 sequence comprising SEQ ID NO: 2, and HCDR3 sequence comprising SEQ ID NO: 245; and the VL region comprises LCDR1 sequence comprising SEQ ID NO: 247 or 248, LCDR2 sequence SEQ ID NO: 250, 251, or 252, and LCDR3 sequence $QHFWGTPLTX_6$ (SEQ ID NO: 253), wherein $X_6$ is present or absence, and if present, is F.

In some instances, the anti-transferrin receptor antibody comprises a VH region and a VL region, in which the VH region comprises HCDR1 sequence comprising SEQ ID NO: 240, HCDR2 sequence comprising SEQ ID NO: 242, and HCDR3 sequence comprising SEQ ID NO: 245; and the VL region comprises LCDR1 sequence comprising SEQ ID NO: 247, LCDR2 sequence $AX_4TNLAX_5$ (SEQ ID NO: 249), and LCDR3 sequence $QHFWGTPLTX_6$ (SEQ ID NO: 253), wherein $X_4$ is selected from A or G, $X_5$ is selected from D or E and $X_6$ is present or absence, and if present, is F.

In some instances, the anti-transferrin receptor antibody comprises a VH region and a VL region, in which the VH region comprises HCDR1 sequence comprising SEQ ID NO: 240, HCDR2 sequence comprising SEQ ID NO: 242, and HCDR3 sequence comprising SEQ ID NO: 245; and the VL region comprises LCDR1 sequence comprising SEQ ID NO: 247, LCDR2 sequence comprising SEQ ID NO: 250, and LCDR3 sequence comprising SEQ ID NO: 254.

In some instances, the anti-transferrin receptor antibody comprises a VH region and a VL region, in which the VH region comprises HCDR1 sequence comprising SEQ ID NO: 240, HCDR2 sequence comprising SEQ ID NO: 242, and HCDR3 sequence comprising SEQ ID NO: 245; and the VL region comprises LCDR1 sequence comprising SEQ ID NO: 247, LCDR2 sequence comprising SEQ ID NO: 242, and LCDR3 sequence comprising SEQ ID NO: 255.

In some instances, the anti-transferrin receptor antibody comprises a VH region and a VL region, in which the VH region comprises HCDR1 sequence comprising SEQ ID NO: 240, HCDR2 sequence comprising SEQ ID NO: 242, and HCDR3 sequence comprising SEQ ID NO: 245; and the VL region comprises LCDR1 sequence comprising SEQ ID NO: 248, LCDR2 sequence comprising SEQ ID NO: 252, and LCDR3 sequence comprising SEQ ID NO: 255.

In some instances, the anti-transferrin receptor antibody comprises a VH region and a VL region, in which the VH region comprises HCDR1 sequence comprising SEQ ID NO: 240, HCDR2 sequence comprising SEQ ID NO: 243, and HCDR3 sequence comprising SEQ ID NO: 245; and the VL region comprises LCDR1 sequence $RTSENIYX_3NLA$ (SEQ ID NO: 246), LCDR2 sequence comprising SEQ ID NO: 250, 251, or 252, and LCDR3 sequence comprising SEQ ID NO: 254 or 255, wherein $X_3$ is selected from N or S.

In some instances, the anti-transferrin receptor antibody comprises a VH region and a VL region, in which the VH region comprises HCDR1 sequence comprising SEQ ID NO: 240, HCDR2 sequence comprising SEQ ID NO: 243, and HCDR3 sequence comprising SEQ ID NO: 245; and the VL region comprises LCDR1 sequence comprising SEQ ID NO: 247 or 248, LCDR2 sequence $AX_4TNLAX_5$ (SEQ ID NO: 249), and LCDR3 sequence comprising SEQ ID NO: 254 or 255, wherein $X_4$ is selected from A or G, and $X_5$ is selected from D or E.

In some instances, the anti-transferrin receptor antibody comprises a VH region and a VL region, in which the VH region comprises HCDR1 sequence comprising SEQ ID NO: 240, HCDR2 sequence comprising SEQ ID NO: 243, and HCDR3 sequence comprising SEQ ID NO: 245; and the VL region comprises LCDR1 sequence comprising SEQ ID NO: 247 or 248, LCDR2 sequence SEQ ID NO: 250, 251, or 252, and LCDR3 sequence $QHFWGTPLTX_6$ (SEQ ID NO: 253), wherein $X_6$ is present or absence, and if present, is F.

In some instances, the anti-transferrin receptor antibody comprises a VH region and a VL region, in which the VH region comprises HCDR1 sequence comprising SEQ ID NO: 240, HCDR2 sequence comprising SEQ ID NO: 243, and HCDR3 sequence comprising SEQ ID NO: 245; and the VL region comprises LCDR1 sequence comprising SEQ ID NO: 247, LCDR2 sequence $AX_4TNLAX_5$ (SEQ ID NO: 249), and LCDR3 sequence $QHFWGTPLTX_6$ (SEQ ID NO: 253), wherein $X_4$ is selected from A or G, $X_5$ is selected from D or E and $X_6$ is present or absence, and if present, is F.

In some instances, the anti-transferrin receptor antibody comprises a VH region and a VL region, in which the VH region comprises HCDR1 sequence comprising SEQ ID NO: 240, HCDR2 sequence comprising SEQ ID NO: 243, and HCDR3 sequence comprising SEQ ID NO: 245; and the VL region comprises LCDR1 sequence comprising SEQ ID NO: 247, LCDR2 sequence comprising SEQ ID NO: 250, and LCDR3 sequence comprising SEQ ID NO: 254.

In some instances, the anti-transferrin receptor antibody comprises a VH region and a VL region, in which the VH region comprises HCDR1 sequence comprising SEQ ID NO: 240, HCDR2 sequence comprising SEQ ID NO: 243, and HCDR3 sequence comprising SEQ ID NO: 245; and the VL region comprises LCDR1 sequence comprising SEQ ID NO: 247, LCDR2 sequence comprising SEQ ID NO: 251, and LCDR3 sequence comprising SEQ ID NO: 255.

In some instances, the anti-transferrin receptor antibody comprises a VH region and a VL region, in which the VH region comprises HCDR1 sequence comprising SEQ ID NO: 240, HCDR2 sequence comprising SEQ ID NO: 243, and HCDR3 sequence comprising SEQ ID NO: 245; and the VL region comprises LCDR1 sequence comprising SEQ ID NO: 248, LCDR2 sequence comprising SEQ ID NO: 252, and LCDR3 sequence comprising SEQ ID NO: 255.

In some instances, the anti-transferrin receptor antibody comprises a VH region and a VL region, in which the VH region comprises HCDR1 sequence comprising SEQ ID NO: 240, HCDR2 sequence comprising SEQ ID NO: 244, and HCDR3 sequence comprising SEQ ID NO: 245; and the VL region comprises LCDR1 sequence $RTSENIYX_3NLA$ (SEQ ID NO: 246), LCDR2 sequence comprising SEQ ID NO: 250, 251, or 252, and LCDR3 sequence comprising SEQ ID NO: 254 or 255, wherein $X_3$ is selected from N or S.

In some instances, the anti-transferrin receptor antibody comprises a VH region and a VL region, in which the VH region comprises HCDR1 sequence comprising SEQ ID NO: 240, HCDR2 sequence comprising SEQ ID NO: 244, and HCDR3 sequence comprising SEQ ID NO: 245; and the VL region comprises LCDR1 sequence comprising SEQ ID NO: 247 or 248, LCDR2 sequence $AX_4TNLAX_5$ (SEQ ID NO: 249), and LCDR3 sequence comprising SEQ ID NO: 254 or 255, wherein $X_4$ is selected from A or G, and $X_5$ is selected from D or E.

In some instances, the anti-transferrin receptor antibody comprises a VH region and a VL region, in which the VH region comprises HCDR1 sequence comprising SEQ ID NO: 240, HCDR2 sequence comprising SEQ ID NO: 244, and HCDR3 sequence comprising SEQ ID NO: 245; and the VL region comprises LCDR1 sequence comprising SEQ ID NO: 247 or 248, LCDR2 sequence SEQ ID NO: 250, 251, or 252, and LCDR3 sequence $QHFWGTPLTX_6$ (SEQ ID NO: 253), wherein $X_6$ is present or absence, and if present, is F.

In some instances, the anti-transferrin receptor antibody comprises a VH region and a VL region, in which the VH region comprises HCDR1 sequence comprising SEQ ID NO: 240, HCDR2 sequence comprising SEQ ID NO: 244, and HCDR3 sequence comprising SEQ ID NO: 245 and the VL region comprises LCDR1 sequence comprising SEQ ID NO: 247, LCDR2 sequence $AX_4TNLAX_5$ (SEQ ID NO: 249), and LCDR3 sequence $QHFWGTPLTX_6$ (SEQ ID NO: 253), wherein $X_4$ is selected from A or G, $X_5$ is selected from D or E and $X_6$ is present or absence, and if present, is F.

In some instances, the anti-transferrin receptor antibody comprises a VH region and a VL region, in which the VH region comprises HCDR1 sequence comprising SEQ ID NO: 240, HCDR2 sequence comprising SEQ ID NO: 244, and HCDR3 sequence comprising SEQ ID NO: 245; and the VL region comprises LCDR1 sequence comprising SEQ ID NO: 247, LCDR2 sequence comprising SEQ ID NO: 250, and LCDR3 sequence comprising SEQ ID NO: 254.

In some instances, the anti-transferrin receptor antibody comprises a VH region and a VL region, in which the VH region comprises HCDR1 sequence comprising SEQ ID NO: 240, HCDR2 sequence comprising SEQ ID NO: 244, and HCDR3 sequence comprising SEQ ID NO: 245; and the VL region comprises LCDR1 sequence comprising SEQ ID NO: 247, LCDR2 sequence comprising SEQ ID NO: 251, and LCDR3 sequence comprising SEQ ID NO: 255.

In some instances, the anti-transferrin receptor antibody comprises a VH region and a VL region, in which the VH region comprises HCDR1 sequence comprising SEQ ID NO: 240, HCDR2 sequence comprising SEQ ID NO: 244, and HCDR3 sequence comprising SEQ ID NO: 245; and the VL region comprises LCDR1 sequence comprising SEQ ID NO: 248, LCDR2 sequence comprising SEQ ID NO: 252, and LCDR3 sequence comprising SEQ ID NO: 255.

In some aspects, the anti-transferrin receptor antibody comprises a VH region and a VL region in which the sequence of the VH region comprises about 80%, 85%, 90%, 95%, 96% 97%, 98%, 99%, or 100% sequence identity to SEQ ID NOs: 256-260 and the sequence of the VL region comprises about 80%, 85%, 90%, 95%, 96% 97%, 98%, 99%, or 100% sequence identity to SEQ ID NOs: 261-265.

In some aspects, the VH region comprises a sequence selected from SEQ ID NOs: 256-260 (Table 3) and the VL region comprises a sequence selected from SEQ ID NOs: 261-264 (Table 4). The underlined regions in Table 3 and Table 4 denote the respective CDR1, CDR2, or CDR3 sequence.

TABLE 3

| NAME | VH SEQUENCE | SEQ ID NO: |
|---|---|---|
| 13E4_VH1 | QVQLVQSGAEVKKPGASVKVSCKASGYTFTNYWMHWVRQAPGQ<br>GLEWMGEINPINGRSNYAQKFQGRVTLTVDTSISTAYMELSRL<br>RSDDTAVYYCARGTRAMHYWGQGTLVTVSS | 256 |
| 13E4_VH2 | QVQLVQSGAEVKKPGASVKVSCKASGYTFTNYWMHWVRQAPGQ<br>GLEWIGEINPINGRSNYAEKFQGRVTLTVDTSSSTAYMELSRL<br>RSDDTAVYYCARGTRAMHYWGQGTLVTVSS | 257 |
| 13E4_VH3 | QVQLVQSGAEVKKPGASVKVSCKASGYTFTNYWMHWVRQAPGQ<br>GLEWMGEINPIQGRSNYAEKFQGRVTLTVDTSSSTAYMELSSL<br>RSEDTATYYCARGTRAMHYWGQGTLVTVSS | 258 |

TABLE 3-continued

| NAME | VH SEQUENCE | SEQ ID NO: |
|---|---|---|
| 13E4_VH4 | QVQLVQSGAEVKKPGASVKVSCKASGYTFTNYWMHWVRQAPGQGLEWMGEINPINGRSNYAEKFQGRVTLTVDTSSSTAYMELSSLRSEDTATYYCARGTRAMHYWGQGTLVTVSS | 259 |
| 13E4_VH | QVQLQQPGAELVKPGASVKLSCKASGYTFTNYWMHWVKQRPGQGLEWIGEINPINGRSNYGERFKTKATLTVDKSSSTAYMQLSSLTSEDSAVYYCARGTRAMHYWGQGTSVTVSS | 260 |

TABLE 4

| NAME | VL SEQUENCE | SEQ ID NO: |
|---|---|---|
| 13E4_VL1 | DIQMTQSPSSLSASVGDRVTITCRTSENIYNNLAWYQQKPGKSPKLLIYAATNLADGVPSRFSGSGSGTDYTLTISSLQPEDFATYYCQHFWGTPLTFGGGTKVEIK | 261 |
| 13E4_VL2 | DIQMTQSPSSLSASVGDRVTITCRTSENIYNNLAWYQQKPGKAPKLLIYAATNLADGVPSRFSGSGSGTDYTLTISSLQPEDFATYYCQHFWGTPLTFGGGTKVEIK | 262 |
| 13E4_VL3 | DIQMTQSPSSLSASVGDRVTITCRTSENIYNNLAWYQQKPGKAPKLLIYAATNLAEGVPSRFSGSGSGTDYTLTISSLQPEDFATYYCQHFWGTPLTFGGGTKVEIK | 263 |
| 13E4_VL4 | DIQMTQSPSSLSASVGDRVTITCRTSENIYSNLAWYQQKPGKAPKLLIYAGTNLADGVPSRFSGSGSGTDYTLTISSLQPEDFANYYCQHFWGTPLTFGGGTKVEIK | 264 |
| 13E4_VL | DIQMTQSPASLSVSVGETVTITCRTSENIYNNLAWYQQKQGKSPQLLVYAATNLADGVPSRFSGSGSGTQYSLKINSLQSEDFGNYYCQHFWGTPLTFGAGTKLELK | 265 |

In some aspects, the anti-transferrin receptor antibody comprises a VH region and a VL region as illustrated in Table 5.

TABLE 5

| | 13E4_VH1 (SEQ ID NO: 266) | 13E4_VH2 (SEQ ID NO: 267) | 13E4_VH3 (SEQ ID NO: 268) | 13E4_VH4 (SEQ ID NO: 269) |
|---|---|---|---|---|
| 13E4_VL1 (SEQ ID NO: 261) | SEQ ID NO: 256 + SEQ ID NO: 261 | SEQ ID NO: 257 + SEQ ID NO: 261 | SEQ ID NO: 258 + SEQ ID NO: 261 | SEQ ID NO: 259 + SEQ ID NO: 261 |
| 13E4_VL2 (SEQ ID NO: 262) | SEQ ID NO: 256 + SEQ ID NO: 262 | SEQ ID NO: 257 + SEQ ID NO: 262 | SEQ ID NO: 258 + SEQ ID NO: 262 | SEQ ID NO: 259 + SEQ ID NO: 262 |
| 13E4_VL3 (SEQ ID NO: 263) | SEQ ID NO: 256 + SEQ ID NO: 263 | SEQ ID NO: 257 + SEQ ID NO: 263 | SEQ ID NO: 258 + SEQ ID NO: 263 | SEQ ID NO: 259 + SEQ ID NO: 263 |
| 13E4_VL4 (SEQ ID NO: 264) | SEQ ID NO: 256 + SEQ ID NO: 264 | SEQ ID NO: 257 + SEQ ID NO: 264 | SEQ ID NO: 258 + SEQ ID NO: 264 | SEQ ID NO: 259 + SEQ ID NO: 264 |

In some aspects, an anti-transferrin receptor antibody described herein comprises an IgG framework, an IgA framework, an IgE framework, or an IgM framework. In some instances, the anti-transferrin receptor antibody comprises an IgG framework (e.g., IgG1, IgG2, IgG3, or IgG4). In some cases, the anti-transferrin receptor antibody comprises an IgG1 framework. In some cases, the anti-transferrin receptor antibody comprises an IgG2 (e.g., an IgG2a or IgG2b) framework. In some cases, the anti-transferrin receptor antibody comprises an IgG2a framework. In some cases, the anti-transferrin receptor antibody comprises an IgG2b framework. In some cases, the anti-transferrin receptor antibody comprises an IgG3 framework. In some cases, the anti-transferrin receptor antibody comprises an IgG4 framework.

In some cases, an anti-transferrin receptor antibody comprises one or more mutations in a framework region, e.g., in the CH1 domain, CH2 domain, CH3 domain, hinge region, or a combination thereof. In some instances, the one or more mutations are to stabilize the antibody and/or to increase half-life. In some instances, the one or more mutations are to modulate Fc receptor interactions, to reduce or eliminate Fc effector functions such as FcγR, antibody-dependent cell-mediated cytotoxicity (ADCC), or complement-dependent cytotoxicity (CDC). In additional instances, the one or more mutations are to modulate glycosylation.

In some aspects, the one or more mutations are located in the Fc region. In some instances, the Fc region comprises a mutation at residue position L234, L235, or a combination thereof. In some instances, the mutations comprise L234 and L235. In some instances, the mutations comprise L234A and L235A. In some cases, the residue positions are in reference to IgG1.

In some instances, the Fc region comprises a mutation at residue position L234, L235, D265, N297, K322, L328, or P329, or a combination thereof. In some instances, the mutations comprise L234 and L235 in combination with a mutation at residue position K322, L328, or P329. In some cases, the Fc region comprises mutations at L234, L235, and K322. In some cases, the Fc region comprises mutations at L234, L235, and L328. In some cases, the Fc region comprises mutations at L234, L235, and P329. In some cases, the Fc region comprises mutations at D265 and N297. In some cases, the residue position is in reference to IgG1.

In some instances, the Fc region comprises L234A, L235A, D265A, N297G, K322G, L328R, or P329G, or a combination thereof. In some instances, the Fc region comprises L234A and L235A in combination with K322G, L328R, or P329G. In some cases, the Fc region comprises L234A, L235A, and K322G. In some cases, the Fc region comprises L234A, L235A, and L328R. In some cases, the Fc region comprises L234A, L235A, and P329G. In some cases, the Fc region comprises D265A and N297G. In some cases, the residue position is in reference to IgG1.

In some instances, the Fc region comprises a mutation at residue position L235, L236, D265, N297, K322, L328, or P329, or a combination of the mutations. In some instances, the Fc region comprises mutations at L235 and L236. In some instances, the Fc region comprises mutations at L235 and L236 in combination with a mutation at residue position K322, L328, or P329. In some cases, the Fc region comprises mutations at L235, L236, and K322. In some cases, the Fc region comprises mutations at L235, L236, and L328. In some cases, the Fc region comprises mutations at L235, L236, and P329. In some cases, the Fc region comprises mutations at D265 and N297. In some cases, the residue position is in reference to IgG2b.

In some aspects, the Fc region comprises L235A, L236A, D265A, N297G, K322G, L328R, or P329G, or a combination thereof. In some instances, the Fc region comprises L235A and L236A. In some instances, the Fc region comprises L235A and L236A in combination with K322G, L328R, or P329G. In some cases, the Fc region comprises L235A, L236A, and K322G. In some cases, the Fc region comprises L235A, L236A, and L328R. In some cases, the Fc region comprises L235A, L236A, and P329G. In some cases, the Fc region comprises D265A and N297G. In some cases, the residue position is in reference to IgG2b.

In some aspects, the Fc region comprises a mutation at residue position L233, L234, D264, N296, K321, L327, or P328, wherein the residues correspond to positions 233, 234, 264, 296, 321, 327, and 328 of SEQ ID NO: 270. In some instances, the Fc region comprises mutations at L233 and L234. In some instances, the Fc region comprises mutations at L233 and L234 in combination with a mutation at residue position K321, L327, or P328. In some cases, the Fc region comprises mutations at L233, L234, and K321. In some cases, the Fc region comprises mutations at L233, L234, and L327. In some cases, the Fc region comprises mutations at L233, L234, and K321. In some cases, the Fc region comprises mutations at L233, L234, and P328. In some instances, the Fc region comprises mutations at D264 and N296. In some cases, equivalent positions to residue L233, L234, D264, N296, K321, L327, or P328 in an IgG1, IgG2, IgG3, or IgG4 framework are contemplated. In some cases, mutations to a residue that corresponds to residue L233, L234, D264, N296, K321, L327, or P328 of SEQ ID NO: 270 in an IgG1, IgG2, or IgG4 framework are also contemplated.

In some aspects, the Fc region comprises L233A, L234A, D264A, N296G, K321G, L327R, or P328G, wherein the residues correspond to positions 233, 234, 264, 296, 321, 327, and 328 of SEQ ID NO: 270. In some instances, the Fc region comprises L233A and L234A. In some instances, the Fc region comprises L233A and L234A in combination with K321G, L327R, or P328G. In some cases, the Fc region comprises L233A, L234A, and K321G. In some cases, the Fc region comprises L233A, L234A, and L327R. In some cases, the Fc region comprises L233A, L234A, and K321G. In some cases, the Fc region comprises L233A, L234A, and P328G. In some instances, the Fc region comprises D264A and N296G.

In some aspects, the human IgG constant region is modified to alter antibody-dependent cellular cytotoxicity (ADCC) and/or complement-dependent cytotoxicity (CDC), e.g., with an amino acid modification described in Natsume et al., 2008 *Cancer Res,* 68(10): 3863-72; Idusogie et al., 2001 *J Immunol,* 166(4): 2571-5; Moore et al., 2010 *mAbs,* 2(2): 181-189; Lazar et al., 2006 *PNAS,* 103(11): 4005-4010, Shields et al., 2001 *JBC,* 276(9): 6591-6604; Stavenhagen et al., 2007 *Cancer Res,* 67(18): 8882-8890; Stavenhagen et al., 2008 *Advan. Enzyme Regul.,* 48: 152-164; Alegre et al, 1992 *J Immunol,* 148: 3461-3468; Reviewed in Kaneko and Niwa, 2011 Biodrugs, 25(1): 1-11.

In some aspects, an anti-transferrin receptor antibody described herein is a full-length antibody, comprising a heavy chain (HC) and a light chain (LC). In some cases, the heavy chain (HC) comprises a sequence selected from Table 6. In some cases, the light chain (LC) comprises a sequence selected from Table 7. The underlined region denotes the respective CDRs.

TABLE 6

| NAME | HC SEQUENCE | SEQ ID NO: |
|---|---|---|
| 13E4_VH1 | QVQLVQSGAEVKKPGASVKVSCKASGYTFTNYWMHWVRQA<br>PGQGLEWMGEINPINGRSNYAQKFQGRVTLTVDTSISTAY<br>MELSRLRSDDTAVYYCARGTRAMHYWGQGTLVTVSSASTK<br>GPSVFPLAPSSKSTSGGTAALGCLVKDYFPEPVTVSWNSG<br>ALTSGVHTFPAVLQSSGLYSLSSVVTVPSSSLGTQTYICN<br>VNHKPSNTKVDKRVEPKSCDKTHTCPPCPAPELLGGPSVF<br>LFPPKPKDTLMISRTPEVTCVVVDVSHEDPEVKFNWYVDG<br>VEVHNAKTKPREEQYNSTYRVVSVLTVLHQDWLNGKEYKC<br>KVSNKALPAPIEKTISKAKGQPREPQVYTLPPSREEMTKN<br>QVSLTCLVKGFYPSDIAVEWESNGQPENNYKTTPPVLDSD<br>GSFFLYSKLTVDKSRWQQGNVFSCSVMHEALHNHYTQKSL<br>SLSPG | 270 |
| 13E4_VH1_a | QVQLVQSGAEVKKPGASVKVSCKASGYTFTNYWMHWVRQA<br>PGQGLEWMGEINPINGRSNYAQKFQGRVTLTVDTSISTAY<br>MELSRLRSDDTAVYYCARGTRAMHYWGQGTLVTVSSASTK<br>GPSVFPLAPSSKSTSGGTAALGCLVKDYFPEPVTVSWNSG<br>ALTSGVHTFPAVLQSSGLYSLSSVVTVPSSSLGTQTYICN<br>VNHKPSNTKVDKRVEPKSCDKTHTCPPCPAPE**AA**GGPSVF<br>LFPPKPKDTLMISRTPEVTCVVVDVSHEDPEVKFNWYVDG<br>VEVHNAKTKPREEQYNSTYRVVSVLTVLHQDWLNGKEYKC | 271 |

TABLE 6-continued

| NAME | HC SEQUENCE | SEQ ID NO: |
| --- | --- | --- |
| | KVSNKALPAPIEKTISKAKGQPREPQVYTLPPSREEMTKN<br>QVSLTCLVKGFYPSDIAVEWESNGQPENNYKTTPPVLDSD<br>GSFFLYSKLTVDKSRWQQGNVFSCSVMHEALHNHYTQKSL<br>SLSPG | |
| 13E4_VH1_b | QVQLVQSGAEVKKPGASVKVSCKASGYTFTNYWMHWVRQA<br>PGQGLEWMGEINPINGRSNYAQKFQGRVTLTVDTSISTAY<br>MELSRLRSDDTAVYYCARGTRAMHYWGQGTLVTVSSASTK<br>GPSVFPLAPSSKSTSGGTAALGCLVKDYFPEPVTVSWNSG<br>ALTSGVHTFPAVLQSSGLYSLSSVVTVPSSSLGTQTYICN<br>VNHKPSNTKVDKRVEPKSCDKTHTCPPCPAPE**AA**GGPSVF<br>LFPPKPKDTLMISRTPEVTCVVVDVSHEDPEVKFNWYVDG<br>VEVHNAKTKPREEQYNSTYRVVSVLTVLHQDWLNGKEYKC<br>**G**VSNKALPAPIEKTISKAKGQPREPQVYTLPPSREEMTKN<br>QVSLTCLVKGFYPSDIAVEWESNGQPENNYKTTPPVLDSD<br>GSFFLYSKLTVDKSRWQQGNVFSCSVMHEALHNHYTQKSL<br>SLSPG | 272 |
| 13E4_VH1_c | QVQLVQSGAEVKKPGASVKVSCKASGYTFTNYWMHWVRQA<br>PGQGLEWMGEINPINGRSNYAQKFQGRVTLTVDTSISTAY<br>MELSRLRSDDTAVYYCARGTRAMHYWGQGTLVTVSSASTK<br>GPSVFPLAPSSKSTSGGTAALGCLVKDYFPEPVTVSWNSG<br>ALTSGVHTFPAVLQSSGLYSLSSVVTVPSSSLGTQTYICN<br>VNHKPSNTKVDKRVEPKSCDKTHTCPPCPAPE**AA**GGPSVF<br>LFPPKPKDTLMISRTPEVTCVVVDVSHEDPEVKFNWYVDG<br>VEVHNAKTKPREEQYNSTYRVVSVLTVLHQDWLNGKEYKC<br>KVSNKA**R**PAPIEKTISKAKGQPREPQVYTLPPSREEMTKN<br>QVSLTCLVKGFYPSDIAVEWESNGQPENNYKTTPPVLDSD<br>GSFFLYSKLTVDKSRWQQGNVFSCSVMHEALHNHYTQKSL<br>SLSPG | 273 |
| 13E4_VH1_d | QVQLVQSGAEVKKPGASVKVSCKASGYTFTNYWMHWVRQA<br>PGQGLEWMGEINPINGRSNYAQKFQGRVTLTVDTSISTAY<br>MELSRLRSDDTAVYYCARGTRAMHYWGQGTLVTVSSASTK<br>GPSVFPLAPSSKSTSGGTAALGCLVKDYFPEPVTVSWNSG<br>ALTSGVHTFPAVLQSSGLYSLSSVVTVPSSSLGTQTYICN<br>VNHKPSNTKVDKRVEPKSCDKTHTCPPCPAPE**AA**GGPSVF<br>LFPPKPKDTLMISRTPEVTCVVVDVSHEDPEVKFNWYVDG<br>VEVHNAKTKPREEQYNSTYRVVSVLTVLHQDWLNGKEYKC<br>KVSNKAL**G**APIEKTISKAKGQPREPQVYTLPPSREEMTKN<br>QVSLTCLVKGFYPSDIAVEWESNGQPENNYKTTPPVLDSD<br>GSFFLYSKLTVDKSRWQQGNVFSCSVMHEALHNHYTQKSL<br>SLSPG | 274 |
| 13E4_VH1_e | QVQLVQSGAEVKKPGASVKVSCKASGYTFTNYWMHWVRQA<br>PGQGLEWMGEINPINGRSNYAQKFQGRVTLTVDTSISTAY<br>MELSRLRSDDTAVYYCARGTRAMHYWGQGTLVTVSSASTK<br>GPSVFPLAPSSKSTSGGTAALGCLVKDYFPEPVTVSWNSG<br>ALTSGVHTFPAVLQSSGLYSLSSVVTVPSSSLGTQTYICN<br>VNHKPSNTKVDKRVEPKSCDKTHTCPPCPAPELLGGPSVF<br>LFPPKPKDTLMISRTPEVTCVVV**A**VSHEDPEVKFNWYVDG<br>VEVHNAKTKPREEQY**G**STYRVVSVLTVLHQDWLNGKEYKC<br>KVSNKALPAPIEKTISKAKGQPREPQVYTLPPSREEMTKN<br>QVSLTCLVKGFYPSDIAVEWESNGQPENNYKTTPPVLDSD<br>GSFFLYSKLTVDKSRWQQGNVFSCSVMHEALHNHYTQKSL<br>SLSPG | 275 |
| 13E4_VH2 | QVQLVQSGAEVKKPGASVKVSCKASGYTFTNYWMHWVRQA<br>PGQGLEWIGEINPINGRSNYAEKFQGRVTLTVDTSSSTAY<br>MELSRLRSDDTAVYYCARGTRAMHYWGQGTLVTVSSASTK<br>GPSVFPLAPSSKSTSGGTAALGCLVKDYFPEPVTVSWNSG<br>ALTSGVHTFPAVLQSSGLYSLSSVVTVPSSSLGTQTYICN<br>VNHKPSNTKVDKRVEPKSCDKTHTCPPCPAPELLGGPSVF<br>LFPPKPKDTLMISRTPEVTCVVVDVSHEDPEVKFNWYVDG<br>VEVHNAKTKPREEQYNSTYRVVSVLTVLHQDWLNGKEYKC<br>KVSNKALPAPIEKTISKAKGQPREPQVYTLPPSREEMTKN<br>QVSLTCLVKGFYPSDIAVEWESNGQPENNYKTTPPVLDSD<br>GSFFLYSKLTVDKSRWQQGNVFSCSVMHEALHNHYTQKSL<br>SLSPG | 276 |
| 13E4_VH2_a | QVQLVQSGAEVKKPGASVKVSCKASGYTFTNYWMHWVRQA<br>PGQGLEWIGEINPINGRSNYAEKFQGRVTLTVDTSSSTAY<br>MELSRLRSDDTAVYYCARGTRAMHYWGQGTLVTVSSASTK<br>GPSVFPLAPSSKSTSGGTAALGCLVKDYFPEPVTVSWNSG<br>ALTSGVHTFPAVLQSSGLYSLSSVVTVPSSSLGTQTYICN<br>VNHKPSNTKVDKRVEPKSCDKTHTCPPCPAPE**AA**GGPSVF<br>LFPPKPKDTLMISRTPEVTCVVVDVSHEDPEVKFNWYVDG<br>VEVHNAKTKPREEQYNSTYRVVSVLTVLHQDWLNGKEYKC | 277 |

TABLE 6-continued

| NAME | HC SEQUENCE | SEQ ID NO: |
|---|---|---|
| | KVSNKALPAPIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPG | |
| 13E4_VH2_b | QVQLVQSGAEVKKPGASVKVSCKASGYTFTNYWMHWVRQA PGQGLEWIGEINPINGRSNYAEKFQGRVTLTVDTSSSTAY MELSRLRSDDTAVYYCARGTRAMHYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICN VNHKPSNTKVDKRVEPKSCDKTHTCPPCPAPE**AA**GGPSVF LFPPKPKDTLMISRTPEVTCVVVDVSHEDPEVKFNWYVDG VEVHNAKTKPREEQYNSTYRVVSVLTVLHQDWLNGKEYKC **G**VSNKALPAPIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPG | 278 |
| 13E4_VH2_c | QVQLVQSGAEVKKPGASVKVSCKASGYTFTNYWMHWVRQA PGQGLEWIGEINPINGRSNYAEKFQGRVTLTVDTSSSTAY MELSRLRSDDTAVYYCARGTRAMHYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICN VNHKPSNTKVDKRVEPKSCDKTHTCPPCPAPE**AA**GGPSVF LFPPKPKDTLMISRTPEVTCVVVDVSHEDPEVKFNWYVDG VEVHNAKTKPREEQYNSTYRVVSVLTVLHQDWLNGKEYKC KVSNKA**R**PAPIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPG | 279 |
| 13E4_VH2_d | QVQLVQSGAEVKKPGASVKVSCKASGYTFTNYWMHWVRQA PGQGLEWIGEINPINGRSNYAEKFQGRVTLTVDTSSSTAY MELSRLRSDDTAVYYCARGTRAMHYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICN VNHKPSNTKVDKRVEPKSCDKTHTCPPCPAPE**AA**GGPSVF LFPPKPKDTLMISRTPEVTCVVVDVSHEDPEVKFNWYVDG VEVHNAKTKPREEQYNSTYRVVSVLTVLHQDWLNGKEYKC KVSNKAL**G**APIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPG | 280 |
| 13E4_VH2_e | QVQLVQSGAEVKKPGASVKVSCKASGYTFTNYWMHWVRQA PGQGLEWIGEINPINGRSNYAEKFQGRVTLTVDTSSSTAY MELSRLRSDDTAVYYCARGTRAMHYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICN VNHKPSNTKVDKRVEPKSCDKTHTCPPCPAPELLGGPSVF LFPPKPKDTLMISRTPEVTCVVV**A**VSHEDPEVKFNWYVDG VEVHNAKTKPREEQY**G**STYRVVSVLTVLHQDWLNGKEYKC KVSNKALPAPIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPG | 281 |
| 13E4_VH3 | QVQLVQSGAEVKKPGASVKVSCKASGYTFTNYWMHWVRQA PGQGLEWMGEINPIQGRSNYAEKFQGRVTLTVDTSSSTAY MELSSLRSEDTATYYCARGTRAMHYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICN VNHKPSNTKVDKRVEPKSCDKTHTCPPCPAPELLGGPSVF LFPPKPKDTLMISRTPEVTCVVVDVSHEDPEVKFNWYVDG VEVHNAKTKPREEQYNSTYRVVSVLTVLHQDWLNGKEYKC KVSNKALPAPIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPG | 282 |
| 13E4_VH3_a | QVQLVQSGAEVKKPGASVKVSCKASGYTFTNYWMHWVRQA PGQGLEWMGEINPIQGRSNYAEKFQGRVTLTVDTSSSTAY MELSSLRSEDTATYYCARGTRAMHYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICN VNHKPSNTKVDKRVEPKSCDKTHTCPPCPAPE**AA**GGPSVF LFPPKPKDTLMISRTPEVTCVVVDVSHEDPEVKFNWYVDG VEVHNAKTKPREEQYNSTYRVVSVLTVLHQDWLNGKEYKC | 283 |

TABLE 6-continued

| NAME | HC SEQUENCE | SEQ ID NO: |
|---|---|---|
| | KVSNKALPAPIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPG | |
| 13E4_VH3_b | QVQLVQSGAEVKKPGASVKVSCKASGYTFTNYWMHWVRQA PGQGLEWMGEINPIQGRSNYAEKFQGRVTLTVDTSSSTAY MELSSLRSEDTATYYCARGTRAMHYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICN VNHKPSNTKVDKRVEPKSCDKTHTCPPCPAPE**AA**GGPSVF LFPPKPKDTLMISRTPEVTCVVVDVSHEDPEVKFNWYVDG VEVHNAKTKPREEQYNSTYRVVSVLTVLHQDWLNGKEYKC **G**VSNKALPAPIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPG | 284 |
| 13E4_VH3_c | QVQLVQSGAEVKKPGASVKVSCKASGYTFTNYWMHWVRQA PGQGLEWMGEINPIQGRSNYAEKFQGRVTLTVDTSSSTAY MELSSLRSEDTATYYCARGTRAMHYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICN VNHKPSNTKVDKRVEPKSCDKTHTCPPCPAPE**AA**GGPSVF LFPPKPKDTLMISRTPEVTCVVVDVSHEDPEVKFNWYVDG VEVHNAKTKPREEQYNSTYRVVSVLTVLHQDWLNGKEYKC KVSNKA**R**PAPIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPG | 285 |
| 13E4_VH3_d | QVQLVQSGAEVKKPGASVKVSCKASGYTFTNYWMHWVRQA PGQGLEWMGEINPIQGRSNYAEKFQGRVTLTVDTSSSTAY MELSSLRSEDTATYYCARGTRAMHYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICN VNHKPSNTKVDKRVEPKSCDKTHTCPPCPAPE**AA**GGPSVF LFPPKPKDTLMISRTPEVTCVVVDVSHEDPEVKFNWYVDG VEVHNAKTKPREEQYNSTYRVVSVLTVLHQDWLNGKEYKC KVSNKAL**G**APIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPG | 286 |
| 13E4_VH3_e | QVQLVQSGAEVKKPGASVKVSCKASGYTFTNYWMHWVRQA PGQGLEWMGEINPIQGRSNYAEKFQGRVTLTVDTSSSTAY MELSSLRSEDTATYYCARGTRAMHYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICN VNHKPSNTKVDKRVEPKSCDKTHTCPPCPAPELLGGPSVF LFPPKPKDTLMISRTPEVTCVVV**A**VSHEDPEVKFNWYVDG VEVHNAKTKPREEQY**G**STYRVVSVLTVLHQDWLNGKEYKC KVSNKALPAPIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPG | 287 |
| 13E4_VH4 | QVQLVQSGAEVKKPGASVKVSCKASGYTFTNYWMHWVRQA PGQGLEWMGEINPINGRSNYAEKFQGRVTLTVDTSSSTAY MELSSLRSEDTATYYCARGTRAMHYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICN VNHKPSNTKVDKRVEPKSCDKTHTCPPCPAPELLGGPSVF LFPPKPKDTLMISRTPEVTCVVVDVSHEDPEVKFNWYVDG VEVHNAKTKPREEQYNSTYRVVSVLTVLHQDWLNGKEYKC KVSNKALPAPIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPG | 288 |
| 13E4_VH4_a | QVQLVQSGAEVKKPGASVKVSCKASGYTFTNYWMHWVRQA PGQGLEWMGEINPINGRSNYAEKFQGRVTLTVDTSSSTAY MELSSLRSEDTATYYCARGTRAMHYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICN VNHKPSNTKVDKRVEPKSCDKTHTCPPCPAPE**AA**GGPSVF LFPPKPKDTLMISRTPEVTCVVVDVSHEDPEVKFNWYVDG VEVHNAKTKPREEQYNSTYRVVSVLTVLHQDWLNGKEYKC | 289 |

TABLE 6-continued

| NAME | HC SEQUENCE | SEQ ID NO: |
|---|---|---|
| | KVSNKALPAPIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPG | |
| 13E4_VH4_b | QVQLVQSGAEVKKPGASVKVSCKASGYTFTNYWMHWVRQA PGQGLEWMGEINPINGRSNYAEKFQGRVTLTVDTSSSTAY MELSSLRSEDTATYYCARGTRAMHYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICN VNHKPSNTKVDKRVEPKSCDKTHTCPPCPAPE**AA**GGPSVF LFPPKPKDTLMISRTPEVTCVVVDVSHEDPEVKFNWYVDG VEVHNAKTKPREEQYNSTYRVVSVLTVLHQDWLNGKEYKC **G**VSNKALPAPIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPG | 290 |
| 13E4_VH4_c | QVQLVQSGAEVKKPGASVKVSCKASGYTFTNYWMHWVRQA PGQGLEWMGEINPINGRSNYAEKFQGRVTLTVDTSSSTAY MELSSLRSEDTATYYCARGTRAMHYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICN VNHKPSNTKVDKRVEPKSCDKTHTCPPCPAPE**AA**GGPSVF LFPPKPKDTLMISRTPEVTCVVVDVSHEDPEVKFNWYVDG VEVHNAKTKPREEQYNSTYRVVSVLTVLHQDWLNGKEYKC KVSNKA**R**PAPIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPG | 291 |
| 13E4_VH4_d | QVQLVQSGAEVKKPGASVKVSCKASGYTFTNYWMHWVRQA PGQGLEWMGEINPINGRSNYAEKFQGRVTLTVDTSSSTAY MELSSLRSEDTATYYCARGTRAMHYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICN VNHKPSNTKVDKRVEPKSCDKTHTCPPCPAPE**AA**GGPSVF LFPPKPKDTLMISRTPEVTCVVVDVSHEDPEVKFNWYVDG VEVHNAKTKPREEQYNSTYRVVSVLTVLHQDWLNGKEYKC KVSNKAL**G**APIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPG | 292 |
| 13E4_VH4_e | QVQLVQSGAEVKKPGASVKVSCKASGYTFTNYWMHWVRQA PGQGLEWMGEINPINGRSNYAEKFQGRVTLTVDTSSSTAY MELSSLRSEDTATYYCARGTRAMHYWGQGTLVTVSSASTK GPSVFPLAPSSKSTSGGTAALGCLVKDYFPEPVTVSWNSG ALTSGVHTFPAVLQSSGLYSLSSVVTVPSSSLGTQTYICN VNHKPSNTKVDKRVEPKSCDKTHTCPPCPAPELLGGPSVF LFPPKPKDTLMISRTPEVTCVVV**A**VSHEDPEVKFNWYVDG VEVHNAKTKPREEQY**G**STYRVVSVLTVLHQDWLNGKEYKC KVSNKALPAPIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPG | 293 |

TABLE 7

| NAME | LC SEQUENCE | SEQ ID NO: |
|---|---|---|
| 13E4_VL1 | DIQMTQSPSSLSASVGDRVTITCRTSENIYNNLAWYQQKPGKS PKLLIYAATNLADGVPSRFSGSGSGTDYTLTISSLQPEDFATY YCQHFWGTPLTFGGGTKVEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC | 294 |
| 13E4_VL2 | DIQMTQSPSSLSASVGDRVTITCRTSENIYNNLAWYQQKPGKA PKLLIYAATNLADGVPSRFSGSGSGTDYTLTISSLQPEDFATY YCQHFWGTPLTFGGGTKVEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC | 295 |

TABLE 7-continued

| NAME | LC SEQUENCE | SEQ ID NO: |
|---|---|---|
| 13E4_VL3 | DIQMTQSPSSLSASVGDRVTITCRTSENIYNNLAWYQQKPGKA PKLLIYAATNLAEGVPSRFSGSGSGTDYTLTISSLQPEDFATY YCQHFWGTPLTFGGGTKVEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC | 296 |
| 13E4_VL4 | DIQMTQSPSSLSASVGDRVTITCRTSENIYSNLAWYQQKPGKA PKLLIYAGTNLADGVPSRFSGSGSGTDYTLTISSLQPEDFANY YCQHFWGTPLTFGGGTKVEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC | 297 |

In some aspects, an anti-transferrin receptor antibody described herein has an improved serum half-life compared to a reference anti-transferrin receptor antibody. In some instances, the improved serum half-life is at least 30 minutes, 1 hour, 1.5 hour, 2 hours, 3 hours, 4 hours, 5 hours, 6 hours, 7 hours, 8 hours, 9 hours, 10 hours, 12 hours, 18 hours, 24 hours, 2 days, 3 days, 4 days, 5 days, 6 days, 7 days, 14 days, 30 days, or longer than reference anti-transferrin receptor antibody.

In some aspects, the binding moiety A is conjugated to a polynucleic acid molecule (B) non-specifically. In some instances, the binding moiety A is conjugated to a polynucleic acid molecule (B) via a lysine residue or a cysteine residue, in a non-site specific manner. In some instances, the binding moiety A is conjugated to a polynucleic acid molecule (B) via a lysine residue (e.g., lysine residue present in the binding moiety A) in a non-site specific manner. In some cases, the binding moiety A is conjugated to a polynucleic acid molecule (B) via a cysteine residue (e.g., cysteine residue present in the binding moiety A) in a non-site specific manner.

In some aspects, the binding moiety A is conjugated to a polynucleic acid molecule (B) in a site-specific manner. In some instances, the binding moiety A is conjugated to a polynucleic acid molecule (B) through a lysine residue, a cysteine residue, at the 5'-terminus, at the 3'-terminus, an unnatural amino acid, or an enzyme-modified or enzyme-catalyzed residue, via a site-specific manner. In some instances, the binding moiety A is conjugated to a polynucleic acid molecule (B) through a lysine residue (e.g., lysine residue present in the binding moiety A) via a site-specific manner. In some instances, the binding moiety A is conjugated to a polynucleic acid molecule (B) through a cysteine residue (e.g., cysteine residue present in the binding moiety A) via a site-specific manner. In some instances, the binding moiety A is conjugated to a polynucleic acid molecule (B) at the 5'-terminus via a site-specific manner. In some instances, the binding moiety A is conjugated to a polynucleic acid molecule (B) at the 3'-terminus via a site-specific manner. In some instances, the binding moiety A is conjugated to a polynucleic acid molecule (B) through an unnatural amino acid via a site-specific manner. In some instances, the binding moiety A is conjugated to a polynucleic acid molecule (B) through an enzyme-modified or enzyme-catalyzed residue via a site-specific manner.

In some aspects, one or more polynucleic acid molecule (B) is conjugated to a binding moiety A. In some instances, about 1, 2, 3, 4, 5, 6, 7, 8, 9, 10, 11, 12, 13, 14, 15, 16, or more polynucleic acid molecules are conjugated to one binding moiety A. In some instances, about 1 polynucleic acid molecule is conjugated to one binding moiety A. In some instances, about 2 polynucleic acid molecules are conjugated to one binding moiety A. In some instances, about 3 polynucleic acid molecules are conjugated to one binding moiety A. In some instances, about 4 polynucleic acid molecules are conjugated to one binding moiety A. In some instances, about 5 polynucleic acid molecules are conjugated to one binding moiety A. In some instances, about 6 polynucleic acid molecules are conjugated to one binding moiety A. In some instances, about 7 polynucleic acid molecules are conjugated to one binding moiety A. In some instances, about 8 polynucleic acid molecules are conjugated to one binding moiety A. In some instances, about 9 polynucleic acid molecules are conjugated to one binding moiety A. In some instances, about 10 polynucleic acid molecules are conjugated to one binding moiety A. In some instances, about 11 polynucleic acid molecules are conjugated to one binding moiety A. In some instances, about 12 polynucleic acid molecules are conjugated to one binding moiety A. In some instances, about 13 polynucleic acid molecules are conjugated to one binding moiety A. In some instances, about 14 polynucleic acid molecules are conjugated to one binding moiety A. In some instances, about 15 polynucleic acid molecules are conjugated to one binding moiety A. In some instances, about 16 polynucleic acid molecules are conjugated to one binding moiety A. In some cases, the one or more polynucleic acid molecules are the same. In other cases, the one or more polynucleic acid molecules are different.

In some aspects, the number of polynucleic acid molecule (B) conjugated to a binding moiety A forms a ratio. In some instances, the ratio is referred to as a DAR (drug-to-antibody) ratio, in which the drug as referred to herein is the polynucleic acid molecule (B). In some instances, the DAR ratio of the polynucleic acid molecule (B) to binding moiety A is about 1, 2, 3, 4, 5, 6, 7, 8, 9, 10, 11, 12, 13, 14, 15, 16, or greater. In some instances, the DAR ratio of the polynucleic acid molecule (B) to binding moiety A is about 1 or greater. In some instances, the DAR ratio of the polynucleic acid molecule (B) to binding moiety A is about 2 or greater. In some instances, the DAR ratio of the polynucleic acid molecule (B) to binding moiety A is about 3 or greater. In some instances, the DAR ratio of the polynucleic acid molecule (B) to binding moiety A is about 4 or greater. In some instances, the DAR ratio of the polynucleic acid molecule (B) to binding moiety A is about 5 or greater. In some instances, the DAR ratio of the polynucleic acid molecule (B) to binding moiety A is about 6 or greater. In some instances, the DAR ratio of the polynucleic acid molecule (B) to binding moiety A is about 7 or greater. In some instances, the DAR ratio of the polynucleic acid molecule (B) to binding moiety A is about 8 or greater. In some instances, the DAR ratio of the polynucleic acid molecule (B) to binding moiety A is about 9 or greater. In some instances, the DAR ratio of the polynucleic acid molecule (B) to binding moiety A is about 10 or greater. In some instances, the DAR ratio of the polynucleic acid molecule (B) to binding moiety A is about 11 or greater. In some instances, the DAR ratio of the polynucleic acid molecule (B) to binding moiety A is about 12 or greater.

In some instances, the DAR ratio of the polynucleic acid molecule (B) to binding moiety A is about 1, 2, 3, 4, 5, 6, 7, 8, 9, 10, 11, 12, 13, 14, 15, or 16. In some instances, the DAR ratio of the polynucleic acid molecule (B) to binding moiety A is about 1. In some instances, the DAR ratio of the polynucleic acid molecule (B) to binding moiety A is about 2. In some instances, the DAR ratio of the polynucleic acid molecule (B) to binding moiety A is about 3. In some instances, the DAR ratio of the polynucleic acid molecule (B) to binding moiety A is about 4. In some instances, the DAR ratio of the polynucleic acid molecule (B) to binding moiety A is about 5. In some instances, the DAR ratio of the polynucleic acid molecule (B) to binding moiety A is about 6. In some instances, the DAR ratio of the polynucleic acid molecule (B) to binding moiety A is about 7. In some instances, the DAR ratio of the polynucleic acid molecule (B) to binding moiety A is about 8. In some instances, the DAR ratio of the polynucleic acid molecule (B) to binding moiety A is about 9. In some instances, the DAR ratio of the polynucleic acid molecule (B) to binding moiety A is about 10. In some instances, the DAR ratio of the polynucleic acid molecule (B) to binding moiety A is about 11. In some instances, the DAR ratio of the polynucleic acid molecule (B) to binding moiety A is about 12. In some instances, the DAR ratio of the polynucleic acid molecule (B) to binding moiety A is about 13. In some instances, the DAR ratio of the polynucleic acid molecule (B) to binding moiety A is about 14. In some instances, the DAR ratio of the polynucleic acid molecule (B) to binding moiety A is about 15. In some instances, the DAR ratio of the polynucleic acid molecule (B) to binding moiety A is about 16.

In some instances, the DAR ratio of the polynucleic acid molecule (B) to binding moiety A is 1, 2, 3, 4, 5, 6, 7, 8, 9, 10, 11, 12, 13, 14, 15, or 16. In some instances, the DAR ratio of the polynucleic acid molecule (B) to binding moiety A is 1. In some instances, the DAR ratio of the polynucleic acid molecule (B) to binding moiety A is 2. In some instances, the DAR ratio of the polynucleic acid molecule (B) to binding moiety A is 4. In some instances, the DAR ratio of the polynucleic acid molecule (B) to binding moiety A is 6. In some instances, the DAR ratio of the polynucleic acid molecule (B) to binding moiety A is 8. In some instances, the DAR ratio of the polynucleic acid molecule (B) to binding moiety A is 12.

In some instances, a conjugate comprising polynucleic acid molecule (B) and binding moiety A has improved activity as compared to a conjugate comprising polynucleic acid molecule (B) without a binding moiety A. In some instances, improved activity results in enhanced biologically relevant functions, e.g., improved stability, affinity, binding, functional activity, and efficacy in treatment or prevention of a disease state. In some instances, the disease state is a result of one or more mutated exons of a gene. In some instances, the conjugate comprising polynucleic acid molecule (B) and binding moiety A results in increased exon skipping of the one or more mutated exons as compared to the conjugate comprising polynucleic acid molecule (B) without a binding moiety A. In some instances, exon skipping is increased by at least or about 5%, 10%, 20%, 25%, 30%, 40%, 50%, 60%, 70%, 80%, 90%, 95%, or more than 95% in the conjugate comprising polynucleic acid molecule (B) and binding moiety A as compared to the conjugate comprising polynucleic acid molecule (B) without a binding moiety A.

In some aspects, an antibody or antigen binding fragment is further modified using conventional techniques known in the art, for example, by using amino acid deletion, insertion, substitution, addition, and/or by recombination and/or any other modification (e.g., posttranslational and chemical modifications, such as glycosylation and phosphorylation) known in the art either alone or in combination. In some instances, the modification further comprises a modification for modulating interaction with Fc receptors. In some instances, the one or more modifications include those described in, for example, International Publication No. WO97/34631, which discloses amino acid residues involved in the interaction between the Fc domain and the FcRn receptor. Methods for introducing such modifications in the nucleic acid sequence underlying the amino acid sequence of an antibody or antigen binding fragment is well known to the person skilled in the art.

In some instances, an antigen binding fragment further encompasses its derivatives and includes polypeptide sequences containing at least one CDR.

In some instances, the term "single-chain" as used herein means that the first and second domains of a bi-specific single chain construct are covalently linked, preferably in the form of a co-linear amino acid sequence encodable by a single nucleic acid molecule.

In some instances, a bispecific single chain antibody construct relates to a construct comprising two antibody derived binding domains. In such embodiments, bi-specific single chain antibody construct is tandem bi-scFv or diabody. In some instances, a scFv contains a VH and VL domain connected by a linker peptide. In some instances, linkers are of a length and sequence sufficient to ensure that each of the first and second domains can, independently from one another, retain their differential binding specificities.

In some aspects, binding to or interacting with as used herein defines a binding/interaction of at least two antigen-interaction-sites with each other. In some instances, antigen-interaction-site defines a motif of a polypeptide that shows the capacity of specific interaction with a specific antigen or a specific group of antigens. In some cases, the binding/interaction is also understood to define a specific recognition. In such cases, specific recognition refers to that the antibody or its antigen binding fragment is capable of specifically interacting with and/or binding to at least two amino acids of each of a target molecule. For example, specific recognition relates to the specificity of the antibody molecule, or to its ability to discriminate between the specific regions of a target molecule. In additional instances, the specific interaction of the antigen-interaction-site with its specific antigen results in an initiation of a signal, e.g. due to the induction of a change of the conformation of the antigen, an oligomerization of the antigen, etc. In further embodiments, the binding is exemplified by the specificity of a "key-lock-principle". Thus in some instances, specific motifs in the amino acid sequence of the antigen-interaction-site and the antigen bind to each other as a result of their primary, secondary or tertiary structure as well as the result of secondary modifications of said structure. In such cases, the specific interaction of the antigen-interaction-site with its specific antigen results as well in a simple binding of the site to the antigen.

In some instances, specific interaction further refers to a reduced cross-reactivity of the antibody or antigen binding fragment or a reduced off-target effect. For example, the antibody or antigen binding fragment that bind to the polypeptide/protein of interest but do not or do not essentially bind to any of the other polypeptides are considered as specific for the polypeptide/protein of interest. Examples for the specific interaction of an antigen-interaction-site with a specific antigen comprise the specificity of a ligand for its receptor, for example, the interaction of an antigenic determinant (epitope) with the antigenic binding site of an antibody.

Additional Binding Moieties

In some aspects, the binding moiety is a plasma protein. In some instances, the plasma protein comprises albumin. In some instances, the binding moiety A is albumin. In some instances, albumin is conjugated by one or more of a conjugation chemistry described herein to a polynucleic acid molecule. In some instances, albumin is conjugated by native ligation chemistry to a polynucleic acid molecule. In some instances, albumin is conjugated by lysine conjugation to a polynucleic acid molecule.

In some instances, the binding moiety is a steroid. Exemplary steroids include cholesterol, phospholipids, di- and triacylglycerols, fatty acids, hydrocarbons that are saturated, unsaturated, comprise substitutions, or combinations thereof. In some instances, the steroid is cholesterol. In some instances, the binding moiety is cholesterol. In some instances, cholesterol is conjugated by one or more of a conjugation chemistry described herein to a polynucleic acid molecule. In some instances, cholesterol is conjugated by native ligation chemistry to a polynucleic acid molecule. In some instances, cholesterol is conjugated by lysine conjugation to a polynucleic acid molecule.

In some instances, the binding moiety is a polymer, including but not limited to polynucleic acid molecule aptamers that bind to specific surface markers on cells. In this instance the binding moiety is a polynucleic acid that does not hybridize to a target gene or mRNA, but instead is capable of selectively binding to a cell surface marker similarly to an antibody binding to its specific epitope of a cell surface marker.

In some cases, the binding moiety is a peptide. In some cases, the peptide comprises between about 1 and about 3 kDa. In some cases, the peptide comprises between about 1.2 and about 2.8 kDa, about 1.5 and about 2.5 kDa, or about 1.5 and about 2 kDa. In some instances, the peptide is a bicyclic peptide. In some cases, the bicyclic peptide is a constrained bicyclic peptide. In some instances, the binding moiety is a bicyclic peptide (e.g., bicycles from Bicycle Therapeutics).

In additional cases, the binding moiety is a small molecule. In some instances, the small molecule is an antibody-recruiting small molecule. In some cases, the antibody-recruiting small molecule comprises a target-binding terminus and an antibody-binding terminus, in which the target-binding terminus is capable of recognizing and interacting with a cell surface receptor. For example, in some instances, the target-binding terminus comprising a glutamate urea compound enables interaction with PSMA, thereby, enhances an antibody interaction with a cell that expresses PSMA. In some instances, a binding moiety is a small molecule described in Zhang et al., "A remote arene-binding site on prostate specific membrane antigen revealed by antibody-recruiting small molecules," J Am Chem Soc. 132(36): 12711-12716 (2010); or McEnaney, et al., "Antibody-recruiting molecules: an emerging paradigm for engaging immune function in treating human disease," ACS Chem Biol. 7(7): 1139-1151 (2012).

Production of Antibodies or Antigen Binding Fragment Thereof

In some aspects, polypeptides described herein (e.g., antibodies and antigen binding fragments) are produced using any method known in the art to be useful for the synthesis of polypeptides (e.g., antibodies), in particular, by chemical synthesis or by recombinant expression, and are preferably produced by recombinant expression techniques.

In some instances, an antibody or antigen binding fragment thereof is expressed recombinantly, and the nucleic acid encoding the antibody or antigen binding fragment is assembled from chemically synthesized oligonucleotides (e.g., as described in Kutmeier et al., 1994, *BioTechniques* 17:242), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody is optionally generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some instances, an antibody or its antigen binding is optionally generated by immunizing an animal, such as a rabbit, to generate polyclonal antibodies or, more preferably, by generating monoclonal antibodies, e.g., as described by Kohler and Milstein (1975, *Nature* 256:495-497) or, as described by Kozbor et al. (1983, *Immunology Today* 4:72) or Cole et al. (1985 in *Monoclonal Antibodies and Cancer Therapy*, Alan R. Liss, Inc., pp. 77-96). Alternatively, a clone encoding at least the Fab portion of the antibody is optionally obtained by screening Fab expression libraries (e.g., as described in Huse et al., 1989, *Science* 246:1275-1281) for clones of Fab fragments that bind the specific antigen or by screening antibody libraries (See, e.g., Clackson et al., 1991, *Nature* 352:624; Hane et al., 1997 *Proc. Natl. Acad. Sci. USA* 94:4937).

In some aspects, techniques developed for the production of "chimeric antibodies" (Morrison et al., 1984, *Proc. Natl. Acad. Sci.* 81:851-855; Neuberger et al., 1984, *Nature* 312:604-608; Takeda et al., 1985, *Nature* 314:452-454) by splicing genes from a mouse antibody molecule of appropriate antigen specificity together with genes from a human antibody molecule of appropriate biological activity are used. A chimeric antibody is a molecule in which different portions are derived from different animal species, such as those having a variable region derived from a murine monoclonal antibody and a human immunoglobulin constant region, e.g., humanized antibodies.

In some aspects, techniques described for the production of single chain antibodies (U.S. Pat. No. 4,694,778; Bird, 1988, *Science* 242:423-42; Huston et al., 1988, *Proc. Natl. Acad. Sci. USA* 85:5879-5883; and Ward et al., 1989, *Nature* 334:544-54) are adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* are also optionally used (Skerra et al., 1988, *Science* 242:1038-1041).

In some aspects, an expression vector comprising the nucleotide sequence of an antibody or the nucleotide sequence of an antibody is transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

In some aspects, a variety of host-expression vector systems is utilized to express an antibody or its antigen binding fragment described herein. Such host-expression systems represent vehicles by which the coding sequences of the antibody is produced and subsequently purified, but also represent cells that are, when transformed or transfected with the appropriate nucleotide coding sequences, express an antibody or its antigen binding fragment in situ. These include, but are not limited to, microorganisms such as bacteria (e.g., *E. coli* and *B. subtilis*) transformed with recombinant bacteriophage DNA, plasmid DNA or cosmid DNA expression vectors containing an antibody or its antigen binding fragment coding sequences; yeast (e.g., *Saccharomyces Pichia*) transformed with recombinant yeast expression vectors containing an antibody or its antigen binding fragment coding sequences; insect cell systems infected with recombinant virus expression vectors (e.g., baculovirus) containing an antibody or its antigen binding fragment coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its antigen binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

For long-term, high-yield production of recombinant proteins, stable expression is preferred. In some instances, cell lines that stably express an antibody are optionally engineered. Rather than using expression vectors that contain viral origins of replication, host cells are transformed with DNA controlled by appropriate expression control elements (e.g., promoter, enhancer, sequences, transcription terminators, polyadenylation sites, etc.), and a selectable marker. Following the introduction of the foreign DNA, engineered cells are then allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn are cloned and expanded into cell lines. This method can advantageously be used to engineer cell lines which express the antibody or its antigen binding fragments.

In some instances, a number of selection systems are used, including but not limited to the herpes simplex virus thymidine kinase (Wigler et al., 1977, *Cell* 11:223), hypoxanthine-guanine phosphoribosyltransferase (Szybalska & Szybalski, 192, *Proc. Natl. Acad. Sci. USA* 48:202), and adenine phosphoribosyltransferase (Lowy et al., 1980, *Cell* 22:817) genes are employed in tk-, hgprt- or aprt-cells, respectively. Also, antimetabolite resistance are used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (Clinical Pharmacy 12:488-505; Wu and Wu, 1991, *Biotherapy* 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May, 1993, *TIB TECH* 11(5):155-215) and hygro, which confers resistance to hygromycin (Santerre et al., 1984, *Gene* 30:147). Methods commonly known in the art of recombinant DNA technology which can be used are described in Ausubel et al. (eds., 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al. (eds), 1994, *Current Protocols in Human Genetics*, John Wiley & Sons, NY.; Colberre-Garapin et al., 1981, *J Mol. Biol.* 150:1).

In some instances, the expression levels of an antibody are increased by vector amplification (for a review, see Bebbington and Hentschel, *The use of vectors based on gene amplification for the expression of cloned genes in mammalian cells in DNA cloning*, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, *Mol. Cell Biol.* 3:257).

In some instances, any method known in the art for purification or analysis of an antibody or antibody conjugates is used, for example, by chromatography (e.g., ion exchange, affinity, particularly by affinity for the specific antigen after Protein A, and sizing column chromatography), centrifugation, differential solubility, or by any other standard technique for the purification of proteins. Exemplary chromatography methods included, but are not limited to, strong anion exchange chromatography, hydrophobic interaction chromatography, size exclusion chromatography, and fast protein liquid chromatography.

Conjugation Chemistry

In some aspects, a polynucleic acid molecule B is conjugated to a binding moiety. In some aspects, a polynucleic acid molecule B is conjugated to a binding moiety in a formula A-X-B (X is a linker conjugating A and B). In some instances, the binding moiety comprises amino acids, peptides, polypeptides, proteins, antibodies, antigens, toxins, hormones, lipids, nucleotides, nucleosides, sugars, carbohydrates, polymers such as polyethylene glycol and polypropylene glycol, as well as analogs or derivatives of all of these classes of substances. Additional examples of binding moiety also include steroids, such as cholesterol, phospholipids, di- and triacylglycerols, fatty acids, hydrocarbons (e.g., saturated, unsaturated, or contains substitutions), enzyme substrates, biotin, digoxigenin, and polysaccharides. In some instances, the binding moiety is an antibody or antigen binding fragment thereof. In some instances, the polynucleic acid molecule is further conjugated to a polymer, and optionally an endosomolytic moiety.

In some aspects, the polynucleic acid molecule is conjugated to the binding moiety by a chemical ligation process. In some instances, the polynucleic acid molecule is conjugated to the binding moiety by a native ligation. In some instances, the conjugation is as described in: Dawson, et al. "Synthesis of proteins by native chemical ligation," *Science* 1994, 266, 776-779; Dawson, et al. "Modulation of Reactivity in Native Chemical Ligation through the Use of Thiol Additives," *J Am. Chem. Soc.* 1997, 119, 4325-4329; Hackeng, et al. "Protein synthesis by native chemical ligation: Expanded scope by using straightforward methodology.," *Proc. Natl. Acad. Sci. USA* 1999, 96, 10068-10073; or Wu, et al. "Building complex glycopeptides: Development of a cysteine-free native chemical ligation protocol," *Angew. Chem. Int. Ed.* 2006, 45, 4116-4125. In some instances, the conjugation is as described in U.S. Pat. No. 8,936,910. In some aspects, the polynucleic acid molecule is conjugated to the binding moiety either site-specifically or non-specifically via native ligation chemistry.

In some instances, the polynucleic acid molecule is conjugated to the binding moiety by a site-directed method utilizing a "traceless" coupling technology (Philochem). In some instances, the "traceless" coupling technology utilizes an N-terminal 1,2-aminothiol group on the binding moiety which is then conjugate with a polynucleic acid molecule containing an aldehyde group. (see Casi et al., "Site-specific traceless coupling of potent cytotoxic drugs to recombinant antibodies for pharmacodelivery," *JACS* 134(13): 5887-5892 (2012))

In some instances, the polynucleic acid molecule is conjugated to the binding moiety by a site-directed method utilizing an unnatural amino acid incorporated into the binding moiety. In some instances, the unnatural amino acid comprises p-acetylphenylalanine (pAcPhe). In some instances, the keto group of pAcPhe is selectively coupled to an alkoxy-amine derivatived conjugating moiety to form an oxime bond. (see Axup et al., "Synthesis of site-specific antibody-drug conjugates using unnatural amino acids," *PNAS* 109(40): 16101-16106 (2012)).

In some instances, the polynucleic acid molecule is conjugated to the binding moiety by a site-directed method utilizing an enzyme-catalyzed process. In some instances, the site-directed method utilizes SMARTag™ technology (Catalent, Inc.). In some instances, the SMARTag™ technology comprises generation of a formylglycine (FGly) residue from cysteine by formylglycine-generating enzyme (FGE) through an oxidation process under the presence of an aldehyde tag and the subsequent conjugation of FGly to an alkylhydraine-functionalized polynucleic acid molecule via hydrazino-Pictet-Spengler (HIPS) ligation. (see Wu et al., "Site-specific chemical modification of recombinant proteins produced in mammalian cells by using the genetically encoded aldehyde tag," *PNAS* 106(9): 3000-3005 (2009); Agarwal, et al., "A Pictet-Spengler ligation for protein chemical modification," *PNAS* 110(1): 46-51 (2013))

In some instances, the enzyme-catalyzed process comprises microbial transglutaminase (mTG). In some cases, the polynucleic acid molecule is conjugated to the binding moiety utilizing a microbial transglutaminase-catalyzed process. In some instances, mTG catalyzes the formation of a covalent bond between the amide side chain of a glutamine within the recognition sequence and a primary amine of a functionalized polynucleic acid molecule. In some instances, mTG is produced from *Streptomyces mobarensis*. (see Strop et al., "Location matters: site of conjugation modulates stability and pharmacokinetics of antibody drug conjugates," *Chemistry and Biology* 20(2) 161-167 (2013))

In some instances, the polynucleic acid molecule is conjugated to the binding moiety by a method as described in PCT Publication No. WO2014/140317, which utilizes a sequence-specific transpeptidase.

In some instances, the polynucleic acid molecule is conjugated to the binding moiety by a method as described in U.S. Patent Publication Nos. 2015/0105539 and 2015/0105540.

Polymer Conjugating Moiety

In some aspects, a polymer moiety C is further conjugated to a polynucleic acid molecule described herein, a binding moiety described herein, or in combinations thereof. In some instances, a polymer moiety C is conjugated a polynucleic acid molecule in a formula A-$X_1$-B—$X_2$—C ($X_1$, $X_2$ as two linkers conjugating A and B, B and C, respectively). In some cases, a polymer moiety C is conjugated to a binding moiety. In other cases, a polymer moiety C is conjugated to a polynucleic acid molecule-binding moiety molecule. In additional cases, a polymer moiety C is conjugated, as illustrated supra.

In some instances, the polymer moiety C is a natural or synthetic polymer, consisting of long chains of branched or unbranched monomers, and/or cross-linked network of monomers in two or three dimensions. In some instances, the polymer moiety C includes a polysaccharide, lignin, rubber, or polyalkylen oxide (e.g., polyethylene glycol). In some instances, the at least one polymer moiety C includes, but is not limited to, alpha-, omega-dihydroxylpolyethyleneglycol, biodegradable lactone-based polymer, e.g. polyacrylic acid, polylactide acid (PLA), poly(glycolic acid) (PGA), polypropylene, polystyrene, polyolefin, polyamide, polycyanoacrylate, polyimide, polyethylene terephthalate (also known as poly(ethylene terephthalate), PET, PETG, or PETE), polytetramethylene glycol (PTG), or polyurethane as well as mixtures thereof. As used herein, a mixture refers to the use of different polymers within the same compound as well as in reference to block copolymers. In some cases, block copolymers are polymers wherein at least one section of a polymer is built up from monomers of another polymer. In some instances, the polymer moiety C comprises polyalkylene oxide. In some instances, the polymer moiety C comprises PEG. In some instances, the polymer moiety C comprises polyethylene imide (PEI) or hydroxy ethyl starch (HES).

In some instances, C is a PEG moiety. In some instances, the PEG moiety is conjugated at the 5' terminus of the polynucleic acid molecule while the binding moiety is conjugated at the 3' terminus of the polynucleic acid molecule. In some instances, the PEG moiety is conjugated at the 3' terminus of the polynucleic acid molecule while the binding moiety is conjugated at the 5' terminus of the polynucleic acid molecule. In some instances, the PEG moiety is conjugated to an internal site of the polynucleic acid molecule. In some instances, the PEG moiety, the binding moiety, or a combination thereof, are conjugated to an internal site of the polynucleic acid molecule. In some instances, the conjugation is a direct conjugation. In some instances, the conjugation is via native ligation.

In some aspects, the polyalkylene oxide (e.g., PEG) is a polydisperse or monodisperse compound. In some instances, polydisperse material comprises disperse distribution of different molecular weight of the material, characterized by mean weight (weight average) size and dispersity. In some instances, the monodisperse PEG comprises one size of molecules. In some aspects, C is poly- or monodispersed polyalkylene oxide (e.g., PEG) and the indicated molecular weight represents an average of the molecular weight of the polyalkylene oxide, e.g., PEG, molecules.

In some aspects, the molecular weight of the polyalkylene oxide (e.g., PEG) is about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da.

In some aspects, C is polyalkylene oxide (e.g., PEG) and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some aspects, C is PEG and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some instances, the molecular weight of C is about 200 Da. In some instances, the molecular weight of C is about 300 Da. In some instances, the molecular weight of C is about 400 Da. In some instances, the molecular weight of C is about 500 Da. In some instances, the molecular weight of C is about 600 Da. In some instances, the molecular weight of C is about 700 Da. In some instances, the molecular weight of C is about 800 Da. In some instances, the molecular weight of C is about 900 Da. In some instances, the molecular weight of C is about 1000 Da. In some instances, the molecular weight of C is about 1100 Da. In some instances, the molecular weight of C is about 1200 Da. In some instances, the molecular weight of C is about 1300 Da. In some instances, the molecular weight of C is about 1400 Da. In some instances, the molecular weight of C is about 1450 Da. In some instances, the molecular weight of C is about 1500 Da. In some instances, the molecular weight of C is about 1600 Da. In some instances, the molecular weight of C is about 1700 Da. In some instances, the molecular weight of C is about 1800 Da. In some instances, the molecular weight of C is about 1900 Da. In some instances, the molecular weight of C is about 2000 Da. In some instances, the molecular weight of C is about 2100 Da. In some instances, the molecular weight of C is about 2200 Da. In some instances, the molecular weight of C is about 2300 Da. In some instances, the molecular weight of C is about 2400 Da. In some instances, the molecular weight of C is about 2500 Da. In some instances, the molecular weight of C is about 2600 Da. In some instances, the molecular weight of C is about 2700 Da. In some instances, the molecular weight of C is about 2800 Da. In some instances, the molecular weight of C is about 2900 Da. In some instances, the molecular weight of C is about 3000 Da. In some instances, the molecular weight of C is about 3250 Da. In some instances, the molecular weight of C is about 3350 Da. In some instances, the molecular weight of C is about 3500 Da. In some instances, the molecular weight of C is about 3750 Da. In some instances, the molecular weight of C is about 4000 Da. In some instances, the molecular weight of C is about 4250 Da. In some instances, the molecular weight of C is about 4500 Da. In some instances, the molecular weight of C is about 4600 Da. In some instances, the molecular weight of C is about 4750 Da. In some instances, the molecular weight of C is about 5000 Da. In some instances, the molecular weight of C is about 5500 Da. In some instances, the molecular weight of C is about 6000 Da. In some instances, the molecular weight of C is about 6500 Da. In some instances, the molecular weight of C is about 7000 Da. In some instances, the molecular weight of C is about 7500 Da. In some instances, the molecular weight of C is about 8000 Da. In some instances, the molecular weight of C is about 10,000 Da. In some instances, the molecular weight of C is about 12,000 Da. In some instances, the molecular weight of C is about 20,000 Da. In some instances, the molecular weight of C is about 35,000 Da. In some instances, the molecular weight of C is about 40,000 Da. In some instances, the molecular weight of C is about 50,000 Da. In some instances, the molecular weight of C is about 60,000 Da. In some instances, the molecular weight of C is about 100,000 Da.

In some aspects, the polyalkylene oxide (e.g., PEG) comprises discrete ethylene oxide units (e.g., four to about 48 ethylene oxide units). In some instances, the polyalkylene oxide comprising the discrete ethylene oxide units is a linear chain. In other cases, the polyalkylene oxide comprising the discrete ethylene oxide units is a branched chain.

In some instances, the polymer moiety C is a polyalkylene oxide (e.g., PEG) comprising discrete ethylene oxide units. In some cases, the polymer moiety C comprises between about 4 and about 48 ethylene oxide units. In some cases, the polymer moiety C comprises about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, or about 48 ethylene oxide units.

In some instances, the polymer moiety C is a discrete PEG comprising, e.g., between about 4 and about 48 ethylene oxide units. In some cases, the polymer moiety C is a discrete PEG comprising, e.g., about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, or about 48 ethylene oxide units. In some cases, the polymer moiety C is a discrete PEG comprising, e.g., about 4 ethylene oxide units. In some cases, the polymer moiety C is a discrete PEG comprising, e.g., about 5 ethylene oxide units. In some cases, the polymer moiety C is a discrete PEG comprising, e.g., about 6 ethylene oxide units. In some cases, the polymer moiety C is a discrete PEG comprising, e.g., about 7 ethylene oxide units. In some cases, the polymer moiety C is a discrete PEG comprising, e.g., about 8 ethylene oxide units. In some cases, the polymer moiety C is a discrete PEG comprising, e.g., about 9 ethylene oxide units. In some cases, the polymer moiety C is a discrete PEG comprising, e.g., about 10 ethylene oxide units. In some cases, the polymer moiety C is a discrete PEG comprising, e.g., about 11 ethylene oxide units. In some cases, the polymer moiety C is a discrete PEG comprising, e.g., about 12 ethylene oxide units. In some cases, the polymer moiety C is a discrete PEG comprising, e.g., about 13 ethylene oxide units. In some cases, the polymer moiety C is a discrete PEG comprising, e.g., about 14 ethylene oxide units. In some cases, the polymer moiety C is a discrete PEG comprising, e.g., about 15 ethylene oxide units. In some cases, the polymer moiety C is a discrete PEG comprising, e.g., about 16 ethylene oxide units. In some cases, the polymer moiety C is a discrete PEG comprising, e.g., about 17 ethylene oxide units. In some cases, the polymer moiety C is a discrete PEG comprising, e.g., about 18 ethylene oxide units. In some cases, the polymer moiety C is a discrete PEG comprising, e.g., about 19 ethylene oxide units. In some cases, the polymer moiety C is a discrete PEG comprising, e.g., about 20 ethylene oxide units. In some cases, the polymer moiety C is a discrete PEG comprising, e.g., about 21 ethylene oxide units. In some cases, the polymer moiety C is a discrete PEG comprising, e.g., about 22 ethylene oxide units. In some cases, the polymer moiety C is a discrete PEG comprising, e.g., about 23 ethylene oxide units. In some cases, the polymer moiety C is a discrete PEG comprising, e.g., about 24 ethylene oxide units. In some cases, the polymer moiety C is a discrete PEG comprising, e.g., about 25 ethylene oxide units. In some cases, the polymer moiety C is a discrete PEG comprising, e.g., about 26 ethylene oxide units. In some cases, the polymer moiety C is a discrete PEG comprising, e.g., about 27 ethylene oxide units. In some cases, the polymer moiety C is a discrete PEG comprising, e.g., about 28 ethylene oxide units. In some cases, the polymer moiety C is a discrete PEG comprising, e.g., about 29 ethylene oxide units. In some cases, the polymer moiety C is a discrete PEG comprising, e.g., about 30 ethylene oxide units. In some cases, the polymer moiety C is a discrete PEG comprising, e.g., about 31 ethylene oxide units. In some cases, the polymer moiety C is a discrete PEG comprising, e.g., about 32 ethylene oxide units. In some cases, the polymer moiety C is a discrete PEG comprising, e.g., about 33 ethylene oxide units. In some cases, the polymer moiety C is a discrete PEG comprising, e.g., about 34 ethylene oxide units. In some cases, the polymer moiety C is a discrete PEG comprising, e.g., about 35 ethylene oxide units. In some cases, the polymer moiety C is a discrete PEG comprising, e.g., about 36 ethylene oxide units. In some cases, the polymer moiety C is a discrete PEG comprising, e.g., about 37 ethylene oxide units. In some cases, the polymer moiety C is a discrete PEG comprising, e.g., about 38 ethylene oxide units. In some cases, the polymer moiety C is a discrete PEG comprising, e.g., about 39 ethylene oxide units. In some cases, the polymer moiety C is a discrete PEG comprising, e.g., about 40 ethylene oxide units. In some cases, the polymer moiety C is a discrete PEG comprising, e.g., about 41 ethylene oxide units. In some cases, the polymer moiety C is a discrete PEG comprising, e.g., about 42 ethylene oxide units. In some cases, the polymer moiety C is a discrete PEG comprising, e.g., about 43 ethylene oxide units. In some cases, the polymer moiety C is a discrete PEG comprising, e.g., about 44 ethylene oxide units. In some cases, the polymer moiety C is a discrete PEG comprising, e.g., about 45 ethylene oxide units. In some cases, the polymer moiety C is a discrete PEG comprising, e.g., about 46 ethylene oxide units. In some cases, the polymer moiety C is a discrete PEG comprising, e.g., about 47 ethylene oxide units. In some cases, the polymer moiety C is a discrete PEG comprising, e.g., about 48 ethylene oxide units.

In some cases, the polymer moiety C is dPEG® (Quanta Biodesign Ltd).

In some aspects, the polymer moiety C comprises a cationic mucic acid-based polymer (cMAP). In some instances, cMAP comprises one or more subunit of at least one repeating subunit, and the subunit structure is represented as Formula (V):

Formula V

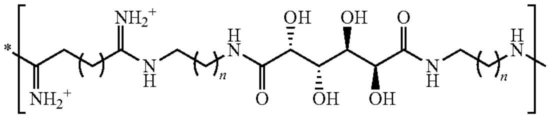

wherein m is independently at each occurrence 1, 2, 3, 4, 5, 6, 7, 8, 9, or 10, preferably 4-6 or 5; and n is independently at each occurrence 1, 2, 3, 4, or 5. In some aspects, m and n are, for example, about 10.

In some instances, cMAP is further conjugated to a PEG moiety, generating a cMAP-PEG copolymer, an mPEG-cMAP-PEGm triblock polymer, or a cMAP-PEG-cMAP triblock polymer. In some instances, the PEG moiety is in a range of from about 500 Da to about 50,000 Da. In some instances, the PEG moiety is in a range of from about 500 Da to about 1000 Da, greater than 1000 Da to about 5000 Da, greater than 5000 Da to about 10,000 Da, greater than 10,000 to about 25,000 Da, greater than 25,000 Da to about 50,000 Da, or any combination of two or more of these ranges.

In some instances, the polymer moiety C is a cMAP-PEG copolymer, an mPEG-cMAP-PEGm triblock polymer, or a cMAP-PEG-cMAP triblock polymer. In some cases, the polymer moiety C is cMAP-PEG copolymer. In other cases, the polymer moiety C is an mPEG-cMAP-PEGm triblock polymer. In additional cases, the polymer moiety C is a cMAP-PEG-cMAP triblock polymer.

In some aspects, the polymer moiety C is conjugated to the polynucleic acid molecule, the binding moiety, and optionally to the endosomolytic moiety as illustrated supra.

Endosomolytic or Cell Membrane Penetration Moiety

In some aspects, a molecule of Formula (I): A-$X_1$-B-$X_2$-C, further comprises an additional conjugating moiety. In some instances, the additional conjugating moiety is an endosomolytic moiety and/or a cell membrane penetration moiety. In some cases, the endosomolytic moiety is a cellular compartmental release component, such as a compound capable of releasing from any of the cellular compartments known in the art, such as the endosome, lysosome, endoplasmic reticulum (ER), Golgi apparatus, microtubule, peroxisome, or other vesicular bodies with the cell. In some cases, the endosomolytic moiety comprises an endosomolytic polypeptide, an endosomolytic polymer, an endosomolytic lipid, or an endosomolytic small molecule. In some cases, the endosomolytic moiety comprises an endosomolytic polypeptide. In other cases, the endosomolytic moiety comprises an endosomolytic polymer. In some cases, the cell membrane penetration moiety comprises a cell penetrating peptide (CPP). In other cases, the cell membrane penetration moiety comprises a cell penetrating lipid. In other cases, the cell membrane penetration moiety comprises a cell penetrating small molecule.

Endosomolytic and Cell Membrane Penetration Polypeptides

In some aspects, a molecule of Formula (I): A-$X_1$-B-$X_2$-C, is further conjugated with an endosomolytic polypeptide. In some cases, the endosomolytic polypeptide is a pH-dependent membrane active peptide. In some cases, the endosomolytic polypeptide is an amphipathic polypeptide. In additional cases, the endosomolytic polypeptide is a peptidomimetic. In some instances, the endosomolytic polypeptide comprises INF, melittin, meucin, or their respective derivatives thereof. In some instances, the endosomolytic polypeptide comprises INF or its derivatives thereof. In other cases, the endosomolytic polypeptide comprises melittin or its derivatives thereof. In additional cases, the endosomolytic polypeptide comprises meucin or its derivatives thereof.

In some instances, INF7 is a polypeptide comprising CGIFGEIEELIEEGLENLIDWGNA (SEQ ID NO: 298), or GLFEAIEGFIENGWEGMIDGWYGC (SEQ ID NO: 299). In some instances, INF7 or its derivatives comprise a sequence of: GLFEAIEGFIENGWEGMIWDYGSGSCG (SEQ ID NO: 300), GLFEAIEGFIENGWEGMIDG WYG-(PEG)6-$NH_2$ (SEQ ID NO: 301), or GLFEAIEGFIENGWEGMIWDYG-SGSC-K(GalNAc)2 (SEQ ID NO: 302).

In some cases, melittin is a polypeptide comprising CLIGAILKVLATGLPTLISWIKNKRKQ (SEQ ID NO: 303), or GIGAVLKVLTTGLPALISWIKRKRQQ (SEQ ID NO: 304). In some instances, melittin comprises a polypeptide sequence as described in U.S. Pat. No. 8,501,930.

In some instances, meucin is an antimicrobial peptide (AMP) derived from the venom gland of the scorpion Mesobuthus eupeus. In some instances, meucin comprises of meucin-13 those sequence comprises IFGAIAGLLKNIF-$NH_2$ (SEQ ID NO: 305) and meucin-18 those sequence comprises FFGHLFKLATKIIPSLFQ (SEQ ID NO: 306).

In some instances, the endosomolytic polypeptide comprises a polypeptide in which its sequence is at least 50%, 60%, 70%, 80%, 90%, 95%, or 99% sequence identity to INF7 or its derivatives thereof, melittin or its derivatives thereof, or meucin or its derivatives thereof. In some instances, the endosomolytic moiety comprises INF7 or its derivatives thereof, melittin or its derivatives thereof, or meucin or its derivatives thereof.

In some instances, the endosomolytic moiety is INF7 or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 298-302. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 298. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 299-302. In some cases, the endosomolytic moiety comprises SEQ ID NO: 298. In some cases, the endosomolytic moiety comprises SEQ ID NO: 299-302. In some cases, the endosomolytic moiety consists of SEQ ID NO: 298. In some cases, the endosomolytic moiety consists of SEQ ID NO: 299-302.

In some instances, the endosomolytic moiety is melittin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 303 or 304. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 303. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 304. In some cases, the endosomolytic moiety comprises SEQ ID NO: 303. In some cases, the endosomolytic moiety comprises SEQ ID NO: 304. In some cases, the endosomolytic moiety consists of SEQ ID NO: 303. In some cases, the endosomolytic moiety consists of SEQ ID NO: 304.

In some instances, the endosomolytic moiety is meucin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 305 or 306. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 305. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 306. In some cases, the endosomolytic moiety comprises SEQ ID NO: 305. In some cases, the endosomolytic moiety comprises SEQ ID NO: 306. In some cases, the endosomolytic moiety consists of SEQ ID NO: 305. In some cases, the endosomolytic moiety consists of SEQ ID NO: 306.

In some instances, the endosomolytic moiety comprises a sequence as illustrated in Table 8.

TABLE 8

| NAME | ORIGIN | AMINO ACID SEQUENCE | SEQ ID NO: | TYPE |
|---|---|---|---|---|
| Pep-1 | NLS from Simian Virus 40 large antigen and Reverse transcriptase of HIV | KETWWETWWTEWSQPKKKRKV | 307 | Primary amphipathic |
| pVEC | VE-cadherin | LLIILRRRRIRKQAHAHSK | 308 | Primary amphipathic |
| VT5 | Synthetic peptide | DPKGDPKGVTVTVTVTVTGKGDPKPD | 309 | β-sheet amphipathic |
| C105Y | 1-antitrypsin | CSIPPEVKFNKPFVYLI | 310 | — |
| Transportan | Galanin and mastoparan | GWTLNSAGYLLGKINLKALAALAKKIL | 311 | Primary amphipathic |
| TP10 | Galanin and mastoparan | AGYLLGKINLKALAALAKKIL | 312 | Primary amphipathic |
| MPG | A hydrophobic domain from the fusion sequence of HIV gp41 and NLS of SV40 T antigen | GALFLGFLGAAGSTMGA | 313 | β-sheet amphipathic |
| gH625 | Glycoprotein gH of HSV type I | HGLASTLTRWAHYNALIRAF | 314 | Secondary amphipathic α-helical |
| CADY | PPTG1 peptide | GLWRALWRLLRSLWRLLWRA | 315 | Secondary amphipathic α-helical |

TABLE 8-continued

| NAME | ORIGIN | AMINO ACID SEQUENCE | SEQ ID NO: | TYPE |
|---|---|---|---|---|
| GALA | Synthetic peptide | WEAALAEA LAEALAEH LAEALAEA LEALAA | 316 | Secondary amphipathic α-helical |
| INF | Influenza HA2 fusion peptide | GLFEAIEG FIENGWEG MIDGWYGC | 317 | Secondary amphipathic α-helical/ pH-dependent membrane active peptide |
| HA2E5-TAT | Influenza HA2 subunit of influenza virus X31 strain fusion peptide | GLFGAIAG FIENGWEG MIDGWYG | 318 | Secondary amphipathic α-helical/ pH-dependent membrane active peptide |
| HA2-pene-tratin | Influenza HA2 subunit of influenza virus X31 strain fusion peptide | GLFGAIAG FIENGWEG MIDGRQIK IWFQNRRM KWKK-amide | 319 | pH-dependent membrane active peptide |
| HA-K4 | Influenza HA2 subunit of influenza virus X31 strain fusion peptide | GLFGAIAG FIENGWEG MIDG-SSK KKK | 320 | pH-dependent membrane active peptide |
| HA2E4 | Influenza HA2 subunit of influenza virus X31 strain fusion peptide | GLFEAIAG FIENGWEG MIDGGGYC | 321 | pH-dependent membrane active peptide |
| H5WYG | HA2 analogue | GLFHAIAH FIHGGWHG LIHGWYG | 322 | pH-dependent membrane active peptide |
| GALA-INF3-(PEG)6-NH | INF3 fusion peptide | GLFEAIEG FIENGWEG LAEALAEA LEALAA-(PEG)6-NH2 | 323 | pH-dependent membrane active peptide |
| CM18-TAT11 | Cecropin-A-Melittin2-12 (CM18) fusion peptide | KWKLFKKI GAVLKVLT TG-YGRKK RRQRRR | 324 | pH-dependent membrane active peptide |

In some cases, the endosomolytic moiety comprises a Bak BH3 polypeptide which induces apoptosis through antagonization of suppressor targets such as Bcl-2 and/or Bcl-xL. In some instances, the endosomolytic moiety comprises a Bak BH3 polypeptide described in Albarran, et al., "Efficient intracellular delivery of a pro-apoptotic peptide with a pH-responsive carrier," *Reactive & Functional Polymers* 71: 261-265 (2011).

In some instances, the endosomolytic moiety comprises a polypeptide (e.g., a cell-penetrating polypeptide) as described in PCT Publication Nos. WO2013/166155 or WO2015/069587.

Endosomolytic Lipids

In some aspects, the endosomolytic moiety is a lipid (e.g., a fusogenic lipid). In some aspects, a molecule of Formula (I): A-$X_1$-B-$X_2$-C, is further conjugated with an endosomolytic lipid (e.g., fusogenic lipid). Exemplary fusogenic lipids include 1,2-dileoyl-sn-3-phosphoethanolamine (DOPE), phosphatidylethanolamine (POPE), palmitoyloleoylphosphatidylcholine (POPC), (6Z,9Z,28Z,31Z)-heptatriaconta-6,9,28,31-tetraen-19-o1 (Di-Lin), N-methyl(2,2-di((9Z,12Z)-octadeca-9,12-dienyl)-1,3-dioxolan-4-γ1)methanamine (DLin-k-DMA) and N-methyl-2-(2,2-di((9Z,12Z)-octadeca-9,12-dienyl)-1,3-dioxolan-4-γ1)ethanamine (XTC).

In some instances, an endosomolytic moiety is a lipid (e.g., a fusogenic lipid) described in PCT Publication No. WO09/126,933.

Endosomolytic Small Molecules

In some aspects, the endosomolytic moiety is a small molecule. In some aspects, a molecule of Formula (I): A-$X_1$-B-$X_2$-C, is further conjugated with an endosomolytic small molecule. Exemplary small molecules suitable as endosomolytic moieties include, but are not limited to, quinine, chloroquine, hydroxychloroquines, amodiaquins (carnoquines), amopyroquines, primaquines, mefloquines, nivaquines, halofantrines, quinone imines, or a combination thereof. In some instances, quinoline endosomolytic moieties include, but are not limited to, 7-chloro-4-(4-diethylamino-1-methylbutyl-amino)quinoline (chloroquine); 7-chloro-4-(4-ethyl-(2-hydroxyethyl)-amino-1-methylbutyl-amino)quinoline (hydroxychloroquine); 7-fluoro-4-(4-diethylamino-1-methylbutyl-amino)quinoline; 4-(4-diethylamino-1-methylbutylamino) quinoline; 7-hydroxy-4-(4-diethyl-amino-1-methylbutylamino)quinoline; 7-chloro-4-(4-diethylamino-1-butylamino)quinoline (desmethylchloroquine); 7-fluoro-4-(4-diethylamino-1-butylamino)quinoline); 4-(4-diethyl-amino-1-butylamino) quinoline; 7-hydroxy-4-(4-diethylamino-1-butylamino)quinoline; 7-chloro-4-(1-carboxy-4-diethylamino-1-butylamino)quinoline; 7-fluoro-4-(1-carboxy-4-diethyl-amino-1-butylamino)quinoline; 4-(1-carboxy-4-diethylamino-1-butylamino) quinoline; 7-hydroxy-4-(1-carboxy-4-diethylamino-1-butylamino)quinoline; 7-chloro-4-(1-carboxy-4-diethylamino-1-methylbutylamino) quinoline; 7-fluoro-4-(1-carboxy-4-diethyl-amino-1-methylbutylamino)quinoline; 4-(1-carboxy-4-diethylamino-1-methylbutylamino)quinoline; 7-hydroxy-4-(1-carboxy-4-diethylamino-1-methylbutylamino)quinoline; 7-fluoro-4-(4-ethyl-(2-hydroxyethyl)-amino-1-methylbutylamino) quinoline; 4-(4-ethyl-(2-hydroxy-ethyl)-amino-1-methylbutylamino-)quinoline; 7-hydroxy-4-(4-ethyl-(2-hydroxyethyl)-amino-1-methylbutylamino)quinoline; hydroxychloroquine phosphate; 7-chloro-4-(4-ethyl-(2-hydroxyethyl-1)-amino-1-butylamino)quinoline (desmethylhydroxychloroquine); 7-fluoro-4-(4-ethyl-(2-hydroxyethyl)-amino-1-butylamino)quinoline; 4-(4-ethyl-(2-hydroxyethyl)-amino-1-butylamino)quinoline; 7-hydroxy-4-(4-ethyl-(2-hydroxyethyl)-amino-1-butylamino) quinoline; 7-chloro-4-(1-carboxy-4-ethyl-(2-hydroxyethyl)-amino-1-butylamino)quinoline; 7-fluoro-4-(1-carboxy-4-ethyl-(2-hydroxyethyl)-amino-1-butylamino)quinoline; 4-(1-carboxy-4-ethyl-(2-hydroxyethyl)-amino-1-butylamino)quinoline; 7-hydroxy-4-(1-carboxy-4-ethyl-(2-hydroxyethyl)-amino-1-butylamino)quinoline; 7-chloro-4-(1-carboxy-4-ethyl-(2-hydroxyethyl)-amino-1-methylbutylamino)quinoline; 7-fluoro-4-(1-carboxy-4-ethyl-(2-hydroxyethyl)-amino-1-methylbutylamino) quinoline; 4-(1-carboxy-4-ethyl-(2-hydroxyethyl)-amino-1-methylbutylamino)quinoline; 7-hydroxy-4-(1-carboxy-4-ethyl-(2-hydroxyethyl)-amino-1-methylbutylamino) quinoline; 8-[(4-aminopentyl)amino-6-methoxydihydrochloride quinoline; 1-acetyl-1,2,3,4-tetrahydroquinoline; 8-[(4-aminopentyl)amino]-6-methoxyquinoline dihydrochloride; 1-butyryl-1,2,3,4-tetrahydroquinoline; 3-chloro-4-(4-hydroxy-alpha,alpha'-bis(2-methyl-1-pyrrolidinyl)-2,5-xylidinoquinoline, 4-[(4-diethyl-amino)-1-methylbutyl-amino]-6-methoxyquinoline; 3-fluoro-4-(4-hydroxy-alpha,alpha'-bis(2-methyl-1-pyrrolidinyl)-2,5-xylidinoquinoline, 4-[(4-diethylamino)-1-methylbutyl-amino]-6-methoxyquinoline; 4-(4-hydroxy-alpha, alpha'-bis(2-methyl-1-pyrrolidinyl)-2,5-xylidinoquinoline; 4-[(4-diethylamino)-1-methylbutyl-amino]-6-methoxyquinoline; 3,4-dihydro-1-(2H)-quinolinecarboxyaldehyde; 1,1'-pentamethylene diquinoleinium diiodide; 8-quinolinol sulfate and amino, aldehyde, carboxylic, hydroxyl, halogen, keto, sulfhydryl and vinyl derivatives or analogs thereof. In some instances, an endosomolytic moiety is a small molecule described in Naisbitt et al (1997, J Pharmacol Exp Therapy 280:884-893) and in U.S. Pat. No. 5,736,557.

Cell Penetrating Polypeptide (CPP)

In some aspects, cell penetrating polypeptide comprises positively charged short peptides with 5-30 amino acids. In some aspects, cell penetrating polypeptide comprises arginine or lysine rich amino acid sequences. In some aspects, cell penetrating polypeptide includes any polypeptide or combination thereof listed in Table 9.

TABLE 9

| Peptide | Sequence | SEQ ID NO: |
|---|---|---|
| Antennapedia Penetratin (43-58) | RQIKIWFQNRRMKWKK | 325 |
| HIV-1 TAT protein (48-60) | GRKKRRQRRRPPQ | 326 |
| pVEC Cadherin (615-632) | LLIILRRRIRKQAHAHSK | 327 |
| Transportan Galanine/Mastoparan | GWTLNSAGYLLGKINLKALAALAKKIL | 328 |
| MPG HIV-gp41/SV40 T-antigen | GALFLGFLGAAGSTMGAWSQPKKKRKV | 329 |
| Pep-1 HIV-reverse transcriptase/SV40 T-antigen | KETWWETWWTEWSQPKKKRKV | 330 |
| Polyarginines | R(n); 6 < n < 12 | 331 |
| MAP | KLALKLALKALKAALKLA | 332 |
| R6W3 | RRWWRRWRR | 333 |
| NLS | CGYGPKKKRKVGG | 334 |
| 8-lysines | KKKKKKKK | 335 |
| ARF (1-22) | MVRRFLVTLRIRRACGPPRVRV | 336 |
| Azurin-p28 | LSTAADMQGVVTDGMASGLDKDYLKPDD | 337 |

Linkers

In some aspects, a linker described herein is a cleavable linker or a non-cleavable linker. In some instances, the linker is a cleavable linker. In other instances, the linker is a non-cleavable linker.

In some cases, the linker is a non-polymeric linker. A non-polymeric linker refers to a linker that does not contain a repeating unit of monomers generated by a polymerization process. Exemplary non-polymeric linkers include, but are not limited to, $C_1$-$C_6$ alkyl group (e.g., a $C_5$, $C_4$, $C_3$, $C_2$, or $C_1$ alkyl group), homobifunctional cross linkers, heterobifunctional cross linkers, peptide linkers, traceless linkers, self-immolative linkers, maleimide-based linkers, or combinations thereof. In some cases, the non-polymeric linker comprises a $C_1$-$C_6$ alkyl group (e.g., a $C_5$, $C_4$, $C_3$, $C_2$, or $C_1$ alkyl group), a homobifunctional cross linker, a heterobifunctional cross linker, a peptide linker, a traceless linker, a self-immolative linker, a maleimide-based linker, or a combination thereof. In additional cases, the non-polymeric linker does not comprise more than two of the same type of linkers, e.g., more than two homobifunctional cross linkers, or more than two peptide linkers. In further cases, the non-polymeric linker optionally comprises one or more reactive functional groups.

In some instances, the non-polymeric linker does not encompass a polymer that is described above. In some instances, the non-polymeric linker does not encompass a polymer encompassed by the polymer moiety C. In some cases, the non-polymeric linker does not encompass a polyalkylene oxide (e.g., PEG). In some cases, the non-polymeric linker does not encompass a PEG.

In some instances, the linker comprises a homobifunctional linker. Exemplary homobifunctional linkers include, but are not limited to, Lomant's reagent dithiobis (succinimidylpropionate) DSP, 3'3'-dithiobis(sulfosuccinimidyl proprionate (DTSSP), disuccinimidyl suberate (DSS), bis (sulfosuccinimidyl)suberate (BS), disuccinimidyl tartrate (DST), disulfosuccinimidyl tartrate (sulfo DST), ethylene glycobis(succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

In some aspects, the linker comprises a heterobifunctional linker. Exemplary heterobifunctional linker include, but are not limited to, amine-reactive and sulfhydryl cross-linkers such as N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio) toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl (4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino)hexanoyl) amino]hexanoate (sIAXX), succinimidyl 4-(((iodoacetyl) amino)methyl)cyclohexane-1-carboxylate (sIAC), succinimidyl 6-((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl)butyric acid hydrazide (MPBH), 4-(N-maleimidomethyl)cyclohexane-1-carboxyl-hydrazide-8 ($M_2C_2H$), 3-(2-pyridyldithio)propionyl hydrazide (PDPH), amine-reactive and photoreactive cross-linkers such as N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido) hexanoate (sulfo-NHs-LC-AsA), sulfosuccinimidyl-2-(ρ-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(ρ-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), ρ-nitrophenyl diazopyruvate (ρNPDP), ρ-nitrophenyl-2-diazo-3,3,3-trifluoropropionate (PNP-DTP), sulfhydryl-reactive and photoreactive cross-linkers such asl-(ρ-Azidosalicylamido)-4-(iodoacetamido)butane (AsIB), N-[4-(ρ-azidosalicylamido) butyl]-3'-(2'-pyridyldithio)propionamide (APDP), benzophenone-4-iodoacetamide, benzophenone-4-maleimide carbonyl-reactive and photoreactive cross-linkers such as ρ-azidobenzoyl hydrazide (ABH), carboxylate-reactive and photoreactive cross-linkers such as 4-(ρ-azidosalicylamido)butylamine (AsBA), and arginine-reactive and photoreactive cross-linkers such as ρ-azidophenyl glyoxal (APG).

In some instances, the linker comprises a reactive functional group. In some cases, the reactive functional group comprises a nucleophilic group that is reactive to an electrophilic group present on a binding moiety. Exemplary electrophilic groups include carbonyl groups-such as aldehyde, ketone, carboxylic acid, ester, amide, enone, acyl halide or acid anhydride. In some aspects, the reactive functional group is aldehyde. Exemplary nucleophilic groups include hydrazide, oxime, amino, hydrazine, thiosemicarbazone, hydrazine carboxylate, and arylhydrazide.

In some aspects, the linker comprises a maleimide group. In some instances, the maleimide group is also referred to as a maleimide spacer. In some instances, the maleimide group further encompasses a caproic acid, forming maleimidocaproyl (mc). In some cases, the linker comprises maleimidocaproyl (mc). In some cases, the linker is maleimidocaproyl (mc). In other instances, the maleimide group comprises a maleimidomethyl group, such as succinimidyl-4-(N-maleimidomethyl)cyclohexane-1-carboxylate (sMCC) or sulfosuccinimidyl-4-(N-maleimidomethyl)cyclohexane-1-carboxylate (sulfo-sMCC) described above.

In some aspects, the maleimide group is a self-stabilizing maleimide. In some instances, the self-stabilizing maleimide utilizes diaminopropionic acid (DPR) to incorporate a basic amino group adjacent to the maleimide to provide intramolecular catalysis of tiosuccinimide ring hydrolysis, thereby eliminating maleimide from undergoing an elimination reaction through a retro-Michael reaction. In some instances, the self-stabilizing maleimide is a maleimide group described in Lyon et al., "Self-hydrolyzing maleimides improve the stability and pharmacological properties of antibody-drug conjugates," *Nat. Biotechnol.* 32(10):1059-1062 (2014). In some instances, the linker comprises a self-stabilizing maleimide. In some instances, the linker is a self-stabilizing maleimide.

In some aspects, the linker comprises a peptide moiety. In some instances, the peptide moiety comprises at least 2, 3, 4, 5, or 6 more amino acid residues. In some instances, the peptide moiety comprises at most 2, 3, 4, 5, 6, 7, or 8 amino acid residues. In some instances, the peptide moiety comprises about 2, about 3, about 4, about 5, or about 6 amino acid residues. In some instances, the peptide moiety is a cleavable peptide moiety (e.g., either enzymatically or chemically). In some instances, the peptide moiety is a non-cleavable peptide moiety. In some instances, the peptide moiety comprises Val-Cit (valine-citrulline), Gly-Gly-Phe-Gly (SEQ ID NO: 338), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 339), or Gly-Phe-Leu-Gly (SEQ ID NO: 340). In some instances, the linker comprises a peptide moiety such as: Val-Cit (valine-citrulline), Gly-Gly-Phe-Gly (SEQ ID NO: 338), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 339), or Gly-Phe-Leu-Gly (SEQ ID NO: 340). In some cases, the linker comprises Val-Cit. In some cases, the linker is Val-Cit.

In some aspects, the linker comprises a benzoic acid group, or its derivatives thereof. In some instances, the benzoic acid group or its derivatives thereof comprise paraaminobenzoic acid (PABA). In some instances, the benzoic acid group or its derivatives thereof comprise gamma-aminobutyric acid (GABA).

In some aspects, the linker comprises one or more of a maleimide group, a peptide moiety, and/or a benzoic acid group, in any combination. In some aspects, the linker comprises a combination of a maleimide group, a peptide moiety, and/or a benzoic acid group. In some instances, the maleimide group is maleimidocaproyl (mc). In some instances, the peptide group is val-cit. In some instances, the benzoic acid group is PABA. In some instances, the linker comprises a mc-val-cit group. In some cases, the linker comprises a val-cit-PABA group. In additional cases, the linker comprises a mc-val-cit-PABA group.

In some aspects, the linker is a self-immolative linker or a self-elimination linker. In some cases, the linker is a self-immolative linker. In other cases, the linker is a self-elimination linker (e.g., a cyclization self-elimination linker). In some instances, the linker comprises a linker described in U.S. Pat. No. 9,089,614 or PCT Publication NO. WO2015038426.

In some aspects, the linker is a dendritic type linker. In some instances, the dendritic type linker comprises a branching, multifunctional linker moiety. In some instances, the dendritic type linker is used to increase the molar ratio of polynucleotide B to the binding moiety A. In some instances, the dendritic type linker comprises PAMAM dendrimers.

In some aspects, the linker is a traceless linker or a linker in which after cleavage does not leave behind a linker moiety (e.g., an atom or a linker group) to a binding moiety A, a polynucleotide B, a polymer C, or an endosomolytic moiety D. Exemplary traceless linkers include, but are not limited to, germanium linkers, silicium linkers, sulfur linkers, selenium linkers, nitrogen linkers, phosphorus linkers, boron linkers, chromium linkers, or phenylhydrazide linker. In some cases, the linker is a traceless aryl-triazene linker as described in Hejesen, et al., "A traceless aryl-triazene linker for DNA-directed chemistry," *Org Biomol Chem* 11(15): 2493-2497 (2013). In some instances, the linker is a traceless linker described in Blaney, et al., "Traceless solid-phase organic synthesis," *Chem. Rev.* 102: 2607-2024 (2002). In some instances, a linker is a traceless linker as described in U.S. Pat. No. 6,821,783.

In some instances, the linker is a linker described in U.S. Pat. Nos. 6,884,869; 7,498,298; 8,288,352; 8,609,105; or 8,697,688; U.S. Patent Publication NOs. 2014/0127239; 2013/028919; 2014/286970; 2013/0309256; 2015/037360; or 2014/0294851; or PCT Publication Nos. WO2015057699; WO2014080251; WO2014197854; WO2014145090; or WO2014177042.

In some aspects, $X_1$ and $X_2$ are each independently a bond or a non-polymeric linker. In some instances, $X_1$ and $X_2$ are each independently a bond. In some cases, $X_1$ and $X_2$ are each independently a non-polymeric linker.

In some instances, $X_1$ is a bond or a non-polymeric linker. In some instances, $X_1$ is a bond. In some instances, $X_1$ is a non-polymeric linker. In some instances, the linker is a $C_1$-$C_6$ alkyl group. In some cases, $X_1$ is a $C_1$-$C_6$ alkyl group, such as for example, a $C_5$, $C_4$, $C_3$, $C_2$, or $C_1$ alkyl group. In some cases, the $C_1$-$C_6$ alkyl group is an unsubstituted $C_1$-$C_6$ alkyl group. As used in the context of a linker, and in particular in the context of $X_1$, alkyl means a saturated straight or branched hydrocarbon radical containing up to six carbon atoms. In some instances, $X_1$ includes a homobifunctional linker or a heterobifunctional linker described supra. In some cases, $X_1$ includes a heterobifunctional linker. In some cases, $X_1$ includes sMCC. In other instances, $X_1$ includes a heterobifunctional linker optionally conjugated to a $C_1$-$C_6$ alkyl group. In other instances, $X_1$ includes sMCC optionally conjugated to a $C_1$-$C_6$ alkyl group. In additional instances, $X_1$ does not include a homobifunctional linker or a heterobifunctional linker described supra.

In some instances, $X_2$ is a bond or a linker. In some instances, $X_2$ is a bond. In other cases, $X_2$ is a linker. In additional cases, $X_2$ is a non-polymeric linker. In some aspects, $X_2$ is a $C_1$-$C_6$ alkyl group. In some instances, $X_2$ is a homobifunctional linker or a heterobifunctional linker described supra. In some instances, $X_2$ is a homobifunctional linker described supra. In some instances, $X_2$ is a heterobifunctional linker described supra. In some instances, $X_2$ comprises a maleimide group, such as maleimidocaproyl (mc) or a self-stabilizing maleimide group described above. In some instances, $X_2$ comprises a peptide moiety, such as Val-Cit. In some instances, $X_2$ comprises a benzoic acid group, such as PABA. In additional instances, $X_2$ comprises a combination of a maleimide group, a peptide moiety, and/or a benzoic acid group. In additional instances, $X_2$ comprises a me group. In additional instances, $X_2$ comprises a mc-val-cit group. In additional instances, $X_2$ comprises a val-cit-PABA group. In additional instances, $X_2$ comprises a me-val-cit-PABA group.

Methods of Use

Muscle atrophy refers to a loss of muscle mass and/or to a progressive weakening and degeneration of muscles. In some cases, the loss of muscle mass and/or the progressive weakening and degeneration of muscles occurs due to a high rate of protein degradation, a low rate of protein synthesis, or a combination of both. In some cases, a high rate of muscle protein degradation is due to muscle protein catabolism (i.e., the breakdown of muscle protein in order to use amino acids as substrates for gluconeogenesis).

In one embodiment, muscle atrophy refers to a significant loss in muscle strength. By significant loss in muscle strength is meant a reduction of strength in diseased, injured, or unused muscle tissue in a subject relative to the same muscle tissue in a control subject. In an embodiment, a significant loss in muscle strength is a reduction in strength of at least 10%, at least 15%, at least 20%, at least 25%, at least 30%, at least 35%, at least 40%, at least 45%, at least 50%, or more relative to the same muscle tissue in a control subject. In another embodiment, by significant loss in muscle strength is meant a reduction of strength in unused muscle tissue relative to the muscle strength of the same muscle tissue in the same subject prior to a period of nonuse. In an embodiment, a significant loss in muscle strength is a reduction of at least 10%, at least 15%, at least 20%, at least 25%, at least 30%, at least 35%, at least 40%, at least 45%, at least 50%, or more relative to the muscle strength of the same muscle tissue in the same subject prior to a period of nonuse.

In some aspects, described herein is a method of treating cardiomyopathy in a subject, which comprises providing polynucleic acid molecule or polynucleic acid molecule conjugate described herein and administering to the subject a therapeutically effective amount of a polynucleic acid molecule described herein or a polynucleic acid molecule conjugate described herein. In some instances, the polynucleic acid molecule or polynucleic acid molecule conjugate is effective to reduce a quantity of the mRNA transcript of human PRKAG2. In some instances, the subject is diagnosed or suspected to have cardiomyopathy. In some instances, the subject has suffered, or is suffering from one or more symptoms of cardiomyopathy. In some instances, the polynucleic acid molecule or polynucleic acid molecule conjugate mediates RNA interference against the human PRKAG2 mRNA as to modulate or treat cardiomyopathy (and/or its symptoms thereof) caused by or associated with a glycogen storage disease in a subject. In some aspects, the polynucleic acid molecule or polynucleic acid molecule conjugate mediates RNA interference against a human PRKAG2 mRNA comprising a mutation. In some instances, the mutation is a point mutation of the human PRKAG2 gene as to modulate cardiomyopathy caused by glycogen storage disease in a subject. In some instances, the subject is a human.

In some aspects, described herein is a method of treating PRKAG2 cardiac syndrome in a subject, which comprises providing polynucleic acid molecule or polynucleic acid molecule conjugate described herein and administering to the subject a therapeutically effective amount of a polynucleic acid molecule or a polynucleic acid molecule conjugate described herein. In some instances, the polynucleic acid molecule or polynucleic acid molecule conjugate is effective to reduce a quantity of the mRNA transcript of human PRKAG2. In some instances, the subject is diagnosed or suspected to have PRKAG2 cardiac syndrome. In some instances, the subject has suffered, or is suffering from one or more symptoms of PRKAG2 cardiac syndrome. In some instances, the polynucleic acid molecule or polynucleic acid molecule conjugate mediates RNA interference against the human PRKAG2 mRNA as to modulate or treat PRKAG2 cardiac syndrome in a subject. In some aspects, the polynucleic acid molecule or polynucleic acid molecule conjugate mediates RNA interference against a human PRKAG2 mRNA comprising a mutation. In some instances, the mutation is a point mutation of the human PRKAG2 gene as to modulate PRKAG2 cardiac syndrome in a subject. In some instances, the subject is a human.

In some aspects, described herein is a method of treating cardiomyopathy in a subject, which comprises providing an siRNA-antibody conjugate (siRNA conjugate) described herein and administering to the subject a therapeutically effective amount of the siRNA-antibody conjugate described herein and reducing the levels of PRKAG2 mRNA transcript of human PRKAG2 in said subject. In some instances, cardiomyopathy is cardiomyopathy caused by a glycogen storage disease. In some instances, cardiomyopathy is cardiomyopathy caused by PRKAG2 syndrome or PRKAG2 cardiac syndrome. In some instances, the siRNA-conjugate mediates RNA interference against the human PRKAG2 mRNA to reduce the levels of mRNA transcript of human PRKAG2 mRNA in the subject, thereby treats cardiomyopathy caused PRKAG2 syndrome or cardiac syndrome, or its symptoms thereof, in the subject. In some instances, the siRNA-conjugate mediates RNA interference against a mutated PRKAG2 variant comprising a point mutation within the PRKAG2 gene to reduce the levels of mRNA transcript of human PRKAG2 in said subject, thereby treating cardiomyopathy caused by PRKAG2 syndrome in the subject.

In some aspects, described herein is a method of treating PRKGA2 cardiac syndrome in a subject, which comprises providing an siRNA-antibody conjugate (siRNA conjugate) described herein and administering to the subject a therapeutically effective amount of the siRNA-antibody conjugate described herein and reducing the levels of PRKAG2 mRNA transcript of human PRKAG2 in said subject. In some instances, the siRNA-conjugate mediates RNA interference to reduce the levels of mRNA transcript of human PRKAG2 mRNA in the subject thereby treats PRKGA2 cardiac syndrome in the subject. In some instances, the siRNA-conjugate mediates RNA interference against a mutated PRKAG2 variant comprising a point mutation within the PRKAG2 gene to reduce the levels of mRNA transcript of human PRKAG2 mRNA comprising the mutation, thereby treats PRKGA2 cardiac syndrome in the subject.

In some aspects, described herein is a method of alleviating symptoms in a subject with cardiomyopathy, which comprises providing a PRKAG2 siRNA-antibody conjugate (PRKAG2-siRNA conjugate or PRKAG2-AOC) described herein and administering to the subject a therapeutically effective amount of the siRNA-antibody conjugate described herein by reducing the levels of mRNA transcript of human PRKAG2. In some instances, the cardiomyopathy is caused by a glycogen storage disease. In another embodiments, described herein is a method of alleviating symptoms in a subject with cardiomyopathy caused PRKAG2 syndrome or PRKAG2 cardiac syndrome by providing an siRNA-antibody conjugate described herein and administering to the patient with cardiomyopathy caused by PRKAG2 syndrome a therapeutically effective amount of the siRNA-antibody conjugate describes herein by targeting a PRKAG2 mutant comprising a point mutation within PRKAG2 gene and reducing the levels of mRNA transcript of human PRKAG2 comprising the mutation or reducing the levels of PRKAG2 protein comprising a mutation.

The symptoms of cardiomyopathy are related to the thickening of the heart muscle or cardiac muscles (e.g., hypertrophied cardiac muscles). In some instances, the symptoms of cardiomyopathy include arrhythmia (irregular heart rate or rhythm). In some instances, the symptoms of cardiomyopathy include chest pain, especially during activity. In some instances, the symptoms of cardiac hypertrophy include fatigue. In some instances, the symptoms of cardiomyopathy include fluttering or pounding feeling in the chest. In some instances, the symptoms of cardiomyopathy include heart murmur. In some instances, the symptoms of cardiomyopathy include lightheadedness or dizziness. In some instances, the symptoms of cardiomyopathy include fainting. In some instances, the symptoms of cardiomyopathy include shortness of breath, especially during activity.

In some aspects, described herein is a method of improving cardiac muscle functions in a patient by administering to the cardiomyopathy patient a therapeutically effective amount of the siRNA conjugate described herein thereby reducing the levels of mRNA transcript of human PRKAG2 or reducing the levels of PRKAG2 protein. In some instances, cardiomyopathy is caused by a glycogen storage disease. In some instances, cardiomyopathy is caused by PRKAG2 syndrome or PRKAG2 cardiac syndrome. In some aspects, described herein is a method of improving cardiac muscle functions or alleviating cardiomyopathy symptoms as described above a patient suffering from cardiomyopathy by administering to the cardiomyopathy caused by PRKAG2 syndrome patient a therapeutically effective amount of the siRNA conjugate described herein thereby reducing the levels of mRNA transcript of human PRKAG2 or reducing the levels of PRKAG2 protein.

In some aspects, described herein is a method of treating cardiomyopathy in a subject, which comprises providing an antisense oligonucleotide (ASO) antibody conjugate (ASO-conjugate) described herein and administering to the subject a therapeutically effective amount of the ASO-conjugate described herein and reducing the levels of PRKAG2 mRNA transcript of human PRKAG2 in said subject. In some instances, cardiomyopathy is caused by or associated with a mutated PRKAG2. In some instances, the ASO-conjugate mediates RNA interference against the human PRKAG2 mRNA to reduce the levels of mRNA transcript of human PRKAG2 in said subject, thereby treats cardiomyopathy caused by or associated with a mutated PRKAG2 in the subject. In some instances, the ASO-conjugate mediates RNA interference against a PRKAG2 mutant comprising a point mutation within the PRKAG2 gene to reduce the levels of mRNA transcript of human PRKAG2 with the mutation in said subject, thereby treats cardiomyopathy in the subject.

In some aspects, described herein is a method of treating cardiomyopathy in a subject. In some instances, the subject with cardiomyopathy suffers from cardiomyopathy caused by a glycogen storage disease. In some instances, the subject with cardiomyopathy suffers from cardiomyopathy caused by PRKAG2 syndrome. In some instances, the subject suffers from PRKAG2 cardiac syndrome. In some instances, the subject with cardiomyopathy suffers from cardiomyopathy caused by a mutation of the PRKAG2 gene. In some instances, the subject with cardiomyopathy subject has muscle cells expressing a mutant PRKAG2 selected from a mutated PRKAG2 which comprises a single point mutation the PRKAG2 gene. In some aspects, the muscle cells are cardiac muscle cells.

In some aspects, described herein is a method of modulating PRKAG2 expression or activity in a muscle cell by contacting the muscle cell with a polynucleotide conjugate (siRNA-antibody conjugate or ASO-antibody conjugate) or a polynucleotide molecule (siRNA or ASO), thereby modulating PRKAG2 expression or activity in the muscle cell. In some instances, the polynucleotide conjugate or the polynucleotide molecule reduces the PRKAG2 expression or activity at least 20%, 30%, 40%, 50%, 60%, 70%, or 80% compared to untreated muscle cells, or before the treatment. In some instances, the effect of reduced PRKAG2 expression or activity is maintained for at least 3 days, 7 days, 14 days, 21 days, 28 days, 60 days, 90 days, 120 days, 5 months, 6 months by maintaining the reduced expression or activity of at least 20%, 30%, 40%, or 50%.

In some aspects, described herein is a method of modulating PRKAG2 expression or activity in a subject (e.g., a patient) by administering the subject with a polynucleotide conjugate (siRNA-antibody conjugate or ASO-antibody conjugate) or a polynucleotide molecule (siRNA or ASO), thereby modulating PRKAG2 expression or activity in the subject. In some instances, the polynucleotide conjugate or the polynucleotide molecule reduces the PRKAG2 expression or activity at least 20%, 30%, 40%, 50%, 60%, 70%, or 80% in the muscle cells (e.g., heart muscle cells, skeletal muscle cells, etc.) in the subject compared to untreated subject, or before the treatment. In some instances, the effect of reduced PRKAG2 expression or activity is maintained for at least 3 days, 7 days, 14 days, 21 days, 28 days, 60 days, 90 days, 120 days, 5 months, 6 months by maintaining the reduced expression or activity of at least 20%, 30%, 40%, or 50%.

Pharmaceutical Formulation

In some aspects, the pharmaceutical formulations described herein are administered to a subject by multiple administration routes, including but not limited to, parenteral (e.g., intravenous, subcutaneous, intramuscular), oral, intranasal, buccal, rectal, or transdermal administration routes. In some instances, the pharmaceutical composition describe herein is formulated for parenteral (e.g., intravenous, subcutaneous, intramuscular, intra-arterial, intraperitoneal, intrathecal, intracerebral, intracerebroventricular, or intracranial) administration. In other instances, the pharmaceutical composition described herein is formulated for oral administration. In still other instances, the pharmaceutical composition described herein is formulated for intranasal administration.

In some aspects, the pharmaceutical formulations include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some instances, the pharmaceutical formulation includes multiparticulate formulations. In some instances, the pharmaceutical formulation includes nanoparticle formulations. In some instances, nanoparticles comprise cMAP, cyclodextrin, or lipids. In some cases, nanoparticles comprise solid lipid nanoparticles, polymeric nanoparticles, self-emulsifying nanoparticles, liposomes, microemulsions, or micellar solutions. Additional exemplary nanoparticles include, but are not limited to, paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes and quantum dots. In some instances, a nanoparticle is a metal nanoparticle, e.g., a nanoparticle of scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, gadolinium, aluminum, gallium, indium, tin, thallium, lead, bismuth, magnesium, calcium, strontium, barium, lithium, sodium, potassium, boron, silicon, phosphorus, germanium, arsenic, antimony, and combinations, alloys or oxides thereof.

In some instances, a nanoparticle includes a core or a core and a shell, as in a core-shell nanoparticle.

In some instances, a nanoparticle is further coated with molecules for attachment of functional elements (e.g., with one or more of a polynucleic acid molecule or binding moiety described herein). In some instances, a coating comprises chondroitin sulfate, dextran sulfate, carboxymethyl dextran, alginic acid, pectin, carragheenan, fucoidan, agaropectin, porphyran, karaya gum, gellan gum, xanthan gum, hyaluronic acids, glucosamine, galactosamine, chitin (or chitosan), polyglutamic acid, polyaspartic acid, lysozyme, cytochrome C, ribonuclease, trypsinogen, chymotrypsinogen, α-chymotrypsin, polylysine, polyarginine, histone, protamine, ovalbumin or dextrin or cyclodextrin. In some instances, a nanoparticle comprises a graphene-coated nanoparticle.

In some cases, a nanoparticle has at least one dimension of less than about 500 nm, 400 nm, 300 nm, 200 nm, or 100 nm.

In some instances, the nanoparticle formulation comprises paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes or quantum dots. In some instances, a polynucleic acid molecule or a binding moiety described herein is conjugated either directly or indirectly to the nanoparticle. In some instances, at least 1, 5, 10, 15, 20, 30, 40, 50, 60, 70, 80, 90, 100 or more polynucleic acid molecules or binding moieties described herein are conjugated either directly or indirectly to a nanoparticle.

In some aspects, the pharmaceutical formulation comprises a delivery vector, e.g., a recombinant vector, the delivery of the polynucleic acid molecule into cells. In some instances, the recombinant vector is DNA plasmid. In other instances, the recombinant vector is a viral vector. Exemplary viral vectors include vectors derived from adeno-associated virus, retrovirus, adenovirus, or alphavirus. In some instances, the recombinant vectors capable of expressing the polynucleic acid molecules provide stable expression in target cells. In additional instances, viral vectors are used that provide for transient expression of polynucleic acid molecules.

In some aspects, the pharmaceutical formulation includes a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins1999).

In some instances, the pharmaceutical formulation further includes pH adjusting agents or buffering agents which include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some instances, the pharmaceutical formulation further includes diluent which are used to stabilize compounds because they provide a more stable environment. Salts dissolved in buffered solutions (which also provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

In some cases, the pharmaceutical formulation includes disintegration agents or disintegrants to facilitate the breakup or disintegration of a substance. The term "disintegrate" include both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some instances, the pharmaceutical formulation includes filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Lubricants and glidants are also optionally included in the pharmaceutical formulations described herein for preventing, reducing or inhibiting adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers also function as dispersing agents or wetting agents.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

Stabilizers include compounds such as any antioxidation agents, buffers, acids, preservatives and the like.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol has a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. Sometimes, surfactants are included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium docusate, triacetin, Tween 80, vitamin E TPGS, ammonium salts and the like.

Therapeutic Regimens

In some aspects, the pharmaceutical compositions described herein are administered for therapeutic applications. In some aspects, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, once in two months, once in three months, once in four months, once in five months, once in six months or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In some aspects, one or more pharmaceutical compositions are administered simultaneously, sequentially, or at an interval period of time. In some aspects, one or more pharmaceutical compositions are administered simultaneously. In some cases, one or more pharmaceutical compositions are administered sequentially. In additional cases, one or more pharmaceutical compositions are administered at an interval period of time (e.g., the first administration of a first pharmaceutical composition is on day one followed by an interval of at least 1, 2, 3, 4, 5, or more days prior to the administration of at least a second pharmaceutical composition).

In some aspects, two or more different pharmaceutical compositions are co-administered. In some instances, the two or more different pharmaceutical compositions are co-administered simultaneously. In some cases, the two or more different pharmaceutical compositions are co-administered sequentially without a gap of time between administrations. In other cases, the two or more different pharmaceutical compositions are co-administered sequentially with a gap of about 0.5 hour, 1 hour, 2 hours, 3 hours, 12 hours, 1 day, 2 days, or more between administrations.

In the case wherein the patient's status does improve, upon the doctor's discretion the administration of the composition is given continuously; alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some aspects, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner.

In some aspects, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in certain embodiments, are kits and articles of manufacture for use with one or more of the compositions and methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include target nucleic acid molecule described herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Certain Terminology

The section headings used herein are for organizational purposes only and are not to be construed as limiting the subject matter described.

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 μL" means "about 5 μL" and also "5 μL." Generally, the term "about" includes an amount that would be expected to be within experimental error.

As used herein, the term "polynucleic acid" is interchangeably used with the term "oligonucleotide" or "polynucleotide"

As used herein, the terms "individual(s)", "subject(s)" and "patient(s)" mean any mammal. In some aspects, the mammal is a human. In some aspects, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

The term "therapeutically effective amount" relates to an amount of a polynucleic acid molecule conjugate that is sufficient to provide a desired therapeutic effect in a mammalian subject. In some cases, the amount is single or multiple dose administration to a patient (such as a human) for treating, preventing, preventing the onset of, curing, delaying, reducing the severity of, ameliorating at least one symptom of a disorder or recurring disorder, or prolonging the survival of the patient beyond that expected in the absence of such treatment. Naturally, dosage levels of the particular polynucleic acid molecule conjugate employed to provide a therapeutically effective amount vary in dependence of the type of injury, the age, the weight, the gender, the medical condition of the subject, the severity of the condition, the route of administration, and the particular inhibitor employed. In some instances, therapeutically effective amounts of polynucleic acid molecule conjugate, as described herein, is estimated initially from cell culture and animal models. For example, $IC_{50}$ values determined in cell culture methods optionally serve as a starting point in animal models, while $IC_{50}$ values determined in animal models are optionally used to find a therapeutically effective dose in humans.

Skeletal muscle, or voluntary muscle, is generally anchored by tendons to bone and is generally used to effect skeletal movement such as locomotion or in maintaining posture. Although some control of skeletal muscle is generally maintained as an unconscious reflex (e.g., postural muscles or the diaphragm), skeletal muscles react to conscious control. Smooth muscle, or involuntary muscle, is found within the walls of organs and structures such as the esophagus, stomach, intestines, uterus, urethra, and blood vessels.

Skeletal muscle is further divided into two broad types: Type I (or "slow twitch") and Type II (or "fast twitch"). Type I muscle fibers are dense with capillaries and are rich in mitochondria and myoglobin, which gives Type I muscle tissue a characteristic red color. In some cases, Type I muscle fibers carry more oxygen and sustain aerobic activity using fats or carbohydrates for fuel. Type I muscle fibers contract for long periods of time but with little force. Type II muscle fibers are further subdivided into three major subtypes (IIa, IIx, and IIb) that vary in both contractile speed and force generated. Type II muscle fibers contract quickly and powerfully but fatigue very rapidly, and therefore produce only short, anaerobic bursts of activity before muscle contraction becomes painful.

Unlike skeletal muscle, smooth muscle is not under conscious control.

Cardiac muscle is also an involuntary muscle but more closely resembles skeletal muscle in structure and is found only in the heart. Cardiac and skeletal muscles are striated in that they contain sarcomeres that are packed into highly regular arrangements of bundles. By contrast, the myofibrils of smooth muscle cells are not arranged in sarcomeres and therefore are not striated.

Muscle cells encompass any cells that contribute to muscle tissue. Exemplary muscle cells include myoblasts, satellite cells, myotubes, and myofibril tissues.

As used here, muscle force is proportional to the cross-sectional area (CSA), and muscle velocity is proportional to muscle fiber length. Thus, comparing the cross-sectional areas and muscle fibers between various kinds of muscles is capable of providing an indication of muscle atrophy. Various methods are known in the art to measure muscle strength and muscle weight, see, for example, "Musculoskeletal assessment: Joint range of motion and manual muscle strength" by Hazel M. Clarkson, published by Lippincott Williams & Wilkins, 2000. The production of tomographic images from selected muscle tissues by computed axial tomography and sonographic evaluation are additional methods of measuring muscle mass.

The term antibody oligonucleotide conjugate (AOC) refers to an antibody conjugated to a nucleotide.

The term siRNA conjugate or siRNA-antibody conjugate refers to an antibody conjugated to a siRNA.

The term PRKAG2 siRNA-conjugate or PRKAG2 siRNA-antibody conjugate refers to an antibody conjugated to an siRNA that is capable of hybridizing to a target sequence of the human PRKAG2 mRNA.

The term PRKAG2-AOC refers to an antibody conjugated to an oligonucleotide (e.g., siRNA) that is capable of hybridizing to a target sequence of the human PRKAG2 mRNA.

The term PRKAG2 cardiac syndrome is an autosomal dominant metabolic heart disease characterized by left ventricular hypertrophy (LVH), progressive conduction abnormalities, and ventricular pre-excitation.

The term glycogen storage disease refers to a disease caused by excessive cellular glucose uptake and pathological glycogen storage cells.

EXAMPLES

These examples are provided for illustrative purposes only and not to limit the scope of the claims provided herein.

Example 1: Identification of siRNAs for the Regulation of Mouse and Human/NHP PRKAG2 Transcript Bioinformatic siRNA library design against mouse and human/NHP PRKAG2 transcript:

Sequences of all siRNAs that can bind to PRKAG2 mRNA, or a pre-determined region of the PRKAG2 mRNA are collected to generate a starting set of PRKAG2 siRNAs. From the starting set of PRKAG2 siRNAs, the first eliminating step comprises eliminating one or more PRKAG2 siRNAs that have a single nucleotide polymorphism (SNP) and/or MEF<−5. Then, the second eliminating step comprises eliminating PRKAG2 siRNAs with 0 and 1 mismatches (MM) in the human/mouse/NHP transcriptomes. Then, the third eliminating step comprises eliminating PRKAG2 siRNAs with 0 mismatches (MM) in the human/mouse/NHP intragenic regions. Then, the next step comprises carrying forward one or more PRKAG2 siRNAs with predicted viability values ≥60. The next eliminating step comprises eliminating one or more PRKAG2 siRNAs with a match to a seed region of known miRNAs 1-1000. Then, the eliminating step continues with eliminating PRKAG2 siRNAs molecule with % GC content values of 75% or higher. The above selection steps yield the final 102 candidates PRKAG2 siRNAs selected from a starting set of more than 2000 PRKAG2 siRNAs. Table 10 summarizes the bioinformatics screening that identified 102 siRNAs (92 were 21/23 bp and 10 were 19/21 bp) that bind specifically to human PRKAG2 (NM_016203.4) (SEQ ID NO: 237) and have 100% homology with mouse (NM_145401.2) (SEQ ID NO: 238) and NHP (XM_005551219.3) (SEQ ID NO: 239). Thymine (T) and Uracil (U) are interchangeably used in Table 10.

TABLE 10

| Target site on transcript NM_016203.4 | Exon | Region Target | Antisense Strand/ Guide Strand Sequence (5'-3') | SEQ ID NO: | Sense strand/ Passenger Strand Sequence (5'-3') | SEQ ID NO: |
|---|---|---|---|---|---|---|
| 1205_1225 | 5 | CDS | CCAGCAUGCCGGCUUCCGCGG | 1 | CCGCGGAAGCCGGCAUGCUGG | 103 |
| 1206_1226 | 5 | CDS | UCCAGCAUGCCGGCUUCCGCG | 2 | CGCGGAAGCCGGCAUGCUGGA | 104 |
| 1207_1227 | 5 | CDS | CUCCAGCAUGCCGGCUUCCGC | 3 | GCGGAAGCCGGCAUGCUGGAG | 105 |
| 1209_1229 | 5 | CDS | UUCUCCAGCAUGCCGGCUUCC | 4 | GGAAGCCGGCAUGCUGGAGAA | 106 |
| 1210_1230 | 5 | CDS | CUUCUCCAGCAUGCCGGCUUC | 5 | GAAGCCGGCAUGCUGGAGAAG | 107 |

TABLE 10-continued

| Target site on transcript NM_016203.4 | Exon | Region Target | Antisense Strand/ Guide Strand Sequence (5'-3') | SEQ ID NO: | Sense strand/ Passenger Strand Sequence (5'-3') | SEQ ID NO: |
|---|---|---|---|---|---|---|
| 1211_1231 | 5 | CDS | GCUUCUCCAGCAUGCCGGCUU | 6 | AAGCCGGCAUGCUGGAGAAGC | 108 |
| 1212_1232 | 5 | CDS | AGCUUCUCCAGCAUGCCGGCU | 7 | AGCCGGCAUGCUGGAGAAGCU | 109 |
| 1213_1233 | 5 | CDS | CAGCUUCUCCAGCAUGCCGGC | 8 | GCCGGCAUGCUGGAGAAGCUG | 110 |
| 1279_1299 | 6 | CDS | GUGUGACCUCAUGAAUCGCAU | 9 | AUGCGAUUCAUGAGGUCACAC | 111 |
| 1280_1300 | 6 | CDS | UGUGUGACCUCAUGAAUCGCA | 10 | UGCGAUUCAUGAGGUCACACA | 112 |
| 1281_1301 | 6 | CDS | UUGUGUGACCUCAUGAAUCGC | 11 | GCGAUUCAUGAGGUCACACAA | 113 |
| 1282_1302 | 6 | CDS | CUUGUGUGACCUCAUGAAUCG | 12 | CGAUUCAUGAGGUCACACAAG | 114 |
| 1283_1303 | 6 | CDS | ACUUGUGUGACCUCAUGAAUC | 13 | GAUUCAUGAGGUCACACAAGU | 115 |
| 1284_1304 | 6 | CDS | CACUUGUGUGACCUCAUGAAU | 14 | AUUCAUGAGGUCACACAAGUG | 116 |
| 1285_1305 | 6 | CDS | ACACUUGUGUGACCUCAUGAA | 15 | UUCAUGAGGUCACACAAGUGU | 117 |
| 1287_1307 | 6 | CDS | UAACACUUGUGUGACCUCAUG | 16 | CAUGAGGUCACACAAGUGUUA | 118 |
| 1289_1309 | 6 | CDS | CAUAACACUUGUGUGACCUCA | 17 | UGAGGUCACACAAGUGUUAUG | 119 |
| 1290_1310 | 6 | CDS | UCAUAACACUUGUGUGACCUC | 18 | GAGGUCACACAAGUGUUAUGA | 120 |
| 1293_1313 | 6 | CDS | AUGUCAUAACACUUGUGUGAC | 19 | GUCACACAAGUGUUAUGACAU | 121 |
| 1296_1316 | 6 | CDS | ACGAUGUCAUAACACUUGUGU | 20 | ACACAAGUGUUAUGACAUCGU | 122 |
| 1297_1317 | 6 | CDS | AACGAUGUCAUAACACUUGUG | 21 | CACAAGUGUUAUGACAUCGUU | 123 |
| 1298_1318 | 6 | CDS | GAACGAUGUCAUAACACUUGU | 22 | ACAAGUGUUAUGACAUCGUUC | 124 |
| 1300_1320 | 6 | CDS | UGGAACGAUGUCAUAACACUU | 23 | AAGUGUUAUGACAUCGUUCCA | 125 |
| 1301_1321 | 6 | CDS | UUGGAACGAUGUCAUAACACU | 24 | AGUGUUAUGACAUCGUUCCAA | 126 |
| 1302_1322 | 6 | CDS | GUUGGAACGAUGUCAUAACAC | 25 | GUGUUAUGACAUCGUUCCAAC | 127 |
| 1303_1323 | 6 | CDS | GGUUGGAACGAUGUCAUAACA | 26 | UGUUAUGACAUCGUUCCAACC | 128 |
| 1304_1324 | 6 | CDS | UGGUUGGAACGAUGUCAUAAC | 27 | GUUAUGACAUCGUUCCAACCA | 129 |
| 1305_1325 | 6 | CDS | CUGGUUGGAACGAUGUCAUAA | 28 | UUAUGACAUCGUUCCAACCAG | 130 |
| 1306_1326 | 6 | CDS | ACUGGUUGGAACGAUGUCAUA | 29 | UAUGACAUCGUUCCAACCAGU | 131 |
| 1307_1327 | 6 | CDS | AACUGGUUGGAACGAUGUCAU | 30 | AUGACAUCGUUCCAACCAGUU | 132 |
| 1308_1328 | 6 | CDS | GAACUGGUUGGAACGAUGUCA | 31 | UGACAUCGUUCCAACCAGUUC | 133 |
| 1309_1329 | 6 | CDS | UGAACUGGUUGGAACGAUGUC | 32 | GACAUCGUUCCAACCAGUUCA | 134 |
| 1310_1330 | 6 | CDS | UUGAACUGGUUGGAACGAUGU | 33 | ACAUCGUUCCAACCAGUUCAA | 135 |
| 1311_1331 | 6 | CDS | UUUGAACUGGUUGGAACGAUG | 34 | CAUCGUUCCAACCAGUUCAAA | 136 |
| 1312_1332 | 6 | CDS | CUUUGAACUGGUUGGAACGAU | 35 | AUCGUUCCAACCAGUUCAAAG | 137 |
| 1313_1333 | 6 | CDS | GCUUUGAACUGGUUGGAACGA | 36 | UCGUUCCAACCAGUUCAAAGC | 138 |
| 1314_1334 | 6 | CDS | AGCUUUGAACUGGUUGGAACG | 37 | CGUUCCAACCAGUUCAAAGCU | 139 |
| 1316_1336 | 6 | CDS | CAAGCUUUGAACUGGUUGGAA | 38 | UUCCAACCAGUUCAAAGCUUG | 140 |
| 1317_1337 | 6 | CDS | ACAAGCUUUGAACUGGUUGGA | 39 | UCCAACCAGUUCAAAGCUUGU | 141 |
| 1654_1674 | 11 | CDS | CCCACUGAUAGGGUCAAUAAC | 40 | GUUAUUGACCCUAUCAGUGGG | 142 |
| 1655_1675 | 11 | CDS | UCCCACUGAUAGGGUCAAUAA | 41 | UUAUUGACCCUAUCAGUGGGA | 143 |
| 1656_1676 | 11 | CDS | UUCCCACUGAUAGGGUCAAUA | 42 | UAUUGACCCUAUCAGUGGGAA | 144 |
| 1695_1715 | 11 | CDS | AACUUGAGGAUUCUUUUGUGG | 43 | CCACAAAAGAAUCCUCAAGUU | 145 |

TABLE 10-continued

| Target site on transcript NM_016203.4 | Exon | Region Target | Antisense Strand/ Guide Strand Sequence (5'-3') | SEQ ID NO: | Sense strand/ Passenger Strand Sequence (5'-3') | SEQ ID NO: |
|---|---|---|---|---|---|---|
| 1700_1720 | 11 | CDS | GGAGGAACUUGAGGAUUCUUU | 44 | AAAGAAUCCUCAAGUUCCUCC | 146 |
| 1709_1729 | 11-12 | CDS | UAAAAAGCUGGAGGAACUUGA | 45 | UCAAGUUCCUCCAGCUUUUUA | 147 |
| 1712_1732 | 11-12 | CDS | ACAUAAAAAGCUGGAGGAACU | 46 | AGUUCCUCCAGCUUUUUAUGU | 148 |
| 1713_1733 | 11-12 | CDS | GACAUAAAAAGCUGGAGGAAC | 47 | GUUCCUCCAGCUUUUUAUGUC | 149 |
| 1714_1734 | 11-12 | CDS | AGACAUAAAAAGCUGGAGGAA | 48 | UUCCUCCAGCUUUUUAUGUCU | 150 |
| 1741_1761 | 12 | CDS | CUUCAUGAAGGCAGGCUUUGG | 49 | CCAAAGCCUGCCUUCAUGAAG | 151 |
| 1750_1770 | 12 | CDS | CAGGUUCUGCUUCAUGAAGGC | 50 | GCCUUCAUGAAGCAGAACCUG | 152 |
| 1752_1772 | 12 | CDS | UCCAGGUUCUGCUUCAUGAAG | 51 | CUUCAUGAAGCAGAACCUGGA | 153 |
| 1753_1773 | 12 | CDS | AUCCAGGUUCUGCUUCAUGAA | 52 | UUCAUGAAGCAGAACCUGGAU | 154 |
| 1758_1778 | 12 | CDS | AGCUCAUCCAGGUUCUGCUUC | 53 | GAAGCAGAACCUGGAUGAGCU | 155 |
| 1759_1779 | 12 | CDS | AAGCUCAUCCAGGUUCUGCUU | 54 | AAGCAGAACCUGGAUGAGCUU | 156 |
| 1760_1780 | 12 | CDS | CAAGCUCAUCCAGGUUCUGCU | 55 | AGCAGAACCUGGAUGAGCUUG | 157 |
| 1761_1781 | 12 | CDS | CCAAGCUCAUCCAGGUUCUGC | 56 | GCAGAACCUGGAUGAGCUUGG | 158 |
| 1884_1904 | 12-13 | CDS | ACAACUUUUCCUGACUCAUCC | 57 | GGAUGAGUCAGGAAAAGUUGU | 159 |
| 1885_1905 | 12-13 | CDS | UACAACUUUUCCUGACUCAUC | 58 | GAUGAGUCAGGAAAAGUUGUA | 160 |
| 1886_1906 | 12-13 | CDS | CUACAACUUUUCCUGACUCAU | 59 | AUGAGUCAGGAAAAGUUGUAG | 161 |
| 1889_1909 | 12-13 | CDS | UAUCUACAACUUUUCCUGACU | 60 | AGUCAGGAAAAGUUGUAGAUA | 162 |
| 1897_1917 | 13 | CDS | GGAAUAAAUAUCUACAACUUU | 61 | AAAGUUGUAGAUAUUUAUUCC | 163 |
| 1898_1918 | 13 | CDS | UGGAAUAAAUAUCUACAACUU | 62 | AAGUUGUAGAUAUUUAUUCCA | 164 |
| 1899_1919 | 13 | CDS | UUGGAAUAAAUAUCUACAACU | 63 | AGUUGUAGAUAUUUAUUCCAA | 165 |
| 1921_1941 | 13-14 | CDS | AGCAAGAUUAAUUACAUCAAA | 64 | UUUGAUGUAAUUAAUCUUGCU | 166 |
| 1927_1947 | 13-14 | CDS | CUCAGCAGCAAGAUUAAUUAC | 65 | GUAAUUAAUCUUGCUGCUGAG | 167 |
| 1928_1948 | 13-14 | CDS | UCUCAGCAGCAAGAUUAAUUA | 66 | UAAUUAAUCUUGCUGCUGAGA | 168 |
| 1929_1949 | 13-14 | CDS | UUCUCAGCAGCAAGAUUAAUU | 67 | AAUUAAUCUUGCUGCUGAGAA | 169 |
| 1931_1951 | 13-14 | CDS | UUUUCUCAGCAGCAAGAUUAA | 68 | UUAAUCUUGCUGCUGAGAAAA | 170 |
| 2148_2168 | 15 | CDS | GGUGUGAGGAUCAGGGCUUGC | 69 | GCAAGCCCUGAUCCUCACACC | 171 |
| 2149_2169 | 15 | CDS | UGGUGUGAGGAUCAGGGCUUG | 70 | CAAGCCCUGAUCCUCACACCA | 172 |
| 2155_2175 | 15-16 | CDS | ACCUGCUGGUGUGAGGAUCAG | 71 | CUGAUCCUCACACCAGCAGGU | 173 |
| 2203_2223 | 16 | 3'UTR-CDS | CGUCUACAUUCACGGCGGUCA | 72 | UGACCGCCGUGAAUGUAGACG | 174 |
| 2204_2224 | 16 | 3'UTR-CDS | GCGUCUACAUUCACGGCGGUC | 73 | GACCGCCGUGAAUGUAGACGC | 175 |
| 2205_2225 | 16 | 3'UTR-CDS | GGCGUCUACAUUCACGGCGGU | 74 | ACCGCCGUGAAUGUAGACGCC | 176 |
| 2206_2226 | 16 | 3'UTR | GGGCGUCUACAUUCACGGCGG | 75 | CCGCCGUGAAUGUAGACGCCC | 177 |
| 2267_2287 | 16 | 3'UTR | UUGCAGCCAGUGUUCAUGAGG | 76 | CCUCAUGAACACUGGCUGCAA | 178 |
| 2367_2387 | 16 | 3'UTR | CUGAAUCUUCAAGCACAUAAA | 77 | UUUAUGUGCUUGAAGAUUCAG | 179 |
| 2368_2388 | 16 | 3'UTR | CCUGAAUCUUCAAGCACAUAA | 78 | UUAUGUGCUUGAAGAUUCAGG | 180 |
| 2369_2389 | 16 | 3'UTR | GCCUGAAUCUUCAAGCACAUA | 79 | UAUGUGCUUGAAGAUUCAGGC | 181 |
| 2370_2390 | 16 | 3'UTR | AGCCUGAAUCUUCAAGCACAU | 80 | AUGUGCUUGAAGAUUCAGGCU | 182 |
| 2434_2454 | 16 | 3'UTR | ACUUUAAUGACAUACAGCAUU | 81 | AAUGCUGUAUGUCAUUAAAGU | 183 |

TABLE 10-continued

| Target site on transcript NM_016203.4 | Exon | Region Target | Antisense Strand/ Guide Strand Sequence (5'-3') | SEQ ID NO: | Sense strand/ Passenger Strand Sequence (5'-3') | SEQ ID NO: |
|---|---|---|---|---|---|---|
| 2436_2456 | 16 | 3'UTR | GCACUUUAAUGACAUACAGCA | 82 | UGCUGUAUGUCAUUAAAGUGC | 184 |
| 2440_2460 | 16 | 3'UTR | CAGUGCACUUUAAUGACAUAC | 83 | GUAUGUCAUUAAAGUGCACUG | 185 |
| 2441_2461 | 16 | 3'UTR | ACAGUGCACUUUAAUGACAUA | 84 | UAUGUCAUUAAAGUGCACUGU | 186 |
| 2442_2462 | 16 | 3'UTR | CACAGUGCACUUUAAUGACAU | 85 | AUGUCAUUAAAGUGCACUGUG | 187 |
| 2443_2463 | 16 | 3'UTR | ACACAGUGCACUUUAAUGACA | 86 | UGUCAUUAAAGUGCACUGUGU | 188 |
| 2444_2464 | 16 | 3'UTR | GACACAGUGCACUUUAAUGAC | 87 | GUCAUUAAAGUGCACUGUGUC | 189 |
| 2445_2465 | 16 | 3'UTR | GGACACAGUGCACUUUAAUGA | 88 | UCAUUAAAGUGCACUGUGUCC | 190 |
| 2446_2466 | 16 | 3'UTR | AGGACACAGUGCACUUUAAUG | 89 | CAUUAAAGUGCACUGUGUCCU | 191 |
| 2447_2467 | 16 | 3'UTR | CAGGACACAGUGCACUUUAAU | 90 | AUUAAAGUGCACUGUGUCCUG | 192 |
| 2448_2468 | 16 | 3'UTR | UCAGGACACAGUGCACUUUAA | 91 | UUAAAGUGCACUGUGUCCUGA | 193 |
| 3170_3190 | 16 | 3'UTR | AGUGUCAACAUUUUCAGAGCA | 92 | UGCUCUGAAAAUGUUGACACU | 194 |
| 1205_1223 | 5 | CDS | AGCAUGCCGGCUUCCGCGG | 93 | CCGCGGAAGCCGGCAUGCU | 195 |
| 1206_1224 | 5 | CDS | CAGCAUGCCGGCUUCCGCG | 94 | CGCGGAAGCCGGCAUGCUG | 196 |
| 1207_1225 | 5 | CDS | CCAGCAUGCCGGCUUCCGC | 95 | GCGGAAGCCGGCAUGCUGG | 197 |
| 1305_1323 | 6 | CDS | GGUUGGAACGAUGUCAUAA | 96 | UUAUGACAUCGUUCCAACC | 198 |
| 1307_1325 | 6 | CDS | CUGGUUGGAACGAUGUCAU | 97 | AUGACAUCGUUCCAACCAG | 199 |
| 1308_1326 | 6 | CDS | ACUGGUUGGAACGAUGUCA | 98 | UGACAUCGUUCCAACCAGU | 200 |
| 1309_1327 | 6 | CDS | AACUGGUUGGAACGAUGUC | 99 | GACAUCGUUCCAACCAGUU | 201 |
| 1310_1328 | 6 | CDS | GAACUGGUUGGAACGAUGU | 100 | ACAUCGUUCCAACCAGUUC | 202 |
| 2205_2223 | 16 | 3'UTR-CDS | CGUCUACAUUCACGGCGGU | 101 | ACCGCCGUGAAUGUAGACG | 203 |
| 2206_2224 | 16 | 3'UTR | GCGUCUACAUUCACGGCGG | 102 | CCGCCGUGAAUGUAGACGC | 204 |

Example 2: In Vitro Evaluation of PRKAG2 siRNAs in Transfected Hs iPS-Cardiomyocytes

Materials and Methods siRNA Sequence and Synthesis

All single strand nucleotides for siRNA synthesis were synthesized following standard solid phase synthesis methods on a MerMade12 synthesizer. Standard 2'-O-methyl-base loaded (A/C/G/U) and Universal CPG 1000A0 solid support were used and phosphoramidites (2'-O-methyl, 2'-MOE, 2'-fluoro, 2'-deoxy, LNA) were dissolved in anhydrous acetonitrile to make 0.1M. 3% Trichloroacetic Acid in Dichloromethane, 0.25M 5-ethylthio Tetrazole in acetonitrile were used as deblock reagent and activation reagent respectively. 0.02M Iodine in pyridine/THF/H2O was used as oxidation reagent and 0.05M (dimethylamino-methylidene)amino)-3H-1,2,4-dithiazoline-3-thione (DDTT) in pyridine/acetonitrile was used as sulfurizing reagent. Acetic Anhydride/THF/2,6-Lutidine (Cap A) and 16% N-Methylimidazole in THF (Cap B) were used as capping reagents. Phosphoryl guanidine (PG) sequences were prepared by replacing the oxidation reagent with 0.25M 2-Azido-1,3-dimethylimidazolinium Hexafluorophosphate in acetonitrile/toluene. After synthesis, solid supports were dried and incubated in Ammonium Hydroxide/40% aqueous Methylamine solution (AMA) for 2 hours at room temperature. The CPG was filtered out and washed with Water/Methanol and the combined filtrate was concentrated under vacuum.

Figure 11:
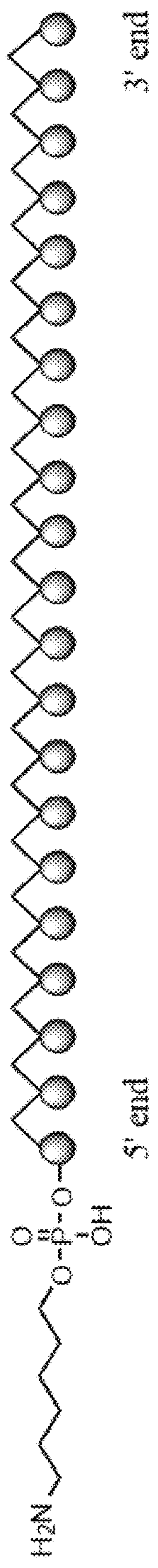
FIG. 11 shows a representative structure of an siRNA passenger strand with a C6-$NH_2$ conjugation handle at the 5' end.
Figure 12:
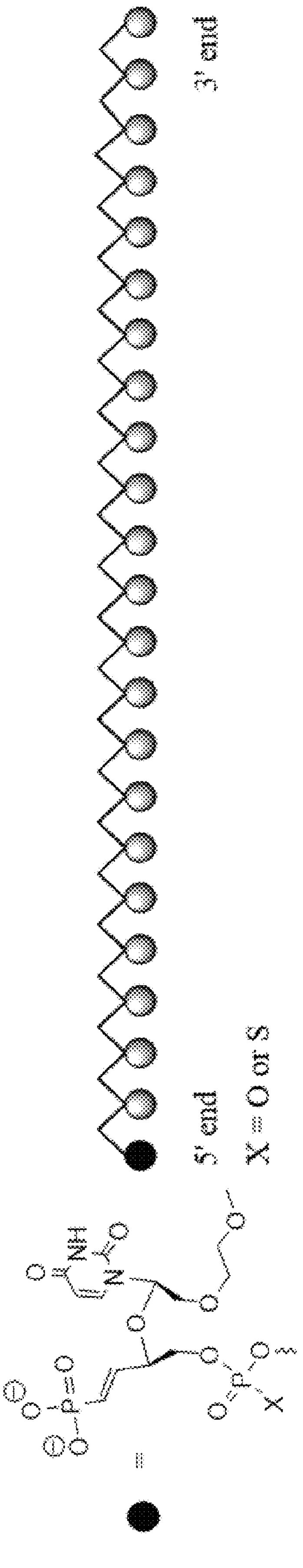
FIG. 12 shows a representative structure of an siRNA guide strand with a 5' (E) vinyl phosphonate.

Purified single strands were duplexed to make double stranded siRNA. siRNA passenger strands were synthesized with or without a C6-NH2 conjugation handle at the 5'end, attached through a phosphodiester linkage. siRNA guide strands were synthesized with or without a 5'-(E)-vinyl phosphonate modified nucleotide. FIG. 11 and FIG. 12 show representative structures of the formats used for in-vivo experiments.

Cholesterol-PRKAG2 siRNA Conjugate

The sequence of the guide/antisense strand was complementary to the gene sequence starting a base position 1897 for the human mRNA transcript for PRKAG2 (GGAAUAAAUAUCUACAACUUU; SEQ ID NO: 61). Base, sugar and phosphate modifications were used to optimize the potency of the duplex and reduce immunogenicity. All siRNA single strands were fully assembled on solid phase using standard phosphoramidite chemistry and purified over HPLC. Purified single strands were duplexed to get the double stranded siRNA. Cholesterol was conjugated to the siRNA at the 5' end of the passenger strand.

Assay

Human iPS-cardiomyocytes-Version 2 (iCM2, Fujifilm-CDI, Cat #C1016, donor #01434) were thawed in Plating Media (PM, Fujifilm-CDI, Cat #M1001)) in gelatin pre-coated plates, at a cell density of 35.000 cells/well in 96-well plates. After 4 hours PM was gently aspirated and replaced with Maintenance Media (Fujifilm-CDI, Cat #M1003). Media change was performed every 2-3 days using Maintenance Media. Cells were cultured for 4 days before siRNA treatment was performed. siRNA transfection was performed using Lipofectamine-RNAiMax (ThermoFisher) and Optimem, according to manufacturer protocol. Transfected cells were incubated in 5% $CO_2$ at 37° C. for 3 or 14 days, then washed with phosphate-buffered saline (PBS), and harvested in 80 μl TRIzol (ThermoFisher) and stored at −80° C. RNA was prepared using a ZYMO 96-well RNA kit (ThermoFisher) and relative RNA expression levels quantified by RT-qPCR using commercially available TaqMan probes (LifeTechnology). Expression data were analyzed using the AACT method normalized to ASHA1, or GAPDH expression, and are presented as % KD relative to mock-transfected cells. Data were analyzed by nonlinear regression using a 3-parameter dose response inhibition function (GraphPad Prism 7.02). All knock down results present the maximal observed KD under these experimental conditions.

Results

All the 102 Human-mouse and NHP cross-reactive siPRKAG2 were tested in a primary in-vitro screening in Human iPS-cardiomyocytes2 (iCM2, Fujifilm-CDI) at 0.1 nM as shown in FIG. 1. A human siPRKAG2 commercially available from Dharmacon™ was used as positive control (Dh1) and a non-targeting siRNA was used as negative control (DhNT). As indicated by the 75% or 90% mRNA knock down (KD) in FIG. 1, several PRKAG2 siRNAs produced 75% or higher PRKAG2 mRNA knock down (KD) at 0.1 nM.

Example 3: In Vitro Evaluation of 13 PRKAG2 siRNAs in Transfected Hs iPS-Cardiomyocytes Materials and Methods The materials and methods are described in Example 2. Top performing siRNAs identified from the primary screening and concentration response in human iPSc-CM2, were validated in a human primary cardiomyocyte (ScienCell, Cat #6200) and mouse primary cardiomyocytes (ScienCell, Cat #6200-57) at 10 nM. A human siPRKAG2 commercially available (Dharmacon™) was used as positive control for human cells and as negative control for mouse cells, due to non-cross-reactivity with mouse. siScramble was used as negative control, and a human siPRKAG2 commercially available from Dharmacon was used as positive control. Two lower performing sequences identified in the primary screening were also tested (21 bp_Seq6 and 21 bp_Seq72).

Results

Figure 2:
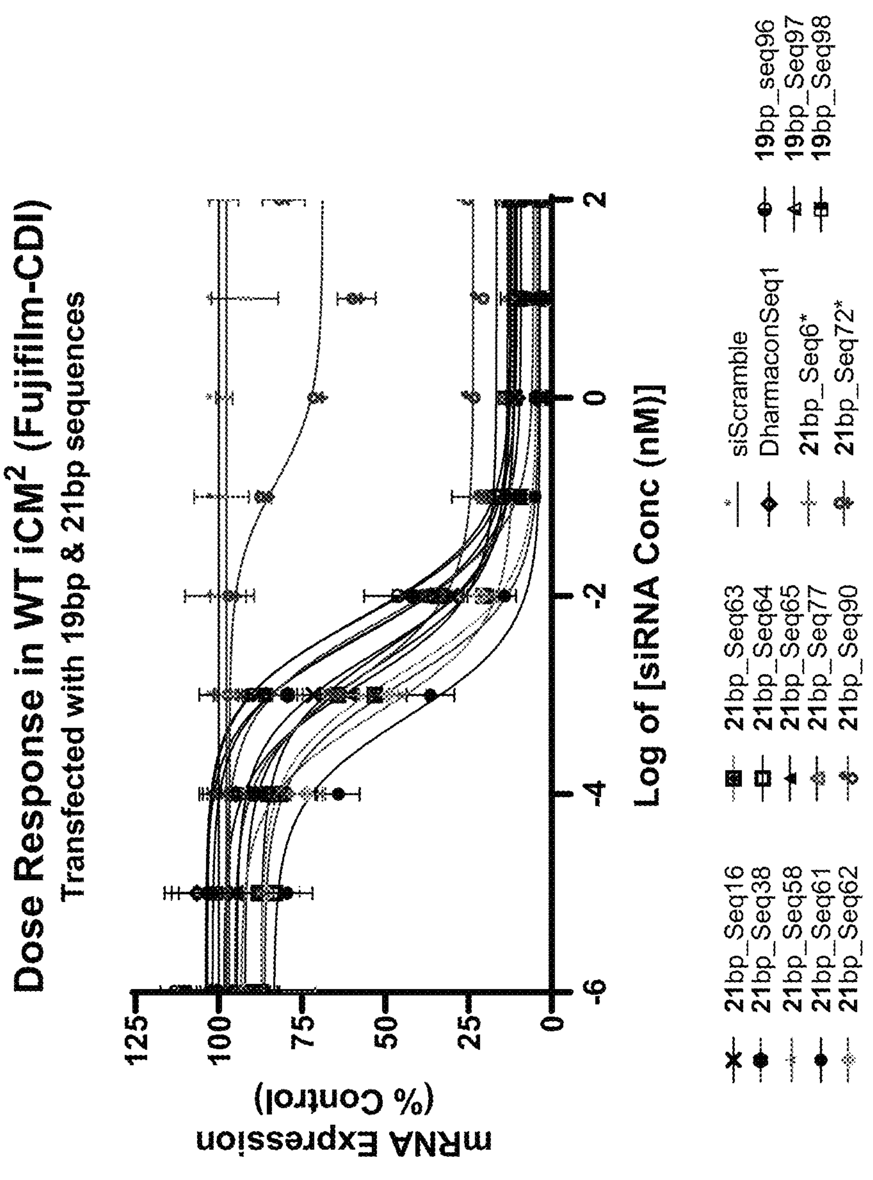
FIG. 2 is a plot showing a representative dose response curve of PRKAG2 mRNA expression levels in iCM2 cells transfected with increasing concentrations of the top 15 performing siRNA PRKAG2 sequences at 3 days post transfection.

The top 15 performing siPRKAG2 identified in the primary screening were tested in a concentration response, with 10-fold dilutions from 100 nM as shown in FIG. 2. All siRNAs have 100% complementarity with human, NHP and mouse transcripts. As shown in FIG. 2, concentration response experiments identified 6 potent siRNAs: siPRKAG2_Seq58 (guide strand base sequence: SEQ ID NO: 58), siPRKAG2_Seq61 (guide strand base sequence: SEQ ID NO: 61), siPRKAG2_Seq62 (guide strand base sequence: SEQ ID NO: 62), siPRKAG2_Seq64 (guide strand base sequence: SEQ ID NO: 64), siPRKAG2_Seq77 (guide strand base sequence: SEQ ID NO: 77), and siPRKAG2_Seq98 (guide strand base sequence: SEQ ID NO: 98) with IC50 on pico-Molar values. The description and activities of these 6 siRNA are summarized in Table TABLE 11.

TABLE 11

| SEQ ID NO: | Target site on transcript NM 016203.4 | Length of PS (bp) | Exon | Region Target | Guide Strand Sequence (5'-3') | IC50 (pM) | mRNA KD % (100 nM) |
|---|---|---|---|---|---|---|---|
| 58 | 1885_1905 | 21 | 12-13 | CDS | UACAACUUUUCC UGACUCAUC | 0.7 | 87.6% |
| 61 | 1897 1917 | 21 | 13 | CDS | GGAAUAAAUAUC UACAACUUU | 0.6 | 99.0% |
| 62 | 1898_1918 | 21 | 13 | CDS | UGGAAUAAAUAU CUACAACUU | 1.3 | 98.9% |
| 64 | 1921 1941 | 21 | 13-14 | CDS | AGCAAGAUUAAU UACAUCAAA | 2.8 | 87.8% |
| 77 | 2367 2387 | 21 | 16 | 3'UTR | CUGAAUCUUCAA GCACAUAAA | 1.3 | 85.7% |
| 98 | 1308 1326 | 19 | 6 | CDS | ACUGGUUGGAAC GAUGUCA | 3.8 | 87.7% |

Example 4: In Vitro Validation of Top 6 Performing siRNA in Mouse and Human Primary Cardiomyocytes

Materials and Methods

The experimental materials and methods are described in Example 2.

Results

Figure 3A:
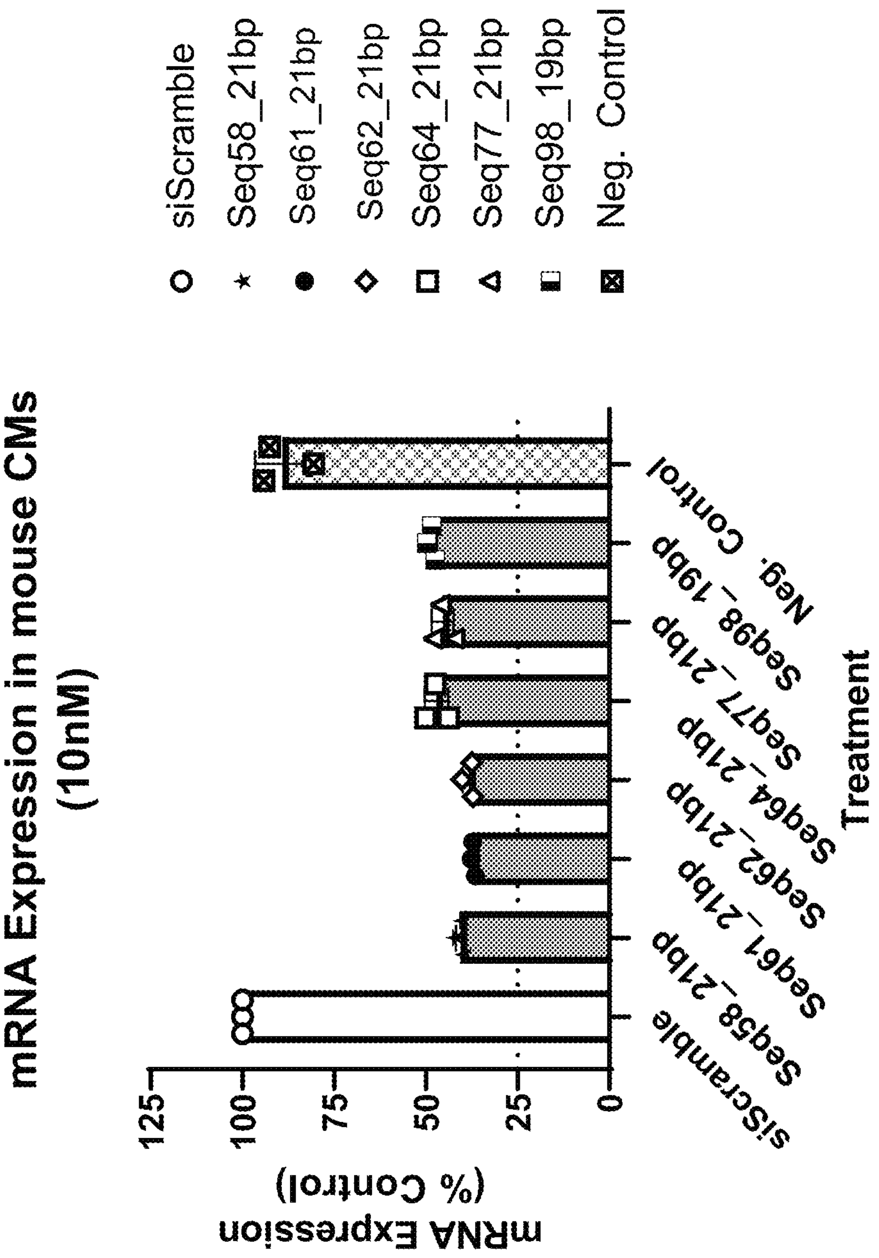
FIGS. 3A and 3B are representative bar graphs showing in vitro PRKAG2 mRNA expression levels in primary mouse cardiomyocytes (FIG. 3A) and primary human cardiomyocytes (FIG. 3B) transfected with PRKAG2 siRNA at a concentration of 10 nM 3 days post transfection.
Figure 3B:
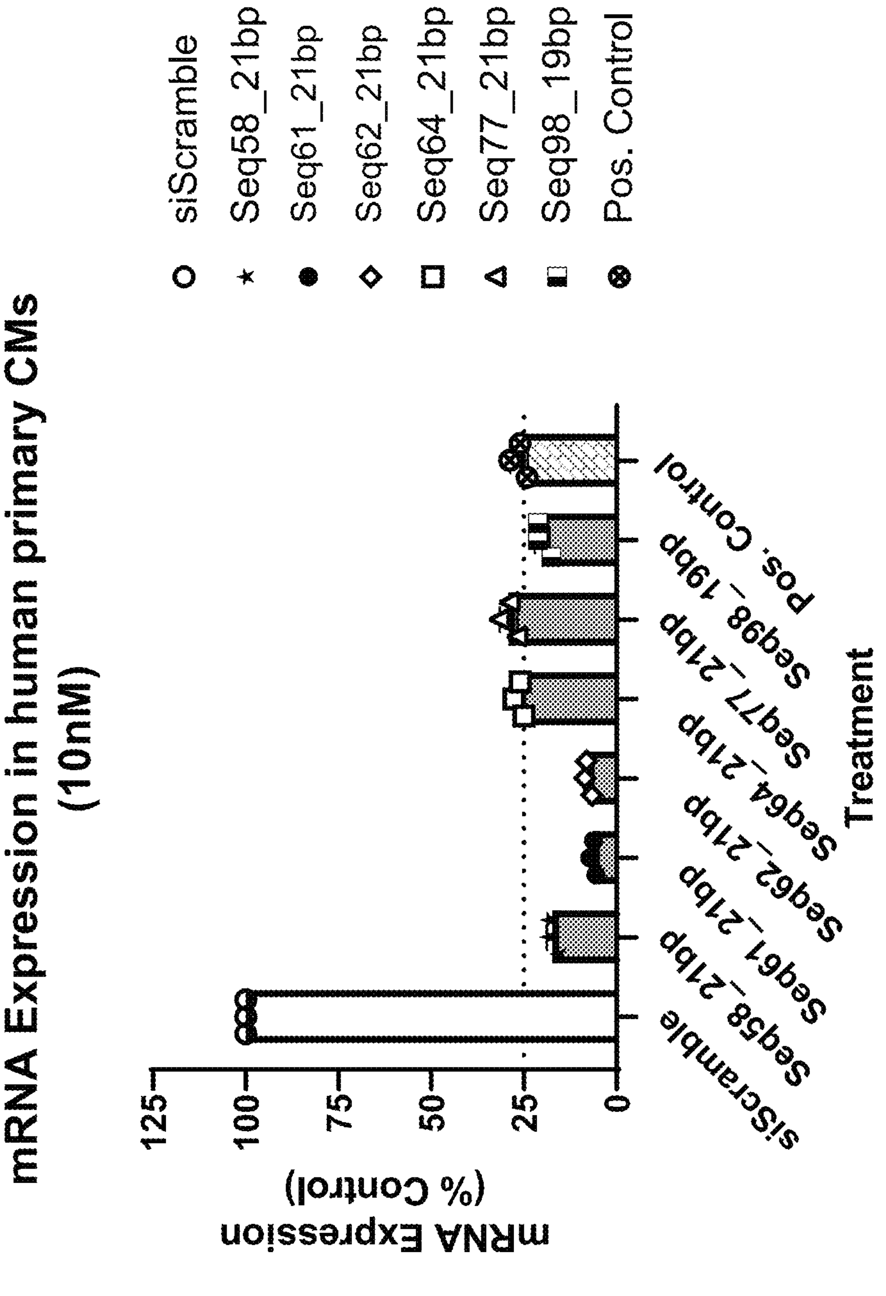

Top 6 performing siRNAs were assessed in mouse and human primary cardiomyocytes at 10 nM (FIGS. 3A and 3B). All 6 PRKAG2 siRNAs were able to knock down the expression of PRKAG2 mRNA in both primary cell types tested. The siRNAs showed greater activities in decreasing PRKAG2 mRNA levels in human primary cardiomyocytes than that of mouse primary cardiomyocytes.

Example 5: Conjugate Synthesis

Anti-Human Transferrin Receptor Antibody

Anti-human transferrin receptor antibody is a human IgG1 monoclonal antibody that binds to the human transferrin receptor 1. The antibody was produced as described in U.S. Pat. No. 10,913,800.

Anti-Mouse Transferrin Receptor Antibody

Anti-mouse transferrin receptor antibody or CD71 mAb is a rat IgG2a subclass monoclonal antibody that binds mouse CD71 or mouse transferrin receptor 1 (mTfR1). The antibody was produced by BioXcell and it is commercially available (Catalog #BE0175).

IgG2a Isotype Control Antibody

Rat IgG2a isotype control antibody was purchased from BioXcell (Clone 2A3, Catalog #BE0089). This antibody is specific to trinitrophenol and does not have any known antigens in mouse.

AOC Synthesis

Antibody cys-MCC-siRNA Conjugation by random cysteine conjugation siRNAs were synthesized on a solid support made of controlled pore glass (CPG) employing the conventional phosphoramidite oligomerization chemistry and purified by high-performance liquid chromatography (HPLC). The passenger strand of the siRNA used for conjugation was synthesized with a C6 amino linker at the 5'-end. Functionalized siRNA (maleimide Linker-siRNA) was obtained by the reaction of linker with siRNA in slightly basic conditions (pH 7.4) in 50% DMSO for 30 min at room temperature, and reaction completion was confirmed by MS. Excess linker and DMSO were removed by spin filtration using AMICON 3K MWCO filters or TFF and buffer exchange with pH 6 sodium acetate buffer. PRKAG2 AOC was generated using a standard random cysteine conjugation method of murine anti-TfR1 monoclonal antibody and PRKAG2 targeted siRNA. In practice, the interchain disulfides of the antibody are partially and mildly reduced with TCEP tris(2-carboxyethyl)phosphine) to reveal cysteines that are highly and selectively reactive with the maleimide linker on the siRNA. This reaction forms a covalent link between the two advanced intermediates. The remaining thiols were capped with N-ethylmaleimide (NEM) prior to purification.

The reaction mixture was purified using strong anion exchange chromatography (SAX) to separate unreacted Ab, a drug-antibody ratio (DAR) species (i.e., one siRNA per antibody is DAR1), and excess siRNA. DAR1 AOC and DAR2 AOC fractions were collected, concentrated, buffer exchanged into PBS, and sterile filtered using a 0.2 μm filter.

Step 1: Antibody Interchain Disulfide Reduction with TCEP and Conjugation

The reduced antibody was made by adding 2 mM EDTA and 4 equivalents of TCEP in PBS to a solution of antibody in PBS or 20 mM Histidine, 145 mM NaCl, and pH 6 buffer. This solution was incubated for 4 hours at 37° C. To the reduced antibody solution, 1.1 eq of MCC-C6-siRNA was added. Analysis of the reaction mixture by analytical SAX column chromatography showed antibody-siRNA conjugate along with unreacted antibody and siRNA.

Step 2: Purification

The crude reaction mixture was purified by AKTA Pure FPLC using strong anion exchange chromatography method-1. Fractions containing DART and DAR>2 antibody-siRNA conjugates were separated, concentrated, buffer exchanged with pH 7.2 PBS, and sterile filtered using 0.2 μm filters.

Step 3: Analysis of the Purified Conjugate

The isolated conjugates were characterized by SEC, SAX chromatography. The purity of the conjugate was assessed by analytical HPLC using either anion exchange chromatography method-2 or anion exchange chromatography method-3 as described herein. Isolated DART conjugates are typically eluted at 9.0±0.3 min on analytical SAX method and are greater than 90% pure. The typical DAR>2 cysteine conjugate contains more than 90% DAR2 and less than 10% DAR3.

Fab' Generation from mAb and Conjugation to siRNA

Figure 13:
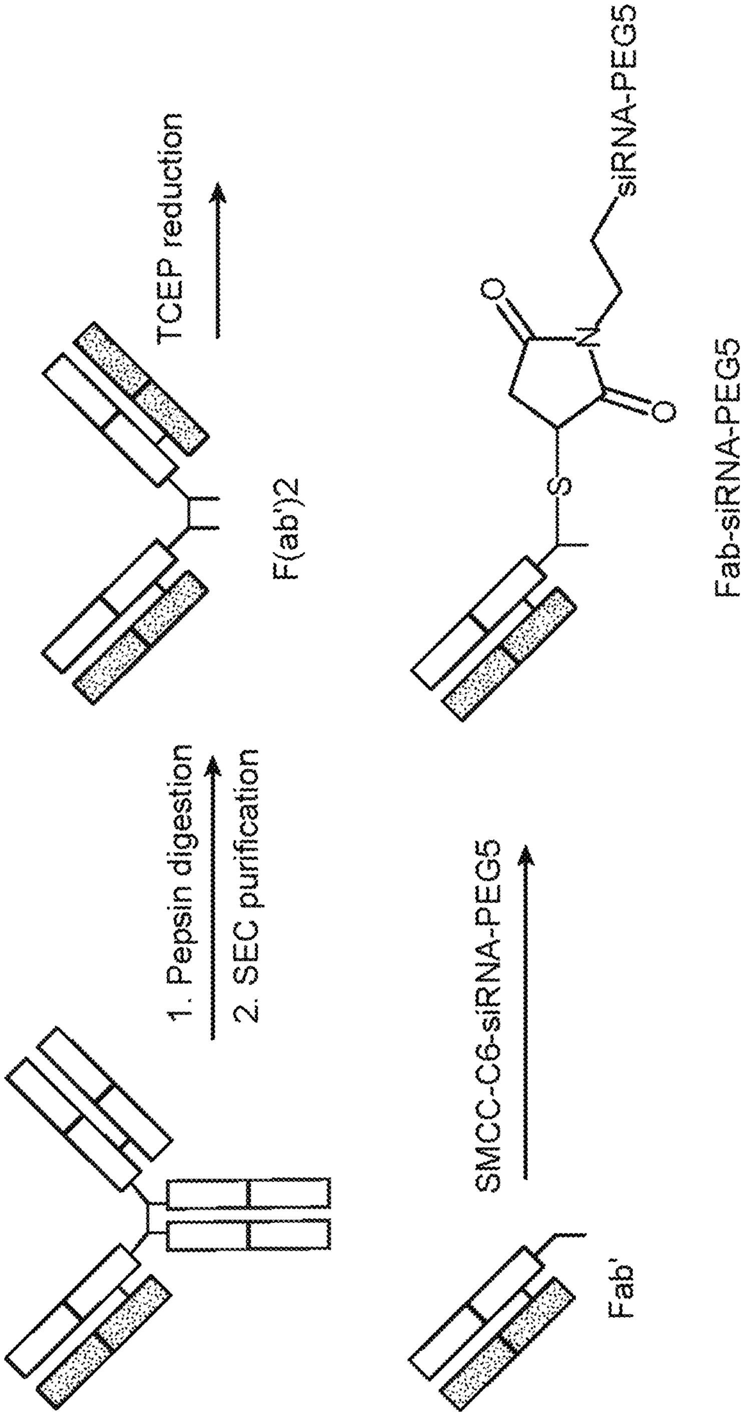
FIG. 13 shows a representative structure of Scheme-3: Fab-siRNA conjugate generation.

Scheme of Fab'-siRNA conjugate is described in FIG. 13.

The antibody was buffer exchanged with pH 4.0, 20 mM sodium acetate/acetic acid buffer and made up to 5 mg/ml concentration. Immobilized pepsin (Thermo Scientific, Prod #20343) was added and incubated for 3 hours at 37° C. The reaction mixture was filtered using 30 kDa MWCO Amicon spin filters and pH 7.4 PBS. The retentate was collected and purified using size exclusion chromatography to isolate F(ab')2. The collected F(ab')2 was then reduced by 10 equivalents of TCEP and conjugated with SMCC-C6-siRNA-PEG5 at room temperature in pH 7.4 PBS. Analysis of reaction mixture on SAX chromatography showed Fab-siRNA conjugate along with unreacted Fab and siRNA-PEG. Fab Oligonucleotide Conjugate Synthesis Method (FabOC)

Step 1: Fab Expression

FabOC antibody fragments were synthesized in-house using CHO or HEK293 expression and purified by protein L.

The sequences of the FabOC antibody fragments of human a-TfR1 antibody are provided in Table 12.

TABLE 12

| Compound | SEQ ID NO: | Sequence |
|---|---|---|
| FabOC peptide | 205 | MEWSWVFLFFLSVTTGVHSQVQLVQSGAEVKKPGASVKVSCKASG YTFTNYWMHWVRQAPGQGLEWMGEINPINGRSNYAQKFQGRVTLT VDTSISTAYMELSRLRSDDTAVYYCARGTRAMHYWGQGTLVTVSS ASTKGPSVFPLAPSSKSTSGGTAALGCLVKDYFPEPVTVSWNSGA |

TABLE 12-continued

| Compound | SEQ ID NO: | Sequence |
|---|---|---|
| | | LTSGVHTFPAVLQSSGLYSLSSVVTVPSSSLGTQTYICNVNHKPS NTKVDKRVEPKSCDKTHTCG |
| FabOC nucleotide | 206 | ATGGAATGGTCATGGGTTTTTTTGTTTTTCCTCTCAGTTACGACT GGTGTCCATAGCCAAGTCCAACTGGTGCAGTCCGGTGCGGAGGTT AAGAAGCCCGGAGCGAGCGTAAAGGTGAGTTGTAAAGCGAGTGGA TACACGTTCACGAACTATTGGATGCATTGGGTTCGACAAGCACCG GGTCAGGGACTTGAGTGGATGGGAGAAATTAATCCGATTAACGGT CGCAGTAACTATGCGCAGAAATTCCAAGGCCGAGTAACTCTCACC GTGGACACGTCCATCTCTACAGCGTACATGGAACTCAGCAGGTTG CGCTCTGACGATACCGCAGTTTATTATTGCGCGCGAGGGACGCGG GCTATGCACTATTGGGGGCAGGGCACCCTCGTCACCGTATCATCT GCGAGTACGAAGGGACCTTCTGTGTTCCCATTGGCTCCCAGCAGC AAAAGTACCAGTGGTGGAACAGCTGCGCTTGGATGCCTGGTGAAA GATTATTTCCCCGAGCCGGTGACAGTCAGCTGGAACAGCGGCGCA CTCACCAGCGGTGTACATACGTTCCCGGCGGTTTTGCAATCTAGT GGCCTCTATTCCCTTAGTTCCGTAGTTACCGTCCCATCTTCAAGC CTCGGAACCCAGACTTACATCTGCAACGTCAATCATAAGCCCAGT AACACAAAAGTTGATAAGAGAGTAGAGCCGAAATCCTGTGATAAG ACCCACACATGTGGG |
| Light chain peptide | 207 | MSVPTQVLGLLLLWLTDARCDIQMTQSPSSLSASVGDRVTITCRT SENIYNNLAWYQQKPGKAPKLLIYAATNLAEGVPSRFSGSGSGTD YTLTISSLQPEDFATYYCQHFWGTPLTFGGGTKVEIKRTVAAPSV FIFPPSDEQLKSGTASVVCLLNNFYPREAKVQWKVDNALQSGNSQ ESVTEQDSKDSTYSLSSTLTLSKADYEKHKVYACEVTHQGLSSPV TKSFNRGEC |
| Light chain nucleotide | 208 | GCCTCCGGACTCTAGAGCCGCCACCATGAGCGTACCAACCCAGGT GCTCGGACTCCTGTTGTTGTGGCTCACCGATGCAAGATGCGATAT ACAAATGACACAAAGCCCAAGTAGTTTGTCAGCCAGCGTAGGGGA TAGAGTTACTATAACTTGCCGAACGTCTGAAAATATATATAATAA CCTCGCGTGGTACCAGCAGAAGCCCGGCAAGGCCCCTAAACTCCT CATTTATGCAGCTACTAACCTCGCTGAAGGAGTACCATCAAGGTT CTCAGGCAGCGGGTCTGGAACTGACTACACATTGACTATTTCAAG CCTTCAGCCAGAGGACTTCGCTACATACTACTGTCAACACTTCTG GGGGACTCCGCTTACTTTCGGAGGCGGTACCAAAGTGGAGATAAA ACGGACGGTTGCTGCTCCGAGCGTTTTTATATTCCCGCCCTCTGA TGAACAGCTGAAATCAGGCACTGCGAGCGTTGTTTGCTTGCTGAA TAACTTTTACCCCCGCGAGGCGAAAGTACAATGGAAGGTAGACAA CGCACTGCAATCTGGGAATAGTCAAGAGAGTGTTACCGAACAAGA TTCAAAAGATTCCACTTATTCCCTTAGTTCTACTTTGACACTGAG CAAAGCAGATTACGAGAAACATAAGGTCTACGCCTGCGAGGTGAC GCACCAGGGCCTGAGCAGCCCAGTTACAAAGTCCTTCAATCGAGG TGAGTGTTAGGCGGCCGCTATAAGGGT |

Step 2: Fab Conjugation to Oligonucleotide

To the purified Fab, 2 mM of EDTA and 1 eq of TCEP in PBS was added. The solution was incubated at 37° C. for 4 hrs. Lyophilized siRNA was reconstituted in 50 mM PBS, pH 7.6 and pH adjusted to pH 7.2 followed by the addition of 8 equivalents of SMCC in DMSO. The reaction mixture was incubated at room temperature (RT) for 40 minutes. The SMCC activation was verified by mass spectrometry. The reaction mixture was treated and buffer exchanged with 10 mM Sodium Acetate buffer, pH 6.0 using 3K MWCO spin filters.

To the reduced Fab, 1 equivalent of SMCC activated siRNA solution was added and the reaction mixture was analyzed by analytical SAX.

Purification of FabOC

The crude reaction mixture was purified by AKTA explorerpure FPLC using anion exchange chromatography method-1. Fractions containing FabOC (DART and DAR2 Fab-siRNA conjugates) were separated, concentrated and buffer exchanged with pH 7.4 PBS.

Step 3: Analysis of the Purified FabOC

The characterization and purity of the isolated conjugate was assessed by analytical HPLC using anion exchange chromatography method-2 or 3 as well as by SEC method-1.

Purification and Analytical Methods

Anion Exchange Chromatography Method (SAX)-1

Column: Tosoh Bioscience, TSKGel SuperQ-5PW, 21.5 mm ID×15 cm, 13 μm

Solvent A: 20 mM TRIS buffer, pH 8.0; Solvent B: 20 mM TRIS, 1.5 M NaCl, pH 8.0;

Flow Rate: 6.0 ml/min

| Gradient: | | |
|---|---|---|
| % A | % B | Column Volume |
| 100 | 0 | 1.00 |
| 60 | 40 | 18.00 |
| 40 | 60 | 2.00 |
| 40 | 60 | 5.00 |
| 0 | 100 | 2.00 |
| 100 | 0 | 2.00 |

Anion Exchange Chromatography (SAX) Method-2

Column: Thermo Scientific, ProPac™ SAX-10, Bio LC™, 4×250 mm

Solvent A: 80% 10 mM TRIS pH 8, 20% ethanol; Solvent B: 80% 10 mM TRIS pH 8, 20% ethanol, 1.5 M NaCl;

Flow Rate: 0.75 ml/min

| Gradient: | | |
|---|---|---|
| Time | % A | % B |
| 0.0 | 90 | 10 |
| 3.00 | 90 | 10 |
| 11.00 | 40 | 60 |
| 13.00 | 40 | 60 |
| 15.00 | 90 | 10 |
| 20.00 | 90 | 10 |

Anion Exchange Chromatography (SAX) Method-3

Column: Thermo Scientific, ProPac™ SAX-10, Bio LC™, 4×250 mm

Solvent A: 80% 10 mM TRIS pH 8, 20% ethanol; Solvent B: 80% 10 mM TRIS pH 8, 20% ethanol, 1.5 M NaCl Flow Rate: 0.75 ml/min

| Gradient: | | |
|---|---|---|
| Time | % A | % B |
| 0.0 | 90 | 10 |
| 3.00 | 90 | 10 |
| 11.00 | 40 | 60 |
| 23.00 | 40 | 60 |
| 25.00 | 90 | 10 |
| 30.00 | 90 | 10 |

Size Exclusion Chromatography (SEC) Method-1

Column: TOSOH Biosciences, TSKgelG3000SW XL, 7.8×300 mm, 5 μM

Mobile phase: 150 mM phosphate buffer

Flow Rate: 1.0 ml/min for 15 mins

Example 6: Evaluation of Selected PRKAG2 siRNAs-AOCs in WT Mice

Materials and Methods

PRKAG2 siRNAs-AOCs

The synthesis and purification of the PRKAG2 siRNAs-AOCs are described in Example 5.

Animals

All animal studies were conducted following protocols in accordance with the Institutional Animal Care and Use Committee (IACUC) at Explora BioLabs, which adhere to the regulations outlined in the USDA Animal Welfare Act as well as the "Guide for the Care and Use of Laboratory Animals" (National Research Council publication, 8th Ed., revised in 2011). Mice were obtained from Charles River Laboratories or from Jackson Laboratories. Wild type $C_{57}$BL/6J or 57BL6NCrl mice (8-10 week old) were dosed via intravenous (iv) infusion with the indicated AOCs and doses.

qPCR mRNA Levels Evaluation in In Vivo Mouse

At scheduled take down day, hearts and gastrocnemius muscles were harvested and snap-frozen in liquid nitrogen. mRNA expression levels in target tissue was determined using a comparative qPCR assay. Total RNA was extracted from the tissue, reverse transcribed and mRNA levels were quantified using TaqMan qPCR, using the appropriately designed primers and probes. PPIB (housekeeping gene) was used as an internal RNA loading control, results were calculated by the comparative Ct method, where the difference between the target gene Ct value and the PPIB Ct value (ΔCt) is calculated and then further normalized relative to the PBS control group by taking a second difference (ΔΔCt).

Chemical Modification of siRNA

Top 6 performing siRNAs identified from the concentration response in in vitro, were synthesized using 7f.8s modifications and with and without VpUq chemical modifications as shown in in Table 13. As used herein, 7f.8s modifications refer a modification pattern of an antisense strand (guide strand): nsNfsnnnNfnnnnnnnNfnNfnnnnnsnsn (XosXfsXoXoXoXfXoXoXoXoXoXoXfXoXf XoXoXoXoXosXosXo), and sense strand (passenger strand): nsnsnnnnnnNfNfNfnnnnnnnnnsnsn (XosXosXoXoXoXoXoXoXfXfXfXoXoXoXoXoX oXoXosXosXo), where Xf or Nf refers to 2'-Fluoro modified nucleotide where X or N is any base, Fluorine at 2' position on ribose; Xo or n refers to 2'-O—$CH_3$ modified nucleotide, where X or n is any base and methylated oxygen at 2' position on ribose; s refers to phosphorothioate modification, phosphorothioate linkage between bases. In some instances, modified guide strand comprises U at the 5' end (e.g., VpUq or U). In some instances, such U replaces the 5' end nucleotides of the base sequence. In some instances, modified guide stranded includes an overhang sequence of "UU" or "dTdT" or "TT".

TABLE 13

| Compound | Modification Pattern | SEQ ID NO: | Base Antisense/ Guide Strand Sequence (5'-3') | SEQ ID NO: | ModifiedA ntisense/ Guide Strand Sequence (5'-3') | SEQ ID NO: | Modified Sense/ Passenger Strand Sequence (5'-3') |
|---|---|---|---|---|---|---|---|
| Seq58 (Seq58 - Vp) | 7f.8s | 58 | UACAACUUUUCC UGACUCAUC | 209 | UosAfsCoAoAoCfUoUoUoUoCoCoU oGfAoCfUoCoAoUoCosUosUo | 221 | (NH2C6)GosAosUoGoAo GoUoCoAfGfGfAoAoAoA oGoUoUoGosUosAo |
| Seq58 + Vp (Seq58 + VpUq) | 7f.8s + VpUq | 58 | UACAACUUUUCC UGACUCAUC | 210 | VpUqsAfsCoAoAoCfUoUoUoUoCoC oUoGfAoCfUoCoAoUoCosUosUo | 222 | (NH2C6)GosAosUoGoAo GoUoCoAfGfGfAoAoAoA oGoUoUoGosUosAo |
| Seq61 (Seq61 - Vp) | 7f.8s | 61 | GGAAUAAAUAUC UACAACUUU | 211 | UosGfsAoAoUoAfAoAoUoAoUoCoU oAfCoAfAoCoUoUoUosUosUo | 223 | AosAosAoGoUoUoGoUoA fGfAfUoAoUoUoUoAoUo UosCosAo |
| Seq61 + Vp (Seq61 + VpUq) | 7f.8s + VpUq | 61 | GGAAUAAAUAUC UACAACUUU | 212 | VpUqsGfsAoAoUoAfAoAoUoAoUoC oUoAfCoAfAoCoUoUoUosUosUo | 224 | AosAosAoGoUoUoGoUoA ofGfAfUoAUoUoUoAoUo UosCosAo |

TABLE 13-continued

| Compound | Modification Pattern | SEQ ID NO: | Base Antisense/ Guide Strand Sequence (5'-3') | SEQ ID NO: | ModifiedA ntisense/ Guide Strand Sequence (5'-3') | SEQ ID NO: | Modified Sense/ Passenger Strand Sequence (5'-3') |
|---|---|---|---|---|---|---|---|
| Seq62 (Seq62 – Vp) | 7f.8s | 62 | UGGAAUAAAUAU CUACAACUU | 213 | UosGfsGoAoAoUfAoAoAoUoAoUoC oUfAoCfAoAoCoUoUosUosUo | 225 | AosAosGoUoUoGoUoAoG fAfUfAoUoUoUoAoUoUo CosCosAo |
| Seq62 + Vp (Seq62 + VpUq) | 7f.8s + VpUq | 62 | UGGAAUAAAUAU CCUAAACUU | 214 | VpUqsGfsGoAoAoUfAoAoAoUoAoU oCoUfAoCfAoAoCoUoUosUosUo | 226 | AosAosGoUoUoGoUoAoG fAfUfAoUoUoUoAoUoUo CosCosAo |
| Seq64 (Seq64 – Vp) | 7f.8s | 64 | AGCAAGAUUAAU UACAUCAAA | 215 | UosGfsCoAoAoGfAoUoUoAoAoUoU oAfCoAfUoCoAoAoAosUosUo | 227 | (NH2C6)UosUosUoGoAo UoGoUoAfAfUfUoAoAoU oCoUoUoGosCosAo |
| Seq64 + Vp (Seq64 + VpUq) | 7f.8s + VpUq | 64 | AGCAAGAUUAAU UACAUCAAA | 216 | VpUqsGfsCoAoAoGfAoUoUoAoAoU oUoAfCoAfUoCoAoAoAosUosUo | 228 | UosUosUoGoAoUoGoUoA fAfUfUoAoAoUoCoUoUo GosCosAo |
| Seq77 (Seq77 – Vp) | 7f.8s | 77 | CUGAAUCUUCAA GCACAUAAA | 217 | UosUfsGoAoAoUfCoUoUoCoAoAoG oCfAoCfAoUoAoAoAosUosUo | 229 | UosUosUoAoUoGoUoGoC fUfUfGoAoAoGoAoUoUo CosAosAo |
| Seq77 + Vp (Seq77 + VpUq) | 7f.8s + VpUq | 77 | CUGAAUCUUCAA GCACAUAAA | 218 | VpUqsUfsGoAoAoUfCoUoUoCoAoA oGoCfAoCfAoUoAoAoAosUosUo | 230 | UosUosUoAoUoGoUoGoC fUfUfGoAoAoGoAoUoUo CosAosAo |
| Seq98 (Seq98 – Vp) | 7f.8s | 98 | ACUGGUUGGAAC GAUGUCA | 219 | UosCfsUoGoGoUfUoGoGoAoAoCoG oAfUoGfUoCoAosUosUo | 231 | UosGosAoCoAoUoCfGfU ofUoCoCoAAoCoCoAosG osAo |
| Seq98 + Vp (Seq98 + VpUq) | 7f.8s + VpUq | 98 | ACUGGUUGGAAC GAUGUCA | 220 | VpUqsCfsUoGoGoUfUoGoGoAoAoC oGoAfUoGfUoCoAosUosUo | 232 | UosGosAoCoAoUoCfGfU fUoCoCoAoAoCoCoAosG osAo |

*Vp refers to 5' Vinyl Phosphonate;
Uq refers to UNA-U Unlocked nucleobase analog to uridine;
Xf refers to 2'-Fluoro modified nucleotide where X is any base, Fluorine at 2' position on ribose;
Xo refers to 2'-O-CH3 modified nucleotide, where X is any base and methylated oxygen at 2' position on ribose;s refers to phosphorothioate modification, phosphorothioate linkage between bases;and (NH2C6) refers to aminohexyl handle/linker.
In some instances, (NH2C6) is coupled to the 5' end of the passenger strand (sense strand).

siRNAs were conjugated to anti-transferrin receptor 1 (TfR1) antibody using a SMCC linker, to produce AOCs and were tested in WT mice. 8 weeks old C57BL mice were injected IV with AOCs, at 3 mg/kg (siRNA dose). Heart and gastrocnemius were collected at 28 and 56 days after AOC treatment. Control animals were injected with PBS.

Results

Top 6 performing siRNAs identified from the concentration response in in vitro, were synthesized using 7f.8s modifications and with and without VpUq chemical modifications (Table 13).

Figure 4:
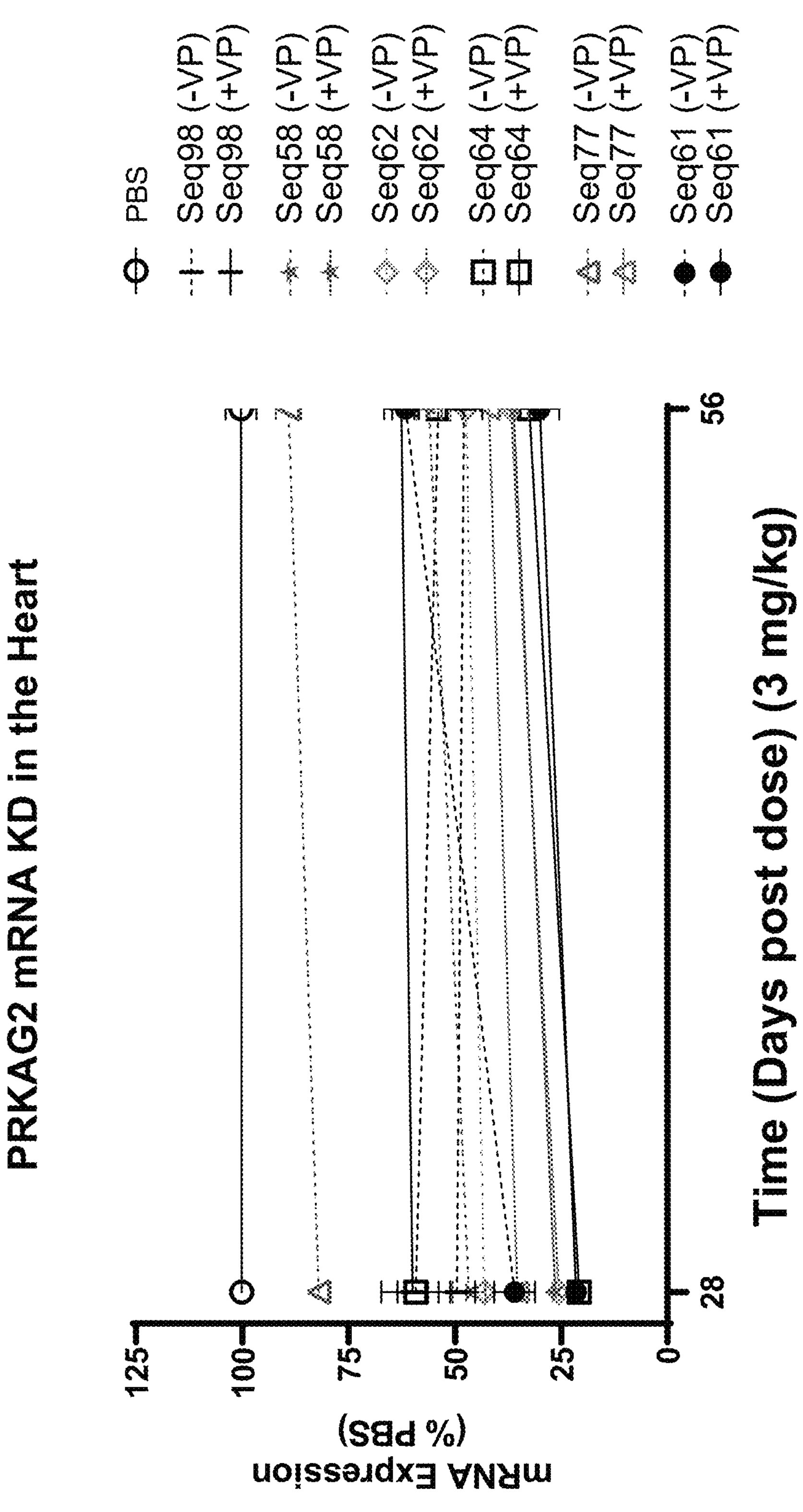
FIG. 4 is a representative plot showing in vivo PRKAG2 mRNA expression levels in heart tissue obtained from wild-type mice at 28 and 56 days after a single IV injection of 3 mg/kg PRKAG2 siRNA AOCs with and without VpUq modification.
Figure 5:
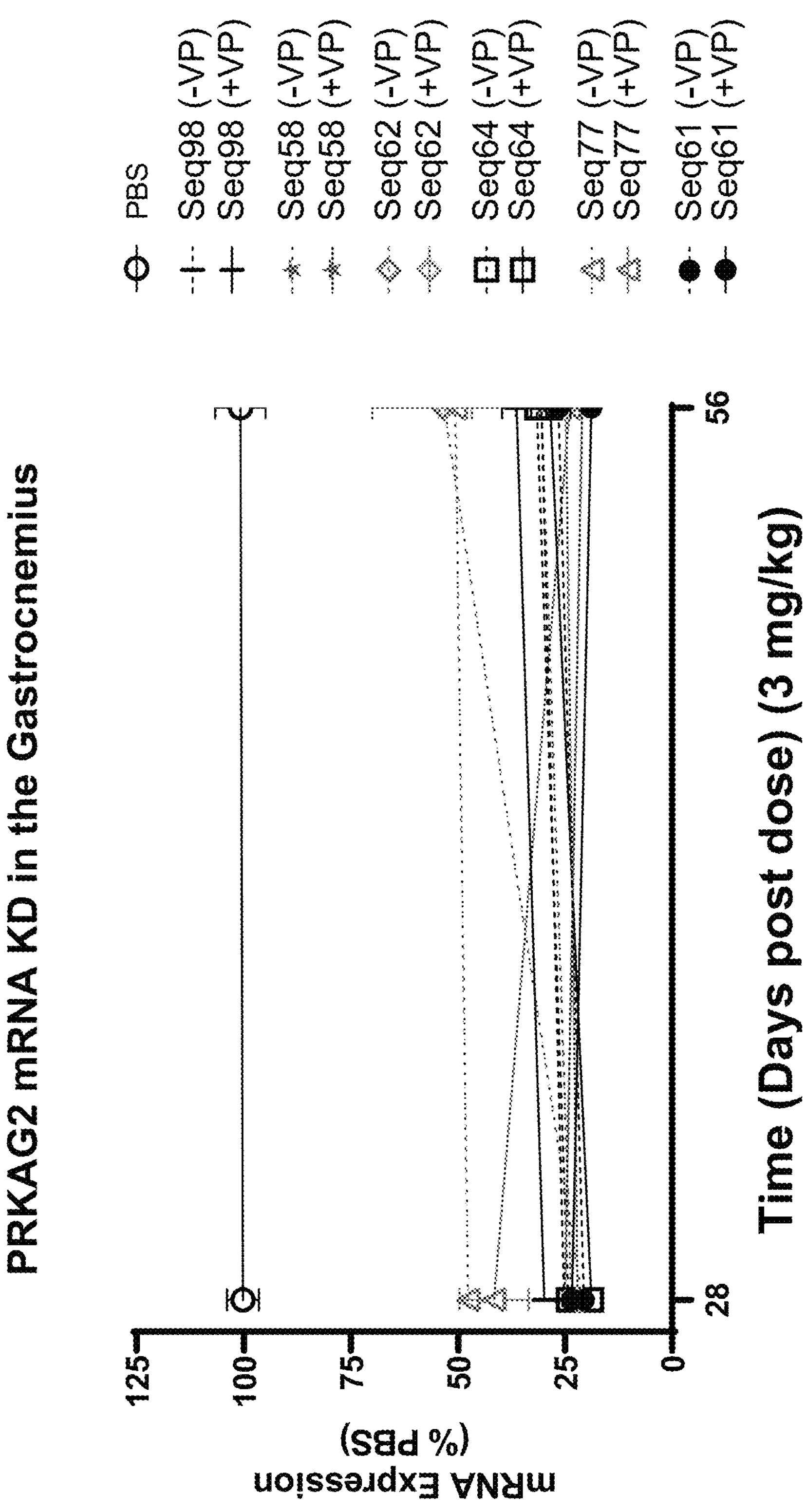
FIG. 5 is a representative plot showing in vivo PRKAG2 mRNA expression levels in gastrocnemius muscle tissue obtained from wild-type mice at 28 and 56 days after a single IV injection of 3 mg/kg PRKAG2 siRNA AOCs with and without VpUq modification.

In the heart, over 75% knockdown (KD) of PRKAG2 mRNA expression was achieved with Seq61+Vp at 28 days, and KD was maintained up to 56 days (FIG. 4). In the gastrocnemius, over 75% KD was achieved with Seq61+Vp at 28 days and maintained up to 56 days (FIG. 5).

Example 7: In Vivo Echocardiography (Echo) Measurement in Conscious Mice

Materials and Methods

The synthesis and purification of the PRKAG2 siRNAs-AOCs are described in Example 5. Wild type $C_{57}$BL/6J or 57BL6NCrl mice (8-10 week old) were dosed via intravenous (IV) infusion with the indicated AOCs and doses.

All animal procedures were performed in accordance with the IACUC protocols. Mice were kept under identical housing conditions (12 hrs light/dark cycle, standard diet ad libitum, 21° C. room temperature prior to echocardiographic assessment. Echo was performed using Vevo 3100 high-resolution Imaging System (Fujifilm VisualSonics, Toronto, Ontario, Canada). In order to obtain more accurate cardiac measurements and avoid the cardio suppressive effects by the use of anesthesia, conscious echo was performed, using oxygen flow at 0.8 L/hr. Animals were naired and restrained. A snout was placed in the nose cone and mice were taped to the platform using surgical tape. Electrode gel was applied to the contact areas between the paws and the electrode surface. Pre-warmed sonography gel was applied to the chest area. LAX B-mode was used to acquire EF %, SV and LV volume measurements. The long axis of the heart was imaged, the LVOT was aligned with the apex and images with wide open aorta and largest diameter of ventricles were acquired. SAX B-mode and M-mode were used for FS %, LV posterior wall thickness and LV diameter. B-model cine loops were generated visualizing the maximum dimension of the LV from apex to base in a parasternal long axis view. After LAX image acquisition, the probe was moved on 900 to capture the SAX B-mode, to image along the short axis of the heart. Heart apex, papillary muscles and atria were localized and images were taken when the largest diameter was seen. An image sequence was acquired. After switching to M-mode, images were acquired when a posterior and the anterior wall were seen, without interfering with papillary muscles. After competition of acquisition, animals were wiped gently with a kimwipe to remove gel, tape was removed, and animals were returned to home cage. All acquired images were digitally stored in raw format (DICOM) for further offline-analysis.

Results

Figure 6A:
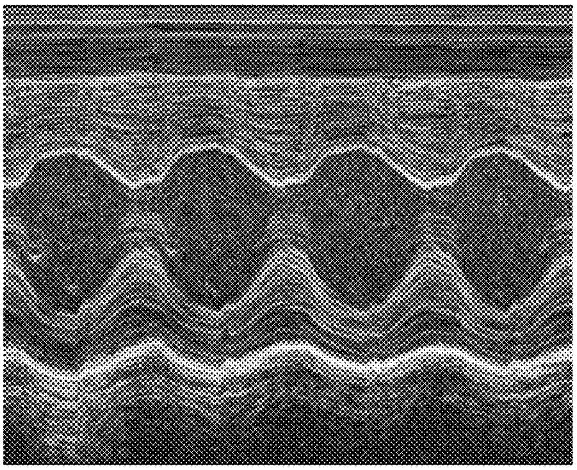
FIGS. 6A-6C show representative M-mode echocardiography images of mice 56 days post single IV dose of PBS (FIG. 6A), 3 mg/kg of AOC PRKAG2_Seq61 without VpUq modification (FIG. 6B), or 3 mg/kg of AOC PRKAG2_Seq61 with VpUq modification (FIG. 6C).
Figure 6B:
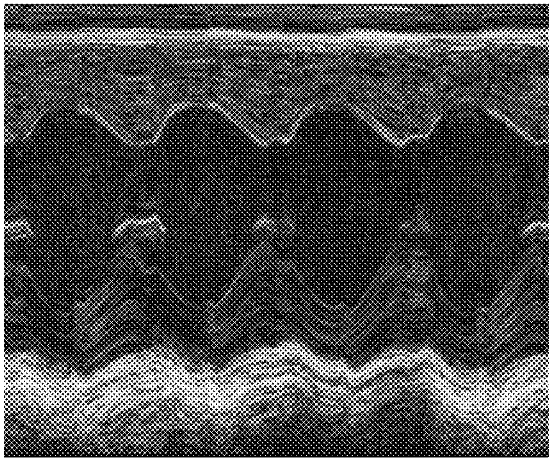
Figure 6C:
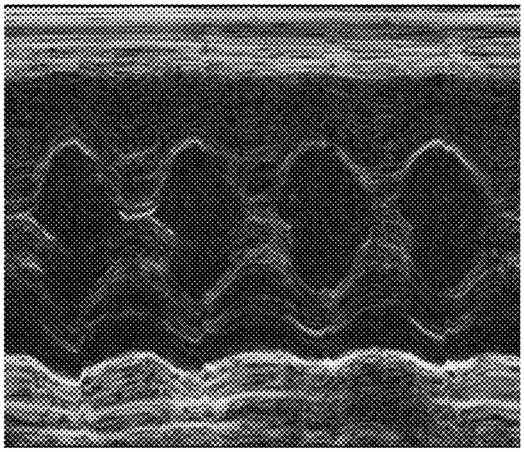
Figure 6D:
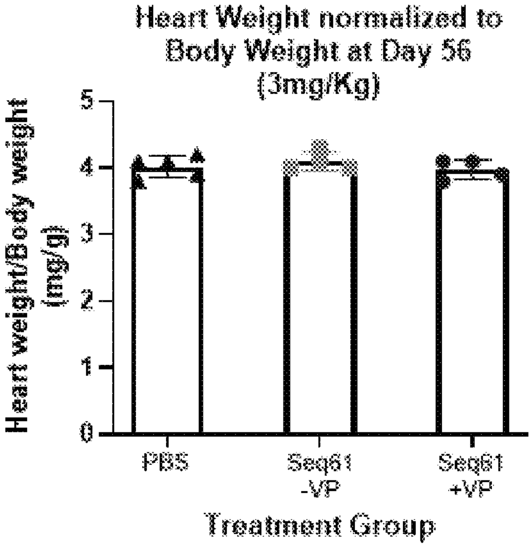
FIG. 6D shows a representative bar graph of a normalized heart to body weight cardiac assessment of mice 56 days post single IV dose of PBS, 3 mg/kg of AOC PRKAG2_Seq61 without VpUq modification, or 3 mg/kg of AOC PRKAG2_Seq61 with VpUq modification.
Figure 6E:
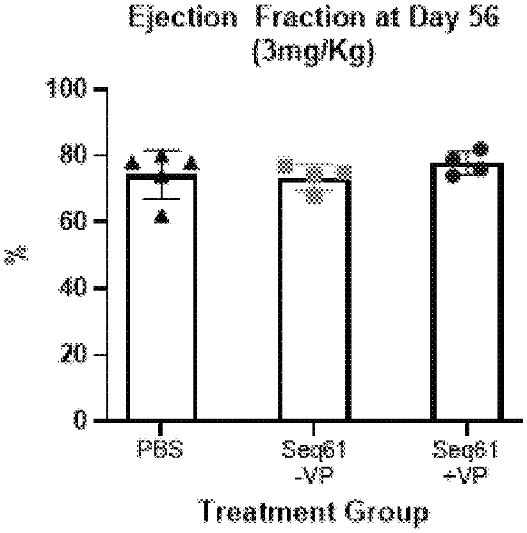
FIG. 6E shows a representative bar graph of a functional (ejection fraction) cardiac assessment of mice 56 days post single IV dose of PBS, 3 mg/kg of AOC PRKAG2_Seq61 without VpUq modification, or 3 mg/kg of AOC PRKAG2_Seq61 with VpUq modification.
Figure 6F:
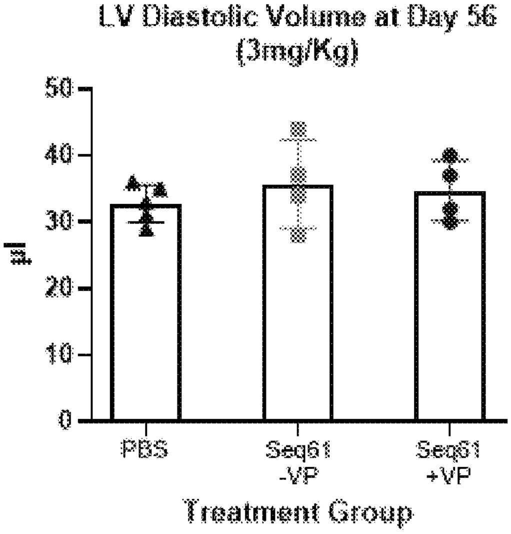
FIG. 6F shows a representative bar graph of a morphological (LV diastolic volume) cardiac assessment of mice 56 days post single IV dose of PBS, 3 mg/kg of AOC PRKAG2_Seq61 without VpUq modification, or 3 mg/kg of AOC PRKAG2_Seq61 with VpUq modification.

To address any potential cardiac adverse events in mice administered siPRKAG2_Seq61-AOC (a-TfR1 antibody-PRKAG2 siRNA (SEQ ID NOs: 211 and 223) conjugate, also referred as PRKAG2_Seq61-VP), cardiac function and cardiac hypertrophy were assessed in these animals. Cardiac function in these mice was measured with echocardiography at 56 days after AOC treatment for animals treated with siPRKAG2_Seq61-AOC or siPRKAG2 Seq61+VpUq-AOC (a-TfR1 antibody-PRKAG2 siRNA+VpUq (SEQ ID NOs: 212 and 224) conjugate, also referred as PRKAG2_Seq61+Vp) (FIGS. 6A-6C). The echocardiograms for these animals showed no observed differences between treatments. Ejection Fraction % and LV diastolic volume were comparable between treatments (see FIGS. 6A-6C). In addition, cardiac hypertrophy was assessed by measuring the weights of the heart of these animals. As shown in FIGS. 6D-6F, hearts weights normalized to body weights were comparable between the AOC treated group and the control group. These results indicate that the administration of siPRKAG2_Seq61-AOC did not affect cardiac function or have any effect related to cardiac hypertrophy.

Example 8: Dose Response of siPRKAG2_Seq61-AOCs in WT Mice

Materials and Methods

The materials and methods are described in Examples 5-7.

Results

Figure 7:
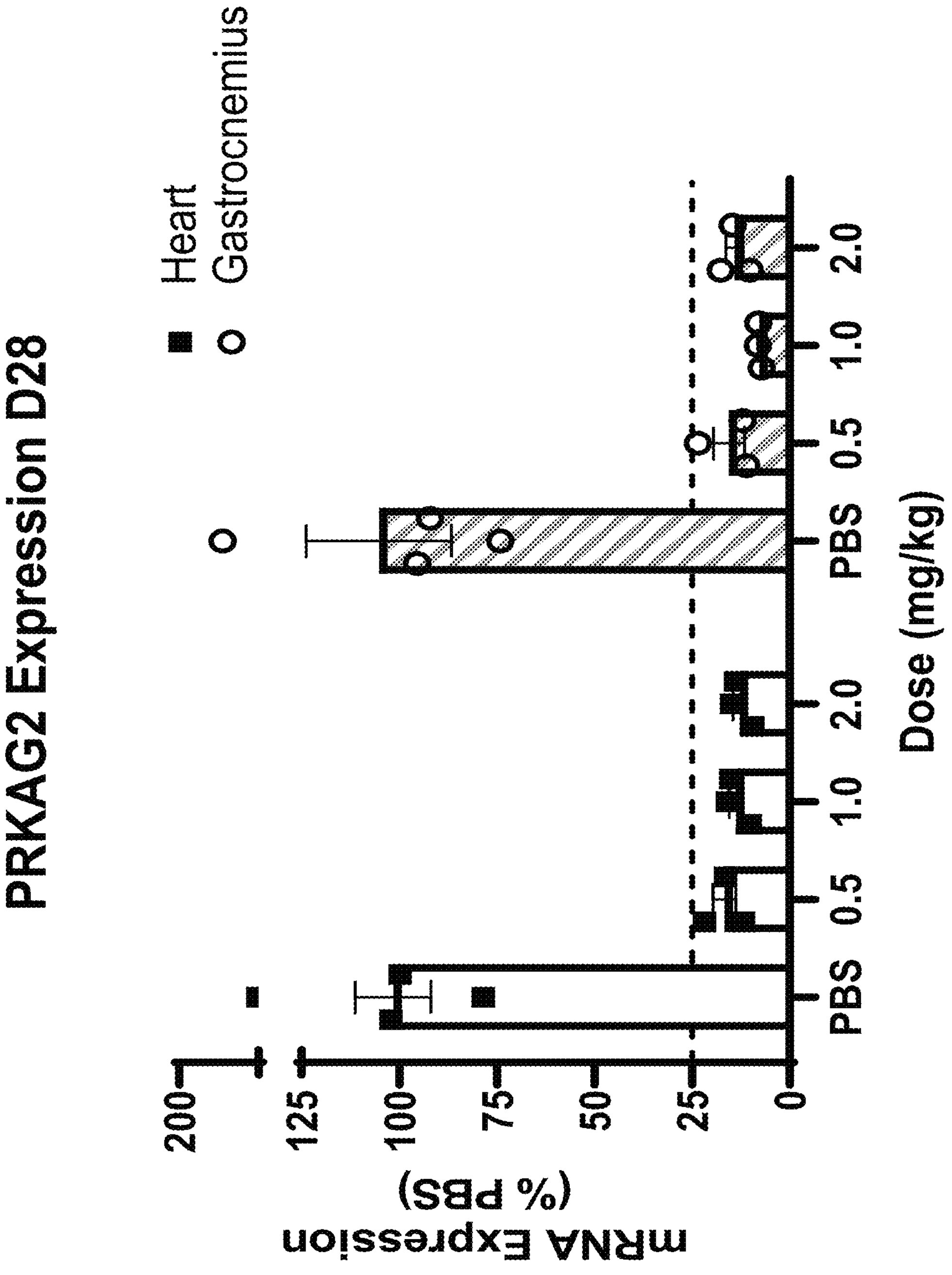
FIG. 7 is a representative bar graph showing in vivo PRKAG2 mRNA expression levels in heart tissue and gastrocnemius muscle tissue obtained from mice at 28 days post lead siRNA PRKAG2_Seq61+VpUq-AOC injection at various dosages, measured with qPCR. (n=4 for PBS; n=3 for AOC).

To address potency of the lead candidate siPRKAG2_Seq61+VpUq-AOC a dose response (2-1-0.5 mg/Kg, siRNA dose) was performed in WT mice, and heart and gastrocnemius tissue samples were collected at 28 days post single AOC injection. Over 75% knockdown (KD) of PRKAG2 mRNA expression PRKAG2 was achieved in heart and gastrocnemius tissues at 0.5 mg/Kg (FIG. 7).

Figure 8:
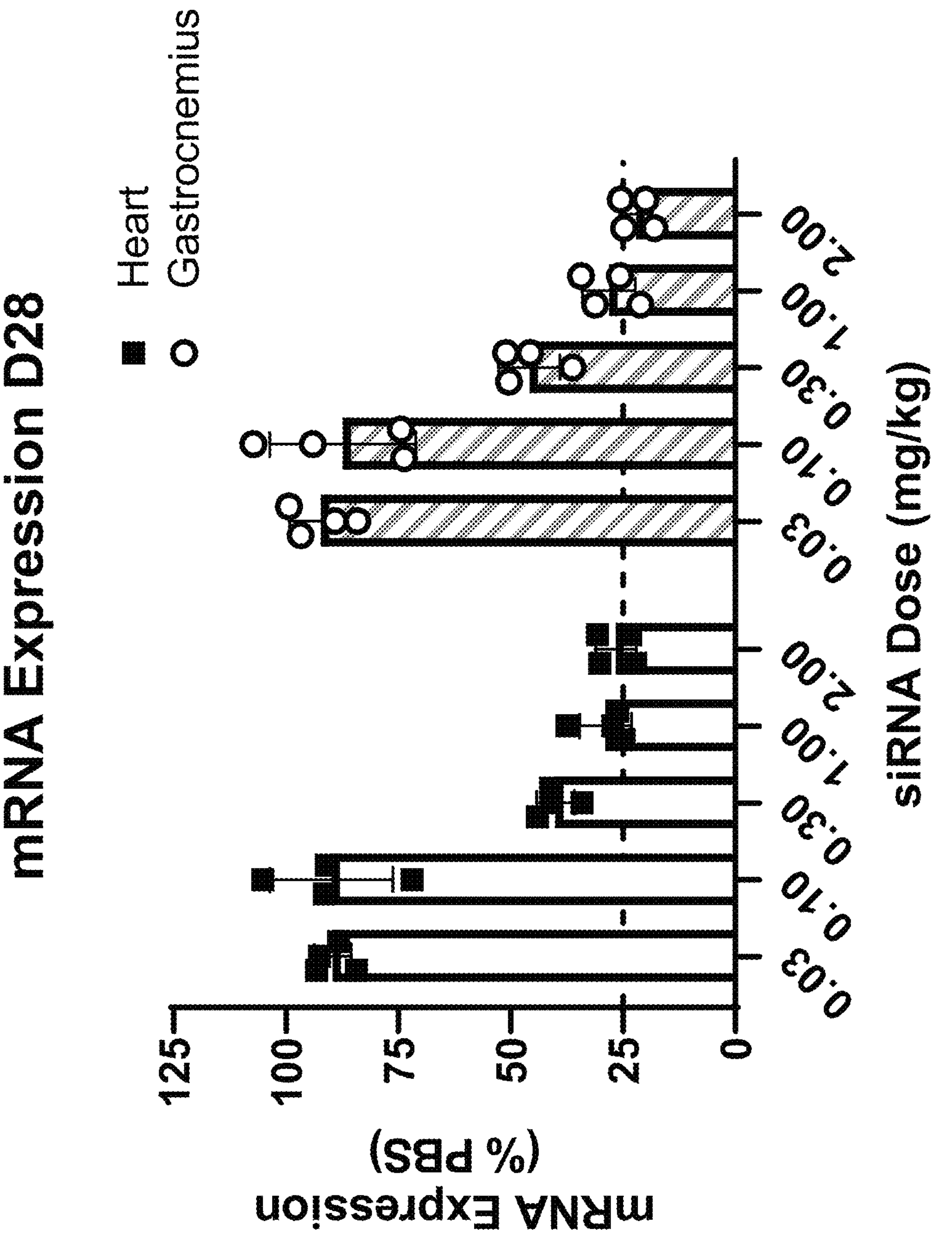
FIG. 8 is a representative bar graph showing in vivo PRKAG2 mRNA expression levels in heart tissue and gastrocnemius muscles obtained from mice at 28 days post injection of lead siPRKAG2_Seq61 AOC with VpUq modification at various dosages, measured with qPCR.

Since maximum KD was still reached at the lowest tested dose (0.5 mg/kg), a second mouse dose response study was performed and lead sequence AOC was tested at 2, 1, 0.3, 0.1, and 0.03 mg/kg (FIG. 8). Maximum PRKAG2 KD, corresponding to 75% was achieved with 2 and 1 mg/Kg doses in heart and gastrocnemius. At 0.3 mg/Kg dose, 60% KD was reached in both tissues. KD levels were comparable between heart and gastrocnemius at each dose tested.

These results indicate that siPRKAG2_Seq61+VpUq-AOC was able to decrease PRKAG2 mRNA levels in the heart tissue and gastrocnemius muscle obtained from mice after 28 days post injection of siPRKAG2_Seq61+VpUq-AOC.

Example 9: In Vitro Evaluation of siPRKAG2 Seq61 KD at Gene and Protein Expression Level

Materials and Methods

JESS Capillary Western Blot

Cardiomyocytes were seeded on 1% Matrigel coated 24-well plates at a starting density of 20,000 cells/well in General Media (Skeletal Muscle Growth Media, Promocell c-23160, Gentamycin 5%, Gibco 15710064). After 3 or 14 days post siRNA transfection, cardiomyocytes lysates were collected. Protein expression levels were measured using JESS-Western Blot (Protein Simple) in Human-iPS-CM2. Cells were washed in PBS and harvested in Pierce RIPA Lysis and Extraction Buffer (Thermo Scientific, Cat #89901) containing one Pierce Protease Inhibitor mini table (Thermo Scientific, Cat #A32953). Total protein concentration was determined using the Pierce BCA Protein Assay Kit (Thermo Scientific, Cat #23225). Samples were run on a 25 capillary cartridge (12-240 kDa separation) on the chemiluminescent channel. Total protein was used as a loading control. A PRKAG2 anti-rabbit primary antibody (Sigma, Diluted 1:50 and an anti-rabbit secondary antibody (Abcam, Diluted 1:20) were used to detect the target protein. The Compass for Simple Western™ software was used to analyze the changes in protein expression.

Figure 9A:
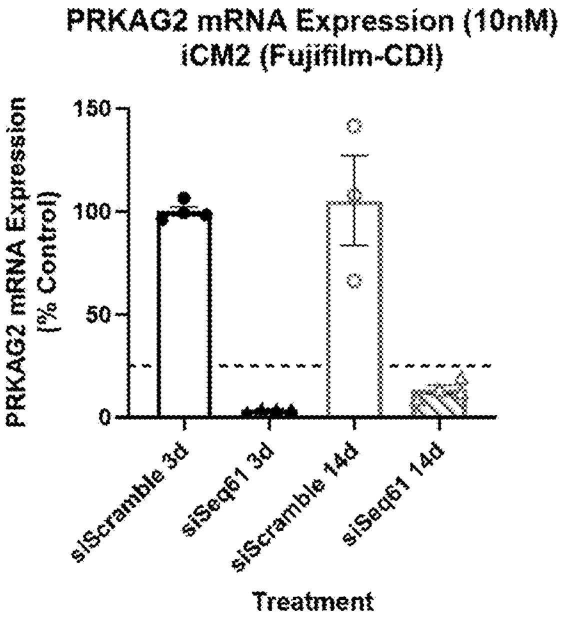
FIG. 9A shows a representative bar graph showing PRKAG2 mRNA expression levels in $iCM^2$ at 3 and 14 days post PRKAG2 siRNA transfection measured by qPCR.
Figure 9B:
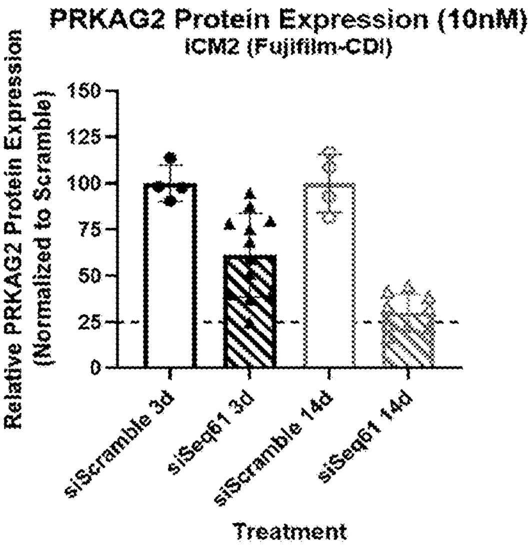
FIG. 9B shows a representative bar graph showing relative PRKAG2 protein expression levels in $iCM^2$ at 3 and 14 days post PRKAG2 siRNA transfection measured by JESS-western blotting.
Figure 9C:
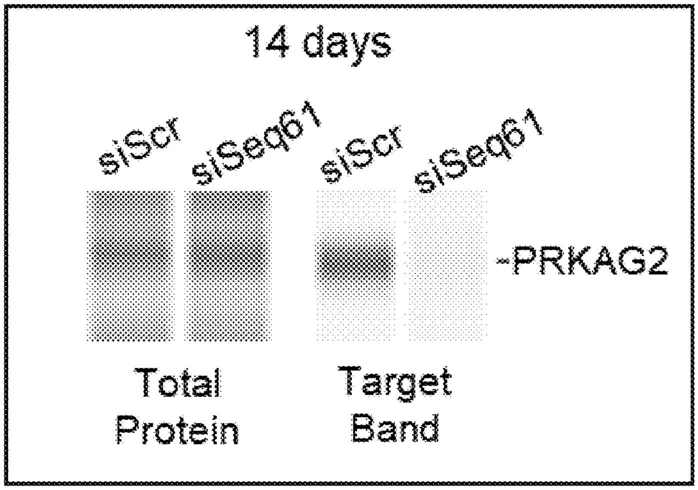
FIG. 9C shows representative western blot images of total protein used a loading control band and a PRKAG2 band, detected by western blotting using a PRKAG2 antibody (Sigma).

Results siPRKAG2_Seq61 was tested in human iPSC-CM2 at 10 nM and samples were collected at 3 and 14 days post siRNA transfection for mRNA and protein expression. A siScramble sequence was used as negative control. Over 95% knockdown (KD) of PRKAG2 mRNA expression was achieved at 3 days and 80% KD was achieved at 14 days post siRNA transfection (FIG. 9A). Proteins levels were measured using JESS capillary WB and about 75% KD was achieved at 14 days (FIGS. 9B and C). These results indicate that decreases in PRKAG2 mRNA levels in iCM2 cells transfected with PRKAG2_Seq 61 siRNA correlated with decreases in PRKAG2 protein levels in these cells as determined by JESS-WB.

Example 10: In-Vitro Treatment with mAb-AOC and Fab-AOC/FabOC

Materials and Methods

The synthesis and purification of the mAb-AOC and Fab-AOCs are described in Example 5. HeLa cells were obtained from ATCC and engineered at Avidity Biosciences to overexpress human transferrin receptor 1 (TfR1).

Assay

HeLa cells were obtained from ATCC and engineered at Avidity Biosciences to overexpress human TfR1. The HeLa cells overexpressing TfR1 were cultured (DMEM, 10% FBS, PenStrep) in 75 $cm^2$ flasks and then seeded in 96 well plates at a cell density of 4,000 cells/well. One day post seeding, the media was refreshed and the cells were treated with either AOC-mAb (monoclonal full length a-TfR1 antibody conjugated with siRNA) or AOC-Fab (Fab fragment of a-TfR1 antibody conjugated with siRNA) in a dose-response manner. Cells were collected two days post AOC treatment and were harvested in 100 μL TRIzol. RNA was prepared using a ZYMO 96-well RNA kit (ThermoFisher) and relative RNA expression levels quantified by RT-qPCR using commercially available TaqMan probes (LifeTechnology). Expression data were analyzed as previously described.

Results

Figure 10A:
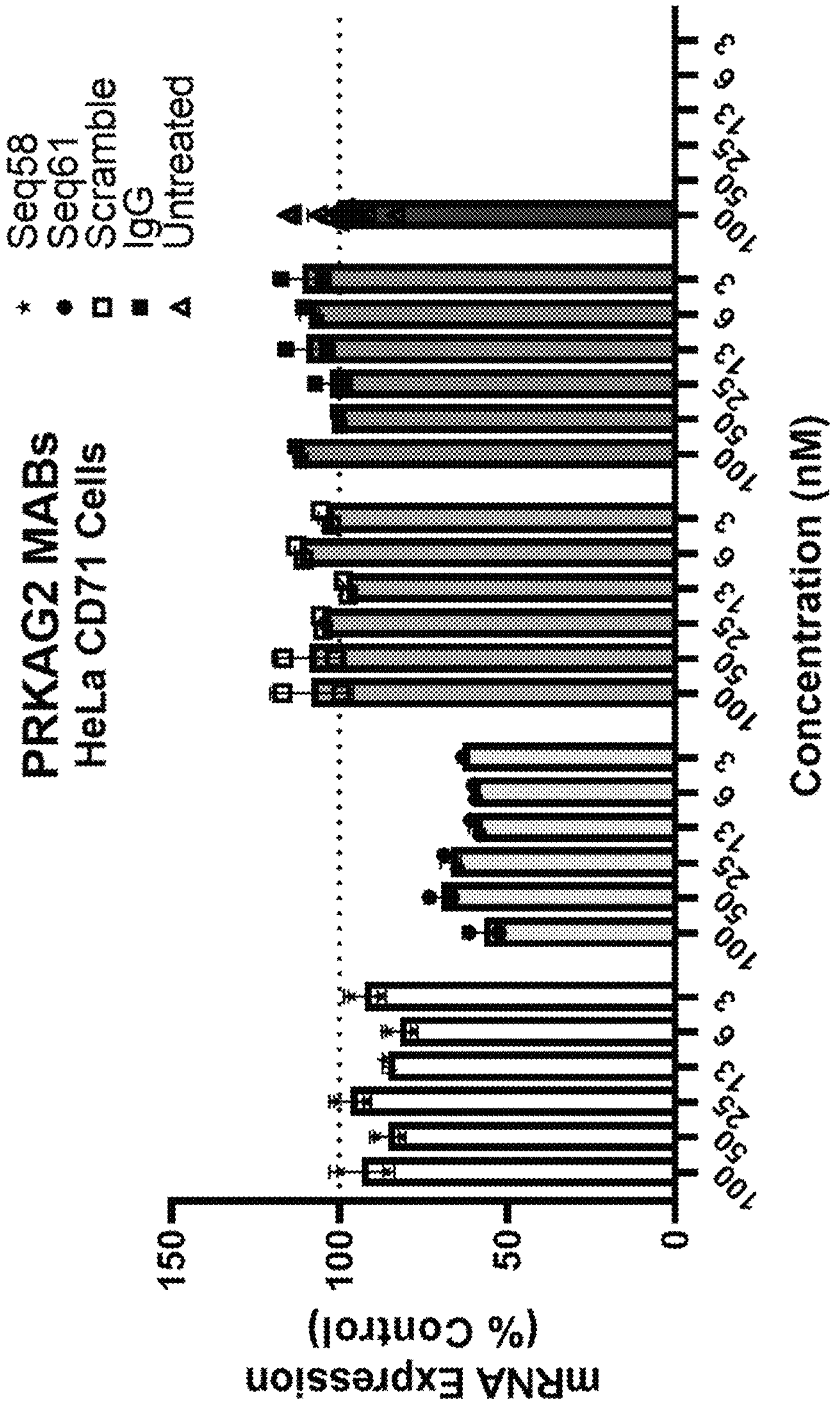
FIGS. 10A-10B show representative bar graphs showing in vitro PRKAG2 mRNA expression levels in HeLa cells overexpressing Transferrin receptor 1 incubated with PRKAG2 siRNA AOC-MAbs (FIG. 10A) and PRKAG2 siRNA AOC-Fabs (FIG. 10B) for 48 hours.
Figure 10B:
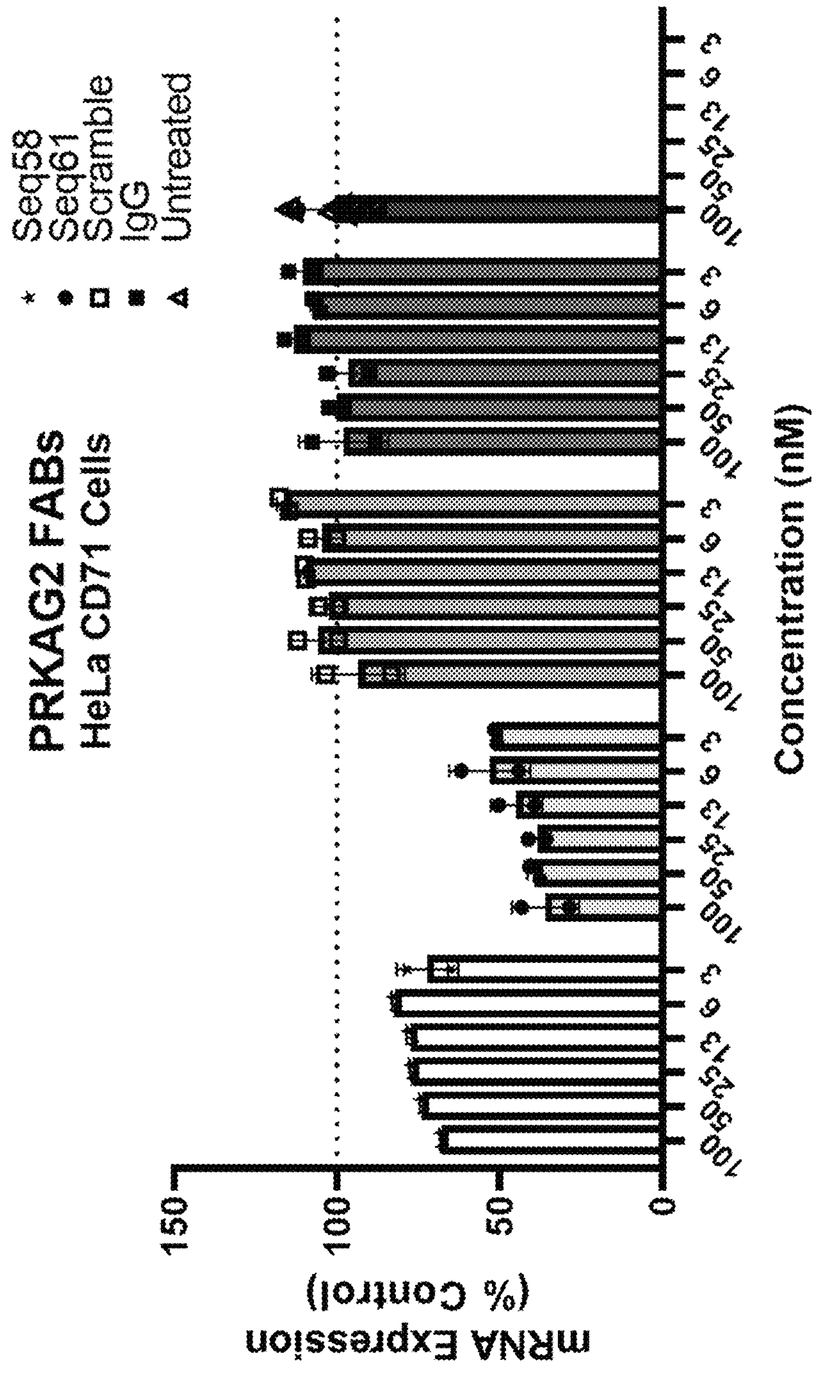

HeLa cells overexpressing TfR1 were treated with AOC-Mab and FabOC, in a concentration response with, using the two siRNAs (seq61 (SEQ ID NOs: 211 and SEQ ID NO: 223) and seq 58 (SEQ ID NO: 209 and SEQ ID NO: 221)). HeLa cells overexpressing the transferrin receptor (TfR1) were treated with the PRKAG2_58 (SEQ ID NOs: 211 and SEQ ID NO: 223) or PRKAG2_61 (SEQ ID NO: 209 and SEQ ID NO: 221) siRNA conjugated to the anti-TfR1 monoclonal antibody (mAb) or the anti-TfR1 fragment antigen-binding (Fab). The results indicate that the PRKAG2_58 or PRKAG2_61 siRNA conjugated to the anti-TfR1 fragment antigen-binding (Fab) were both able to decrease PRKAG2 mRNA levels in HeLa cells overexpressing TfR1 (FIG. 10A, 10B). However, the PRKAG2_61 siRNA conjugated to the anti-TfR1 monoclonal antibody (mAb) was able to decrease PRKAG2 mRNA levels in HeLa cells overexpressing TfR1 but not the PRKAG2_58 siRNA conjugated to the anti-TfR1 monoclonal antibody (mAb). The PRKAG2 mRNA knock down levels with the PRKAG2_61 conjugated with anti-TfR1 Fab are greater than that of the PRKAG2_61 conjugated with anti-TfR1 mAb in this cell assay.

Example 11: In Vitro Transfection of PRKAG2 siRNA AOC in NHP Cardiac Fibroblasts Materials and Methods Non-human primate cardiac fibroblasts were obtained from Creative Biolabs (Cat #NHP-PC110). PRKAG2 siSeq61+Vp is described in Example 3 and Example 6. Cells were thawed and cultured in Cell Culture Growth Medium (Creative Biolabs, Cat #NHP-PC 110-M) supplemented with Cell Growth Supplements (Creative Biolabs), and expanded for at least 4 passages in flasks coated with 1% gelatin (Stem Cell Technologies, Cat #7903) before cells were seeded in 96 wells plates and transfection occurred. Cells were lifted using TrypLE (Thermofisher, Cat #12604013) and TrypLE was inhibited using complete growth medium. 12,000 cells were seeded per well in a 96 well plate. One day after seeding, cells were transfected with PRKAG2 siRNA Seq61 modified with vinyl phosphonate (siSeq61+Vp), using Optimem Reduced Serum Medium (Gibco, Life Technologies, Cat #31985-062) and Lipofectamine RNAiMAX (Invitrogen, Cat #13778-150), in a 1:50 ratio. Cells were collected in Trizol 3 days post siRNA transfection. RNA was extracted using Direct-zol-96 RNA (Zymo Research, Cat #R2056). RNA was treated with DNase and eluted into water following manufacturer's instructions. RNA was transcribed to cDNA using the High-Capacity cDNA Reverse Transcription Kit (ThermoFisher, Cat #4368813). mRNA expression levels were assessed for PRKAG2 and PPIP (Housekeeping gene) using QuantStudio Real-Time PCR. TaqMan probes used were purchased at ThermoFisher. NHP PRKAG2: Mf00697321_m1 and NHP PPIβ: Mf02802985_m1.

Results

Figure 14:
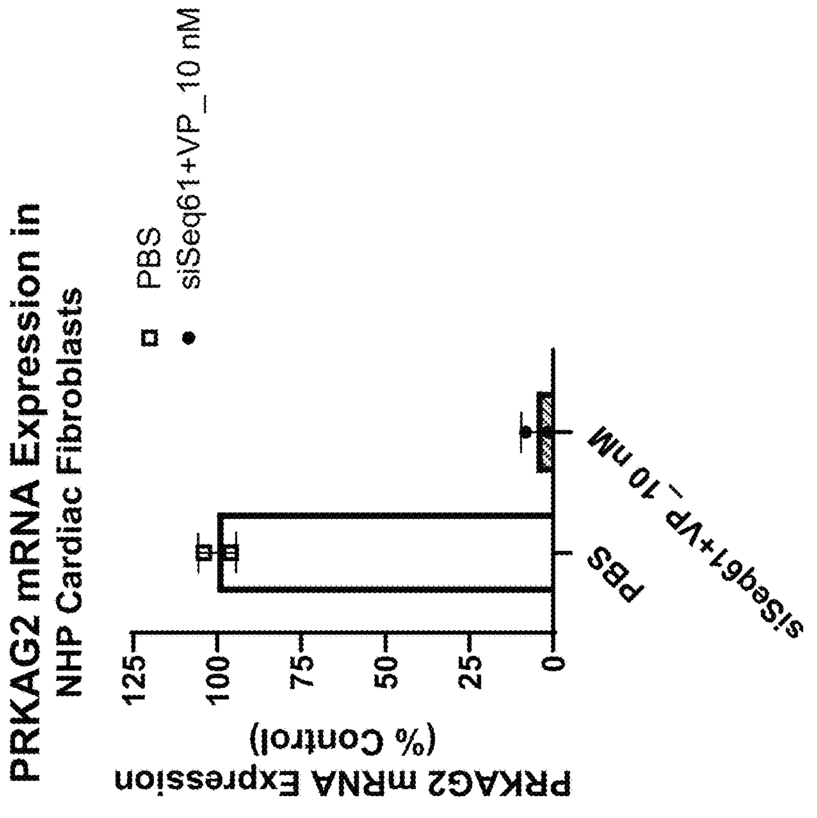
FIG. 14 is a representative bar graph showing PRKAG2 mRNA expression levels in NHP cardiac fibroblasts in 72 hours after transfection with PRKAG2 siRNA with VpUq modification (siSeq61+Vp) at a concentration of 10 nM.

NHP cardiac fibroblasts were transfected with PRKAG2 siSeq61+Vp at a concentration of 10 nM and PRKAG2 mRNA levels were analyzed by qPCR analysis in 72 hours after transfection. The results indicated that PRKAG2 siSeq61+Vp decreased PRKAG2 mRNA expressed levels by more than 80% in NHP cardiac fibroblasts compared to levels in control cells (FIG. 14). Overall, the PRKAG2 siSeq61+Vp were observed to significantly reduce PRKAG2 mRNA expression levels in NHP cardiac fibroblasts in vitro.

Example 12: In Vitro Transfection of PRKAG2 siRNA in NHP Skeletal Muscle Cells

Materials and Methods

Non-human primate (NHP) skeletal muscle cells were obtained from Creative Biolabs (Cat #NHP-PC163). PRKAG2 siSeq61+Vp is described in Example 3 and Example 6. Cells were thawed using Cell Culture Growth Basal Medium (Creative Biolabs, Cat #NHP-PC163-M) supplemented with 10 μM ROCK Inhibitor (Y-27632 dihydrochloride, Biotechne, Tocris, at #1254). PRKAG2 siSeq61+Vp is described in Example 3 and Example 6. Cells were cultured in Cell Culture Growth Basal Medium (Creative Biolabs, Cat #NHP-PC163-M) supplemented with Cell Growth Supplements (Creative Biolabs), following vendor's instructions, and expanded for at least 2 passages in flasks coated with 1% gelatin (Stem Cell Technologies, Cat #7903) before cells were seeded in 96 well plates and transfected. Cells were lifted using TrypLE (Thermofisher, Cat #12604013) and TrypLE was inhibited using complete growth medium. 12,000 cells were seeded per well in a 96 well plate. One day after seeding, cells were transfected with PRKAG2 siRNAs, using Optimem Reduced Serum Medium (Gibco, Life Technologies, Cat #31985-062) and Lipofectamine RNAiMAX (Invitrogen, Cat #13778-150), in a 1:50 ratio. Cells were collected in Trizol 2 days post siRNA transfection. RNA was extracted using Direct-zol-96 RNA (Zymo Research, Cat #R2056). RNA was treated with DNase and eluted into water following manufacturer's instructions. RNA was transcribed to cDNA using the High-Capacity cDNA Reverse Transcription Kit (ThermoFisher, Cat #4368813). mRNA expression was assessed for PRKAG2 and SSB (Housekeeping gene) using QuantStudio Real-Time PCR. TaqMan probes used were purchased at ThermoFisher. NHP PRKAG2: Mf00697321_m1 and NHP SSB: Mf04187362_g2.

Results

Figure 15:
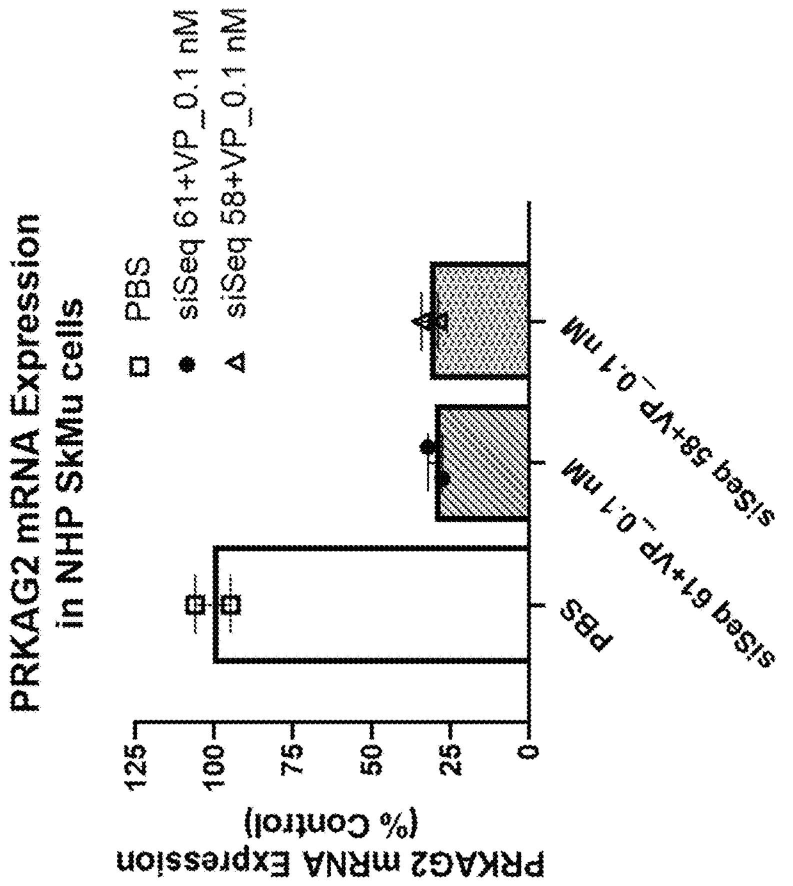
FIG. 15 illustrates representative bar graphs showing PRKAG2 mRNA expression levels in NHP skeletal muscle (NHP-PC163) in 48 hours after transfection with PRKAG2 siSeq61+Vp and PRKAG2 siSeq58+Vp at a concentration of 0.1 nM.

NHP skeletal muscle cells were transfected with PRKAG2 siSeq61+Vp and PRKAG2 siSeq58+Vp for 48 hours and PRKAG2 mRNA expression levels were determined by qPCR. The results showed that two PRKAG2 siRNAs, PRKAG2 siSeq61+Vp and PRKAG2 siSeq58+Vp, decreased PRKAG2 mRNA expression levels by over 65% in NHP cells compared to PRKAG2 mRNA expression levels in control cells treated with PBS (FIG. 15). Overall, PRKAG2 siRNAs were observed to significantly decrease PRKAG2 mRNA expression levels in NHP skeletal muscle cells compared to PRKAG2 mRNA levels in control cells in vitro.

Example 13: In Vitro Transfection of Lead siRNA in Human Neonatal Dermal Fibroblasts (HndFib)

Materials and Methods

Human Neonatal Dermal Fibroblasts (HndFib) cells were obtained from ATCC (Cat #PCS-201-010). PRKAG2 siSeq61+Vp is described in Example 3 and Example 6. Cells were thawed using Fibroblasts Culturing Media (FCM) (composed of DMEM-high glucose with L-glutamine (ATCC, Cat #ATCC-30-2002), 10% FBS (Corning, Cat #35-015-CV) and 1% Pen/Strep ATCC, Cat #ATCC 30-2300). Cells were cultured in FCM and expanded for at least 4 passages in flasks coated with 1% gelatin (Stem Cell Technologies, Cat #7903) before cells were seeded in 96 wells plates and transfection occurred. Cells were lifted using TrypLE (Thermofisher, Cat #12604013) and TrypLE was inhibited using FCM. 8,000 cells were seeded per well in a 96 well plate. One day after seeding, cells were transfected with PRKAG2 siSeq61+Vp, using Optimem Reduced Serum Medium (Gibco, Life Technologies, Cat #31985-062) and Lipofectamine RNAiMAX (Invitrogen, Cat #13778-150), in a 1:50 ratio. Cells were collected in Trizol 2 days post siRNA transfection. RNA was subsequently extracted using Direct-zol-96 RNA (Zymo Research, Cat #R2056). The extracted RNA was then treated with DNase and eluted into water in accordance with the manufacturer's instructions. The treated RNA was transcribed into cDNA using the High-Capacity cDNA Reverse Transcription Kit (ThermoFisher, Cat #4368813). mRNA expression was assessed for PRKAG2 and AHSA1 (Housekeeping gene) using QuantStudio Real-Time PCR. TaqMan probes used were obtained from ThermoFisher. Hs PRKAG2: Hs00211903_m1 and Hs AHSA1: Hs00201602_m1.

Results

Figure 16:
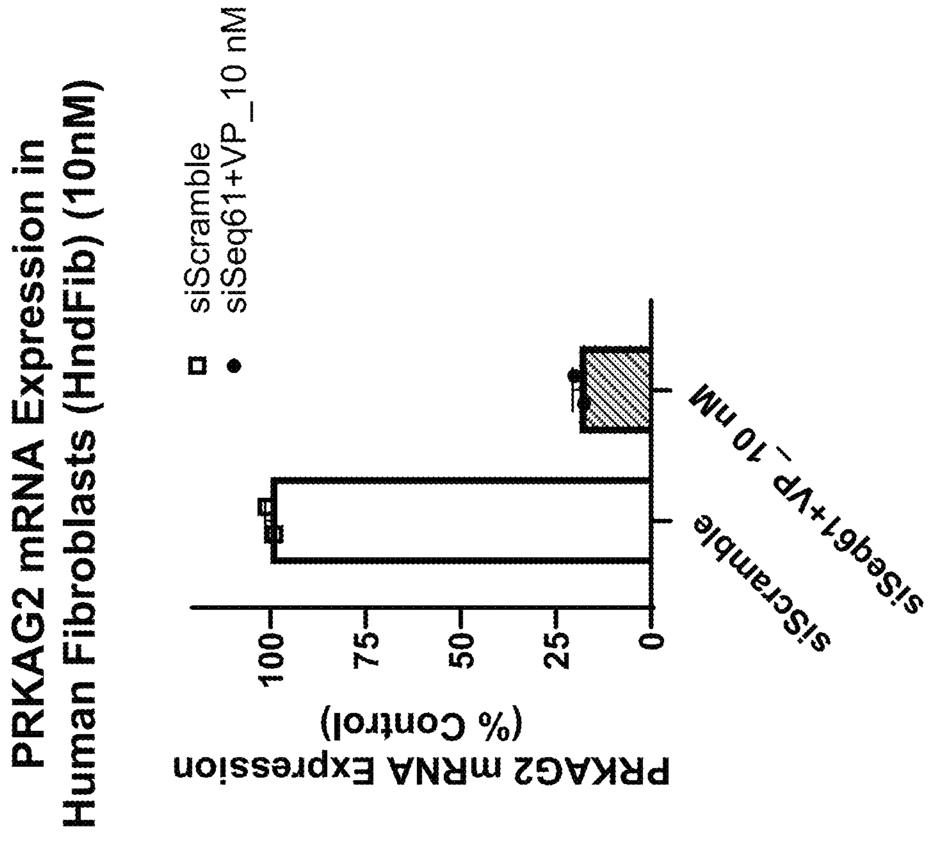
FIG. 16 is a representative bar graph showing PRKAG2 mRNA expression levels in human neonatal dermal fibroblasts (HndFib) in 48 hours after transfection with PRKAG2 siSeq61+Vp at a concentration of 10 nM for 48 hours.

Human neonatal dermal fibroblasts (HndFib) were transfected with PRKAG2 siSeq61+Vp at a concentration of 10 nM and PRKAG2 mRNA levels were determined by qPCR analysis in 48 hours after transfection. The results showed that PRKAG2 siSeq61+Vp was observed to decrease PRKAG2 mRNA expression levels by over 75% in human fibroblast cells compared to levels in control cells treated with PBS (FIG. 16). Overall, PRKAG2 siSeq61+Vp was observed to significantly decrease PRKAG2 mRNA expression levels in human neonatal dermal fibroblasts in vitro.

Example 14: In Vitro Transfection of Antisense Oligonucleotides (ASOs) in Human iPS-Cardiomyocytes ($iCM^2$)

Materials and Methods

Human iPS-cardiomyocytes-Version 2 ($iCM^2$, Fujifilm-CDI, Cat #$C_{1016}$, donor #01434) were thawed in Plating Media (PM, Fujifilm-CDI, Cat #M1001) in gelatin pre-coated plates, at a cell density of 35,000 cells/well in 96-well plates. After 4 hours, PM was gently aspirated and replaced with Maintenance Media (MM, Fujifilm-CDI, Cat #M1003). Media change was performed every 2-3 days using MM. Cells were cultured for 4 days before ASOs treatment was performed. PRKAG2 ASO Seq58 and PRKAG2 ASO Seq61 are antisense oligonucleotides described in Table 14. PRKAG2 ASO transfection was performed using Lipofectamine-RNAiMax (ThermoFisher) and Optimem, according to manufacturer protocol. Transfected cells were incubated in 5% $CO_2$ at 37° C. for 3 days, then washed with PBS, and harvested in 80 µl TRIzol (ThermoFisher) and stored at −80° C. RNA was prepared using a ZYMO 96-well RNA kit (ThermoFisher) and relative RNA expression levels quantified by RT-qPCR using commercially available TaqMan probes (LifeTechnology) Human PRKAG2: Hs00211903_m1; AHSA1: Hs00201602_m1. Expression data were analyzed using the AACT method normalized to ASHA1, expression, and are presented as % expression relative to mock-transfected cells. Data were analyzed by nonlinear regression using a 3-parameter dose response inhibition function (GraphPad Prism 7.02).

TABLE 14

| ASO Compound | SEQ ID NO: | Base ASO Sequence | SEQ ID NO: | Modified ASO sequence |
|---|---|---|---|---|
| PRKAG2_ 1885_ASO_ Seq58.seq | 233 | TACAACTT TTCCTGAC TCAT | 235 | (Tm)s(Am)s(Cm)s(Am)s(Am)s CsTsTsTsTsCsCsTsGsAs(Cm)s (Tm)s(Cm)s(Am)s(Tm) |
| PRKAG2_ 1897_ASO_ Seq61.seq | 234 | GGAATAAA TATCTACA ACTT | 236 | (Gm)s(Gm)s(Am)s(Am)s(Tm)s AsAsAsTsAsTsCsTsAsCs(Am)s (Am)s(Cm)s(Tm)s(Tm) |

Figure 17:
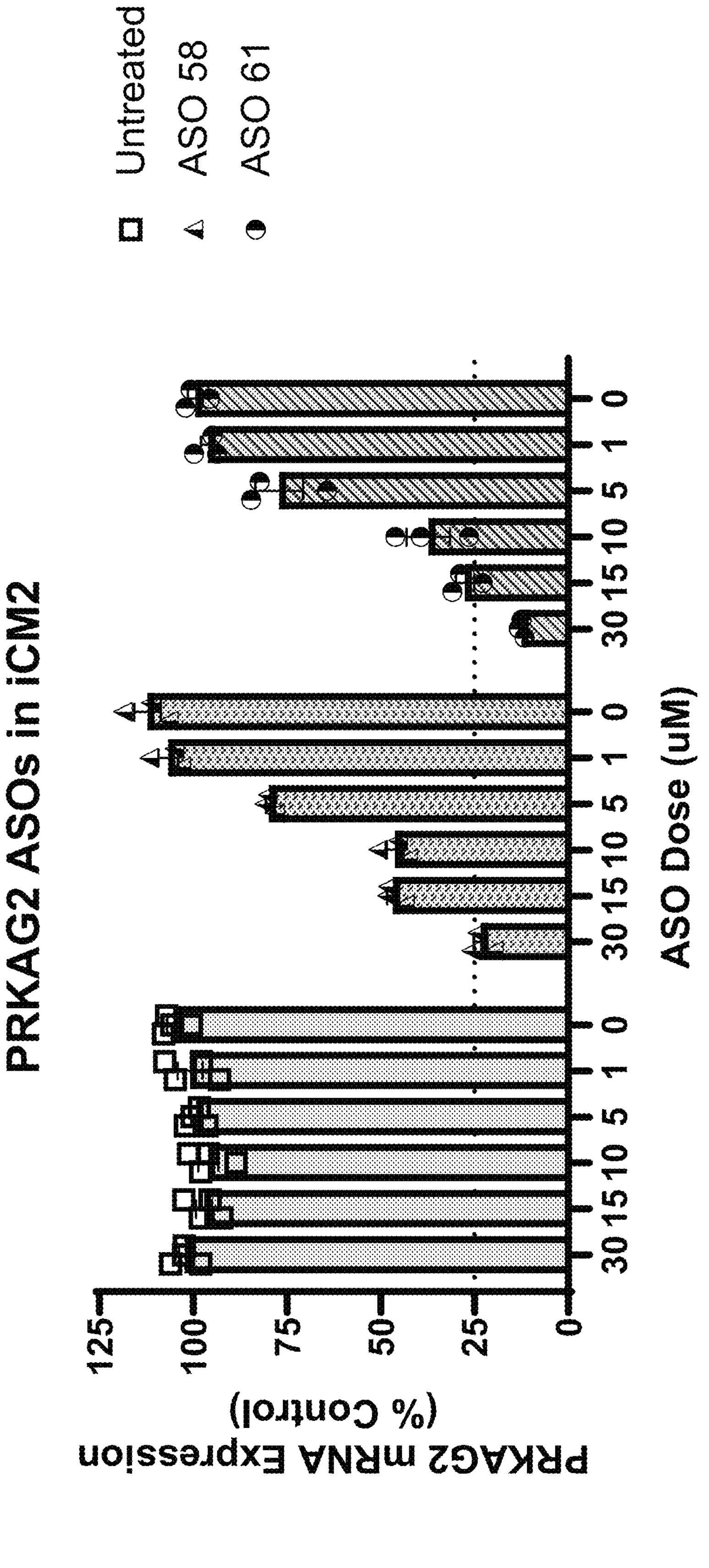
FIG. 17 illustrates representative bar graphs showing PRKAG2 mRNA expression levels in human iPS-cardiomyocytes ($iCM^2$) in 72 hours after treated with PRKAG2 ASO Seq 58 or PRKAG2 ASO Seq 6 at concentrations of 1 μM, 5 μM, 10 μM, 15 μM and 30 μM.

Nm = 2'-MOE;
s = phosphorothioate backbone modification;
In some instances, 5' end of the ASO is coupled to (5'NH2C6) to conjugate with the antibody Results Human iPS-cardiomyocytes ($iCM^2$) were transfected with increasing concentrations (e.g., 1 µM, 5 µM, 10 µM, 15 µM or 30 µM) of PRKAG2 ASO Seq 58 or ASO PRKAG2 ASO Seq61 for 72 hours. The results showed that the antisense oligonucleotides (ASO) PRKAG2 Seq 58 or PRKAG2 Seq 61 were observed to decrease PRKAG2 mRNA expression levels in a concentration dependent manner (FIG. 17). At the highest concentration of 30 µM, PRKAG2 ASO Seq 58 ASO was observed to decrease PRKAG2 mRNA expression levels by 75% and PRKAG2 ASO Seq 61 was observed to decrease PRKAG2 mRNA expression levels by 80% in human iPS-cardiomyocytes ($iCM^2$). Overall, the antisense oligonucleotides (ASOs) PRKAG2 Seq 58 and PRKAG2 Seq 61 were observed to decrease PRKAG2 mRNA expression levels in a concentration dependent manner in human iPS-cardiomyocytes ($iCM^2$) in vitro.

Example 15: In Vitro PRKAG2 siRNA-Fab Conjugate Treatment in Primary Human Adult Ventricular Cardiomyocytes (AVCMs)

Materials and Methods

Primary Human Adult Ventricular Cardiomyocytes (AVCMs) were obtained from AnaBios (AnaBios Donor ID: 230203HHB, 38 years, female, African American, Cause of Death: Anoxia/Drug Intoxication). Cells culture and cell treatment with PRKAG2 siRNAs-Fab was performed at AnaBios, according AnaBios proprietary protocols. 200,000 viable cells were seeded in each well of a 6 well plate. The siRNA, PRKAG2 siSeq61, PRKAG2 siSeq58, and PRKAG2 siRNA-Fab conjugates are described in Example 3 and Example 5. Cells were paced with intermittent stimulation per AnaBios protocols. 4 hours after seeding, cells received first AOC-Fab treatment at 30 nM in media containing Insulin-Transferrin-Selenium (ITS, ThermoFisher, Cat #41400045) and a second treatment was performed at day 2 in media without ITS. Cells were collected at day 3 in TryZol for RNA extraction, cDNA synthesis and qPCR. Human PRKAG2: Hs00211903 ml; AHSA1: Hs00201602_m1.

Results

Figure 18:
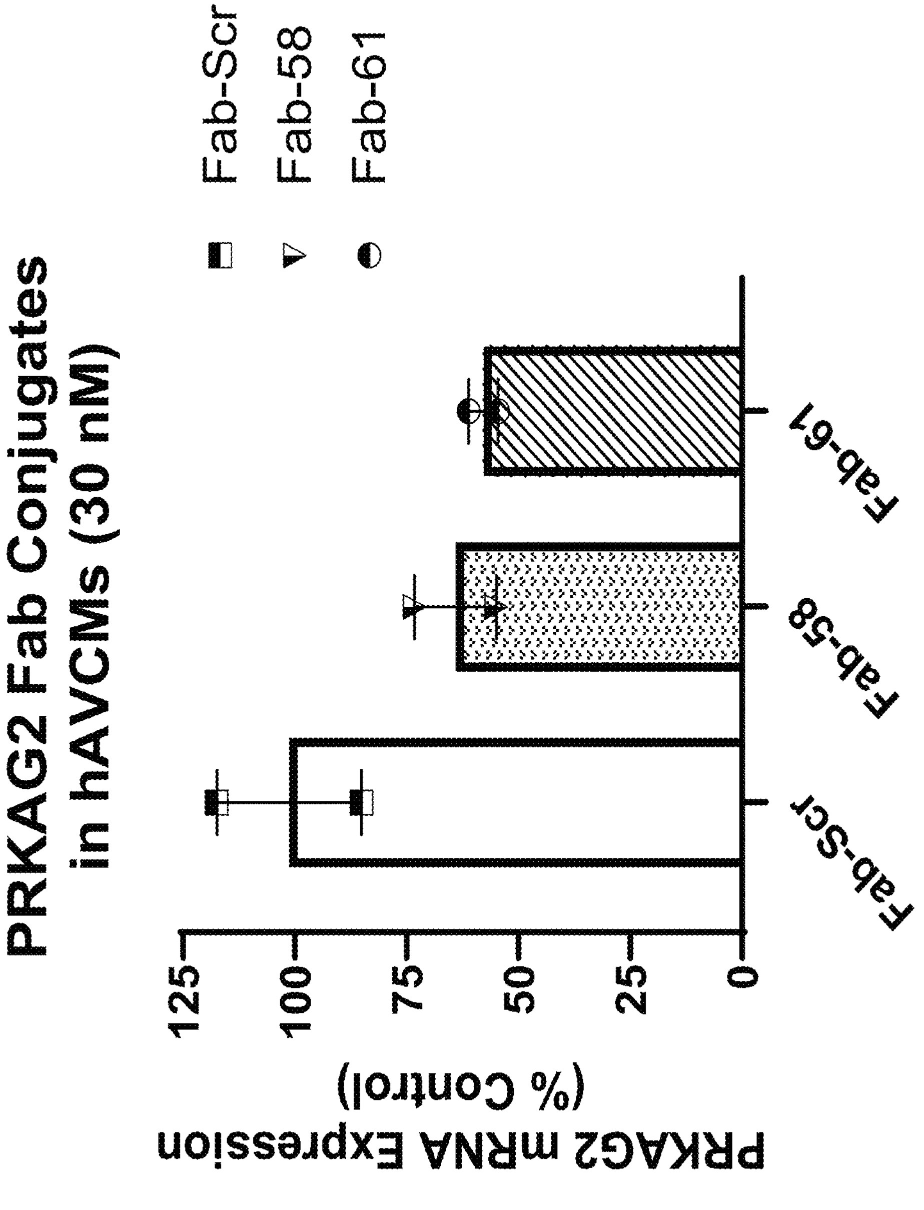
FIG. 18 illustrates representative bar graphs showing in vitro PRKAG2 mRNA expression levels in human primary Adult Ventricular Cardiomyocytes (AVCMs) in 72 hours after treated with PRKAG2siSeq61-Fab, PRKAG2 siSeq 58-Fab conjugates, or siScramble-Fab at a concentration of 30 nM.

Human primary Adult Ventricular Cardiomyocytes (AVCMs) were treated at Day 0 and at Day 2 with siSeq61-Fab conjugate, siSeq 58-Fab conjugate, or siScramble-Fab conjugate (control), at a concentration of 30 nM. PRKAG2 mRNA expression levels were determined by qPCR analysis at Day 3. The results demonstrated an observed reduction in PRKAG2 mRNA levels by about 40% in human AVCMs treated by siSeq58-Fab conjugates or siSeq61-Fab conjugates relative to the control. (FIG. 18). Overall, siPRKAG2-Fab conjugates were observed to significantly decrease PRKAG2 mRNA expression levels in human AVCMs.

Example 16: Evaluation of PRKAG2 AOC with Lead PRKAG2 siRNA in a Cardiac Mouse Model in Vivo Materials and Methods Trans-Aortic Constriction (TAC) is a model of pressure overload-induced cardiac hypertrophy and failure in mice. The degree of constriction ("tightness") dictates the TAC severity and it is determined by the gauge (g) of needle used. TAC surgery was performed at Envigo, using a 26 g needle, causing a moderate heart injury, according Envigo's procedures and animal IACUC protocols. WT male mice, ($C_{57}$BL/6NCrl), 9-10 weeks of age underwent TAC surgery. After 10-14 days, mice (n=16) received a single 3 mg/kg dose of PRKAG2 AOC (siRNA dose). The sham mice (n=8) and control TAC mice (n=13) were administered PBS. PRKAG2 AOC was made with PRKAG2 siRNA Seq 61+Vp conjugated to a mouse TfR1 antibody (BioXcell InVivo mAb, Cat #BE0175) using a SMCC linker. The PRKAG2 siSeq61+Vp and PRKAG2 antibody-oligonucleotide conjugates (AOC) are described in Example 5 and Example 6.

6 weeks after PRKAG2 AOC injection (corresponding to 8 weeks after TAC surgery), echocardiogram was performed, and animals were sacrificed, and hearts were collected for analysis. Echocardiography (Echo) was performed 8 weeks post TAC in conscious mice, according to IACUC protocols. Echo was performed using Vevo 3100 high-resolution Imaging System (Fujifilm VisualSonics, Toronto, Ontario, Canada). To obtain more accurate cardiac measurements and avoid the cardio suppressive effects of anesthesia, conscious echo was performed, using oxygen flow at 0.8 L/hr. Animal fur was removed in chest area with nair, snout was placed in a nose cone and mice were restrained to the Echo platform with surgical tape. Electrode gel was applied to the contact areas between the paws and the electrode surface. Pre-warmed sonography gel was applied to the chest area. LAX B-mode was used to acquire EF %, SV and LV volume measurements. The long axis of the heart was imaged, the LVOT was aligned with the apex and images with wide open aorta and largest diameter of ventricles were acquired. SAX B-mode and M-mode were used for FS %, LV posterior wall thickness and LV diameter. B-model cine loops were generated visualizing the maximum dimension of the LV from apex to base in a parasternal long axis view. After LAX image acquisition, the probe was moved on 900 to capture the SAX B-mode, to image along the short axis of the heart. Heart apex, papillary muscles and atria were localized and images were taken when the largest diameter was seen. An image sequence was acquired. After switching to M-mode, images were acquired when a posterior and the anterior wall were seen, without interfering with papillary muscles. After completion of acquisition animals were wiped gently with a kimwipe to remove gel, tape was removed, and animals were returned to home cage. All acquired images were digitally stored in raw format (DICOM) for further offline-analysis.

A specific stem-loop real-time quantitative polymerase chain reaction (SL-RT-qPCR) assay was designed to measure the amount of guide strand of siRNA Seq61 in tissue homogenate. The SL-RT-qPCR assay along with the general primer and TaqMan probe have been previously described (Chen, 2005). Briefly, calibration standards for an 8-point standard curve were generated by a 1:10 serial dilution of siRNA Seq61 in TRIzol (Thermo Fisher). Study samples were diluted in assay diluent (TE Buffer with 0.1% Triton-X) up to the recommended Minimum Required Dilution (MRD; 1:100). The calibration standards were diluted in assay diluent. A siRNA-specific reverse transcription (RT) primer (custom from Integrated DNA Technologies) was added to the calibration standards and study samples, followed by an annealing and a reverse transcription step (Fisher Scientific, #43-665-97) on a thermocycler. The RT products were quantified via conventional TaqMan RT-PCR (Fisher Scientific, #44-445-58) which includes a siRNA-specific forward primer (custom from Integrated DNA Technologies), a universal reverse primer (custom from Integrated DNA Technologies), and a dye labeled siRNA-specific TaqMan probe (custom from Thermo Fisher). Raw Ct values were exported using the QuantStudio Real-Time PCR and Excel software. The standard curve of Ct values vs. log base 10 of corresponding siRNA concentrations was generated in GraphPad Prism 9.3.1. A simple linear regression of the siRNA standard curve was performed in GraphPad Prism, and the linear equation was used to interpolate study sample plasma concentrations in Excel. The lower limit of quantification was 5 μM. Sample values are reported as the average of technical replicates. qPCR Taqman Assays were performed to detect Mouse PRKAG2: Mm00513977_m1, Mouse SERCA2: Mm01201431_m1, Mouse PPIB: Mm00478295_m1.

Results

Figure 19A:
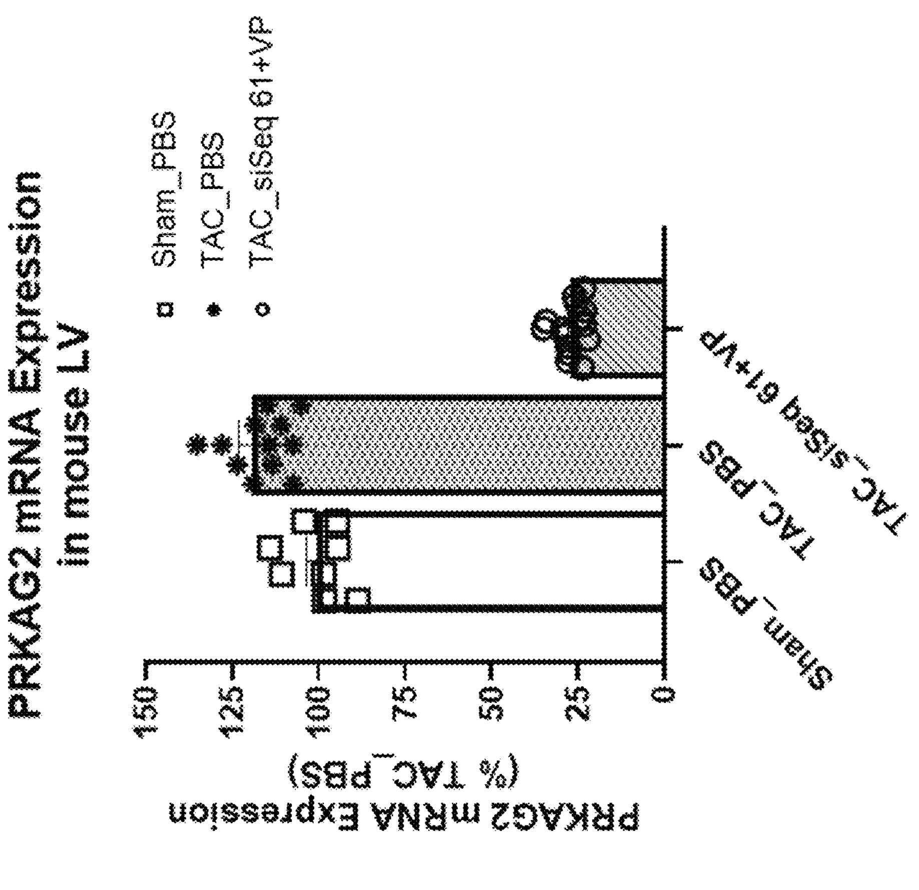
FIGS. 19A-19F are representative graphs showing the cardiac improvements in a trans-aortic constriction (TAC) mouse model that that has been administered an injection of PRKAG2 AOC (PRKAG2 siSeq 61+Vp conjugated to a mouse TfR1 antibody). 10-14 days after TAC cardiac surgery, WT mice received a single 3 mg/kg dose of PRKAG2 AOC, made with lead PRKAG2 siSeq 61+Vp conjugated to a mouse TfR1 antibody. 8 weeks after TAC surgery, an echocardiogram was performed, and animals were sacrificed, and hearts were collected for analysis.
Figure 19B:
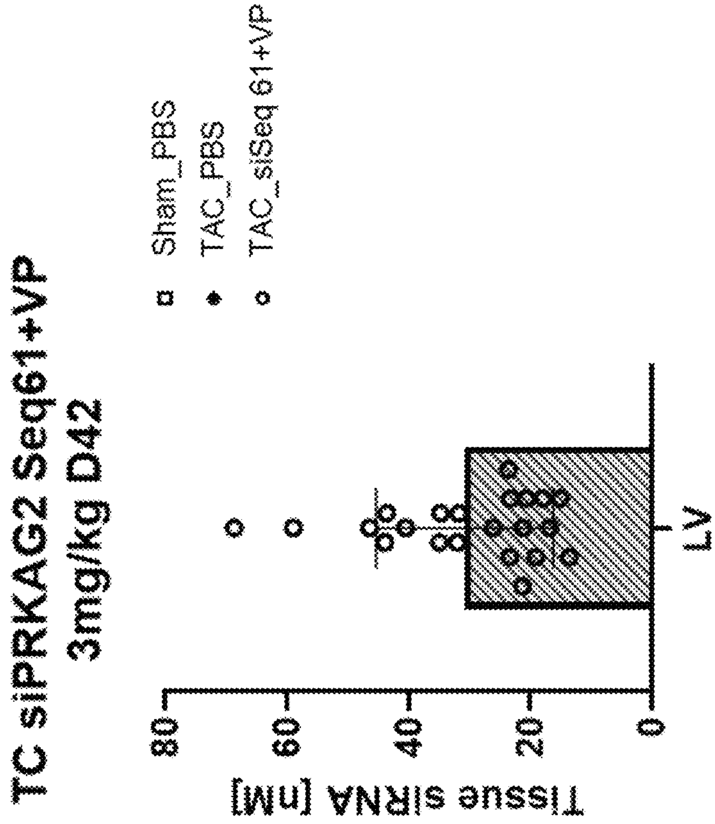
Figure 19C:
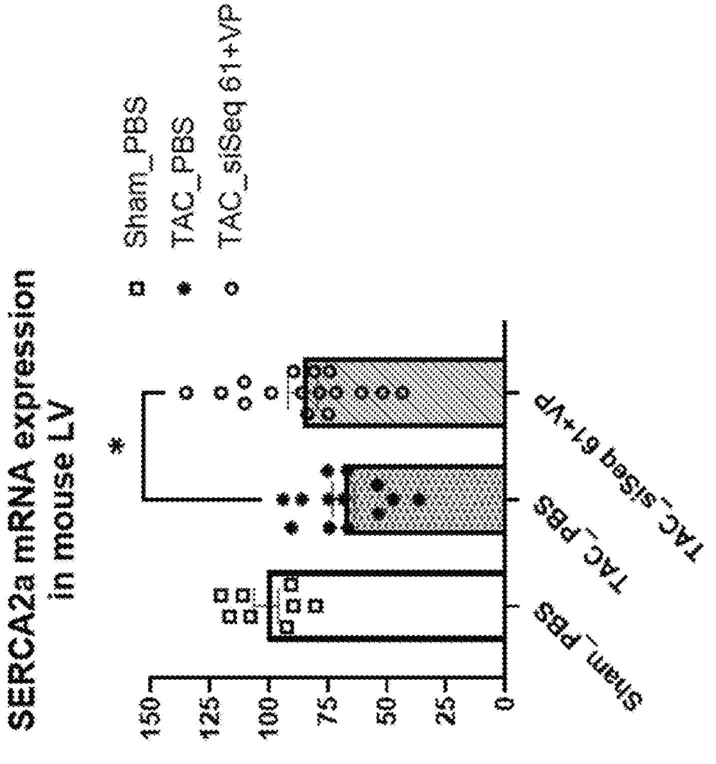
Figure 19D:
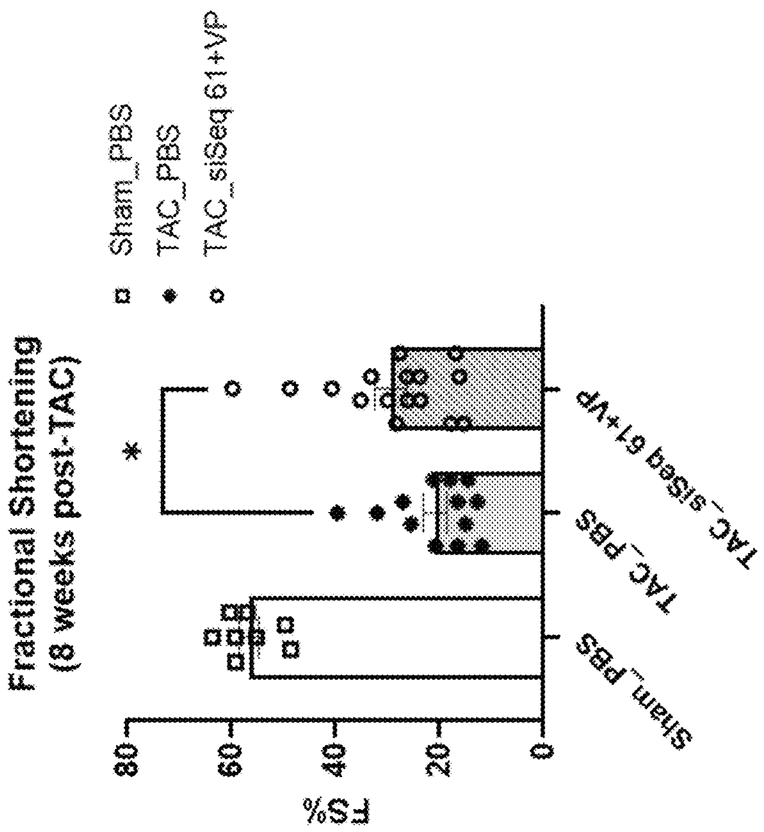
Figure 19E:
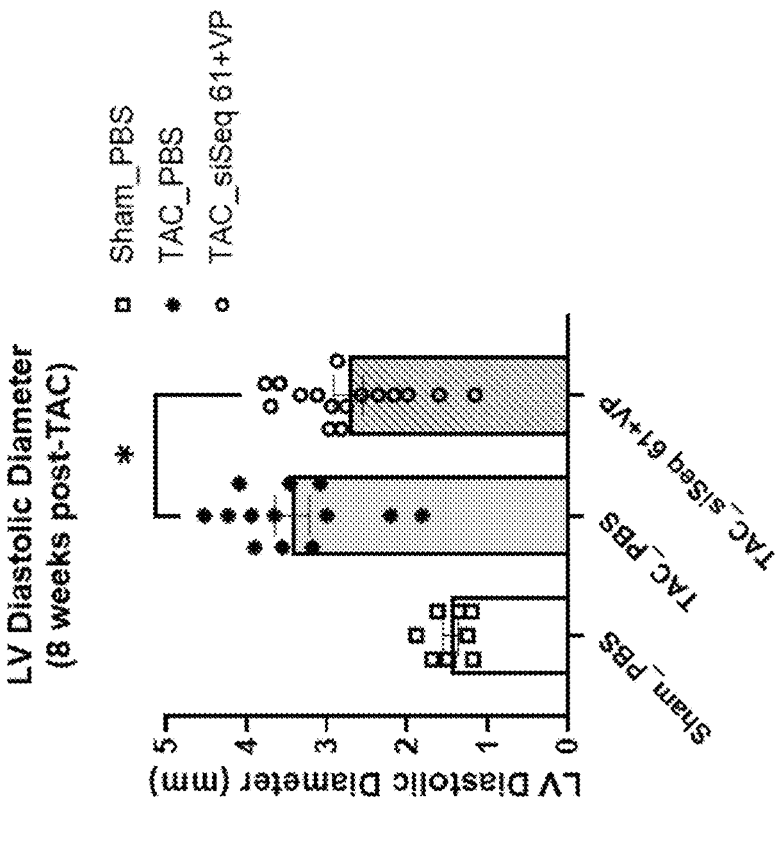
Figure 19F:
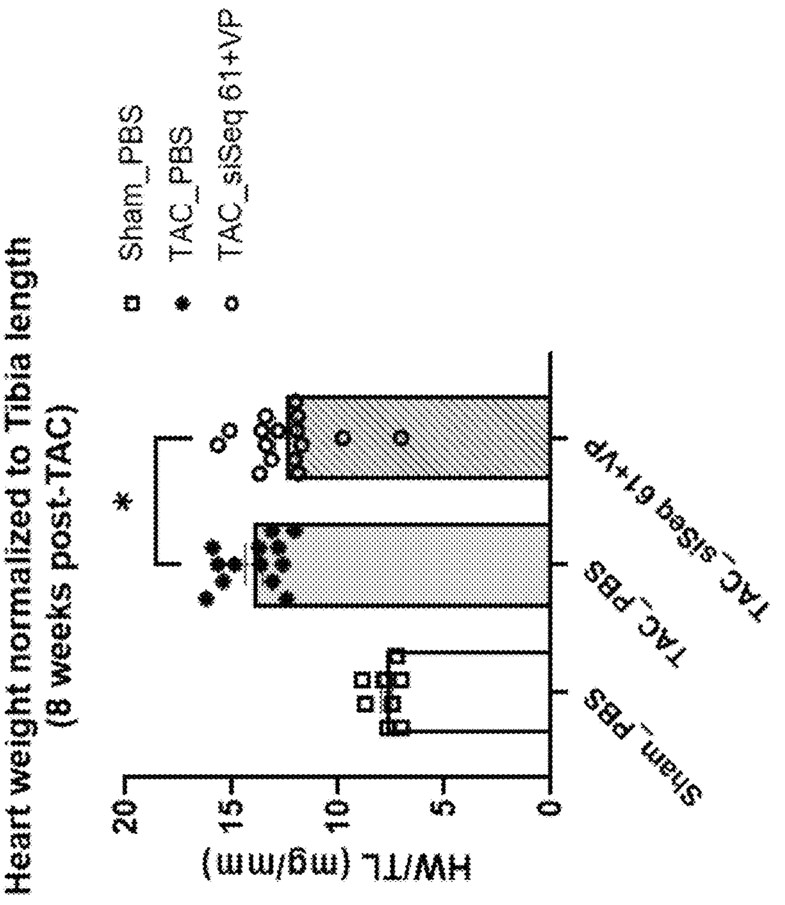

The PRKAG2 AOC (PRKAG2 siSeq 61+Vp conjugated to a mouse TfR1 antibody) was evaluated in the TAC mouse model in vivo. A single dose of 3 mg/kg of PRKAG2 AOC was administered to TAC mice 10-14 days after TAC cardiac surgery. Wild-type mice received a dose of PBS. The results showed that the administration PRKAG2 AOC reduced PRKAG2 expression levels of 75% in hearts obtained from TAC mice compared to the levels of control mice (FIG. 19A). In addition, cardiac tissue concentrations of siRNA were about 30 nM as measured in the left ventricle of the hearts (LV) after a single injection of 3 mg/kg dose of PRKAG2 AOC (FIG. 19B). Furthermore, relative expression levels of the cardiac biomarker Serca2a in LV were measured by qPCR 6 weeks after PRKAG2 AOC injection. Serca2a expression levels were downregulated upon TAC injury to an average of 70%, but the single injection of PRKAG2 AOC in TAC injured mice was able to restore Serca2a expression levels to about 80% (FIG. 19C). In addition, TAC injury decreased the percentage of fractional shortening (FS %) from an average of 57% in WT sham mice to 20%, indicating that the TAC heart injury was properly causing a cardiac damage. However, PRKAG2 AOC treated TAC injured mice had a FS % of 30%, showing that the AOC can improve cardiac function after severe heart damage as measured by FS % (FIG. 19D). Furthermore, sham operated mice have a left ventricular diastolic diameter (LVDD) average of 1.3 mm, while TAC-PBS mice have an average of 3.5 mm, indicating cardiac hypertrophy. However, PRKAG2 AOC treatment reduced the LVDD in TAC mice to an average of 2.7 mm (FIG. 19E). Finally, TAC mice injected with PBS have a higher normalized heart weight ratio compared to sham mice suggesting TAC mice have cardiac hypertrophy. However, TAC mice injected with PRKAG2 AOC have an improved normalized heart weight ratio compared to the one of TAC mice injected with PBS (FIG. 19F). Overall, these results suggest that the administration of PRKAG2 AOC (PRKAG2 siSeq61+Vp conjugated to anti-TfR1 antibody) improves cardiac functions in a TAC mouse model for heart failure.

Example 17: PRKAG2 AOC has a Long-Lasting Duration of Action in Mice

Materials and Methods 8-10 weeks old, male $C_{57}$BL/6NCrl WT mice (n=4) received a single injection of PRKAG2 AOC (lead sequence siSeq61+Vp conjugated to a mouse TfR1 antibody) at a dose of 1 mg/kg or 2 mg/kg (siRNA dose) or control PBS (n=4). Samples were collected at 2, 4, and 6 months after dosing. Echocardiogram was performed before the 6 months after dosing. The PRKAG2 siSeq61+Vp and PRKAG2 antibody-oligonucleotide conjugates (AOC) are described in Example 5 and Example 6.

A specific stem-loop real-time quantitative polymerase chain reaction (SL-RT-qPCR) assay was designed to measure the guide strand of siRNA Seq61 in tissue homogenate. The SL-RT-qPCR assay along with the general primer and TaqMan probe have been previously described (Chen, 2005). Briefly, calibration standards for an 8-point standard curve were generated by a 1:10 serial dilution of PRKAG2 siRNA-Seq61 in TRIzol (Thermo Fisher). Study samples were diluted in assay diluent (TE Buffer with 0.1% Triton-X) up to the recommended Minimum Required Dilution (MRD; 1:100). The calibration standards were diluted in assay diluent. A siRNA-specific reverse transcription (RT) primer (custom from Integrated DNA Technologies) was added to the calibration standards and study samples, followed by an annealing and a reverse transcription step (Fisher Scientific, #43-665-97) on a thermocycler. The RT products were quantified via conventional TaqMan RT-PCR (Fisher Scientific, #44-445-58) which includes a siRNA-specific forward primer (custom from Integrated DNA Technologies), a universal reverse primer (custom from Integrated DNA Technologies), and a dye labeled siRNA-specific TaqMan probe (custom from Thermo Fisher). Raw Ct values were exported using the QuantStudio Real-Time PCR and Excel software. The standard curve of Ct values vs. log base 10 of corresponding siRNA concentrations was generated in GraphPad Prism 9.3.1. A simple linear regression of the siRNA standard curve was performed in GraphPad Prism, and the linear equation was used to interpolate study sample plasma concentrations in Excel. The lower limit of quantification was 5 μM. Sample values are reported as the average of technical replicates. qPCR Taqman Assays were performed to detect Mouse PRKAG2: Mm00513977_m1, Mouse PPIB: Mm00478295_m1.

Results

Figure 20:
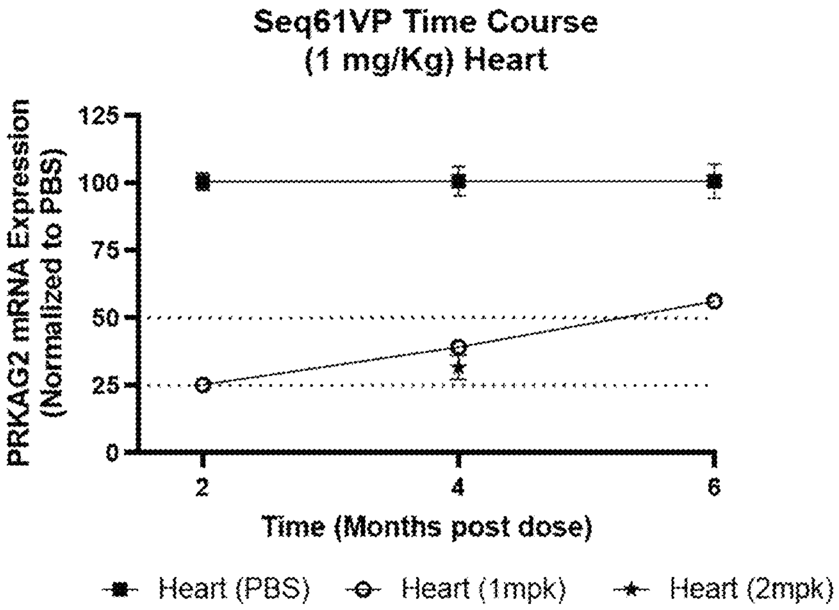
FIG. 20 is plot showing in vivo time dependence of PRKAG2 mRNA expression levels in hearts obtained from wild-type mice after a single injection of PRKAG2 AOC (siRNA Seq 61+Vp conjugated to a mouse TfR1 antibody) at a concentration of 1 mg/kg of AOC (siRNA dose) at 2 months, 4 months, and 6 months post-dose, or 2 mg/kg of AOC (siRNA dose) at 4 months post-dose.

The results showed that PRKAG2 mRNA expression levels in the mouse cardiac cells were reduced to about 25% at 2 months and about 50% at 6 months after a single injection of PRKAG2 AOC at a dose of 1 mg/kg compared to PRKAG2 mRNA expression levels in control mice (FIG. 20).

Overall, the results indicated that a single administration of PRKAG2 AOC in mice was observed to have a duration of action up to 6 months in cardiac tissues.

Example 18: In Vivo Evaluation of PRKAG2 AOC with Lead PRKAG2 siRNA in Non-Human Primate (NHP)

Materials and Methods

Animal study was performed following Institutional Animal Care and Use Committee (IACUC) protocols. Throughout the study, animals were housed individually in a stainless-steel wire cages (720 W×700 L×800H mm). The animals had access to about 60 g of diet (Teklad Global Certified 20% Protein Primate Diet 2050C, Envigo, USA), twice daily. The animals had ad libitum access to filtered, ultraviolet light-irradiated municipal tap water at all times.

Pharmacokinetics (PK) and Pharmacodynamics (PD) profiles of PRKAG2 antibody-oligonucleotide conjugates (AOC), AOC siSeq61+Vp conjugated with human a-TfR1 antibody, following a single intravenous (IV) administration was evaluated in WT cynomolgus monkeys (naïve). The PRKAG2 siSeq61+Vp and PRKAG2 antibody-oligonucleotide conjugates (AOC) are described in Example 4 and Example 5.

Male Cynomolgus monkeys, approximately 2 to 4 years of age at receipt, and approximately 2 to 4 kg body weight at the start of treatment received either doses of vehicle (saline) control (n=2) or PRKAG2 siRNA AOC at 3 mg/kg (siRNA dose) (n=3) on Day 1. Heart tissue samples were collected at necropsy on Day 29.

Tissue samples were evaluated for mRNA expression using a comparative RT-qPCR assay. Tissues samples ranging from 25-50 mg were homogenized in 1 mL of TRIzol (Thermo Fisher) on the OMNI Bead Ruptor Elite system (OMNI International). Total RNA was isolated from tissue homogenate supernatant using the Direct-zol-96 RNA kit (Zymo Research) according to the manufacturer's instructions. 250 ng of purified RNA was reverse transcribed to cDNA using the HighCapacity cDNA Reverse Transcription Kit (Applied Biosystem) and SimpliAmp Thermal Cycler (Applied Biosystem). The amount of cDNA used per qPCR reaction was 50 ng for muscle analysis. qPCR was performed using TaqMan Fast Universal Master Mix II (Thermo Fisher) and commercially available Taqman Assays (PRKAG2 Mf04185244_m1-FAM; SSB Mf04187362_g1-VIC). Each sample was run in technical duplicates in a Quant Studio instrument (Thermo Fisher). qPCR data was analyzed using the ΔΔCt method with gene of interest normalized to Small RNA Binding Exonuclease Protection Factor La gene (SSB) expression. PRKAG2 expression in heart was calculated using formula: 100*[2^−(ΔCt sample−Average ΔCt1M001, 1M002)]. PRKAG2 expression in skeletal muscle was calculated using formula: 100*[2^−(ΔCt sample−ΔCt Predose)]; where Ct is the qPCR cycle threshold. Data was analyzed using GraphPad Prism 10 and is expressed as mean±SD.

A specific stem-loop real-time quantitative polymerase chain reaction (SL-RT-qPCR) assay was designed to measure the amount of guide strand of PRKAG2 siRNA Seq61 in cynomolgus monkey plasma. The SL-RT-qPCR assay along with the general primer and TaqMan probe have been previously described (Chen, 2005). Briefly, calibration standards for an 8-point standard curve were generated by a 1:10 serial dilution of PRKAG2 siRNA Seq61 in Cynomolgus Monkey gendered pooled plasma (BIOIVT Cat #NHP01PLKP2N). Study samples were diluted in assay diluent (TE Buffer with 0.1% Triton-X) up to the recommended Minimum Required Dilution (MRD; 1:100). The calibration standards were diluted in assay diluent. A siRNA-specific reverse transcription (RT) primer (custom from Integrated DNA Technologies) was added to the calibration standards and study samples, followed by an annealing and a reverse transcription step (Fisher Scientific, #43-665-97) on a thermocycler. The RT products were quantified via conventional TaqMan RT-PCR (Fisher Scientific, #44-445-58) which includes a siRNA-specific forward primer (custom from Integrated DNA Technologies), a universal reverse primer (custom from Integrated DNA Technologies), and a dye labeled siRNA-specific TaqMan probe (custom from Thermo Fisher). Raw Ct values were exported using the QuantStudio Real-Time PCR and Excel software. The standard curve of Ct values vs. log base 10 of corresponding siRNA concentrations was generated in GraphPad Prism 9.3.1. A simple linear regression of the siRNA standard curve was performed in GraphPad Prism, and the linear equation was used to interpolate study sample plasma concentrations in Excel. The lower limit of quantification was 5 μM. Sample values are reported as the average of technical replicates.

Body weights were measured weekly. Heart weights were collected at necropsy. Heart/body weight ratios were calculated for each animal.

Results

Figure 21B:
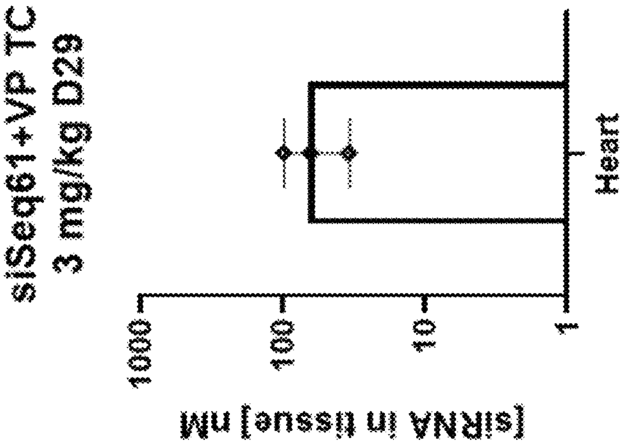
FIGS. 21A-21E are representative graphs showing cardiac parameters in NHP administered a single injection of PRKAG2 AOC (siRNA Seq61+Vp conjugated to a humanTfR1 antibody) at a dose of 3 mg/kg of AOC.
Figure 21A:
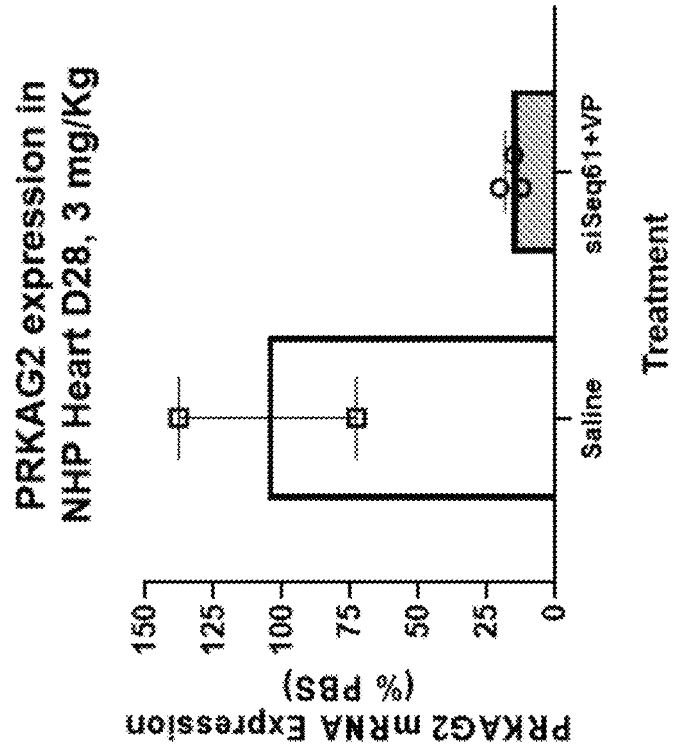
Figure 21C:
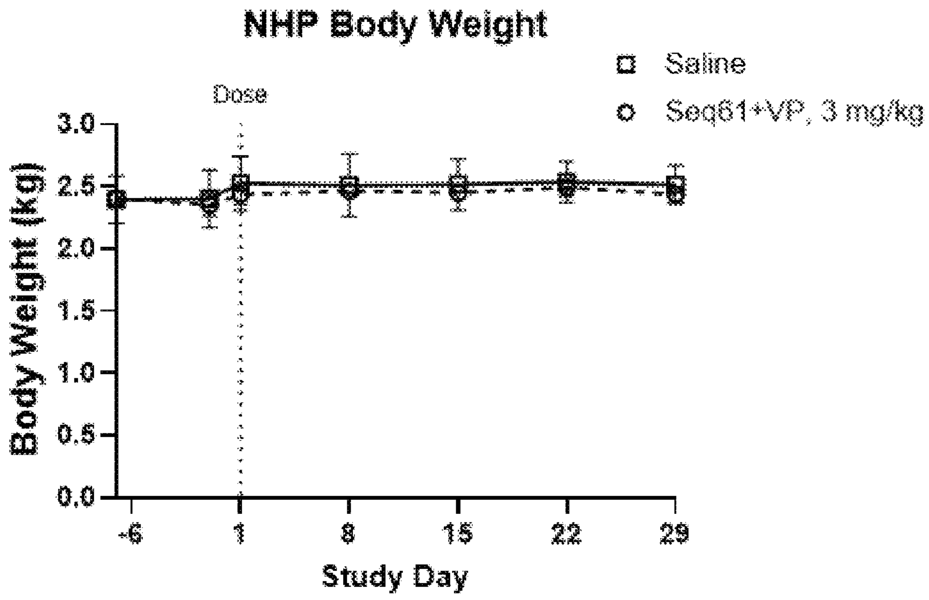
Figure 21D:
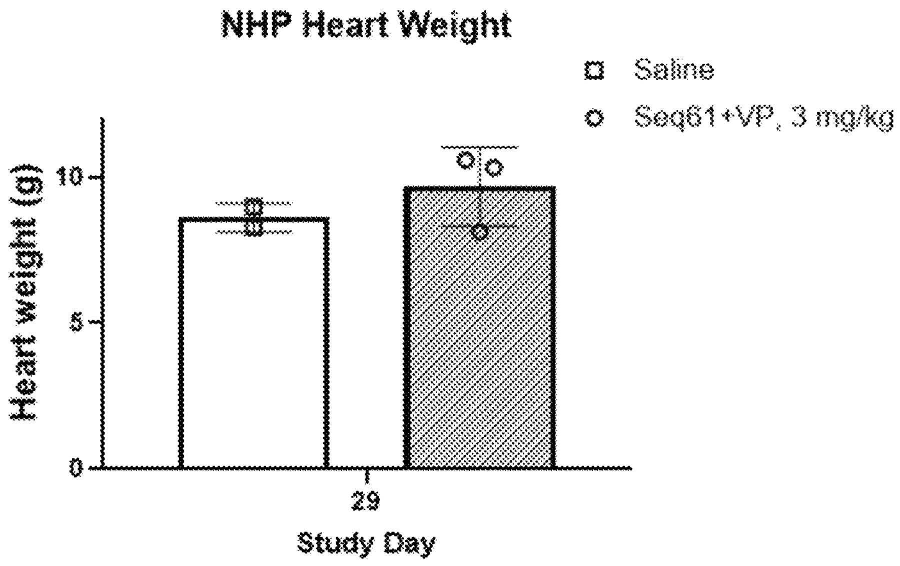
Figure 21E:
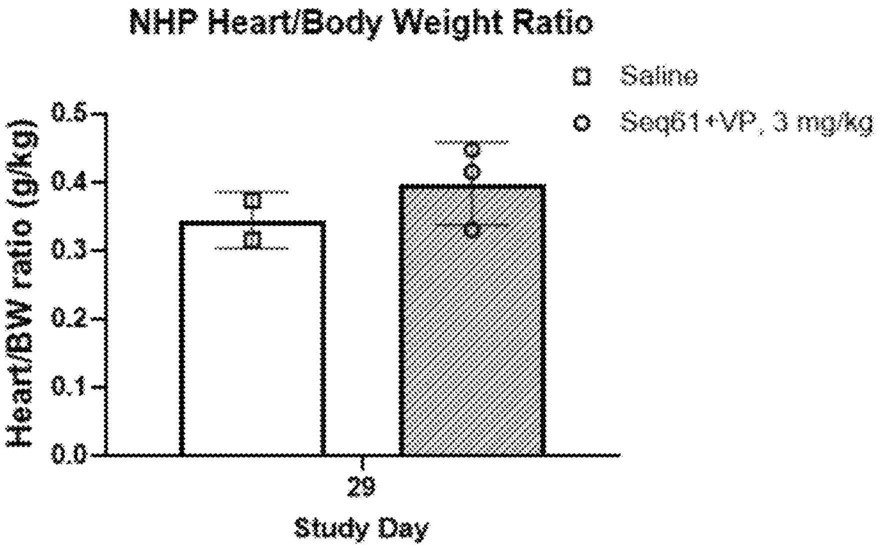

Male Cynomolgus monkey received a single 3 mg/kg (siRNA dose) IV injection of PRKAG2 siRNA AOC (siRNA Seq 61+Vp conjugated to a human TfR1 antibody) (n=3) or saline (n=2) and muscle tissues were collected 28 days post-injection of the PRKAG2 siRNA AOC. The results indicated PRKAG2 mRNA expression levels were observed to decrease by about 80% in cardiac muscle in comparison to PRKAG2 mRNA expression levels of control animals (FIG. 21A). In addition, PRKAG2 siRNA tissue concentrations were about 100 nM in cardiac tissue at Day 29 (FIG. 21B). Thus, administration of PRKAG2 siRNA AOC was observed to deliver high levels of siRNA to cardiac tissue. In addition, animal body weights were measured weekly and no significant differences were observed between PRKAG2 siRNA AOC-injected animals and control animals (FIG. 21C). Furthermore, no significant differences were observed between heart weights of PRKAG2 siRNA AOC-injected animals and control animals (FIG. 21D). Heart/body weight ratios were also observed to be comparable for PRKAG2 siRNA AOC-injected animals and control animals (FIG. 21E). Overall, the administration of PRKAG2 siRNA AOC in NHP was observed to decrease PRKAG2 mRNA expression levels in cardiac tissue, and was not observed to have significant measurable effects on body weight or heart weight.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

SEQUENCE LISTING

```
Sequence total quantity: 340
SEQ ID NO: 1          moltype = RNA  length = 21
FEATURE               Location/Qualifiers
source                1..21
                      mol_type = other RNA
                      organism = synthetic construct
SEQUENCE: 1
ccagcatgcc ggcttccgcg g                                            21

SEQ ID NO: 2          moltype = RNA  length = 21
FEATURE               Location/Qualifiers
source                1..21
                      mol_type = other RNA
                      organism = synthetic construct
SEQUENCE: 2
tccagcatgc cggcttccgc g                                            21

SEQ ID NO: 3          moltype = RNA  length = 21
FEATURE               Location/Qualifiers
source                1..21
                      mol_type = other RNA
                      organism = synthetic construct
SEQUENCE: 3
ctccagcatg ccggcttccg c                                            21

SEQ ID NO: 4          moltype = RNA  length = 21
FEATURE               Location/Qualifiers
source                1..21
                      mol_type = other RNA
                      organism = synthetic construct
SEQUENCE: 4
ttctccagca tgccggcttc c                                            21
```

```
SEQ ID NO: 5            moltype = RNA  length = 21
FEATURE                 Location/Qualifiers
source                  1..21
                        mol_type = other RNA
                        organism = synthetic construct
SEQUENCE: 5
cttctccagc atgccggctt c                                              21

SEQ ID NO: 6            moltype = RNA  length = 21
FEATURE                 Location/Qualifiers
source                  1..21
                        mol_type = other RNA
                        organism = synthetic construct
SEQUENCE: 6
gcttctccag catgccggct t                                              21

SEQ ID NO: 7            moltype = RNA  length = 21
FEATURE                 Location/Qualifiers
source                  1..21
                        mol_type = other RNA
                        organism = synthetic construct
SEQUENCE: 7
agcttctcca gcatgccggc t                                              21

SEQ ID NO: 8            moltype = RNA  length = 21
FEATURE                 Location/Qualifiers
source                  1..21
                        mol_type = other RNA
                        organism = synthetic construct
SEQUENCE: 8
cagcttctcc agcatgccgg c                                              21

SEQ ID NO: 9            moltype = RNA  length = 21
FEATURE                 Location/Qualifiers
source                  1..21
                        mol_type = other RNA
                        organism = synthetic construct
SEQUENCE: 9
gtgtgacctc atgaatcgca t                                              21

SEQ ID NO: 10           moltype = RNA  length = 21
FEATURE                 Location/Qualifiers
source                  1..21
                        mol_type = other RNA
                        organism = synthetic construct
SEQUENCE: 10
tgtgtgacct catgaatcgc a                                              21

SEQ ID NO: 11           moltype = RNA  length = 21
FEATURE                 Location/Qualifiers
source                  1..21
                        mol_type = other RNA
                        organism = synthetic construct
SEQUENCE: 11
ttgtgtgacc tcatgaatcg c                                              21

SEQ ID NO: 12           moltype = RNA  length = 21
FEATURE                 Location/Qualifiers
source                  1..21
                        mol_type = other RNA
                        organism = synthetic construct
SEQUENCE: 12
cttgtgtgac ctcatgaatc g                                              21

SEQ ID NO: 13           moltype = RNA  length = 21
FEATURE                 Location/Qualifiers
source                  1..21
                        mol_type = other RNA
                        organism = synthetic construct
SEQUENCE: 13
acttgtgtga cctcatgaat c                                              21

SEQ ID NO: 14           moltype = RNA  length = 21
FEATURE                 Location/Qualifiers
source                  1..21
                        mol_type = other RNA
                        organism = synthetic construct
SEQUENCE: 14
cacttgtgtg acctcatgaa t                                              21
```

```
SEQ ID NO: 15          moltype = RNA  length = 21
FEATURE                Location/Qualifiers
source                 1..21
                       mol_type = other RNA
                       organism = synthetic construct
SEQUENCE: 15
acacttgtgt gacctcatga a                                              21

SEQ ID NO: 16          moltype = RNA  length = 21
FEATURE                Location/Qualifiers
source                 1..21
                       mol_type = other RNA
                       organism = synthetic construct
SEQUENCE: 16
taacacttgt gtgacctcat g                                              21

SEQ ID NO: 17          moltype = RNA  length = 21
FEATURE                Location/Qualifiers
source                 1..21
                       mol_type = other RNA
                       organism = synthetic construct
SEQUENCE: 17
cataacactt gtgtgacctc a                                              21

SEQ ID NO: 18          moltype = RNA  length = 21
FEATURE                Location/Qualifiers
source                 1..21
                       mol_type = other RNA
                       organism = synthetic construct
SEQUENCE: 18
tcataacact tgtgtgacct c                                              21

SEQ ID NO: 19          moltype = RNA  length = 21
FEATURE                Location/Qualifiers
source                 1..21
                       mol_type = other RNA
                       organism = synthetic construct
SEQUENCE: 19
atgtcataac acttgtgtga c                                              21

SEQ ID NO: 20          moltype = RNA  length = 21
FEATURE                Location/Qualifiers
source                 1..21
                       mol_type = other RNA
                       organism = synthetic construct
SEQUENCE: 20
acgatgtcat aacacttgtg t                                              21

SEQ ID NO: 21          moltype = RNA  length = 21
FEATURE                Location/Qualifiers
source                 1..21
                       mol_type = other RNA
                       organism = synthetic construct
SEQUENCE: 21
aacgatgtca taacacttgt g                                              21

SEQ ID NO: 22          moltype = RNA  length = 21
FEATURE                Location/Qualifiers
source                 1..21
                       mol_type = other RNA
                       organism = synthetic construct
SEQUENCE: 22
gaacgatgtc ataacacttg t                                              21

SEQ ID NO: 23          moltype = RNA  length = 21
FEATURE                Location/Qualifiers
source                 1..21
                       mol_type = other RNA
                       organism = synthetic construct
SEQUENCE: 23
tggaacgatg tcataacact t                                              21

SEQ ID NO: 24          moltype = RNA  length = 21
FEATURE                Location/Qualifiers
source                 1..21
                       mol_type = other RNA
                       organism = synthetic construct
SEQUENCE: 24
```

```
ttggaacgat gtcataacac t                                            21

SEQ ID NO: 25          moltype = RNA  length = 21
FEATURE                Location/Qualifiers
source                 1..21
                       mol_type = other RNA
                       organism = synthetic construct
SEQUENCE: 25
gttggaacga tgtcataaca c                                            21

SEQ ID NO: 26          moltype = RNA  length = 21
FEATURE                Location/Qualifiers
source                 1..21
                       mol_type = other RNA
                       organism = synthetic construct
SEQUENCE: 26
ggttggaacg atgtcataac a                                            21

SEQ ID NO: 27          moltype = RNA  length = 21
FEATURE                Location/Qualifiers
source                 1..21
                       mol_type = other RNA
                       organism = synthetic construct
SEQUENCE: 27
tggttggaac gatgtcataa c                                            21

SEQ ID NO: 28          moltype = RNA  length = 21
FEATURE                Location/Qualifiers
source                 1..21
                       mol_type = other RNA
                       organism = synthetic construct
SEQUENCE: 28
ctggttggaa cgatgtcata a                                            21

SEQ ID NO: 29          moltype = RNA  length = 21
FEATURE                Location/Qualifiers
source                 1..21
                       mol_type = other RNA
                       organism = synthetic construct
SEQUENCE: 29
actggttgga acgatgtcat a                                            21

SEQ ID NO: 30          moltype = RNA  length = 21
FEATURE                Location/Qualifiers
source                 1..21
                       mol_type = other RNA
                       organism = synthetic construct
SEQUENCE: 30
aactggttgg aacgatgtca t                                            21

SEQ ID NO: 31          moltype = RNA  length = 21
FEATURE                Location/Qualifiers
source                 1..21
                       mol_type = other RNA
                       organism = synthetic construct
SEQUENCE: 31
gaactggttg gaacgatgtc a                                            21

SEQ ID NO: 32          moltype = RNA  length = 21
FEATURE                Location/Qualifiers
source                 1..21
                       mol_type = other RNA
                       organism = synthetic construct
SEQUENCE: 32
tgaactggtt ggaacgatgt c                                            21

SEQ ID NO: 33          moltype = RNA  length = 21
FEATURE                Location/Qualifiers
source                 1..21
                       mol_type = other RNA
                       organism = synthetic construct
SEQUENCE: 33
ttgaactggt tggaacgatg t                                            21

SEQ ID NO: 34          moltype = RNA  length = 21
FEATURE                Location/Qualifiers
source                 1..21
                       mol_type = other RNA
                       organism = synthetic construct
```

-continued

```
SEQUENCE: 34
tttgaactgg ttggaacgat g                                              21

SEQ ID NO: 35          moltype = RNA  length = 21
FEATURE                Location/Qualifiers
source                 1..21
                       mol_type = other RNA
                       organism = synthetic construct
SEQUENCE: 35
ctttgaactg gttggaacga t                                              21

SEQ ID NO: 36          moltype = RNA  length = 21
FEATURE                Location/Qualifiers
source                 1..21
                       mol_type = other RNA
                       organism = synthetic construct
SEQUENCE: 36
gctttgaact ggttggaacg a                                              21

SEQ ID NO: 37          moltype = RNA  length = 21
FEATURE                Location/Qualifiers
source                 1..21
                       mol_type = other RNA
                       organism = synthetic construct
SEQUENCE: 37
agctttgaac tggttggaac g                                              21

SEQ ID NO: 38          moltype = RNA  length = 21
FEATURE                Location/Qualifiers
source                 1..21
                       mol_type = other RNA
                       organism = synthetic construct
SEQUENCE: 38
caagctttga actggttgga a                                              21

SEQ ID NO: 39          moltype = RNA  length = 21
FEATURE                Location/Qualifiers
source                 1..21
                       mol_type = other RNA
                       organism = synthetic construct
SEQUENCE: 39
acaagctttg aactggttgg a                                              21

SEQ ID NO: 40          moltype = RNA  length = 21
FEATURE                Location/Qualifiers
source                 1..21
                       mol_type = other RNA
                       organism = synthetic construct
SEQUENCE: 40
cccactgata gggtcaataa c                                              21

SEQ ID NO: 41          moltype = RNA  length = 21
FEATURE                Location/Qualifiers
source                 1..21
                       mol_type = other RNA
                       organism = synthetic construct
SEQUENCE: 41
tcccactgat agggtcaata a                                              21

SEQ ID NO: 42          moltype = RNA  length = 21
FEATURE                Location/Qualifiers
source                 1..21
                       mol_type = other RNA
                       organism = synthetic construct
SEQUENCE: 42
ttcccactga tagggtcaat a                                              21

SEQ ID NO: 43          moltype = RNA  length = 21
FEATURE                Location/Qualifiers
source                 1..21
                       mol_type = other RNA
                       organism = synthetic construct
SEQUENCE: 43
aacttgagga ttcttttgtg g                                              21

SEQ ID NO: 44          moltype = RNA  length = 21
FEATURE                Location/Qualifiers
source                 1..21
                       mol_type = other RNA
```

-continued

```
                        organism = synthetic construct
SEQUENCE: 44
ggaggaactt gaggattctt t                                              21

SEQ ID NO: 45           moltype = RNA  length = 21
FEATURE                 Location/Qualifiers
source                  1..21
                        mol_type = other RNA
                        organism = synthetic construct
SEQUENCE: 45
taaaaagctg gaggaacttg a                                              21

SEQ ID NO: 46           moltype = RNA  length = 21
FEATURE                 Location/Qualifiers
source                  1..21
                        mol_type = other RNA
                        organism = synthetic construct
SEQUENCE: 46
acataaaaag ctggaggaac t                                              21

SEQ ID NO: 47           moltype = RNA  length = 21
FEATURE                 Location/Qualifiers
source                  1..21
                        mol_type = other RNA
                        organism = synthetic construct
SEQUENCE: 47
gacataaaaa gctggaggaa c                                              21

SEQ ID NO: 48           moltype = RNA  length = 21
FEATURE                 Location/Qualifiers
source                  1..21
                        mol_type = other RNA
                        organism = synthetic construct
SEQUENCE: 48
agacataaaa agctggagga a                                              21

SEQ ID NO: 49           moltype = RNA  length = 21
FEATURE                 Location/Qualifiers
source                  1..21
                        mol_type = other RNA
                        organism = synthetic construct
SEQUENCE: 49
cttcatgaag gcaggctttg g                                              21

SEQ ID NO: 50           moltype = RNA  length = 21
FEATURE                 Location/Qualifiers
source                  1..21
                        mol_type = other RNA
                        organism = synthetic construct
SEQUENCE: 50
caggttctgc ttcatgaagg c                                              21

SEQ ID NO: 51           moltype = RNA  length = 21
FEATURE                 Location/Qualifiers
source                  1..21
                        mol_type = other RNA
                        organism = synthetic construct
SEQUENCE: 51
tccaggttct gcttcatgaa g                                              21

SEQ ID NO: 52           moltype = RNA  length = 21
FEATURE                 Location/Qualifiers
source                  1..21
                        mol_type = other RNA
                        organism = synthetic construct
SEQUENCE: 52
atccaggttc tgcttcatga a                                              21

SEQ ID NO: 53           moltype = RNA  length = 21
FEATURE                 Location/Qualifiers
source                  1..21
                        mol_type = other RNA
                        organism = synthetic construct
SEQUENCE: 53
agctcatcca ggttctgctt c                                              21

SEQ ID NO: 54           moltype = RNA  length = 21
FEATURE                 Location/Qualifiers
source                  1..21
```

-continued

```
                      mol_type = other RNA
                      organism = synthetic construct
SEQUENCE: 54
aagctcatcc aggttctgct t                                              21

SEQ ID NO: 55         moltype = RNA  length = 21
FEATURE               Location/Qualifiers
source                1..21
                      mol_type = other RNA
                      organism = synthetic construct
SEQUENCE: 55
caagctcatc caggttctgc t                                              21

SEQ ID NO: 56         moltype = RNA  length = 21
FEATURE               Location/Qualifiers
source                1..21
                      mol_type = other RNA
                      organism = synthetic construct
SEQUENCE: 56
ccaagctcat ccaggttctg c                                              21

SEQ ID NO: 57         moltype = RNA  length = 21
FEATURE               Location/Qualifiers
source                1..21
                      mol_type = other RNA
                      organism = synthetic construct
SEQUENCE: 57
acaacttttc ctgactcatc c                                              21

SEQ ID NO: 58         moltype = RNA  length = 21
FEATURE               Location/Qualifiers
source                1..21
                      mol_type = other RNA
                      organism = synthetic construct
SEQUENCE: 58
tacaactttt cctgactcat c                                              21

SEQ ID NO: 59         moltype = RNA  length = 21
FEATURE               Location/Qualifiers
source                1..21
                      mol_type = other RNA
                      organism = synthetic construct
SEQUENCE: 59
ctacaacttt tcctgactca t                                              21

SEQ ID NO: 60         moltype = RNA  length = 21
FEATURE               Location/Qualifiers
source                1..21
                      mol_type = other RNA
                      organism = synthetic construct
SEQUENCE: 60
tatctacaac ttttcctgac t                                              21

SEQ ID NO: 61         moltype = RNA  length = 21
FEATURE               Location/Qualifiers
source                1..21
                      mol_type = other RNA
                      organism = synthetic construct
SEQUENCE: 61
ggaataaata tctacaactt t                                              21

SEQ ID NO: 62         moltype = RNA  length = 21
FEATURE               Location/Qualifiers
source                1..21
                      mol_type = other RNA
                      organism = synthetic construct
SEQUENCE: 62
tggaataaat atctacaact t                                              21

SEQ ID NO: 63         moltype = RNA  length = 21
FEATURE               Location/Qualifiers
source                1..21
                      mol_type = other RNA
                      organism = synthetic construct
SEQUENCE: 63
ttggaataaa tatctacaac t                                              21

SEQ ID NO: 64         moltype = RNA  length = 21
FEATURE               Location/Qualifiers
```

-continued

```
source                1..21
                      mol_type = other RNA
                      organism = synthetic construct
SEQUENCE: 64
agcaagatta attacatcaa a                                                21

SEQ ID NO: 65         moltype = RNA  length = 21
FEATURE               Location/Qualifiers
source                1..21
                      mol_type = other RNA
                      organism = synthetic construct
SEQUENCE: 65
ctcagcagca agattaatta c                                                21

SEQ ID NO: 66         moltype = RNA  length = 21
FEATURE               Location/Qualifiers
source                1..21
                      mol_type = other RNA
                      organism = synthetic construct
SEQUENCE: 66
tctcagcagc aagattaatt a                                                21

SEQ ID NO: 67         moltype = RNA  length = 21
FEATURE               Location/Qualifiers
source                1..21
                      mol_type = other RNA
                      organism = synthetic construct
SEQUENCE: 67
ttctcagcag caagattaat t                                                21

SEQ ID NO: 68         moltype = RNA  length = 21
FEATURE               Location/Qualifiers
source                1..21
                      mol_type = other RNA
                      organism = synthetic construct
SEQUENCE: 68
ttttctcagc agcaagatta a                                                21

SEQ ID NO: 69         moltype = RNA  length = 21
FEATURE               Location/Qualifiers
source                1..21
                      mol_type = other RNA
                      organism = synthetic construct
SEQUENCE: 69
ggtgtgagga tcagggcttg c                                                21

SEQ ID NO: 70         moltype = RNA  length = 21
FEATURE               Location/Qualifiers
source                1..21
                      mol_type = other RNA
                      organism = synthetic construct
SEQUENCE: 70
tggtgtgagg atcagggctt g                                                21

SEQ ID NO: 71         moltype = RNA  length = 21
FEATURE               Location/Qualifiers
source                1..21
                      mol_type = other RNA
                      organism = synthetic construct
SEQUENCE: 71
acctgctggt gtgaggatca g                                                21

SEQ ID NO: 72         moltype = RNA  length = 21
FEATURE               Location/Qualifiers
source                1..21
                      mol_type = other RNA
                      organism = synthetic construct
SEQUENCE: 72
cgtctacatt cacggcggtc a                                                21

SEQ ID NO: 73         moltype = RNA  length = 21
FEATURE               Location/Qualifiers
source                1..21
                      mol_type = other RNA
                      organism = synthetic construct
SEQUENCE: 73
gcgtctacat tcacggcggt c                                                21

SEQ ID NO: 74         moltype = RNA  length = 21
```

```
FEATURE                Location/Qualifiers
source                 1..21
                       mol_type = other RNA
                       organism = synthetic construct
SEQUENCE: 74
ggcgtctaca ttcacggcgg t                                            21

SEQ ID NO: 75          moltype = RNA  length = 21
FEATURE                Location/Qualifiers
source                 1..21
                       mol_type = other RNA
                       organism = synthetic construct
SEQUENCE: 75
gggcgtctac attcacggcg g                                            21

SEQ ID NO: 76          moltype = RNA  length = 21
FEATURE                Location/Qualifiers
source                 1..21
                       mol_type = other RNA
                       organism = synthetic construct
SEQUENCE: 76
ttgcagccag tgttcatgag g                                            21

SEQ ID NO: 77          moltype = RNA  length = 21
FEATURE                Location/Qualifiers
source                 1..21
                       mol_type = other RNA
                       organism = synthetic construct
SEQUENCE: 77
ctgaatcttc aagcacataa a                                            21

SEQ ID NO: 78          moltype = RNA  length = 21
FEATURE                Location/Qualifiers
source                 1..21
                       mol_type = other RNA
                       organism = synthetic construct
SEQUENCE: 78
cctgaatctt caagcacata a                                            21

SEQ ID NO: 79          moltype = RNA  length = 21
FEATURE                Location/Qualifiers
source                 1..21
                       mol_type = other RNA
                       organism = synthetic construct
SEQUENCE: 79
gcctgaatct tcaagcacat a                                            21

SEQ ID NO: 80          moltype = RNA  length = 21
FEATURE                Location/Qualifiers
source                 1..21
                       mol_type = other RNA
                       organism = synthetic construct
SEQUENCE: 80
agcctgaatc ttcaagcaca t                                            21

SEQ ID NO: 81          moltype = RNA  length = 21
FEATURE                Location/Qualifiers
source                 1..21
                       mol_type = other RNA
                       organism = synthetic construct
SEQUENCE: 81
actttaatga catacagcat t                                            21

SEQ ID NO: 82          moltype = RNA  length = 21
FEATURE                Location/Qualifiers
source                 1..21
                       mol_type = other RNA
                       organism = synthetic construct
SEQUENCE: 82
gcactttaat gacatacagc a                                            21

SEQ ID NO: 83          moltype = RNA  length = 21
FEATURE                Location/Qualifiers
source                 1..21
                       mol_type = other RNA
                       organism = synthetic construct
SEQUENCE: 83
cagtgcactt taatgacata c                                            21
```

-continued

```
SEQ ID NO: 84          moltype = RNA  length = 21
FEATURE                Location/Qualifiers
source                 1..21
                       mol_type = other RNA
                       organism = synthetic construct
SEQUENCE: 84
acagtgcact ttaatgacat a                                           21

SEQ ID NO: 85          moltype = RNA  length = 21
FEATURE                Location/Qualifiers
source                 1..21
                       mol_type = other RNA
                       organism = synthetic construct
SEQUENCE: 85
cacagtgcac tttaatgaca t                                           21

SEQ ID NO: 86          moltype = RNA  length = 21
FEATURE                Location/Qualifiers
source                 1..21
                       mol_type = other RNA
                       organism = synthetic construct
SEQUENCE: 86
acacagtgca ctttaatgac a                                           21

SEQ ID NO: 87          moltype = RNA  length = 21
FEATURE                Location/Qualifiers
source                 1..21
                       mol_type = other RNA
                       organism = synthetic construct
SEQUENCE: 87
gacacagtgc actttaatga c                                           21

SEQ ID NO: 88          moltype = RNA  length = 21
FEATURE                Location/Qualifiers
source                 1..21
                       mol_type = other RNA
                       organism = synthetic construct
SEQUENCE: 88
ggacacagtg cactttaatg a                                           21

SEQ ID NO: 89          moltype = RNA  length = 21
FEATURE                Location/Qualifiers
source                 1..21
                       mol_type = other RNA
                       organism = synthetic construct
SEQUENCE: 89
aggacacagt gcactttaat g                                           21

SEQ ID NO: 90          moltype = RNA  length = 21
FEATURE                Location/Qualifiers
source                 1..21
                       mol_type = other RNA
                       organism = synthetic construct
SEQUENCE: 90
caggacacag tgcactttaa t                                           21

SEQ ID NO: 91          moltype = RNA  length = 21
FEATURE                Location/Qualifiers
source                 1..21
                       mol_type = other RNA
                       organism = synthetic construct
SEQUENCE: 91
tcaggacaca gtgcacttta a                                           21

SEQ ID NO: 92          moltype = RNA  length = 21
FEATURE                Location/Qualifiers
source                 1..21
                       mol_type = other RNA
                       organism = synthetic construct
SEQUENCE: 92
agtgtcaaca ttttcagagc a                                           21

SEQ ID NO: 93          moltype = RNA  length = 19
FEATURE                Location/Qualifiers
source                 1..19
                       mol_type = other RNA
                       organism = synthetic construct
SEQUENCE: 93
agcatgccgg cttccgcgg                                              19
```

```
SEQ ID NO: 94           moltype = RNA  length = 19
FEATURE                 Location/Qualifiers
source                  1..19
                        mol_type = other RNA
                        organism = synthetic construct
SEQUENCE: 94
cagcatgccg gcttccgcg                                               19

SEQ ID NO: 95           moltype = RNA  length = 19
FEATURE                 Location/Qualifiers
source                  1..19
                        mol_type = other RNA
                        organism = synthetic construct
SEQUENCE: 95
ccagcatgcc ggcttccgc                                               19

SEQ ID NO: 96           moltype = RNA  length = 19
FEATURE                 Location/Qualifiers
source                  1..19
                        mol_type = other RNA
                        organism = synthetic construct
SEQUENCE: 96
ggttggaacg atgtcataa                                               19

SEQ ID NO: 97           moltype = RNA  length = 19
FEATURE                 Location/Qualifiers
source                  1..19
                        mol_type = other RNA
                        organism = synthetic construct
SEQUENCE: 97
ctggttggaa cgatgtcat                                               19

SEQ ID NO: 98           moltype = RNA  length = 19
FEATURE                 Location/Qualifiers
source                  1..19
                        mol_type = other RNA
                        organism = synthetic construct
SEQUENCE: 98
actggttgga acgatgtca                                               19

SEQ ID NO: 99           moltype = RNA  length = 19
FEATURE                 Location/Qualifiers
source                  1..19
                        mol_type = other RNA
                        organism = synthetic construct
SEQUENCE: 99
aactggttgg aacgatgtc                                               19

SEQ ID NO: 100          moltype = RNA  length = 19
FEATURE                 Location/Qualifiers
source                  1..19
                        mol_type = other RNA
                        organism = synthetic construct
SEQUENCE: 100
gaactggttg gaacgatgt                                               19

SEQ ID NO: 101          moltype = RNA  length = 19
FEATURE                 Location/Qualifiers
source                  1..19
                        mol_type = other RNA
                        organism = synthetic construct
SEQUENCE: 101
cgtctacatt cacggcggt                                               19

SEQ ID NO: 102          moltype = RNA  length = 19
FEATURE                 Location/Qualifiers
source                  1..19
                        mol_type = other RNA
                        organism = synthetic construct
SEQUENCE: 102
gcgtctacat tcacggcgg                                               19

SEQ ID NO: 103          moltype = RNA  length = 21
FEATURE                 Location/Qualifiers
source                  1..21
                        mol_type = other RNA
                        organism = synthetic construct
SEQUENCE: 103
```

```
ccgcggaagc cggcatgctg g                                              21

SEQ ID NO: 104         moltype = RNA  length = 21
FEATURE                Location/Qualifiers
source                 1..21
                       mol_type = other RNA
                       organism = synthetic construct
SEQUENCE: 104
cgcggaagcc ggcatgctgg a                                              21

SEQ ID NO: 105         moltype = RNA  length = 21
FEATURE                Location/Qualifiers
source                 1..21
                       mol_type = other RNA
                       organism = synthetic construct
SEQUENCE: 105
gcggaagccg gcatgctgga g                                              21

SEQ ID NO: 106         moltype = RNA  length = 21
FEATURE                Location/Qualifiers
source                 1..21
                       mol_type = other RNA
                       organism = synthetic construct
SEQUENCE: 106
ggaagccggc atgctggaga a                                              21

SEQ ID NO: 107         moltype = RNA  length = 21
FEATURE                Location/Qualifiers
source                 1..21
                       mol_type = other RNA
                       organism = synthetic construct
SEQUENCE: 107
gaagccggca tgctggagaa g                                              21

SEQ ID NO: 108         moltype = RNA  length = 21
FEATURE                Location/Qualifiers
source                 1..21
                       mol_type = other RNA
                       organism = synthetic construct
SEQUENCE: 108
aagccggcat gctggagaag c                                              21

SEQ ID NO: 109         moltype = RNA  length = 21
FEATURE                Location/Qualifiers
source                 1..21
                       mol_type = other RNA
                       organism = synthetic construct
SEQUENCE: 109
agccggcatg ctggagaagc t                                              21

SEQ ID NO: 110         moltype = RNA  length = 21
FEATURE                Location/Qualifiers
source                 1..21
                       mol_type = other RNA
                       organism = synthetic construct
SEQUENCE: 110
gccggcatgc tggagaagct g                                              21

SEQ ID NO: 111         moltype = RNA  length = 21
FEATURE                Location/Qualifiers
source                 1..21
                       mol_type = other RNA
                       organism = synthetic construct
SEQUENCE: 111
atgcgattca tgaggtcaca c                                              21

SEQ ID NO: 112         moltype = RNA  length = 21
FEATURE                Location/Qualifiers
source                 1..21
                       mol_type = other RNA
                       organism = synthetic construct
SEQUENCE: 112
tgcgattcat gaggtcacac a                                              21

SEQ ID NO: 113         moltype = RNA  length = 21
FEATURE                Location/Qualifiers
source                 1..21
                       mol_type = other RNA
                       organism = synthetic construct
```

```
SEQUENCE: 113
gcgattcatg aggtcacaca a                                             21

SEQ ID NO: 114          moltype = RNA  length = 21
FEATURE                 Location/Qualifiers
source                  1..21
                        mol_type = other RNA
                        organism = synthetic construct
SEQUENCE: 114
cgattcatga ggtcacacaa g                                             21

SEQ ID NO: 115          moltype = RNA  length = 21
FEATURE                 Location/Qualifiers
source                  1..21
                        mol_type = other RNA
                        organism = synthetic construct
SEQUENCE: 115
gattcatgag gtcacacaag t                                             21

SEQ ID NO: 116          moltype = RNA  length = 21
FEATURE                 Location/Qualifiers
source                  1..21
                        mol_type = other RNA
                        organism = synthetic construct
SEQUENCE: 116
attcatgagg tcacacaagt g                                             21

SEQ ID NO: 117          moltype = RNA  length = 21
FEATURE                 Location/Qualifiers
source                  1..21
                        mol_type = other RNA
                        organism = synthetic construct
SEQUENCE: 117
ttcatgaggt cacacaagtg t                                             21

SEQ ID NO: 118          moltype = RNA  length = 21
FEATURE                 Location/Qualifiers
source                  1..21
                        mol_type = other RNA
                        organism = synthetic construct
SEQUENCE: 118
catgaggtca cacaagtgtt a                                             21

SEQ ID NO: 119          moltype = RNA  length = 21
FEATURE                 Location/Qualifiers
source                  1..21
                        mol_type = other RNA
                        organism = synthetic construct
SEQUENCE: 119
tgaggtcaca caagtgttat g                                             21

SEQ ID NO: 120          moltype = RNA  length = 21
FEATURE                 Location/Qualifiers
source                  1..21
                        mol_type = other RNA
                        organism = synthetic construct
SEQUENCE: 120
gaggtcacac aagtgttatg a                                             21

SEQ ID NO: 121          moltype = RNA  length = 21
FEATURE                 Location/Qualifiers
source                  1..21
                        mol_type = other RNA
                        organism = synthetic construct
SEQUENCE: 121
gtcacacaag tgttatgaca t                                             21

SEQ ID NO: 122          moltype = RNA  length = 21
FEATURE                 Location/Qualifiers
source                  1..21
                        mol_type = other RNA
                        organism = synthetic construct
SEQUENCE: 122
acacaagtgt tatgacatcg t                                             21

SEQ ID NO: 123          moltype = RNA  length = 21
FEATURE                 Location/Qualifiers
source                  1..21
                        mol_type = other RNA
```

```
                       organism = synthetic construct
SEQUENCE: 123
cacaagtgtt atgacatcgt t                                    21

SEQ ID NO: 124         moltype = RNA  length = 21
FEATURE                Location/Qualifiers
source                 1..21
                       mol_type = other RNA
                       organism = synthetic construct
SEQUENCE: 124
acaagtgtta tgacatcgtt c                                    21

SEQ ID NO: 125         moltype = RNA  length = 21
FEATURE                Location/Qualifiers
source                 1..21
                       mol_type = other RNA
                       organism = synthetic construct
SEQUENCE: 125
aagtgttatg acatcgttcc a                                    21

SEQ ID NO: 126         moltype = RNA  length = 21
FEATURE                Location/Qualifiers
source                 1..21
                       mol_type = other RNA
                       organism = synthetic construct
SEQUENCE: 126
agtgttatga catcgttcca a                                    21

SEQ ID NO: 127         moltype = RNA  length = 21
FEATURE                Location/Qualifiers
source                 1..21
                       mol_type = other RNA
                       organism = synthetic construct
SEQUENCE: 127
gtgttatgac atcgttccaa c                                    21

SEQ ID NO: 128         moltype = RNA  length = 21
FEATURE                Location/Qualifiers
source                 1..21
                       mol_type = other RNA
                       organism = synthetic construct
SEQUENCE: 128
tgttatgaca tcgttccaac c                                    21

SEQ ID NO: 129         moltype = RNA  length = 21
FEATURE                Location/Qualifiers
source                 1..21
                       mol_type = other RNA
                       organism = synthetic construct
SEQUENCE: 129
gttatgacat cgttccaacc a                                    21

SEQ ID NO: 130         moltype = RNA  length = 21
FEATURE                Location/Qualifiers
source                 1..21
                       mol_type = other RNA
                       organism = synthetic construct
SEQUENCE: 130
ttatgacatc gttccaacca g                                    21

SEQ ID NO: 131         moltype = RNA  length = 21
FEATURE                Location/Qualifiers
source                 1..21
                       mol_type = other RNA
                       organism = synthetic construct
SEQUENCE: 131
tatgacatcg ttccaaccag t                                    21

SEQ ID NO: 132         moltype = RNA  length = 21
FEATURE                Location/Qualifiers
source                 1..21
                       mol_type = other RNA
                       organism = synthetic construct
SEQUENCE: 132
atgacatcgt tccaaccagt t                                    21

SEQ ID NO: 133         moltype = RNA  length = 21
FEATURE                Location/Qualifiers
source                 1..21
```

```
                        mol_type = other RNA
                        organism = synthetic construct
SEQUENCE: 133
tgacatcgtt ccaaccagtt c                                              21

SEQ ID NO: 134          moltype = RNA  length = 21
FEATURE                 Location/Qualifiers
source                  1..21
                        mol_type = other RNA
                        organism = synthetic construct
SEQUENCE: 134
gacatcgttc caaccagttc a                                              21

SEQ ID NO: 135          moltype = RNA  length = 21
FEATURE                 Location/Qualifiers
source                  1..21
                        mol_type = other RNA
                        organism = synthetic construct
SEQUENCE: 135
acatcgttcc aaccagttca a                                              21

SEQ ID NO: 136          moltype = RNA  length = 21
FEATURE                 Location/Qualifiers
source                  1..21
                        mol_type = other RNA
                        organism = synthetic construct
SEQUENCE: 136
catcgttcca accagttcaa a                                              21

SEQ ID NO: 137          moltype = RNA  length = 21
FEATURE                 Location/Qualifiers
source                  1..21
                        mol_type = other RNA
                        organism = synthetic construct
SEQUENCE: 137
atcgttccaa ccagttcaaa g                                              21

SEQ ID NO: 138          moltype = RNA  length = 21
FEATURE                 Location/Qualifiers
source                  1..21
                        mol_type = other RNA
                        organism = synthetic construct
SEQUENCE: 138
tcgttccaac cagttcaaag c                                              21

SEQ ID NO: 139          moltype = RNA  length = 21
FEATURE                 Location/Qualifiers
source                  1..21
                        mol_type = other RNA
                        organism = synthetic construct
SEQUENCE: 139
cgttccaacc agttcaaagc t                                              21

SEQ ID NO: 140          moltype = RNA  length = 21
FEATURE                 Location/Qualifiers
source                  1..21
                        mol_type = other RNA
                        organism = synthetic construct
SEQUENCE: 140
ttccaaccag ttcaaagctt g                                              21

SEQ ID NO: 141          moltype = RNA  length = 21
FEATURE                 Location/Qualifiers
source                  1..21
                        mol_type = other RNA
                        organism = synthetic construct
SEQUENCE: 141
tccaaccagt tcaaagcttg t                                              21

SEQ ID NO: 142          moltype = RNA  length = 21
FEATURE                 Location/Qualifiers
source                  1..21
                        mol_type = other RNA
                        organism = synthetic construct
SEQUENCE: 142
gttattgacc ctatcagtgg g                                              21

SEQ ID NO: 143          moltype = RNA  length = 21
FEATURE                 Location/Qualifiers
```

```
source                  1..21
                        mol_type = other RNA
                        organism = synthetic construct
SEQUENCE: 143
ttattgaccc tatcagtggg a                                            21

SEQ ID NO: 144          moltype = RNA  length = 21
FEATURE                 Location/Qualifiers
source                  1..21
                        mol_type = other RNA
                        organism = synthetic construct
SEQUENCE: 144
tattgaccct atcagtggga a                                            21

SEQ ID NO: 145          moltype = RNA  length = 21
FEATURE                 Location/Qualifiers
source                  1..21
                        mol_type = other RNA
                        organism = synthetic construct
SEQUENCE: 145
ccacaaaaga atcctcaagt t                                            21

SEQ ID NO: 146          moltype = RNA  length = 21
FEATURE                 Location/Qualifiers
source                  1..21
                        mol_type = other RNA
                        organism = synthetic construct
SEQUENCE: 146
aaagaatcct caagttcctc c                                            21

SEQ ID NO: 147          moltype = RNA  length = 21
FEATURE                 Location/Qualifiers
source                  1..21
                        mol_type = other RNA
                        organism = synthetic construct
SEQUENCE: 147
tcaagttcct ccagcttttt a                                            21

SEQ ID NO: 148          moltype = RNA  length = 21
FEATURE                 Location/Qualifiers
source                  1..21
                        mol_type = other RNA
                        organism = synthetic construct
SEQUENCE: 148
agttcctcca gctttttatg t                                            21

SEQ ID NO: 149          moltype = RNA  length = 21
FEATURE                 Location/Qualifiers
source                  1..21
                        mol_type = other RNA
                        organism = synthetic construct
SEQUENCE: 149
gttcctccag ctttttatgt c                                            21

SEQ ID NO: 150          moltype = RNA  length = 21
FEATURE                 Location/Qualifiers
source                  1..21
                        mol_type = other RNA
                        organism = synthetic construct
SEQUENCE: 150
ttcctccagc tttttatgtc t                                            21

SEQ ID NO: 151          moltype = RNA  length = 21
FEATURE                 Location/Qualifiers
source                  1..21
                        mol_type = other RNA
                        organism = synthetic construct
SEQUENCE: 151
ccaaagcctg ccttcatgaa g                                            21

SEQ ID NO: 152          moltype = RNA  length = 21
FEATURE                 Location/Qualifiers
source                  1..21
                        mol_type = other RNA
                        organism = synthetic construct
SEQUENCE: 152
gccttcatga agcagaacct g                                            21

SEQ ID NO: 153          moltype = RNA  length = 21
```

```
FEATURE                Location/Qualifiers
source                 1..21
                       mol_type = other RNA
                       organism = synthetic construct
SEQUENCE: 153
cttcatgaag cagaacctgg a                                          21

SEQ ID NO: 154         moltype = RNA  length = 21
FEATURE                Location/Qualifiers
source                 1..21
                       mol_type = other RNA
                       organism = synthetic construct
SEQUENCE: 154
ttcatgaagc agaacctgga t                                          21

SEQ ID NO: 155         moltype = RNA  length = 21
FEATURE                Location/Qualifiers
source                 1..21
                       mol_type = other RNA
                       organism = synthetic construct
SEQUENCE: 155
gaagcagaac ctggatgagc t                                          21

SEQ ID NO: 156         moltype = RNA  length = 21
FEATURE                Location/Qualifiers
source                 1..21
                       mol_type = other RNA
                       organism = synthetic construct
SEQUENCE: 156
aagcagaacc tggatgagct t                                          21

SEQ ID NO: 157         moltype = RNA  length = 21
FEATURE                Location/Qualifiers
source                 1..21
                       mol_type = other RNA
                       organism = synthetic construct
SEQUENCE: 157
agcagaacct ggatgagctt g                                          21

SEQ ID NO: 158         moltype = RNA  length = 21
FEATURE                Location/Qualifiers
source                 1..21
                       mol_type = other RNA
                       organism = synthetic construct
SEQUENCE: 158
gcagaacctg gatgagcttg g                                          21

SEQ ID NO: 159         moltype = RNA  length = 21
FEATURE                Location/Qualifiers
source                 1..21
                       mol_type = other RNA
                       organism = synthetic construct
SEQUENCE: 159
ggatgagtca ggaaaagttg t                                          21

SEQ ID NO: 160         moltype = RNA  length = 21
FEATURE                Location/Qualifiers
source                 1..21
                       mol_type = other RNA
                       organism = synthetic construct
SEQUENCE: 160
gatgagtcag gaaaagttgt a                                          21

SEQ ID NO: 161         moltype = RNA  length = 21
FEATURE                Location/Qualifiers
source                 1..21
                       mol_type = other RNA
                       organism = synthetic construct
SEQUENCE: 161
atgagtcagg aaaagttgta g                                          21

SEQ ID NO: 162         moltype = RNA  length = 21
FEATURE                Location/Qualifiers
source                 1..21
                       mol_type = other RNA
                       organism = synthetic construct
SEQUENCE: 162
agtcaggaaa agttgtagat a                                          21
```

-continued

```
SEQ ID NO: 163         moltype = RNA  length = 21
FEATURE                Location/Qualifiers
source                 1..21
                       mol_type = other RNA
                       organism = synthetic construct
SEQUENCE: 163
aaagttgtag atatttattc c                                            21

SEQ ID NO: 164         moltype = RNA  length = 21
FEATURE                Location/Qualifiers
source                 1..21
                       mol_type = other RNA
                       organism = synthetic construct
SEQUENCE: 164
aagttgtaga tatttattcc a                                            21

SEQ ID NO: 165         moltype = RNA  length = 21
FEATURE                Location/Qualifiers
source                 1..21
                       mol_type = other RNA
                       organism = synthetic construct
SEQUENCE: 165
agttgtagat atttattcca a                                            21

SEQ ID NO: 166         moltype = RNA  length = 21
FEATURE                Location/Qualifiers
source                 1..21
                       mol_type = other RNA
                       organism = synthetic construct
SEQUENCE: 166
tttgatgtaa ttaatcttgc t                                            21

SEQ ID NO: 167         moltype = RNA  length = 21
FEATURE                Location/Qualifiers
source                 1..21
                       mol_type = other RNA
                       organism = synthetic construct
SEQUENCE: 167
gtaattaatc ttgctgctga g                                            21

SEQ ID NO: 168         moltype = RNA  length = 21
FEATURE                Location/Qualifiers
source                 1..21
                       mol_type = other RNA
                       organism = synthetic construct
SEQUENCE: 168
taattaatct tgctgctgag a                                            21

SEQ ID NO: 169         moltype = RNA  length = 21
FEATURE                Location/Qualifiers
source                 1..21
                       mol_type = other RNA
                       organism = synthetic construct
SEQUENCE: 169
aattaatctt gctgctgaga a                                            21

SEQ ID NO: 170         moltype = RNA  length = 21
FEATURE                Location/Qualifiers
source                 1..21
                       mol_type = other RNA
                       organism = synthetic construct
SEQUENCE: 170
ttaatcttgc tgctgagaaa a                                            21

SEQ ID NO: 171         moltype = RNA  length = 21
FEATURE                Location/Qualifiers
source                 1..21
                       mol_type = other RNA
                       organism = synthetic construct
SEQUENCE: 171
gcaagccctg atcctcacac c                                            21

SEQ ID NO: 172         moltype = RNA  length = 21
FEATURE                Location/Qualifiers
source                 1..21
                       mol_type = other RNA
                       organism = synthetic construct
SEQUENCE: 172
caagccctga tcctcacacc a                                            21
```

```
SEQ ID NO: 173          moltype = RNA  length = 21
FEATURE                 Location/Qualifiers
source                  1..21
                        mol_type = other RNA
                        organism = synthetic construct
SEQUENCE: 173
ctgatcctca caccagcagg t                                            21

SEQ ID NO: 174          moltype = RNA  length = 21
FEATURE                 Location/Qualifiers
source                  1..21
                        mol_type = other RNA
                        organism = synthetic construct
SEQUENCE: 174
tgaccgccgt gaatgtagac g                                            21

SEQ ID NO: 175          moltype = RNA  length = 21
FEATURE                 Location/Qualifiers
source                  1..21
                        mol_type = other RNA
                        organism = synthetic construct
SEQUENCE: 175
gaccgccgtg aatgtagacg c                                            21

SEQ ID NO: 176          moltype = RNA  length = 21
FEATURE                 Location/Qualifiers
source                  1..21
                        mol_type = other RNA
                        organism = synthetic construct
SEQUENCE: 176
accgccgtga atgtagacgc c                                            21

SEQ ID NO: 177          moltype = RNA  length = 21
FEATURE                 Location/Qualifiers
source                  1..21
                        mol_type = other RNA
                        organism = synthetic construct
SEQUENCE: 177
ccgccgtgaa tgtagacgcc c                                            21

SEQ ID NO: 178          moltype = RNA  length = 21
FEATURE                 Location/Qualifiers
source                  1..21
                        mol_type = other RNA
                        organism = synthetic construct
SEQUENCE: 178
cctcatgaac actggctgca a                                            21

SEQ ID NO: 179          moltype = RNA  length = 21
FEATURE                 Location/Qualifiers
source                  1..21
                        mol_type = other RNA
                        organism = synthetic construct
SEQUENCE: 179
tttatgtgct tgaagattca g                                            21

SEQ ID NO: 180          moltype = RNA  length = 21
FEATURE                 Location/Qualifiers
source                  1..21
                        mol_type = other RNA
                        organism = synthetic construct
SEQUENCE: 180
ttatgtgctt gaagattcag g                                            21

SEQ ID NO: 181          moltype = RNA  length = 21
FEATURE                 Location/Qualifiers
source                  1..21
                        mol_type = other RNA
                        organism = synthetic construct
SEQUENCE: 181
tatgtgcttg aagattcagg c                                            21

SEQ ID NO: 182          moltype = RNA  length = 21
FEATURE                 Location/Qualifiers
source                  1..21
                        mol_type = other RNA
                        organism = synthetic construct
SEQUENCE: 182
```

```
atgtgcttga agattcaggc t                                              21

SEQ ID NO: 183          moltype = RNA  length = 21
FEATURE                 Location/Qualifiers
source                  1..21
                        mol_type = other RNA
                        organism = synthetic construct
SEQUENCE: 183
aatgctgtat gtcattaaag t                                              21

SEQ ID NO: 184          moltype = RNA  length = 21
FEATURE                 Location/Qualifiers
source                  1..21
                        mol_type = other RNA
                        organism = synthetic construct
SEQUENCE: 184
tgctgtatgt cattaaagtg c                                              21

SEQ ID NO: 185          moltype = RNA  length = 21
FEATURE                 Location/Qualifiers
source                  1..21
                        mol_type = other RNA
                        organism = synthetic construct
SEQUENCE: 185
gtatgtcatt aaagtgcact g                                              21

SEQ ID NO: 186          moltype = RNA  length = 21
FEATURE                 Location/Qualifiers
source                  1..21
                        mol_type = other RNA
                        organism = synthetic construct
SEQUENCE: 186
tatgtcatta aagtgcactg t                                              21

SEQ ID NO: 187          moltype = RNA  length = 21
FEATURE                 Location/Qualifiers
source                  1..21
                        mol_type = other RNA
                        organism = synthetic construct
SEQUENCE: 187
atgtcattaa agtgcactgt g                                              21

SEQ ID NO: 188          moltype = RNA  length = 21
FEATURE                 Location/Qualifiers
source                  1..21
                        mol_type = other RNA
                        organism = synthetic construct
SEQUENCE: 188
tgtcattaaa gtgcactgtg t                                              21

SEQ ID NO: 189          moltype = RNA  length = 21
FEATURE                 Location/Qualifiers
source                  1..21
                        mol_type = other RNA
                        organism = synthetic construct
SEQUENCE: 189
gtcattaaag tgcactgtgt c                                              21

SEQ ID NO: 190          moltype = RNA  length = 21
FEATURE                 Location/Qualifiers
source                  1..21
                        mol_type = other RNA
                        organism = synthetic construct
SEQUENCE: 190
tcattaaagt gcactgtgtc c                                              21

SEQ ID NO: 191          moltype = RNA  length = 21
FEATURE                 Location/Qualifiers
source                  1..21
                        mol_type = other RNA
                        organism = synthetic construct
SEQUENCE: 191
cattaaagtg cactgtgtcc t                                              21

SEQ ID NO: 192          moltype = RNA  length = 21
FEATURE                 Location/Qualifiers
source                  1..21
                        mol_type = other RNA
                        organism = synthetic construct
```

```
SEQUENCE: 192
attaaagtgc actgtgtcct g                                               21

SEQ ID NO: 193          moltype = RNA  length = 21
FEATURE                 Location/Qualifiers
source                  1..21
                        mol_type = other RNA
                        organism = synthetic construct
SEQUENCE: 193
ttaaagtgca ctgtgtcctg a                                               21

SEQ ID NO: 194          moltype = RNA  length = 21
FEATURE                 Location/Qualifiers
source                  1..21
                        mol_type = other RNA
                        organism = synthetic construct
SEQUENCE: 194
tgctctgaaa atgttgacac t                                               21

SEQ ID NO: 195          moltype = RNA  length = 19
FEATURE                 Location/Qualifiers
source                  1..19
                        mol_type = other RNA
                        organism = synthetic construct
SEQUENCE: 195
ccgcggaagc cggcatgct                                                  19

SEQ ID NO: 196          moltype = RNA  length = 19
FEATURE                 Location/Qualifiers
source                  1..19
                        mol_type = other RNA
                        organism = synthetic construct
SEQUENCE: 196
cgcggaagcc ggcatgctg                                                  19

SEQ ID NO: 197          moltype = RNA  length = 19
FEATURE                 Location/Qualifiers
source                  1..19
                        mol_type = other RNA
                        organism = synthetic construct
SEQUENCE: 197
gcggaagccg gcatgctgg                                                  19

SEQ ID NO: 198          moltype = RNA  length = 19
FEATURE                 Location/Qualifiers
source                  1..19
                        mol_type = other RNA
                        organism = synthetic construct
SEQUENCE: 198
ttatgacatc gttccaacc                                                  19

SEQ ID NO: 199          moltype = RNA  length = 19
FEATURE                 Location/Qualifiers
source                  1..19
                        mol_type = other RNA
                        organism = synthetic construct
SEQUENCE: 199
atgacatcgt tccaaccag                                                  19

SEQ ID NO: 200          moltype = RNA  length = 19
FEATURE                 Location/Qualifiers
source                  1..19
                        mol_type = other RNA
                        organism = synthetic construct
SEQUENCE: 200
tgacatcgtt ccaaccagt                                                  19

SEQ ID NO: 201          moltype = RNA  length = 19
FEATURE                 Location/Qualifiers
source                  1..19
                        mol_type = other RNA
                        organism = synthetic construct
SEQUENCE: 201
gacatcgttc caaccagtt                                                  19

SEQ ID NO: 202          moltype = RNA  length = 19
FEATURE                 Location/Qualifiers
source                  1..19
                        mol_type = other RNA
```

-continued

```
                     organism = synthetic construct
SEQUENCE: 202
acatcgttcc aaccagttc                                        19

SEQ ID NO: 203       moltype = RNA  length = 19
FEATURE              Location/Qualifiers
source               1..19
                     mol_type = other RNA
                     organism = synthetic construct
SEQUENCE: 203
accgccgtga atgtagacg                                        19

SEQ ID NO: 204       moltype = RNA  length = 19
FEATURE              Location/Qualifiers
source               1..19
                     mol_type = other RNA
                     organism = synthetic construct
SEQUENCE: 204
ccgccgtgaa tgtagacgc                                        19

SEQ ID NO: 205       moltype = AA  length = 245
FEATURE              Location/Qualifiers
source               1..245
                     mol_type = protein
                     organism = synthetic construct
SEQUENCE: 205
MEWSWVFLFF LSVTTGVHSQ VQLVQSGAEV KKPGASVKVS CKASGYTFTN YWMHWVRQAP  60
GQGLEWMGEI NPINGRSNYA QKFQGRVTLT VDTSISTAYM ELSRLRSDDT AVYYCARGTR  120
AMHYWGQGTL VTVSSASTKG PSVFPLAPSS KSTSGGTAAL GCLVKDYFPE PVTVSWNSGA  180
LTSGVHTFPA VLQSSGLYSL SSVVTVPSSS LGTQTYICNV NHKPSNTKVD KRVEPKSCDK  240
THTCG                                                        245

SEQ ID NO: 206       moltype = DNA  length = 735
FEATURE              Location/Qualifiers
source               1..735
                     mol_type = other DNA
                     organism = synthetic construct
SEQUENCE: 206
atggaatggt catgggtttt tttgtttttc ctctcagtta cgactggtgt ccatagccaa  60
gtccaactgg tgcagtccgg tgcggaggtt aagaagcccg gagcgagcgt aaaggtgagt  120
tgtaaagcga gtggatacac gttcacgaac tattggatgc attgggttcg acaagcaccg  180
ggtcagggac ttgagtggat gggagaaatt aatccgatta acggtcgcag taactatgcg  240
cagaaattcc aaggccgagt aactctcacc gtggacacgt ccatctctac agcgtacatg  300
gaactcagca ggttgcgctc tgacgatacc gcagtttatt attgcgcgcg agggacgcgg  360
gctatgcact attgggggca gggcaccctc gtcaccgtat catctgcgag tacgaaggga  420
ccttctgtgt tcccattggc tcccagcagc aaaagtacca gtggtggaac agctgcgctt  480
ggatgcctgg tgaaagatta tttccccgag ccggtgacag tcagctggaa cagcggcgca  540
ctcaccagcg gtgtacatac gttcccggcg gttttgcaat ctagtggcct ctattccctt  600
agttccgtag ttaccgtccc atcttcaagc ctcggaaccc agacttacat ctgcaacgtc  660
aatcataagc ccagtaacac aaaagttgat aagagagtag agccgaaatc ctgtgataag  720
acccacacat gtggg                                             735

SEQ ID NO: 207       moltype = AA  length = 234
FEATURE              Location/Qualifiers
source               1..234
                     mol_type = protein
                     organism = synthetic construct
SEQUENCE: 207
MSVPTQVLGL LLLWLTDARC DIQMTQSPSS LSASVGDRVT ITCRTSENIY NNLAWYQQKP  60
GKAPKLLIYA ATNLAEGVPS RFSGSGSGTD YTLTISSLQP EDFATYYCQH FWGTPLTFGG  120
GTKVEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 208       moltype = DNA  length = 747
FEATURE              Location/Qualifiers
source               1..747
                     mol_type = other DNA
                     organism = synthetic construct
SEQUENCE: 208
gcctccggac tctagagccg ccaccatgag cgtaccaacc caggtgctcg gactcctgtt  60
gttgtggctc accgatgcaa gatgcgatat acaaatgaca caaagcccaa gtagtttgtc  120
agccagcgta ggggatagag ttactataac ttgccgaacg tctgaaaata tatataataa  180
cctcgcgtgg taccagcaga agcccggcaa ggcccctaaa ctcctcattt atgcagctac  240
taacctcgct gaaggagtac catcaaggtt ctcaggcagc gggtctggaa ctgactacac  300
attgactatt tcaagccttc agccagagga cttcgctaca tactactgtc aacacttctg  360
ggggactccg cttactttcg gaggcggtac caaagtggag ataaaacgga cggttgctgc  420
tccgagcgtt tttatattcc cgccctctga tgaacagctg aaatcaggca ctgcgagcgt  480
tgtttgcttg ctgaataact tttacccccg cgaggcgaaa gtacaatgga aggtagacaa  540
cgcactgcaa tctgggaata gtcaagagag tgttaccgaa caagattcaa aagattccac  600
```

-continued

```
ttattccctt agttctactt tgacactgag caaagcagat tacgagaaac ataaggtcta  660
cgcctgcgag gtgacgcacc agggcctgag cagcccagtt acaaagtcct tcaatcgagg  720
tgagtgttag gcggccgcta taagggt                                      747

SEQ ID NO: 209          moltype = RNA  length = 23
FEATURE                 Location/Qualifiers
modified_base           6
                        mod_base = OTHER
                        note = 2'-fluoro ribonucleotide
modified_base           21..23
                        mod_base = OTHER
                        note = phosphorothioate linkage
modified_base           3..5
                        mod_base = OTHER
                        note = 2'-O-methyl ribonucleotide
modified_base           2
                        mod_base = OTHER
                        note = 2'-fluoro ribonucleotide
modified_base           1..3
                        mod_base = OTHER
                        note = phosphorothioate linkage
modified_base           14
                        mod_base = OTHER
                        note = 2'-fluoro ribonucleotide
modified_base           7..13
                        mod_base = OTHER
                        note = 2'-O-methyl ribonucleotide
modified_base           17..23
                        mod_base = OTHER
                        note = 2'-O-methyl ribonucleotide
modified_base           1
                        mod_base = OTHER
                        note = 2'-O-methyl ribonucleotide
modified_base           15
                        mod_base = OTHER
                        note = 2'-O-methyl ribonucleotide
source                  1..23
                        mol_type = other RNA
                        organism = synthetic construct
modified_base           16
                        mod_base = OTHER
                        note = 2'-fluoro ribonucleotide
SEQUENCE: 209
tacaactttt cctgactcat ctt                                          23

SEQ ID NO: 210          moltype = RNA  length = 23
FEATURE                 Location/Qualifiers
modified_base           1..3
                        mod_base = OTHER
                        note = phosphorothioate linkage
modified_base           14
                        mod_base = OTHER
                        note = 2'-fluoro ribonucleotide
modified_base           1
                        mod_base = OTHER
                        note = unlocked nucleobase analog to uridine with 5' vinyl
                         phosphonate
modified_base           17..23
                        mod_base = OTHER
                        note = 2'-O-methyl ribonucleotide
modified_base           7..13
                        mod_base = OTHER
                        note = 2'-O-methyl ribonucleotide
modified_base           16
                        mod_base = OTHER
                        note = 2'-fluoro ribonucleotide
modified_base           15
                        mod_base = OTHER
                        note = 2'-O-methyl ribonucleotide
modified_base           2
                        mod_base = OTHER
                        note = 2'-fluoro ribonucleotide
source                  1..23
                        mol_type = other RNA
                        organism = synthetic construct
modified_base           3..5
                        mod_base = OTHER
                        note = 2'-O-methyl ribonucleotide
modified_base           21..23
```

```
                         mod_base = OTHER
                         note = phosphorothioate linkage
modified_base            6
                         mod_base = OTHER
                         note = 2'-fluoro ribonucleotide
SEQUENCE: 210
tacaactttt cctgactcat ctt                                          23

SEQ ID NO: 211           moltype = RNA  length = 23
FEATURE                  Location/Qualifiers
modified_base            6
                         mod_base = OTHER
                         note = 2'-fluoro ribonucleotide
modified_base            15
                         mod_base = OTHER
                         note = 2'-O-methyl ribonucleotide
modified_base            2
                         mod_base = OTHER
                         note = 2'-fluoro ribonucleotide
modified_base            16
                         mod_base = OTHER
                         note = 2'-fluoro ribonucleotide
modified_base            1..3
                         mod_base = OTHER
                         note = phosphorothioate linkage
modified_base            3..5
                         mod_base = OTHER
                         note = 2'-O-methyl ribonucleotide
modified_base            7..13
                         mod_base = OTHER
                         note = 2'-O-methyl ribonucleotide
modified_base            1
                         mod_base = OTHER
                         note = 2'-O-methyl ribonucleotide
source                   1..23
                         mol_type = other RNA
                         organism = synthetic construct
modified_base            21..23
                         mod_base = OTHER
                         note = phosphorothioate linkage
modified_base            14
                         mod_base = OTHER
                         note = 2'-fluoro ribonucleotide
modified_base            17..23
                         mod_base = OTHER
                         note = 2'-O-methyl ribonucleotide
SEQUENCE: 211
tgaataaata tctacaactt ttt                                          23

SEQ ID NO: 212           moltype = RNA  length = 23
FEATURE                  Location/Qualifiers
modified_base            17..23
                         mod_base = OTHER
                         note = 2'-O-methyl ribonucleotide
modified_base            14
                         mod_base = OTHER
                         note = 2'-fluoro ribonucleotide
modified_base            3..5
                         mod_base = OTHER
                         note = 2'-O-methyl ribonucleotide
modified_base            7..13
                         mod_base = OTHER
                         note = 2'-O-methyl ribonucleotide
modified_base            1..3
                         mod_base = OTHER
                         note = phosphorothioate linkage
modified_base            1
                         mod_base = OTHER
                         note = unlocked nucleobase analog to uridine with 5' vinyl
                          phosphonate
modified_base            15
                         mod_base = OTHER
                         note = 2'-O-methyl ribonucleotide
modified_base            2
                         mod_base = OTHER
                         note = 2'-fluoro ribonucleotide
modified_base            21..23
                         mod_base = OTHER
                         note = phosphorothioate linkage
```

```
modified_base          16
                       mod_base = OTHER
                       note = 2'-fluoro ribonucleotide
source                 1..23
                       mol_type = other RNA
                       organism = synthetic construct
modified_base          6
                       mod_base = OTHER
                       note = 2'-fluoro ribonucleotide
SEQUENCE: 212
tgaataaata tctacaactt ttt                                          23

SEQ ID NO: 213         moltype = RNA  length = 23
FEATURE                Location/Qualifiers
modified_base          3..5
                       mod_base = OTHER
                       note = 2'-O-methyl ribonucleotide
modified_base          17..23
                       mod_base = OTHER
                       note = 2'-O-methyl ribonucleotide
modified_base          15
                       mod_base = OTHER
                       note = 2'-O-methyl ribonucleotide
modified_base          6
                       mod_base = OTHER
                       note = 2'-fluoro ribonucleotide
modified_base          16
                       mod_base = OTHER
                       note = 2'-fluoro ribonucleotide
modified_base          2
                       mod_base = OTHER
                       note = 2'-fluoro ribonucleotide
modified_base          7..13
                       mod_base = OTHER
                       note = 2'-O-methyl ribonucleotide
source                 1..23
                       mol_type = other RNA
                       organism = synthetic construct
modified_base          14
                       mod_base = OTHER
                       note = 2'-fluoro ribonucleotide
modified_base          1..3
                       mod_base = OTHER
                       note = phosphorothioate linkage
modified_base          21..23
                       mod_base = OTHER
                       note = phosphorothioate linkage
modified_base          1
                       mod_base = OTHER
                       note = 2'-O-methyl ribonucleotide
SEQUENCE: 213
tggaataaat atctacaact ttt                                          23

SEQ ID NO: 214         moltype = RNA  length = 23
FEATURE                Location/Qualifiers
modified_base          16
                       mod_base = OTHER
                       note = 2'-fluoro ribonucleotide
modified_base          2
                       mod_base = OTHER
                       note = 2'-fluoro ribonucleotide
modified_base          1..3
                       mod_base = OTHER
                       note = phosphorothioate linkage
modified_base          6
                       mod_base = OTHER
                       note = 2'-fluoro ribonucleotide
modified_base          14
                       mod_base = OTHER
                       note = 2'-fluoro ribonucleotide
source                 1..23
                       mol_type = other RNA
                       organism = synthetic construct
modified_base          7..13
                       mod_base = OTHER
                       note = 2'-O-methyl ribonucleotide
modified_base          15
                       mod_base = OTHER
                       note = 2'-O-methyl ribonucleotide
```

```
modified_base          17..23
                       mod_base = OTHER
                       note = 2'-O-methyl ribonucleotide
modified_base          1
                       mod_base = OTHER
                       note = unlocked nucleobase analog to uridine with 5' vinyl
                        phosphonate
modified_base          3..5
                       mod_base = OTHER
                       note = 2'-O-methyl ribonucleotide
modified_base          21..23
                       mod_base = OTHER
                       note = phosphorothioate linkage
SEQUENCE: 214
tggaataaat atctacaact ttt                                            23

SEQ ID NO: 215         moltype = RNA  length = 23
FEATURE                Location/Qualifiers
modified_base          1
                       mod_base = OTHER
                       note = 2'-O-methyl ribonucleotide
modified_base          21..23
                       mod_base = OTHER
                       note = phosphorothioate linkage
modified_base          14
                       mod_base = OTHER
                       note = 2'-fluoro ribonucleotide
modified_base          6
                       mod_base = OTHER
                       note = 2'-fluoro ribonucleotide
modified_base          15
                       mod_base = OTHER
                       note = 2'-O-methyl ribonucleotide
modified_base          1..3
                       mod_base = OTHER
                       note = phosphorothioate linkage
source                 1..23
                       mol_type = other RNA
                       organism = synthetic construct
modified_base          16
                       mod_base = OTHER
                       note = 2'-fluoro ribonucleotide
modified_base          2
                       mod_base = OTHER
                       note = 2'-fluoro ribonucleotide
modified_base          7..13
                       mod_base = OTHER
                       note = 2'-O-methyl ribonucleotide
modified_base          17..23
                       mod_base = OTHER
                       note = 2'-O-methyl ribonucleotide
modified_base          3..5
                       mod_base = OTHER
                       note = 2'-O-methyl ribonucleotide
SEQUENCE: 215
tgcaagatta attacatcaa att                                            23

SEQ ID NO: 216         moltype = RNA  length = 23
FEATURE                Location/Qualifiers
modified_base          2
                       mod_base = OTHER
                       note = 2'-fluoro ribonucleotide
source                 1..23
                       mol_type = other RNA
                       organism = synthetic construct
modified_base          7..13
                       mod_base = OTHER
                       note = 2'-O-methyl ribonucleotide
modified_base          16
                       mod_base = OTHER
                       note = 2'-fluoro ribonucleotide
modified_base          17..23
                       mod_base = OTHER
                       note = 2'-O-methyl ribonucleotide
modified_base          6
                       mod_base = OTHER
                       note = 2'-fluoro ribonucleotide
modified_base          3..5
                       mod_base = OTHER
```

```
                         note = 2'-O-methyl ribonucleotide
modified_base            14
                         mod_base = OTHER
                         note = 2'-fluoro ribonucleotide
modified_base            21..23
                         mod_base = OTHER
                         note = phosphorothioate linkage
modified_base            1..3
                         mod_base = OTHER
                         note = phosphorothioate linkage
modified_base            1
                         mod_base = OTHER
                         note = unlocked nucleobase analog to uridine with 5' vinyl
                          phosphonate
modified_base            15
                         mod_base = OTHER
                         note = 2'-O-methyl ribonucleotide
SEQUENCE: 216
tgcaagatta attacatcaa att                                              23

SEQ ID NO: 217           moltype = RNA  length = 23
FEATURE                  Location/Qualifiers
modified_base            1..3
                         mod_base = OTHER
                         note = phosphorothioate linkage
modified_base            3..5
                         mod_base = OTHER
                         note = 2'-O-methyl ribonucleotide
modified_base            7..13
                         mod_base = OTHER
                         note = 2'-O-methyl ribonucleotide
modified_base            1
                         mod_base = OTHER
                         note = 2'-O-methyl ribonucleotide
modified_base            2
                         mod_base = OTHER
                         note = 2'-fluoro ribonucleotide
modified_base            21..23
                         mod_base = OTHER
                         note = phosphorothioate linkage
modified_base            17..23
                         mod_base = OTHER
                         note = 2'-O-methyl ribonucleotide
modified_base            15
                         mod_base = OTHER
                         note = 2'-O-methyl ribonucleotide
modified_base            14
                         mod_base = OTHER
                         note = 2'-fluoro ribonucleotide
source                   1..23
                         mol_type = other RNA
                         organism = synthetic construct
modified_base            6
                         mod_base = OTHER
                         note = 2'-fluoro ribonucleotide
modified_base            16
                         mod_base = OTHER
                         note = 2'-fluoro ribonucleotide
SEQUENCE: 217
ttgaatcttc aagcacataa att                                              23

SEQ ID NO: 218           moltype = RNA  length = 23
FEATURE                  Location/Qualifiers
modified_base            7..13
                         mod_base = OTHER
                         note = 2'-O-methyl ribonucleotide
modified_base            2
                         mod_base = OTHER
                         note = 2'-fluoro ribonucleotide
modified_base            3..5
                         mod_base = OTHER
                         note = 2'-O-methyl ribonucleotide
modified_base            6
                         mod_base = OTHER
                         note = 2'-fluoro ribonucleotide
modified_base            15
                         mod_base = OTHER
                         note = 2'-O-methyl ribonucleotide
source                   1..23
```

-continued

```
                        mol_type = other RNA
                        organism = synthetic construct
modified_base           21..23
                        mod_base = OTHER
                        note = phosphorothioate linkage
modified_base           16
                        mod_base = OTHER
                        note = 2'-fluoro ribonucleotide
modified_base           1
                        mod_base = OTHER
                        note = unlocked nucleobase analog to uridine with 5' vinyl
                         phosphonate
modified_base           17..23
                        mod_base = OTHER
                        note = 2'-O-methyl ribonucleotide
modified_base           1..3
                        mod_base = OTHER
                        note = phosphorothioate linkage
modified_base           14
                        mod_base = OTHER
                        note = 2'-fluoro ribonucleotide
SEQUENCE: 218
ttgaatcttc aagcacataa att                                             23

SEQ ID NO: 219          moltype = RNA  length = 21
FEATURE                 Location/Qualifiers
modified_base           15
                        mod_base = OTHER
                        note = 2'-O-methyl ribonucleotide
modified_base           19..21
                        mod_base = OTHER
                        note = phosphorothioate linkage
modified_base           3..5
                        mod_base = OTHER
                        note = 2'-O-methyl ribonucleotide
modified_base           2
                        mod_base = OTHER
                        note = 2'-fluoro ribonucleotide
modified_base           1..3
                        mod_base = OTHER
                        note = phosphorothioate linkage
modified_base           16
                        mod_base = OTHER
                        note = 2'-fluoro ribonucleotide
modified_base           7..13
                        mod_base = OTHER
                        note = 2'-O-methyl ribonucleotide
modified_base           6
                        mod_base = OTHER
                        note = 2'-fluoro ribonucleotide
modified_base           14
                        mod_base = OTHER
                        note = 2'-fluoro ribonucleotide
modified_base           17..21
                        mod_base = OTHER
                        note = 2'-O-methyl ribonucleotide
source                  1..21
                        mol_type = other RNA
                        organism = synthetic construct
modified_base           1
                        mod_base = OTHER
                        note = 2'-O-methyl ribonucleotide
SEQUENCE: 219
tctggttgga acgatgtcat t                                               21

SEQ ID NO: 220          moltype = RNA  length = 21
FEATURE                 Location/Qualifiers
modified_base           14
                        mod_base = OTHER
                        note = 2'-fluoro ribonucleotide
modified_base           17..21
                        mod_base = OTHER
                        note = 2'-O-methyl ribonucleotide
source                  1..21
                        mol_type = other RNA
                        organism = synthetic construct
modified_base           2
                        mod_base = OTHER
                        note = 2'-fluoro ribonucleotide
```

-continued

```
modified_base          1..3
                       mod_base = OTHER
                       note = phosphorothioate linkage
modified_base          19..21
                       mod_base = OTHER
                       note = phosphorothioate linkage
modified_base          7..13
                       mod_base = OTHER
                       note = 2'-O-methyl ribonucleotide
modified_base          6
                       mod_base = OTHER
                       note = 2'-fluoro ribonucleotide
modified_base          16
                       mod_base = OTHER
                       note = 2'-fluoro ribonucleotide
modified_base          3..5
                       mod_base = OTHER
                       note = 2'-O-methyl ribonucleotide
modified_base          1
                       mod_base = OTHER
                       note = unlocked nucleobase analog to uridine with 5' vinyl
                        phosphonate
modified_base          15
                       mod_base = OTHER
                       note = 2'-O-methyl ribonucleotide
SEQUENCE: 220
tctggttgga acgatgtcat t                                            21

SEQ ID NO: 221         moltype = RNA  length = 21
FEATURE                Location/Qualifiers
modified_base          12..21
                       mod_base = OTHER
                       note = 2'-O-methyl ribonucleotide
modified_base          19..21
                       mod_base = OTHER
                       note = phosphorothioate linkage
modified_base          1..3
                       mod_base = OTHER
                       note = phosphorothioate linkage
modified_base          9..11
                       mod_base = OTHER
                       note = 2'-fluoro ribonucleotide
modified_base          1..8
                       mod_base = OTHER
                       note = 2'-O-methyl ribonucleotide
source                 1..21
                       mol_type = other RNA
                       organism = synthetic construct
SEQUENCE: 221
gatgagtcag gaaaagttgt a                                            21

SEQ ID NO: 222         moltype = RNA  length = 21
FEATURE                Location/Qualifiers
modified_base          9..11
                       mod_base = OTHER
                       note = 2'-fluoro ribonucleotide
modified_base          1..8
                       mod_base = OTHER
                       note = 2'-O-methyl ribonucleotide
modified_base          1..3
                       mod_base = OTHER
                       note = phosphorothioate linkage
modified_base          12..21
                       mod_base = OTHER
                       note = 2'-O-methyl ribonucleotide
modified_base          19..21
                       mod_base = OTHER
                       note = phosphorothioate linkage
source                 1..21
                       mol_type = other RNA
                       organism = synthetic construct
SEQUENCE: 222
gatgagtcag gaaaagttgt a                                            21

SEQ ID NO: 223         moltype = RNA  length = 21
FEATURE                Location/Qualifiers
modified_base          9..11
                       mod_base = OTHER
                       note = 2'-fluoro ribonucleotide
```

```
modified_base          19..21
                       mod_base = OTHER
                       note = phosphorothioate linkage
source                 1..21
                       mol_type = other RNA
                       organism = synthetic construct
modified_base          1..8
                       mod_base = OTHER
                       note = 2'-O-methyl ribonucleotide
modified_base          1..3
                       mod_base = OTHER
                       note = phosphorothioate linkage
modified_base          12..21
                       mod_base = OTHER
                       note = 2'-O-methyl ribonucleotide
SEQUENCE: 223
aaagttgtag atatttattc a                                     21

SEQ ID NO: 224         moltype = RNA  length = 21
FEATURE                Location/Qualifiers
modified_base          19..21
                       mod_base = OTHER
                       note = phosphorothioate linkage
modified_base          12..21
                       mod_base = OTHER
                       note = 2'-O-methyl ribonucleotide
modified_base          1..3
                       mod_base = OTHER
                       note = phosphorothioate linkage
modified_base          1..8
                       mod_base = OTHER
                       note = 2'-O-methyl ribonucleotide
source                 1..21
                       mol_type = other RNA
                       organism = synthetic construct
modified_base          9..11
                       mod_base = OTHER
                       note = 2'-fluoro ribonucleotide
SEQUENCE: 224
aaagttgtag atatttattc a                                     21

SEQ ID NO: 225         moltype = RNA  length = 21
FEATURE                Location/Qualifiers
source                 1..21
                       mol_type = other RNA
                       organism = synthetic construct
modified_base          9..11
                       mod_base = OTHER
                       note = 2'-fluoro ribonucleotide
modified_base          19..21
                       mod_base = OTHER
                       note = phosphorothioate linkage
modified_base          1..8
                       mod_base = OTHER
                       note = 2'-O-methyl ribonucleotide
modified_base          12..21
                       mod_base = OTHER
                       note = 2'-O-methyl ribonucleotide
modified_base          1..3
                       mod_base = OTHER
                       note = phosphorothioate linkage
SEQUENCE: 225
aagttgtaga tatttattcc a                                     21

SEQ ID NO: 226         moltype = RNA  length = 21
FEATURE                Location/Qualifiers
modified_base          12..21
                       mod_base = OTHER
                       note = 2'-O-methyl ribonucleotide
modified_base          1..3
                       mod_base = OTHER
                       note = phosphorothioate linkage
source                 1..21
                       mol_type = other RNA
                       organism = synthetic construct
modified_base          9..11
                       mod_base = OTHER
                       note = 2'-fluoro ribonucleotide
modified_base          19..21
```

```
                        mod_base = OTHER
                        note = phosphorothioate linkage
modified_base           1..8
                        mod_base = OTHER
                        note = 2'-O-methyl ribonucleotide
SEQUENCE: 226
aagttgtaga tatttattcc a                                       21

SEQ ID NO: 227          moltype = RNA  length = 21
FEATURE                 Location/Qualifiers
modified_base           1..8
                        mod_base = OTHER
                        note = 2'-O-methyl ribonucleotide
modified_base           9..11
                        mod_base = OTHER
                        note = 2'-fluoro ribonucleotide
modified_base           1..3
                        mod_base = OTHER
                        note = phosphorothioate linkage
source                  1..21
                        mol_type = other RNA
                        organism = synthetic construct
modified_base           12..21
                        mod_base = OTHER
                        note = 2'-O-methyl ribonucleotide
modified_base           19..21
                        mod_base = OTHER
                        note = phosphorothioate linkage
SEQUENCE: 227
tttgatgtaa ttaatcttgc a                                       21

SEQ ID NO: 228          moltype = RNA  length = 21
FEATURE                 Location/Qualifiers
source                  1..21
                        mol_type = other RNA
                        organism = synthetic construct
modified_base           1..3
                        mod_base = OTHER
                        note = phosphorothioate linkage
modified_base           19..21
                        mod_base = OTHER
                        note = phosphorothioate linkage
modified_base           1..8
                        mod_base = OTHER
                        note = 2'-O-methyl ribonucleotide
modified_base           12..21
                        mod_base = OTHER
                        note = 2'-O-methyl ribonucleotide
modified_base           9..11
                        mod_base = OTHER
                        note = 2'-fluoro ribonucleotide
SEQUENCE: 228
tttgatgtaa ttaatcttgc a                                       21

SEQ ID NO: 229          moltype = RNA  length = 21
FEATURE                 Location/Qualifiers
source                  1..21
                        mol_type = other RNA
                        organism = synthetic construct
modified_base           1..3
                        mod_base = OTHER
                        note = phosphorothioate linkage
modified_base           9..11
                        mod_base = OTHER
                        note = 2'-fluoro ribonucleotide
modified_base           12..21
                        mod_base = OTHER
                        note = 2'-O-methyl ribonucleotide
modified_base           19..21
                        mod_base = OTHER
                        note = phosphorothioate linkage
modified_base           1..8
                        mod_base = OTHER
                        note = 2'-O-methyl ribonucleotide
SEQUENCE: 229
tttatgtgct tgaagattca a                                       21

SEQ ID NO: 230          moltype = RNA  length = 21
FEATURE                 Location/Qualifiers
```

```
modified_base          9..11
                       mod_base = OTHER
                       note = 2'-fluoro ribonucleotide
modified_base          1..3
                       mod_base = OTHER
                       note = phosphorothioate linkage
modified_base          1..8
                       mod_base = OTHER
                       note = 2'-O-methyl ribonucleotide
source                 1..21
                       mol_type = other RNA
                       organism = synthetic construct
modified_base          12..21
                       mod_base = OTHER
                       note = 2'-O-methyl ribonucleotide
modified_base          19..21
                       mod_base = OTHER
                       note = phosphorothioate linkage
SEQUENCE: 230
tttatgtgct tgaagattca a                                              21

SEQ ID NO: 231         moltype = RNA  length = 19
FEATURE                Location/Qualifiers
modified_base          7..9
                       mod_base = OTHER
                       note = 2'-fluoro ribonucleotide
modified_base          10..19
                       mod_base = OTHER
                       note = 2'-O-methyl ribonucleotide
modified_base          17..19
                       mod_base = OTHER
                       note = phosphorothioate linkage
source                 1..19
                       mol_type = other RNA
                       organism = synthetic construct
modified_base          1..3
                       mod_base = OTHER
                       note = phosphorothioate linkage
modified_base          1..6
                       mod_base = OTHER
                       note = 2'-O-methyl ribonucleotide
SEQUENCE: 231
tgacatcgtt ccaaccaga                                                 19

SEQ ID NO: 232         moltype = RNA  length = 19
FEATURE                Location/Qualifiers
source                 1..19
                       mol_type = other RNA
                       organism = synthetic construct
modified_base          1..3
                       mod_base = OTHER
                       note = phosphorothioate linkage
modified_base          10..19
                       mod_base = OTHER
                       note = 2'-O-methyl ribonucleotide
modified_base          1..6
                       mod_base = OTHER
                       note = 2'-O-methyl ribonucleotide
modified_base          17..19
                       mod_base = OTHER
                       note = phosphorothioate linkage
modified_base          7..9
                       mod_base = OTHER
                       note = 2'-fluoro ribonucleotide
SEQUENCE: 232
tgacatcgtt ccaaccaga                                                 19

SEQ ID NO: 233         moltype = DNA  length = 20
FEATURE                Location/Qualifiers
source                 1..20
                       mol_type = other DNA
                       organism = synthetic construct
SEQUENCE: 233
tacaactttt cctgactcat                                                20

SEQ ID NO: 234         moltype = DNA  length = 20
FEATURE                Location/Qualifiers
source                 1..20
                       mol_type = other DNA
```

```
                         organism = synthetic construct
SEQUENCE: 234
ggaataaata tctacaactt                                              20

SEQ ID NO: 235           moltype = DNA  length = 20
FEATURE                  Location/Qualifiers
modified_base            16..20
                         mod_base = OTHER
                         note = 2'-methoxyethyl ribonucleotide
modified_base            1..20
                         mod_base = OTHER
                         note = phosphorothioate linkage
misc_feature             6..15
                         note = DNA
misc_feature             1..5
                         note = RNA
modified_base            1..5
                         mod_base = OTHER
                         note = 2'-methoxyethyl ribonucleotide
misc_feature             16..20
                         note = RNA
source                   1..20
                         mol_type = other DNA
                         organism = synthetic construct
SEQUENCE: 235
tacaactttt cctgactcat                                              20

SEQ ID NO: 236           moltype = DNA  length = 20
FEATURE                  Location/Qualifiers
modified_base            16..20
                         mod_base = OTHER
                         note = 2'-methoxyethyl ribonucleotide
modified_base            1..20
                         mod_base = OTHER
                         note = phosphorothioate linkage
misc_feature             6..15
                         note = DNA
source                   1..20
                         mol_type = other DNA
                         organism = synthetic construct
misc_feature             16..20
                         note = RNA
misc_feature             1..5
                         note = RNA
modified_base            1..5
                         mod_base = OTHER
                         note = 2'-methoxyethyl ribonucleotide
SEQUENCE: 236
ggaataaata tctacaactt                                              20

SEQ ID NO: 237           moltype = RNA  length = 3279
FEATURE                  Location/Qualifiers
source                   1..3279
                         mol_type = genomic RNA
                         organism = Homo sapiens
SEQUENCE: 237
attctgcggc cgaggattac atttatgcac gaacgggctt actggttcca gattccccac  60
ttgggcacag gcataggagg cttgttttcc aaattgctgg ttttaattgc acctgccttt  120
cagattacct ctgggaatct gtgggaggag ccgagagggt ggaaaatgtt tcttagcttt  180
gcaaaaggaa gaaaactttg tcacccagcg ggagacctca gccacgagta acccggggag  240
acaccagaac cgggacgggc tttgactgat ttgcctacga gggttccgta ggaaaggacg  300
cttgaattcg gcgcttcggc ggcggcggcg gccgcgcgag ttccctgctc accctccctc  360
tccgcggaag tccccacgag gtggcttcag ggtgtaacag agcgcgcggc tccagtccga  420
aggcagcggc cgggggaggg aaggagggga ccgaaccccc gaggagtttc gcagaatcaa  480
cttctggtta gagttatggg aagcgcggtt atggacacca agaagaaaaa agatgtttcc  540
agccccggcg ggagcggcgg caagaaaaat gccagccaga agaggcgttc gctgcgcgtg  600
cacattccgg acctgagctc cttcgccatg ccgctcctgg acggagacct ggagggttcc  660
ggaaagcatt cctctcgaaa ggtggacagc cccttcggcc cgggcagccc ctccaaaggg  720
ttcttctcca gaggccccca gccccggccc tccagcccca tgtctgcacc tgtgaggccc  780
aagaccagcc ccggctctcc caaaaccgtg ttcccgttct cctaccagga gtccccgcca  840
cgctcccctc gacgcatgag cttcagtggg atcttccgct cctcctccaa agagtcttcc  900
cccaactcca accctgctac ctcgcccggg ggcatcaggt tttctcccg ctccagaaaa  960
acctccggcc tctcctcctc tccgtcaaca cccacccaag tgaccaagca gcacacgttt  1020
cccctggaat cctataagca cgagcctgaa cggttagaga atcgcatcta tgcctcgtct  1080
tccccccccgg acacagggca gaggttctgc ccgtcttcct tccagagccc gaccaggcct  1140
ccactggcat caccgacaca ctatgctccc tccaaagccg cggcgctggc ggcggccctg  1200
ggacccgcgg aagccggcat gctggagaag ctggagttcg aggacgaagc agtagaagac  1260
tcagaaagtg gtgtttacat gcgattcatg aggtcacaca agtgttatga catcgttcca  1320
accagttcaa agcttgttgt ctttgatact acattacaag ttaaaaaggc cttctttgct  1380
```

-continued

```
ttggtagcca acggtgtccg agcagcgcca ctgtgggaga gtaaaaaaca aagttttgta  1440
ggaatgctaa caattacaga tttcataaat atactacata gatactataa atcacctatg  1500
gtacagattt atgaattaga ggaacataaa attgaaacat ggagggagct ttatttacaa  1560
gaaacattta agcctttagt gaatatatct ccagatgcaa gcctcttcga tgctgtatac  1620
tccttgatca aaaataaaat ccacagattg cccgttattg accctatcag tgggaatgca  1680
ctttatatac ttacccacaa aagaatcctc aagttcctcc agctttttat gtctgatatg  1740
ccaaagcctg ccttcatgaa gcagaacctg gatgagcttg gaataggaac gtaccacaac  1800
attgccttca tacatccaga cactcccatc atcaaagcct tgaacatatt tgtggaaaga  1860
cgaatatcag ctctgcctgt tgtggatgag tcaggaaaag ttgtagatat ttattccaaa  1920
tttgatgtaa ttaatcttgc tgctgagaaa acatacaata acctagatat cacggtgacc  1980
caggcccttc agcaccgttc acagtatttt gaaggtgttg tgaagtgcaa taagctggaa  2040
atactggaga ccatcgtgga cagaatagta agagctgagg tccatcggct ggtggtggta  2100
aatgaagcag atagtattgt gggtattatt tccctgtcgg acattctgca agccctgatc  2160
ctcacaccag caggtgccaa acaaaaggag acagaaacgg agtgaccgcc gtgaatgtag  2220
acgccctagg aggagaactt gaacaaagtc tctgggtcac gtttgcctcc atgaacactg  2280
gctgcaagtg gttaagaatg tatatcaggg tttaacaata ggtatttctt ccagtgatgt  2340
tgaaattaag cttaaaaaag aaagatttta tgtgcttgaa gattcaggct tgcattaaaa  2400
gactgttttc agacctttgt ctgaaggatt ttaaatgctg tatgtcatta aagtgcactg  2460
tgtcctgaag ttttcattat ttttcatttc aaagaattca ctggtatgga acaggtgatg  2520
tggcataagg tgagtgcacg gtatgttcag atcacagtgc cttatgtccg aatacagcaa  2580
tatgtcaccg ccgcagccgg ggcgcacgcg tgtgaaacaa caccgagctt gaatgtggaa  2640
gtctttgaac cttttaccaa atcagtttgt tttctttaga tttgtcaaaa agttgtaatt  2700
tgaatataaa taattacttt aaaattgtaa tgacactttt acacgtaagt gttttgttct  2760
gggctaccgt gtcaacgagg ctgctttaca acagctttat ttatttttac tttcatgcaa  2820
tttttttaca catcttttgg tggagtaaac ttcaccacat ccatgaataa actctcagtt  2880
attttgaaat ggcaaatttc tcattattta agtttggatc tggaaaggac atgacttctg  2940
aaatagccgc tgctgggttt taaaagctga ggtctctcaa agtgtggagg agacgttgcc  3000
gtcaggcggg agccaagtgc cgggaagatg tctatttttt ttcttgtgta ttgaaatgta  3060
aaatcatgat gtttgttatg actgctgatg cgattgtttt tgtaaatttt attgtggcat  3120
atacagtatt gtcatacagt tgaagagaaa caatgtttcc taatgtaagt gctctgaaaa  3180
tgttgacact gtatatatat atatgaggat agtttgtttt ttttttgttt tgggtttttt  3240
tttttcagat tgaaaaatta aaatagatcc tactatcta                         3279

SEQ ID NO: 238          moltype = AA  length = 566
FEATURE                 Location/Qualifiers
source                  1..566
                        mol_type = protein
                        organism = Mus musculus
SEQUENCE: 238
MGSAAMDTKK KKEVSSPGGS SGKKNPSLKR RSLRVHIPDL SSFAMPLLDG DVENSEKHSS  60
RKVDSPFSSG SPSRGLFSRG PQPRPSSPVS APVRPKTSPG SPKTVFPFSY QESPPRSPRR  120
MSFSGIFRSS SKESSPNSNP STSPGGIRFF SRSRKTSSVS SSPSTPTQVT KQHPFPLESY  180
KQEPERPESR IYASSSPPDT GQRFCLAFQS PARPPLASPT YHAPLRTAVL AAAPGPAEAG  240
MLEKLEFQEE EDSESGVYMR FMRSHKCYDI VPTSSKLVVF DTTLQVKKAF FALVANGVRA  300
APLWESKKQS FVGMLTITDF INILHRYYKS PMVQIYELEE HKIETWRELY LQETFKPLVN  360
ISPDASLFDA VYSLIKNKIH RLPVIDPISG NALYILTHKR ILKFLQLFMS DMPKPAFMKQ  420
NLDELGIGTY HNIAFIHPDT PIIKALNIFV ERRISALPVV DESGKVVDIY SKFDVINLAA  480
EKTYNNLDIT VTQALQHRSQ YFEGVVKCSK LETLETIVDR IVRAEVHRLV VVNEADSIVG  540
IISLSDILQA LILTPAGAKQ KETETE                                       566

SEQ ID NO: 239          moltype = RNA  length = 3263
FEATURE                 Location/Qualifiers
source                  1..3263
                        mol_type = genomic RNA
                        organism = Macaca fascicularis
SEQUENCE: 239
attctgcggc cgaggattac atttatgcac gaacggtctc gctggctcca gattccccac  60
ttgggcacag gctaggaggg ttgttttcca aattgctggt tttaattgca cctgcctttc  120
agattacctc tgggaatctg tgggaggagc cgagagggtg gaaaatgttt cttctctttg  180
caaaaggaag aaaactttgt cacccagcgg gagacctcag ccacgcgtaa cccgcgagac  240
accagaaccg ggacgggctt tgactgattc tgcctgcgag agttccgtag gaaaggacgc  300
ttgaactcgg cgctccggcg gcggcggcac gagttccctg ctcactctcc ctccccgcgg  360
aagtccccac gaggtggctt cggggtgtaa cagagcgcgc ggctccagtc cgacggcagc  420
ggccggggca gggaaggagg ggaccgaacc cccgaggagt tacccagaat caacttctgg  480
ttagagttat gggaagcgcg gttatggaca ccaagaagaa aaaagatgtt tccagccccg  540
gcgggagcgg cggcaagaaa aatgccagcc agaagaggcg ttctctgcgc gtgcacattc  600
cggacctgag ctcctttgcc atgccgctcc tggacggaga cctggagggt tccggaaagc  660
attcctctcg aaaggtggac agccccttcg gcccgggcag cccctccaaa gggttcttct  720
ccagaggccc ccagccccgg ccctccagcc ccatgtctgc acccgtgagg cccaagacca  780
gccccggctc tccgaaaacc gtgttcccgt tctcctacca ggagtccccg ccgcgctccc  840
ctcgacgcat gagcttcagc gggatcttcc gctcctcctc caaagagtct tcccccaact  900
ccaaccctgc tacctcgccc gggggcatca ggtttttctc ccgctccaga aaaacctccg  960
gcctctcctc ctctccgtca acacccaccc aagtgaccaa gcagcacaca tttcccctgg  1020
aatcctataa gcacgagcct gaacggttag agaatcgcat ctatgcctcg tcttcccctc  1080
cggacacagg gcagaggttc tgcccgtctt ccttccagag cccgaccagg cctccactgg  1140
catcaccgac acactatgct ccctccaaag ccgcggcgct ggcggcggcc ccgggacccg  1200
cggaagccgg catgctggag aagctggagt tcgaggacga agcagaagac tcagaaagtg  1260
gtgtttacat gcgattcatg aggtcacaca agtgttatga catcgttcca accagttcaa  1320
agcttgtcgt ctttgatact acattacaag ttaaaaaggc cttctttgct ttggtagcca  1380
```

-continued

```
acggtgtccg agcagcacca ctgtgggaga gtaaaaaaca aagttttgta ggaatgctaa  1440
caattacaga tttcataaat atactacata gatactataa atcgcctatg gtacagattt  1500
atgaattaga ggaacataaa attgaaacct ggagggagct ttatttacaa gaaacattta  1560
agcctttagt gaatatatct ccagatgcaa gcctcttcga tgctgtatac tccttgatca  1620
aaaataaaat ccacagattg ccagttattg accctatcag tgggaatgca ctttatatac  1680
tcacccacaa aagaatcctc aagttcctcc agctttttat gtctgatatg ccaaagcctg  1740
ccttcatgaa gcagaacctg gatgagcttg gaataggaac gtaccacaac attgccttca  1800
tacatccaga cactcccatc attaaagcct tgaacatatt tgtggaaaga cgaatatcag  1860
ctctgcctgt tgtggatgag tcaggaaaag ttgtagatat ttattccaaa tttgatgtaa  1920
ttaatcttgc tgctgagaaa acatacaata acctagatat cacagtgacc caggcccttc  1980
agcaccgttc acagtatttt gaaggtgttg taaagtgcaa taagctggaa atactggaga  2040
ccattgtgga cagaatagtg agagctgagg tccatcggct ggtggtggta aatgaagcag  2100
atagtatcgt gggtattatt tccctgtcgg atattctgca agccctgatc ctcacaccag  2160
caggtgccaa acaaaaggag acggaaacag agtgaccgcc gtgaatgtag acgccctagg  2220
aggagaactt gaacaaagtt tctgggtcac gttttgcctc atgaacactg gctgcaagtg  2280
gttaagaatg tatatcaggg tttaatgatg ggtatttctt ccagtgatgt tggaattaag  2340
cttaaaaaag aaagatttta tgtgcttgaa gattcaggct tgcattaaaa gactgttttc  2400
agacctttgt ctgacggatt ttaaatgctg tatgtcatta aagtgcactg tgtcctgaag  2460
ttttcattat ttttcatttc aaagagttca ctggtatgga acaggtgatg cgacataagg  2520
tgagtgcacg gcatgttcag atcacagtgc cttatgtccg aatacagcaa tatgtcacct  2580
ccgcagccgg ggcgcacgcg tgcgaagcca caccgagctt gaatgtggaa gtctttgaac  2640
cttttaccaa atcagtttgt tttcattaga tttgtcaaaa agttgtcatt tgaatataac  2700
gaatgacttt aaaactgtaa tgacactttt acacgtgttt cgttccgggc taccgtgtca  2760
acaaggctgc tttacaacag ctttatttag ttttactttc atgccatttt tttacacatc  2820
ttttggtggg gtaaacttca ccacacccat gaataaactc tcagttattt tgaaatggca  2880
aatttctcat tatttaagtt tggatctgga aaggacatga cttctgaaac agccgctgct  2940
gggttttcaa agctgaggtc tcaaacgtgt aggagacgtt gccgtcaggc gggagccaag  3000
tgccgggaag atgtctattt tttttcttgt gtattaaaat gtaaaatcat gatgtttgta  3060
tgactgccga tgcgattgtg tttgtaaatt ttattgtggc atatacagta ttgtcataca  3120
gttgaagaga aacaatgttt cctaatgtaa gtgctctgaa aatgttgaca ctgtatatat  3180
atatatgagg atagtttggg tttttttgt ttttgggttt ttttttcaga ttgaaaaatt  3240
aaaataaatc ctactatcta cca                                          3263

SEQ ID NO: 240         moltype = AA  length = 9
FEATURE                Location/Qualifiers
source                 1..9
                       mol_type = protein
                       organism = synthetic construct
SEQUENCE: 240
YTFTNYWMH                                                          9

SEQ ID NO: 241         moltype = AA  length = 17
FEATURE                Location/Qualifiers
VARIANT                6
                       note = N or Q
source                 1..17
                       mol_type = protein
                       organism = synthetic construct
SEQUENCE: 241
EINPIXGRSN YAZKFQG                                                 17

SEQ ID NO: 242         moltype = AA  length = 17
FEATURE                Location/Qualifiers
source                 1..17
                       mol_type = protein
                       organism = synthetic construct
SEQUENCE: 242
EINPINGRSN YAQKFQG                                                 17

SEQ ID NO: 243         moltype = AA  length = 17
FEATURE                Location/Qualifiers
source                 1..17
                       mol_type = protein
                       organism = synthetic construct
SEQUENCE: 243
EINPINGRSN YAEKFQG                                                 17

SEQ ID NO: 244         moltype = AA  length = 17
FEATURE                Location/Qualifiers
source                 1..17
                       mol_type = protein
                       organism = synthetic construct
SEQUENCE: 244
EINPIQGRSN YAEKFQG                                                 17

SEQ ID NO: 245         moltype = AA  length = 7
FEATURE                Location/Qualifiers
source                 1..7
                       mol_type = protein
```

```
                        organism = synthetic construct
SEQUENCE: 245
GTRAMHY                                                                       7

SEQ ID NO: 246          moltype = AA  length = 11
FEATURE                 Location/Qualifiers
VARIANT                 8
                        note = N or S
source                  1..11
                        mol_type = protein
                        organism = synthetic construct
SEQUENCE: 246
RTSENIYXNL A                                                                  11

SEQ ID NO: 247          moltype = AA  length = 11
FEATURE                 Location/Qualifiers
source                  1..11
                        mol_type = protein
                        organism = synthetic construct
SEQUENCE: 247
RTSENIYNNL A                                                                  11

SEQ ID NO: 248          moltype = AA  length = 11
FEATURE                 Location/Qualifiers
source                  1..11
                        mol_type = protein
                        organism = synthetic construct
SEQUENCE: 248
RTSENIYSNL A                                                                  11

SEQ ID NO: 249          moltype = AA  length = 7
FEATURE                 Location/Qualifiers
VARIANT                 2
                        note = A or G
source                  1..7
                        mol_type = protein
                        organism = synthetic construct
VARIANT                 7
                        note = D or E
SEQUENCE: 249
AXTNLAX                                                                       7

SEQ ID NO: 250          moltype = AA  length = 7
FEATURE                 Location/Qualifiers
source                  1..7
                        mol_type = protein
                        organism = synthetic construct
SEQUENCE: 250
AATNLAD                                                                       7

SEQ ID NO: 251          moltype = AA  length = 7
FEATURE                 Location/Qualifiers
source                  1..7
                        mol_type = protein
                        organism = synthetic construct
SEQUENCE: 251
AATNLAE                                                                       7

SEQ ID NO: 252          moltype = AA  length = 7
FEATURE                 Location/Qualifiers
source                  1..7
                        mol_type = protein
                        organism = synthetic construct
SEQUENCE: 252
AGTNLAD                                                                       7

SEQ ID NO: 253          moltype = AA  length = 10
FEATURE                 Location/Qualifiers
source                  1..10
                        mol_type = protein
                        organism = synthetic construct
VARIANT                 10
                        note = May be deleted
SEQUENCE: 253
QHFWGTPLTF                                                                    10

SEQ ID NO: 254          moltype = AA  length = 9
FEATURE                 Location/Qualifiers
source                  1..9
```

```
                        mol_type = protein
                        organism = synthetic construct
SEQUENCE: 254
QHFWGTPLT                                                    9

SEQ ID NO: 255          moltype = AA  length = 10
FEATURE                 Location/Qualifiers
source                  1..10
                        mol_type = protein
                        organism = synthetic construct
SEQUENCE: 255
QHFWGTPLTF                                                   10

SEQ ID NO: 256          moltype = AA  length = 116
FEATURE                 Location/Qualifiers
source                  1..116
                        mol_type = protein
                        organism = synthetic construct
SEQUENCE: 256
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSS      116

SEQ ID NO: 257          moltype = AA  length = 116
FEATURE                 Location/Qualifiers
source                  1..116
                        mol_type = protein
                        organism = synthetic construct
SEQUENCE: 257
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSS      116

SEQ ID NO: 258          moltype = AA  length = 116
FEATURE                 Location/Qualifiers
source                  1..116
                        mol_type = protein
                        organism = synthetic construct
SEQUENCE: 258
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSS      116

SEQ ID NO: 259          moltype = AA  length = 116
FEATURE                 Location/Qualifiers
source                  1..116
                        mol_type = protein
                        organism = synthetic construct
SEQUENCE: 259
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSS      116

SEQ ID NO: 260          moltype = AA  length = 116
FEATURE                 Location/Qualifiers
source                  1..116
                        mol_type = protein
                        organism = synthetic construct
SEQUENCE: 260
QVQLQQPGAE LVKPGASVKL SCKASGYTFT NYWMHWVKQR PGQGLEWIGE INPINGRSNY  60
GERFKTKATL TVDKSSSTAY MQLSSLTSED SAVYYCARGT RAMHYWGQGT SVTVSS      116

SEQ ID NO: 261          moltype = AA  length = 107
FEATURE                 Location/Qualifiers
source                  1..107
                        mol_type = protein
                        organism = synthetic construct
SEQUENCE: 261
DIQMTQSPSS LSASVGDRVT ITCRTSENIY NNLAWYQQKP GKSPKLLIYA ATNLADGVPS  60
RFSGSGSGTD YTLTISSLQP EDFATYYCQH FWGTPLTFGG GTKVEIK                107

SEQ ID NO: 262          moltype = AA  length = 107
FEATURE                 Location/Qualifiers
source                  1..107
                        mol_type = protein
                        organism = synthetic construct
SEQUENCE: 262
DIQMTQSPSS LSASVGDRVT ITCRTSENIY NNLAWYQQKP GKAPKLLIYA ATNLADGVPS  60
RFSGSGSGTD YTLTISSLQP EDFATYYCQH FWGTPLTFGG GTKVEIK                107

SEQ ID NO: 263          moltype = AA  length = 107
FEATURE                 Location/Qualifiers
source                  1..107
```

-continued

```
                        mol_type = protein
                        organism = synthetic construct
SEQUENCE: 263
DIQMTQSPSS LSASVGDRVT ITCRTSENIY NNLAWYQQKP GKAPKLLIYA ATNLAEGVPS  60
RFSGSGSGTD YTLTISSLQP EDFATYYCQH FWGTPLTFGG GTKVEIK                107

SEQ ID NO: 264          moltype = AA  length = 107
FEATURE                 Location/Qualifiers
source                  1..107
                        mol_type = protein
                        organism = synthetic construct
SEQUENCE: 264
DIQMTQSPSS LSASVGDRVT ITCRTSENIY SNLAWYQQKP GKAPKLLIYA GTNLADGVPS  60
RFSGSGSGTD YTLTISSLQP EDFANYYCQH FWGTPLTFGG GTKVEIK                107

SEQ ID NO: 265          moltype = AA  length = 107
FEATURE                 Location/Qualifiers
source                  1..107
                        mol_type = protein
                        organism = synthetic construct
SEQUENCE: 265
DIQMTQSPAS LSVSVGETVT ITCRTSENIY NNLAWYQQKQ GKSPQLLVYA ATNLADGVPS  60
RFSGSGSGTQ YSLKINSLQS EDFGNYYCQH FWGTPLTFGA GTKLELK                107

SEQ ID NO: 266          moltype =   length =
SEQUENCE: 266
000

SEQ ID NO: 267          moltype =   length =
SEQUENCE: 267
000

SEQ ID NO: 268          moltype =   length =
SEQUENCE: 268
000

SEQ ID NO: 269          moltype =   length =
SEQUENCE: 269
000

SEQ ID NO: 270          moltype = AA  length = 445
FEATURE                 Location/Qualifiers
source                  1..445
                        mol_type = protein
                        organism = synthetic construct
SEQUENCE: 270
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 271          moltype = AA  length = 445
FEATURE                 Location/Qualifiers
source                  1..445
                        mol_type = protein
                        organism = synthetic construct
SEQUENCE: 271
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 272          moltype = AA  length = 445
FEATURE                 Location/Qualifiers
source                  1..445
                        mol_type = protein
                        organism = synthetic construct
SEQUENCE: 272
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
```

-continued

```
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC GVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 273          moltype = AA  length = 445
FEATURE                 Location/Qualifiers
source                  1..445
                        mol_type = protein
                        organism = synthetic construct
SEQUENCE: 273
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKARPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 274          moltype = AA  length = 445
FEATURE                 Location/Qualifiers
source                  1..445
                        mol_type = protein
                        organism = synthetic construct
SEQUENCE: 274
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 275          moltype = AA  length = 445
FEATURE                 Location/Qualifiers
source                  1..445
                        mol_type = protein
                        organism = synthetic construct
SEQUENCE: 275
QVQLVQSGAE VKKPGASVKV SCKASGYTFT NYWMHWVRQA PGQGLEWMGE INPINGRSNY  60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVAVSHEDP EVKFNWYVDG VEVHNAKTKP REEQYGSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 276          moltype = AA  length = 445
FEATURE                 Location/Qualifiers
source                  1..445
                        mol_type = protein
                        organism = synthetic construct
SEQUENCE: 276
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 277          moltype = AA  length = 445
FEATURE                 Location/Qualifiers
source                  1..445
                        mol_type = protein
                        organism = synthetic construct
SEQUENCE: 277
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
```

-continued

```
VFSCSVMHEA LHNHYTQKSL SLSPG                                    445

SEQ ID NO: 278         moltype = AA  length = 445
FEATURE                Location/Qualifiers
source                 1..445
                       mol_type = protein
                       organism = synthetic construct
SEQUENCE: 278
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC GVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                    445

SEQ ID NO: 279         moltype = AA  length = 445
FEATURE                Location/Qualifiers
source                 1..445
                       mol_type = protein
                       organism = synthetic construct
SEQUENCE: 279
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKARPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                    445

SEQ ID NO: 280         moltype = AA  length = 445
FEATURE                Location/Qualifiers
source                 1..445
                       mol_type = protein
                       organism = synthetic construct
SEQUENCE: 280
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                    445

SEQ ID NO: 281         moltype = AA  length = 445
FEATURE                Location/Qualifiers
source                 1..445
                       mol_type = protein
                       organism = synthetic construct
SEQUENCE: 281
QVQLVQSGAE VKKPGASVKV SCKASGYTFT NYWMHWVRQA PGQGLEWIGE INPINGRSNY  60
AEKFQGRVTL TVDTSSSTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVAVSHEDP EVKFNWYVDG VEVHNAKTKP REEQYGSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                    445

SEQ ID NO: 282         moltype = AA  length = 445
FEATURE                Location/Qualifiers
source                 1..445
                       mol_type = protein
                       organism = synthetic construct
SEQUENCE: 282
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                    445

SEQ ID NO: 283         moltype = AA  length = 445
FEATURE                Location/Qualifiers
```

-continued

```
source                1..445
                      mol_type = protein
                      organism = synthetic construct
SEQUENCE: 283
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 284        moltype = AA  length = 445
FEATURE               Location/Qualifiers
source                1..445
                      mol_type = protein
                      organism = synthetic construct
SEQUENCE: 284
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC GVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 285        moltype = AA  length = 445
FEATURE               Location/Qualifiers
source                1..445
                      mol_type = protein
                      organism = synthetic construct
SEQUENCE: 285
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKARPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 286        moltype = AA  length = 445
FEATURE               Location/Qualifiers
source                1..445
                      mol_type = protein
                      organism = synthetic construct
SEQUENCE: 286
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 287        moltype = AA  length = 445
FEATURE               Location/Qualifiers
source                1..445
                      mol_type = protein
                      organism = synthetic construct
SEQUENCE: 287
QVQLVQSGAE VKKPGASVKV SCKASGYTFT NYWMHWVRQA PGQGLEWMGE INPIQGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVAVSHEDP EVKFNWYVDG VEVHNAKTKP REEQYGSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 288        moltype = AA  length = 445
FEATURE               Location/Qualifiers
source                1..445
                      mol_type = protein
                      organism = synthetic construct
SEQUENCE: 288
```

-continued

```
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 289         moltype = AA  length = 445
FEATURE                Location/Qualifiers
source                 1..445
                       mol_type = protein
                       organism = synthetic construct
SEQUENCE: 289
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 290         moltype = AA  length = 445
FEATURE                Location/Qualifiers
source                 1..445
                       mol_type = protein
                       organism = synthetic construct
SEQUENCE: 290
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC GVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 291         moltype = AA  length = 445
FEATURE                Location/Qualifiers
source                 1..445
                       mol_type = protein
                       organism = synthetic construct
SEQUENCE: 291
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKARPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 292         moltype = AA  length = 445
FEATURE                Location/Qualifiers
source                 1..445
                       mol_type = protein
                       organism = synthetic construct
SEQUENCE: 292
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 293         moltype = AA  length = 445
FEATURE                Location/Qualifiers
source                 1..445
                       mol_type = protein
                       organism = synthetic construct
SEQUENCE: 293
QVQLVQSGAE VKKPGASVKV SCKASGYTFT NYWMHWVRQA PGQGLEWMGE INPINGRSNY  60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
```

-continued

```
LFPPKPKDTL MISRTPEVTC VVVAVSHEDP EVKFNWYVDG VEVHNAKTKP REEQYGSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 294         moltype = AA  length = 214
FEATURE                Location/Qualifiers
source                 1..214
                       mol_type = protein
                       organism = synthetic construct
SEQUENCE: 294
DIQMTQSPSS LSASVGDRVT ITCRTSENIY NNLAWYQQKP GKSPKLLIYA ATNLADGVPS  60
RFSGSGSGTD YTLTISSLQP EDFATYYCQH FWGTPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 295         moltype = AA  length = 214
FEATURE                Location/Qualifiers
source                 1..214
                       mol_type = protein
                       organism = synthetic construct
SEQUENCE: 295
DIQMTQSPSS LSASVGDRVT ITCRTSENIY NNLAWYQQKP GKAPKLLIYA ATNLADGVPS  60
RFSGSGSGTD YTLTISSLQP EDFATYYCQH FWGTPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 296         moltype = AA  length = 214
FEATURE                Location/Qualifiers
source                 1..214
                       mol_type = protein
                       organism = synthetic construct
SEQUENCE: 296
DIQMTQSPSS LSASVGDRVT ITCRTSENIY NNLAWYQQKP GKAPKLLIYA ATNLAEGVPS  60
RFSGSGSGTD YTLTISSLQP EDFATYYCQH FWGTPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 297         moltype = AA  length = 214
FEATURE                Location/Qualifiers
source                 1..214
                       mol_type = protein
                       organism = synthetic construct
SEQUENCE: 297
DIQMTQSPSS LSASVGDRVT ITCRTSENIY SNLAWYQQKP GKAPKLLIYA GTNLADGVPS  60
RFSGSGSGTD YTLTISSLQP EDFANYYCQH FWGTPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 298         moltype = AA  length = 24
FEATURE                Location/Qualifiers
source                 1..24
                       mol_type = protein
                       organism = synthetic construct
SEQUENCE: 298
CGIFGEIEEL IEEGLENLID WGNA                                         24

SEQ ID NO: 299         moltype = AA  length = 24
FEATURE                Location/Qualifiers
source                 1..24
                       mol_type = protein
                       organism = synthetic construct
SEQUENCE: 299
GLFEAIEGFI ENGWEGMIDG WYGC                                         24

SEQ ID NO: 300         moltype = AA  length = 27
FEATURE                Location/Qualifiers
source                 1..27
                       mol_type = protein
                       organism = synthetic construct
SEQUENCE: 300
GLFEAIEGFI ENGWEGMIWD YGSGSCG                                      27

SEQ ID NO: 301         moltype = AA  length = 23
FEATURE                Location/Qualifiers
source                 1..23
                       mol_type = protein
                       organism = synthetic construct
SEQUENCE: 301
```

```
GLFEAIEGFI ENGWEGMIDG WYG                                         23

SEQ ID NO: 302          moltype = AA  length = 27
FEATURE                 Location/Qualifiers
source                  1..27
                        mol_type = protein
                        organism = synthetic construct
SEQUENCE: 302
GLFEAIEGFI ENGWEGMIWD YGSGSCK                                     27

SEQ ID NO: 303          moltype = AA  length = 27
FEATURE                 Location/Qualifiers
source                  1..27
                        mol_type = protein
                        organism = synthetic construct
SEQUENCE: 303
CLIGAILKVL ATGLPTLISW IKNKRKQ                                     27

SEQ ID NO: 304          moltype = AA  length = 26
FEATURE                 Location/Qualifiers
source                  1..26
                        mol_type = protein
                        organism = synthetic construct
SEQUENCE: 304
GIGAVLKVLT TGLPALISWI KRKRQQ                                      26

SEQ ID NO: 305          moltype = AA  length = 13
FEATURE                 Location/Qualifiers
SITE                    13
                        note = amidated phenylalanine
source                  1..13
                        mol_type = protein
                        organism = synthetic construct
SEQUENCE: 305
IFGAIAGLLK NIF                                                    13

SEQ ID NO: 306          moltype = AA  length = 18
FEATURE                 Location/Qualifiers
source                  1..18
                        mol_type = protein
                        organism = synthetic construct
SEQUENCE: 306
FFGHLFKLAT KIIPSLFQ                                               18

SEQ ID NO: 307          moltype = AA  length = 21
FEATURE                 Location/Qualifiers
source                  1..21
                        mol_type = protein
                        organism = synthetic construct
SEQUENCE: 307
KETWWETWWT EWSQPKKKRK V                                           21

SEQ ID NO: 308          moltype = AA  length = 19
FEATURE                 Location/Qualifiers
source                  1..19
                        mol_type = protein
                        organism = synthetic construct
SEQUENCE: 308
LLIILRRRRI RKQAHAHSK                                              19

SEQ ID NO: 309          moltype = AA  length = 26
FEATURE                 Location/Qualifiers
source                  1..26
                        mol_type = protein
                        organism = synthetic construct
SEQUENCE: 309
DPKGDPKGVT VTVTVTVTGK GDPKPD                                      26

SEQ ID NO: 310          moltype = AA  length = 17
FEATURE                 Location/Qualifiers
source                  1..17
                        mol_type = protein
                        organism = synthetic construct
SEQUENCE: 310
CSIPPEVKFN KPFVYLI                                                17

SEQ ID NO: 311          moltype = AA  length = 27
FEATURE                 Location/Qualifiers
source                  1..27
```

```
                      mol_type = protein
                      organism = synthetic construct
SEQUENCE: 311
GWTLNSAGYL LGKINLKALA ALAKKIL                                      27

SEQ ID NO: 312        moltype = AA  length = 21
FEATURE               Location/Qualifiers
source                1..21
                      mol_type = protein
                      organism = synthetic construct
SEQUENCE: 312
AGYLLGKINL KALAALAKKI L                                            21

SEQ ID NO: 313        moltype = AA  length = 17
FEATURE               Location/Qualifiers
source                1..17
                      mol_type = protein
                      organism = synthetic construct
SEQUENCE: 313
GALFLGFLGA AGSTMGA                                                 17

SEQ ID NO: 314        moltype = AA  length = 20
FEATURE               Location/Qualifiers
source                1..20
                      mol_type = protein
                      organism = synthetic construct
SEQUENCE: 314
HGLASTLTRW AHYNALIRAF                                              20

SEQ ID NO: 315        moltype = AA  length = 20
FEATURE               Location/Qualifiers
source                1..20
                      mol_type = protein
                      organism = synthetic construct
SEQUENCE: 315
GLWRALWRLL RSLWRLLWRA                                              20

SEQ ID NO: 316        moltype = AA  length = 30
FEATURE               Location/Qualifiers
source                1..30
                      mol_type = protein
                      organism = synthetic construct
SEQUENCE: 316
WEAALAEALA EALAEHLAEA LAEALEALAA                                   30

SEQ ID NO: 317        moltype = AA  length = 24
FEATURE               Location/Qualifiers
source                1..24
                      mol_type = protein
                      organism = synthetic construct
SEQUENCE: 317
GLFEAIEGFI ENGWEGMIDG WYGC                                         24

SEQ ID NO: 318        moltype = AA  length = 23
FEATURE               Location/Qualifiers
source                1..23
                      mol_type = protein
                      organism = synthetic construct
SEQUENCE: 318
GLFGAIAGFI ENGWEGMIDG WYG                                          23

SEQ ID NO: 319        moltype = AA  length = 36
FEATURE               Location/Qualifiers
source                1..36
                      mol_type = protein
                      organism = synthetic construct
SITE                  36
                      note = amidated lysine
SEQUENCE: 319
GLFGAIAGFI ENGWEGMIDG RQIKIWFQNR RMKWKK                            36

SEQ ID NO: 320        moltype = AA  length = 26
FEATURE               Location/Qualifiers
source                1..26
                      mol_type = protein
                      organism = synthetic construct
SEQUENCE: 320
GLFGAIAGFI ENGWEGMIDG SSKKKK                                       26
```

```
SEQ ID NO: 321          moltype = AA  length = 24
FEATURE                 Location/Qualifiers
source                  1..24
                        mol_type = protein
                        organism = synthetic construct
SEQUENCE: 321
GLFEAIAGFI ENGWEGMIDG GGYC                                            24

SEQ ID NO: 322          moltype = AA  length = 23
FEATURE                 Location/Qualifiers
source                  1..23
                        mol_type = protein
                        organism = synthetic construct
SEQUENCE: 322
GLFHAIAHFI HGGWHGLIHG WYG                                             23

SEQ ID NO: 323          moltype = AA  length = 30
FEATURE                 Location/Qualifiers
source                  1..30
                        mol_type = protein
                        organism = synthetic construct
SEQUENCE: 323
GLFEAIEGFI ENGWEGLAEA LAEALEALAA                                      30

SEQ ID NO: 324          moltype = AA  length = 29
FEATURE                 Location/Qualifiers
source                  1..29
                        mol_type = protein
                        organism = synthetic construct
SEQUENCE: 324
KWKLFKKIGA VLKVLTTGYG RKKRRQRRR                                       29

SEQ ID NO: 325          moltype = AA  length = 16
FEATURE                 Location/Qualifiers
source                  1..16
                        mol_type = protein
                        organism = synthetic construct
SEQUENCE: 325
RQIKIWFQNR RMKWKK                                                     16

SEQ ID NO: 326          moltype = AA  length = 13
FEATURE                 Location/Qualifiers
source                  1..13
                        mol_type = protein
                        organism = synthetic construct
SEQUENCE: 326
GRKKRRQRRR PPQ                                                        13

SEQ ID NO: 327          moltype = AA  length = 18
FEATURE                 Location/Qualifiers
source                  1..18
                        mol_type = protein
                        organism = synthetic construct
SEQUENCE: 327
LLIILRRRIR KQAHAHSK                                                   18

SEQ ID NO: 328          moltype = AA  length = 27
FEATURE                 Location/Qualifiers
source                  1..27
                        mol_type = protein
                        organism = synthetic construct
SEQUENCE: 328
GWTLNSAGYL LGKINLKALA ALAKKIL                                         27

SEQ ID NO: 329          moltype = AA  length = 27
FEATURE                 Location/Qualifiers
source                  1..27
                        mol_type = protein
                        organism = synthetic construct
SEQUENCE: 329
GALFLGFLGA AGSTMGAWSQ PKKKRKV                                         27

SEQ ID NO: 330          moltype = AA  length = 21
FEATURE                 Location/Qualifiers
source                  1..21
                        mol_type = protein
                        organism = synthetic construct
SEQUENCE: 330
KETWWETWWT EWSQPKKKRK V                                               21
```

```
SEQ ID NO: 331          moltype = AA  length = 11
FEATURE                 Location/Qualifiers
source                  1..11
                        mol_type = protein
                        organism = synthetic construct
VARIANT                 8..11
                        note = Residues may be deleted
SEQUENCE: 331
RRRRRRRRRR R                                                        11

SEQ ID NO: 332          moltype = AA  length = 18
FEATURE                 Location/Qualifiers
source                  1..18
                        mol_type = protein
                        organism = synthetic construct
SEQUENCE: 332
KLALKLALKA LKAALKLA                                                 18

SEQ ID NO: 333          moltype = AA  length = 9
FEATURE                 Location/Qualifiers
source                  1..9
                        mol_type = protein
                        organism = synthetic construct
SEQUENCE: 333
RRWWRRWRR                                                           9

SEQ ID NO: 334          moltype = AA  length = 13
FEATURE                 Location/Qualifiers
source                  1..13
                        mol_type = protein
                        organism = synthetic construct
SEQUENCE: 334
CGYGPKKKRK VGG                                                      13

SEQ ID NO: 335          moltype = AA  length = 8
FEATURE                 Location/Qualifiers
source                  1..8
                        mol_type = protein
                        organism = synthetic construct
SEQUENCE: 335
KKKKKKKK                                                            8

SEQ ID NO: 336          moltype = AA  length = 28
FEATURE                 Location/Qualifiers
source                  1..28
                        mol_type = protein
                        organism = synthetic construct
SEQUENCE: 336
LSTAADMQGV VTDGMASGLD KDYLKPDD                                      28

SEQ ID NO: 337          moltype = AA  length = 4
FEATURE                 Location/Qualifiers
source                  1..4
                        mol_type = protein
                        organism = synthetic construct
SEQUENCE: 337
GGFG                                                                4

SEQ ID NO: 338          moltype = AA  length = 4
FEATURE                 Location/Qualifiers
source                  1..4
                        mol_type = protein
                        organism = synthetic construct
SEQUENCE: 338
ALAL                                                                4

SEQ ID NO: 339          moltype = AA  length = 22
FEATURE                 Location/Qualifiers
source                  1..22
                        mol_type = protein
                        organism = synthetic construct
```

-continued

```
SEQUENCE: 339
MVRRFLVTLR IRRACGPPRV RV                                           22

SEQ ID NO: 340          moltype = AA  length = 4
FEATURE                 Location/Qualifiers
source                  1..4
                        mol_type = protein
                        organism = synthetic construct
SEQUENCE: 340
GFLG                                                               4
```

What is claimed is:

1. A polynucleotide conjugate comprising an anti-transferrin receptor antibody or antigen-binding fragment thereof conjugated to a polynucleotide that hybridizes to a target sequence of a human PRKAG2 mRNA and mediates down-regulation of the human PRKAG2 mRNA in a cardiac muscle cell, wherein the polynucleotide is a double-stranded small interfering RNA (siRNA) comprising a guide strand and a passenger strand, wherein the guide strand comprises the nucleic acid sequence selected from SEQ ID NOs: 61 and 65.

2. The polynucleotide conjugate of claim 1, wherein the target sequence is a human PRKAG2 mRNA having a gain of function mutation.

3. The polynucleotide conjugate of claim 1, wherein the passenger strand comprises the nucleic acid sequence selected from SEQ ID NOs: 163 and 167.

4. The polynucleotide conjugate of claim 1, wherein the polynucleotide comprises at least one 2' modified nucleotide, at least one modified internucleotide linkage, or at least one inverted abasic moiety.

5. The polynucleotide conjugate of claim 4, wherein the at least one 2' modified nucleotide comprises:

2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified nucleotide, a locked nucleic acid (LNA), an ethylene nucleic acid (ENA), or a combination thereof.

6. The polynucleotide conjugate of claim 4, wherein the at least one modified internucleotide linkage comprises a phosphorothioate linkage or a phosphorodithioate linkage.

7. The polynucleotide conjugate of claim 1, wherein the polynucleotide comprises a 5'-terminal vinylphosphonate modified nucleotide.

8. The polynucleotide conjugate of claim 4, wherein the passenger strand comprises the nucleic acid sequence selected from SEQ ID NOs: 223 and 224.

9. The polynucleotide conjugate of claim 4, wherein the guide strand comprises the nucleic acid sequence selected from SEQ ID NOs: 211 and 212.

10. The polynucleotide conjugate of claim 4, wherein the guide strand comprises the nucleic acid sequence of SEQ ID NO: 211 or 212 and the passenger strand comprises the nucleic acid sequence of SEQ ID NO: 223 or 224.

11. The polynucleotide conjugate of claim 1, wherein the polynucleotide conjugate has a polynucleotide to antibody ratio of from about 1 to about 4.

12. The polynucleotide conjugate of claim 1, wherein the anti-transferrin receptor antibody or antigen binding fragment thereof comprises a non-human antibody or antigen binding fragment thereof, a human antibody or antigen binding fragment thereof, a humanized antibody or antigen binding fragment thereof, a chimeric antibody or antigen binding fragment thereof, a monoclonal antibody or antigen binding fragment thereof, a monovalent Fab', a divalent Fab2, a single-chain variable fragment (scFv), a diabody, a minibody, a nanobody, a single-domain antibody (sdAb), or a camelid antibody or antigen binding fragment thereof.

13. The polynucleotide conjugate of claim 1, wherein polynucleotide conjugate comprises a linker connecting the anti-transferrin receptor antibody or antigen-binding fragment thereof to the polynucleotide.

14. A polynucleotide molecule for modulating human PRKAG2 mRNA expression, wherein the polynucleotide molecule is a double-stranded siRNA comprising a guide strand and a passenger strand, wherein the guide strand comprises the nucleic acid sequence selected from SEQ ID NOs: 61 and 65.

15. A method of treating cardiomyopathy in a subject in need thereof comprising administering to said subject a polynucleotide conjugate comprising an anti-transferrin receptor antibody or antigen-binding fragment thereof conjugated to a polynucleotide that hybridizes to a target sequence of a human PRKAG2 mRNA, thereby treating cardiomyopathy in said subject, and wherein the polynucleotide is a double-stranded siRNA comprising a guide strand and a passenger strand, wherein the guide strand comprises the nucleic acid sequence selected from SEQ ID NOs: 61 and 65.

16. The method of claim 15, wherein the cardiomyopathy is caused by at least one of: a glycogen storage disease, PRKAG2 syndrome or PRKAG2 cardiac syndrome.

17. The method of claim 16, wherein the PRKAG2 syndrome or the PRKAG2 cardiac syndrome is caused by a mutated human PRKAG2 mRNA that has a gain of function.

18. A conjugate comprising an anti-transferrin receptor antibody or antigen-binding fragment thereof conjugated to an siRNA that decreases human PRKAG2 mRNA levels in a cardiac muscle cell, wherein the anti-transferrin receptor antibody or antigen-binding fragment thereof comprises the VH sequence of SEQ ID NO: 256, 257, 258, 259, or 260, and the VL sequence of SEQ ID NO: 261, 262, 263, 264, or 265, and wherein the guide strand sequence of the siRNA is selected from the group consisting of SEQ ID NOs: 61 and 65, and the passenger strand sequence of the siRNA is selected from the group consisting of SEQ ID NOs: 163 and 167.

19. The conjugate of claim 18, wherein the passenger strand or the guide strand of the siRNA comprises a 5'-terminal vinylphosphonate modified nucleotide.

20. The conjugate of claim 18, wherein the conjugate comprises a linker connecting the anti-transferrin receptor antibody or antigen-binding fragment thereof to the siRNA.

21. The conjugate of claim 20, wherein the linker comprises a maleimide group.

22. The conjugate of claim 18, wherein the siRNA comprises the guide strand sequence of SEQ ID NO:61 and the passenger strand sequence of SEQ ID NO:163.

* * * * *